(12) United States Patent
Danishefsky et al.

(10) Patent No.: US 7,531,181 B2
(45) Date of Patent: May 12, 2009

(54) GP120 SPECIFIC ANTIGENS AND USES THEREOF

(75) Inventors: Samuel J. Danishefsky, Englewood, NJ (US); Vadim Dudkin, New York, NY (US); Xudong Geng, New York, NY (US); Mihirbaran Mandal, New York, NY (US); Isaac Kraus, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 138 days.

(21) Appl. No.: 11/145,084

(22) Filed: Jun. 3, 2005

(65) Prior Publication Data

US 2006/0229432 A1 Oct. 12, 2006

Related U.S. Application Data

(63) Continuation-in-part of application No. PCT/US03/38471, filed on Dec. 3, 2003.

(60) Provisional application No. 60/500,708, filed on Sep. 5, 2003, provisional application No. 60/500,161, filed on Sep. 4, 2003, provisional application No. 60/430,822, filed on Dec. 3, 2002.

(51) Int. Cl.
*A61K 39/21* (2006.01)
*A61K 39/00* (2006.01)
*A61K 39/12* (2006.01)
*A61K 45/00* (2006.01)

(52) U.S. Cl. .............. 424/208.1; 424/184.1; 424/186.1; 424/187.1; 424/188.1; 424/278.1; 424/279.1

(58) Field of Classification Search ....................... None
See application file for complete search history.

(56) References Cited

U.S. PATENT DOCUMENTS

| 5,606,030 A | 2/1997 | Emini et al. |
| 5,623,057 A | 4/1997 | Marburg et al. |
| 5,977,081 A | 11/1999 | Marciani |
| 6,080,725 A | 6/2000 | Marciani |

FOREIGN PATENT DOCUMENTS

| WO | WO 2004033663 A | * | 4/2004 |
| WO | WO-2004/050711 | | 6/2004 |
| WO | WO-2004/060915 | | 7/2004 |

OTHER PUBLICATIONS

Henner, et al. Glycoprotein Biosynthesis in Calf Pituitary. J Biol Chem. 1981;256(12):5997-6003.*
Snippe, et al. Immunogenic Properties in Mice of Hexasaccharide from the Capsular Polysaccharide of *Streptococcus pneumoniae* Type 3. Infect. Immun. 1983; 40(3):856-861.*
Sanders, et al. The Mannose-Dependent Epitope for Neutralizing Antibody 2G12 on Human Immunodeficiency Virus Type 1 Glycoprotein gp120. J Virol. 2002; 76(14);7293-7305*
Scanlan, et al. The Broadly Neutralizing Anti-Human Immunodeficiency Virus Type 1 Antibody 2G12 Recognizes a Cluster of an alpha1—>2 Mannose Residues on the Outer Face of gp120. J Virol. 2002; 76(14)7306-7321.*
Kudryachov, et al. Toward optimized carbohydrate-based anticancer vaccines: Epitope clustering, carrier structure and adjuvant all influence antibody responses to Lewis-y conjugates in mice. PNAS. 2001; 98(6):3264-3269.*
Ratner et al., Eur. J. Org. Chem., 2002, pp. 826-833.
Sprengard et al., Angew. Chem. Int. Ed. Engl., 1996, pp. 321-324, vol. 35. No. 3.
U.S. Appl. No. 11/145,002, filed Jun. 3, 2005, Danishefsky et al.
Arsequell, et al., J. Chem. Soc.—Perkin Trans., 1:1739-1745, 1995.
Adluri, et al., Cancer Immunol. Immun., 41:185-192, 1995.
Ajisaka, et al., Biosci. Biotechnol. Biochem., 65:1240-1243, 2001.
Anisfeld, et al., J. Org. Chem., 55:5560-5562, 1990.
Armbruster, et al., AIDS, 16:227-233, 2002.
Bernstein, et al., Carbohydrate Research, 78:C1, 1980.
Bewley, et al., J. Am. Chem. Soc., 123(17):2001.
Botos, et al., J. Biol. Chem., 227:34336-34342, 2002.
Bu, et al., Tetrahedron Letters, 43:2419-2422, 2002.
Burton, Proc. Natl. Acad. Sci. U.S.A., 94:10018-10023, 1997.
Calarese, et al., Science, 300:2065-2071, 2003.
Canne, et al., Tetrahedron Letters, 36:1217-1220, 1995.

Chan, et al., Fmoc Solid Phase Peptide Synthesis: A Practical Appraoch, Oxford University Press, New York, pp. 50 and pp. 217, 2000.
Chen, et al., J. Am. Chem. Soc., 120:7760-7769, 1998.
Chhabra, et al., Tetrahedron Letters, 39:1603-1606, 1998.
Clippingdale, et al., J. Pept. Sci., 6:225-234, 2000.
Cohen-Anisfeld, et al., J. Am. Chem. Soc., 115(23):10531-10537, 1993.
Danishefsky, et al., Angew. Chem. Int. Ed. Engl., 39:836-863, 2000.
Davis, Chemical Reviews, American Chemical Society, 102(2):579-602, 2002.
Dawson et al., Annu. Rev. Biochem., 69:923-960, 2000.
Dawson, et al., J. Am. Chem. Soc., 119:4325-4329, 1997.
Dawson, et al., Science, 266:776-779, 1994.
Dudkin, et al., J. Am. Chem. Soc., 126:9560-9562, 2004.
Dudkin, et al., Tetrahedron Letters, 44:1791-1793, 2003.
Dumy, et al., Org. Lett., 5:243-246, 2003.
Dumy, et al., Tetrahedron Letters, 36:1225-1258, 1995.
Espinosa, et al., Protein Sci., 11:1492, 2002.
Examination Report, European Patent Application No. 03810054, mailed Jun. 5, 2007.
Feinberg, et al., Science, 294:2163-2166, 2001.
Glunz, et al., J. Am. Chem. Soc., 122:7273-7279, 2000.
Greene, et al., Protective Groups in Organic Synthesis, John Wiley and Sons, New York, Chapter 6, 1999.
Hackeng, et al., Proc. Natl. Acad. Sci. U.S.A., 96:10068-10073, 1999.
Hang, et al., Acc. Chem. Res., 34:727-736, 2001.
Harris, et al., Micron, 30:597-623, 1999.
Helling, et al., Cancer Res., 54:197-203, 1994.
Hojo, et al., Bull. Chem. Soc. Jpn., 64:111-117, 1991.
Inazu, et al., J. Syn. Org. Chem. Jpn., 56:210-220, 1998.
Ingenito, et al., J. Am. Chem. Soc., 121:11369-11374, 1999.
International Search Report, PCT/US03/38471, mailed on Feb. 12, 2004.
Kellner, et al., Biol. Chem. Hoppe-Seyler, 373:51-55, 1992.
Kensil, et al., J. Immunol., 146:431-437, 1991.
Kent, et al., Annu, Rev. Biochem., 57:957-989, 1988.
Koeller, et al., J. Am. Chem. Soc., 122:4241-4242, 2000.
Kudryashov, et al., Proc. Natl. Acad. Sci. U.S.A., 98:3264-3269, 2001.
Kwong, et al., Nature, 420:678-682, 2002.
Lemieux, Chem. Soc. Rev., 7:423, 1978.
Li, et al., Tetrahedron Letters, 39:8669-8672, 1998.
Likhosherstov, et al., Carbohydrate Research, 146:C1-C5, 1986.
Livingston, et al., Vaccine, 12:1275-1280, 1994.
Macmillan, et al., Tetrahedron, 56:9515-9525, 2000.
Mandal, et al., Angew. Chem. Int. Ed. Engl., 2562, 2004.
Marcaurelle, et al., Chem. Eur. J., 7:1129-1132, 2001.
Marciani, et al., Vaccine, 18:3141, 2000.
Marra, et al., Synlett, 572-574, 1990.
Mascola, et al., J. Virol., 73:4009-4018, 1999.
Mascola, et al., Nature Med., 6:207-210, 2000.
Matsuo, et al., J. Am. Chem. Soc., 125:3402-3403, 2003.
Meinjohanns, et al., J. Am. Chem. Soc., Perkin Transactions 1: Organic and Bio-Organic Chemistry, 3:549-560, 1998.
Metzger, et al., Int. J. Pept. Protein Res., 37:46-57, 1991.
Miller, et al., Angew. Chemie. Int. Ed., 42:431-434, 2003.
Musselli, et al., J. Cancer Res. Clin. Oncol., 127:R20-R26, 2001.
Okada, et al., Biophys. Acta-Gen. Subj., 1525:149-160, 2001.
Prakash, et al., Glycobiology, 10:173-176, 2000.
Ragupathi, Cancer Immunol. Immun., 43:152-157, 1996.
Ragupathi, et al., Cancer Immunol. Immun., 48:1-8, 1999.
Renard, et al., Helv. Chim. Act., 86:3638-3647, 2003.
Sanders, et al., J. of Virol., 76(14):7293-7305, 2002.
Scanlan, et al., J. of Virol., 76(14):7306-7321, 2002.
Shankaramma, et al., Chem. Commun., 1842-1843, 2003.
Shin, et al., J. Am. Chem. Soc., 121:11684-11689, 1999.
Singh, et al., Bioorganic and Medicinal Chemistry, 13(3):327-330, 2003.
Spearman, et al., Curr. HIV Res., 1:101-120, 2003.
Stiegler, et al., AIDS, 16:2019-2025, 2002.
Tam, et al., J. Am. Chem. Soc., 117:12058-12063, 1995.
Thaler, et al., Helv. Chim. Acta, 74:628-643, 1991.
Trkola, et al., J. Virol., 70:1100-1108, 1996.

Wang, et al., Abstracts of Papers American Chemical Society, 224(1-2): CARB 15, 2002.
Wang, et al., Angew. Chem. Int. Ed., 40:1728-1732, 2001.
Wang, et al., Chem. Bio., 11:127-134, 2004.
Wang, et al., J. Am. Chem. Soc., 119(46):11137-11146, 1997.
Wei, et al., Nature, 422:307-312, 2003.
Wolbank, et al., J. Virol., 77:4095-4103, 2003.
Zhang, et al., Cancer Res., 56:3315-3319, 1996.
Zhang, et al., Carbohydrate Research, 236:73-88, 1992.

* cited by examiner

*Primary Examiner*—Bruce Campell
*Assistant Examiner*—Stuart W. Snyder
(74) *Attorney, Agent, or Firm*—Choate, Hall & Stewart LLP; C. Hunter Baker

(57) ABSTRACT

The present invention provides multi-antigenic constructs comprising one or more carbohydrate antigens having the formula:

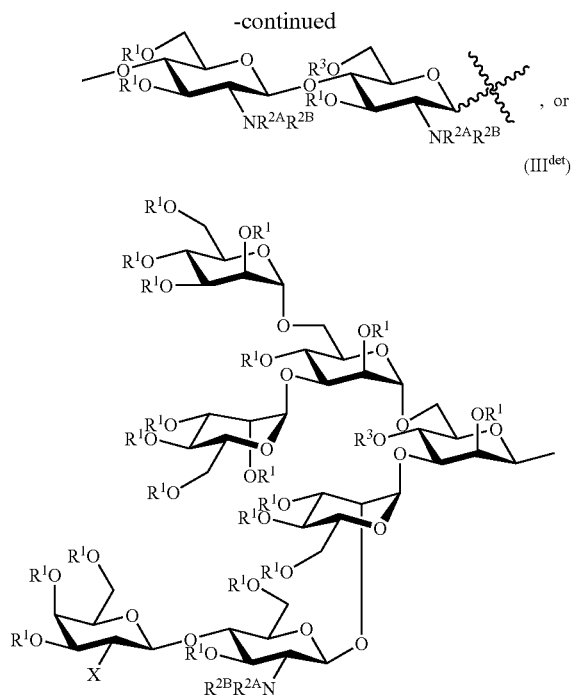

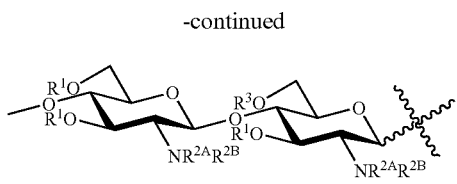

wherein $R^1$, $R^{2A}$, $R^{2B}$, $R^3$, $R^4$, $W^1$, $W^2$ and $W^3$ are as defined herein; and additionally provides compositions thereof, and methods for their use in the treatment and/or prevention of HIV infection, and methods for inducing HIV-specific antibodies in a subject, comprising administering to a subject in need thereof, an effective amount of any of the inventive compounds as disclosed herein, either in conjugated form or unconjugated and in combination with a suitable immunogenic carrier. In another aspect, the invention provides an antibody or antibody fragment which binds specifically to a gp120 glycan or glycopeptide of the invention.

45 Claims, 2 Drawing Sheets

1

2

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Sequence derived from HIV gp120 protein

<400> SEQUENCE: 1

Ala Lys Trp Asn Ser Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Sequence derived from HIV gp120 protein

<400> SEQUENCE: 2
```

```
Ala Lys Trp Asn Asn Thr Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Sequence derived from HIV gp120 protein

<400> SEQUENCE: 3

Cys Asn Ile Ser Arg
1               5

<210> SEQ ID NO 4
<211> LENGTH: 20
<212> TYPE: PRT
<213> ORGANISM: Artificial Sequence
<220> FEATURE:
<223> OTHER INFORMATION: Sequence derived from HIV gp120 protein

<400> SEQUENCE: 4

Ala Phe Val Thr Ile Gly Lys Ile Gly Asn Met Arg Gln Ala His Cys
1               5                   10                  15

Asn Ile Ser Arg
            20

<210> SEQ ID NO 5
<211> LENGTH: 15
<212> TYPE: PRT
<213> ORGANISM: Artificial Sequence
<220> FEATURE:
<223> OTHER INFORMATION: Sequence derived from HIV gp120 protein

<400> SEQUENCE: 5

Ala Phe Val Thr Ile Gly Lys Ile Gly Asn Met Arg Gln Ala His
1               5                   10                  15

<210> SEQ ID NO 6
<211> LENGTH: 5
<212> TYPE: PRT
<213> ORGANISM: Artificial Sequence
<220> FEATURE:
<223> OTHER INFORMATION: Sequence derived from HIV gp120 protein

<400> SEQUENCE: 6

Cys Asp Ile Ser Arg
1               5
```

GP120 SPECIFIC ANTIGENS AND USES THEREOF

PRIORITY

This application is a Continuation-In-Part and claims the benefit under 35 U.S.C. § 120 of co-pending International Application PCT/US03/38471, filed Dec. 3, 2003, and published in English under PCT Article 21(2), which claims priority to U.S. Provisional Application Nos. 60/500,708, filed Sep. 5, 2003; 60/500,161, filed Sep. 4, 2003; and 60/430,822, filed Dec. 3, 2002. Each of the above applications is hereby incorporated by reference in its entirety.

GOVERNMENT SUPPORT

The invention was made with U.S. government support under grants BC020513 and BC022120 awarded by the U.S. Army (DOD) Breast Cancer Research Foundation; and grant 1 F32 AI63976-01 awarded by the National Institutes of Health/National Institute of Allergy and Infectious Diseases. The U.S. government has certain rights in this invention.

BACKGROUND OF THE INVENTION

Despite enormous scientific effort, the development of a vaccine against HIV has proven to be a largely elusive goal. There are several major factors complicating the creation of such vaccine.

One problem stems from a very low immunogenicity of the viral surface. Pairs of the envelope spike proteins (gp120 and gp41) form a trimer, inside of which much of the potentially antigenic surface of the unprocessed precursor protein (gp160) is buried. Moreover, the "outer" face of gp120 is extensively glycosylated (and therefore unavailable for peptide—recognizing antibodies), further complicating the problem.

Secondly, the mature envelope oligomer is itself a very weak antigen. Many explanations have been proposed to explain the unusually low antigenicity of the viral envelope spikes. The "glycan shield" concept implies that steric hindrance created by N-linked carbohydrates of gp120 prevents the immune system form generating antibodies with a broadly neutralizing action. Another hypothesis states that binding of neutralizing antibodies to the CD4 site of gp120 leads to conformational changes and is entropically disfavored, thereby allowing for HIV neutralization escape. It has also been suggested that a very strong initial immune response to gp160, which does not lead to broadly neutralizing antibody production (vide supra) suppresses response to the mature oligomer, which is expressed in much lower concentrations.

In addition, extremely high degree and rate of viral variation provide a powerful mechanism for HIV to escape immune defense.

Accordingly, commonly utilized vaccine formulations have been unable to elicit a potent and broadly neutralizing antibody response. Administration of the whole virus in attenuated or inactivated form presents safety issues as well as the problem of low antigenicity. Immunization with a part of HIV DNA in a carrier is more promising, however it requires a very careful choice of the carrier virus. Also, low envelope antigenicity still remains a serious obstacle to the success of this method. A solution may lie in the use of artificial HIV antigens based on the epitopes of known broadly neutralizing antibodies. A highly focused immune response may be developed with this approach, potentially circumventing the problem of low antigenicity. The biggest challenge in this case is the design and synthesis of the antigens.

Gp120 surface carbohydrates can be seen as an attractive target for such design. There are a number of molecules that can efficiently bind to HIV envelope glycans. Among them, the dendritic cell receptor DC-SIGN has been demonstrated to recognize the internal tri-mannose segment of the N-linked oligosaccharides. A bacterial protein cyanovirin-N efficiently binds high-mannose type gp120 carbohydrates. Also, one of the most potent broadly neutralizing antibodies known to date, the 2g12, has been shown to have a carbohydrate epitope. Administering synthetic antigens containing one or more glycans on a part of gp120 peptide backbone or appropriately chosen linker system and further conjugated to an antigenic carrier could elicit strong immune response ultimately aimed at the real viral envelope. Some of the N-linked carbohydrates of gp120 appear to be conserved in most of HIV primary isolates. Since the glycans recognized by these molecules are located on the outer, "silent" face of the oligomer, they are easily accessible for antibody binding. Entropically disfavored interaction does not present a problem since the epitope does not overlap with the CD4-binding site. Finally, an extensive glycosylation of the envelope is an advantage, rather than a problem for such antigen design.

Accordingly, there remains a need for novel synthetic methods leading to the preparation of gp120 glycans and conjugates thereof, and their evaluation in immunologic and therapeutic studies.

SUMMARY OF THE INVENTION

In recognition of the need to provide access to synthetically unavailable gp120 glycans and glycoconjugates thereof, the present invention, in one aspect, provides novel gp120 glycans and glycoconjugates thereof, and methods for the synthesis and use thereof.

In one aspect, the invention provides clustered glycoconjugates comprising a cyclic or acyclic backbone made up of two or more amino acids or other structural units, wherein one or more of said amino acids or structural units is/are independently substituted with a glycosidic moiety having the structure:

$$\boxed{A} - L^1 -\xi$$

wherein each occurrence of $L^1$ is independently a substituted or unsubstituted, linear or branched, cyclic or acyclic, saturated or unsaturated aliphatic or heteroaliphatic moiety; and and each occurrence of A is independently a carbohydrate domain having the structure:

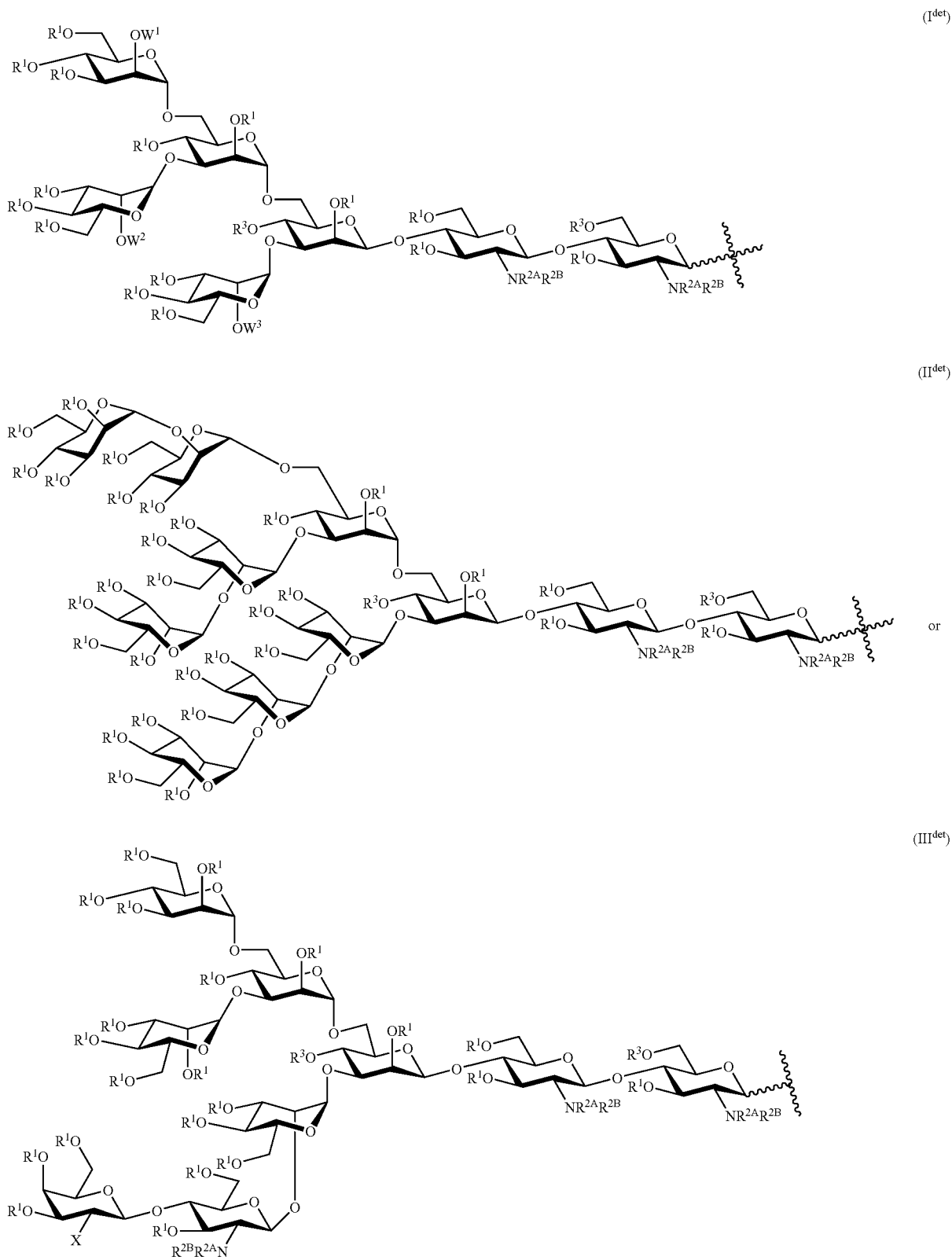
wherein each occurrence of $R^1$ is independently hydrogen or an oxygen protecting group;
each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

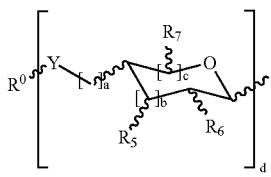

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently optionally substituted mannose, galactose or lactosamine moieties.

In another aspect, the invention encompasses clustered multi-antigenic constructs having the structure:

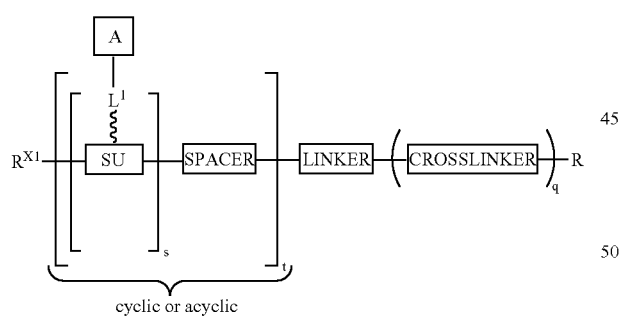

wherein q is 0 or 1;
each occurrence of s is independently an integer from 1-20;
t is an integer from 1-6;
wherein t+s>2;
$R^{X1}$ is hydrogen, alkyl, acyl, aryl, heteroaryl, -alkyl(aryl), -alkyl(heteroaryl) or a nitrogen protecting group; or $R^{X1}$ is covalently bound to a substituent on the last occurrence of the spacer, thereby forming a cyclic backbone;
R is hydrogen or an immunogenic carrier;
each occurrence of the structural unit SU is independently a substituted or unsubstituted aliphatic, heteroaliphatic, aryl, heteroaryl or peptidic moiety;

each occurrence of the spacer is independently a substituted or unsubstituted aliphatic, heteroaliphatic, aryl, heteroaryl or peptidic moiety;
the linker is absent, or is —O—, —$NR_G$—, —$NR_G(CR_HR_J)_kNR_K$—, $NR_G(CR_HR_J)_kNR_K(C=O)(CR_HR_J)_k$S—, —$(CR_HR_J)_kNR_K$—, —$O(CR_HR_J)_kNR_K$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5;
wherein each occurrence of $R_G$, $R_H$, $R_J$ or $R_K$ is independently hydrogen, a linear or branched, substituted or unsubstituted, cyclic or acyclic alkyl moiety, or a substituted or unsubstituted aryl moiety;
the crosslinker is a moiety derived from a crosslinking reagent capable of conjugating the carrier with the linker, or when the linker is absent, with the t braketed structure;
the carrier is a peptide, protein, protein complex or lipid;
each occurrence of $L^1$ is independently a substituted or unsubstituted aliphatic or heteroaliphatic moiety; and
each occurrence of A is independently a carbohydrate domain of formula ($I^{det}$), ($II^{det}$) or ($III^{det}$).

In certain embodiments, the t bracketed structure of the above constructs is a cyclic glycopeptide having the structure:

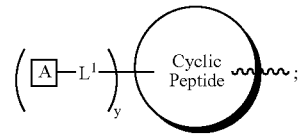

where y is an integer from 1-50; and
each occurrence of A is independently a carbohydrate domain of formula ($I^{det}$), ($II^{det}$) or ($III^{det}$).

In yet another aspect, the invention provides dimeric glycopeptides having the structure:

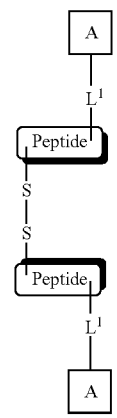

wherein each peptide may be the same or different; each occurrence of $L^1$ may be the same or different and is as defined above; each occurrence of A is independently a carbohydrate domain of formula ($I^{det}$), ($II^{det}$) or ($III^{det}$).

In another aspect, the invention provides compositions of above multimeric antigenic constructs.

In another aspect, the invention provides methods for the use of the above multimeric antigenic constructs in the treatment of HIV, methods for the prevention of HIV, and methods for inducing antibodies in a subject, comprising administering to a subject in need thereof, an effective amount of any of the inventive compounds as disclosed herein, either in conjugated form or unconjugated and in combination with a suitable immunogenic carrier.

In another aspect, the invention provides an antibody or antibody fragment which is specific to one or more of the inventive gp120 glycans and/or glycoconjugates thereof described herein, said antibody being a purified polyclonal antibody or a monoclonal antibody.

DEFINITIONS

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position unless otherwise indicated. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and/or prevention of HIV, or in the inducement of antibodies, as described herein. The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples, which are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

It will be appreciated that additional examples of generally applicable substitutents are illustrated by the specific embodiments shown in the Examples which are described herein, but are not limited to these Examples.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "adjuvant" or "immunogenic stimulant" refers to a moiety, which, when co-administered with an immunogen, enhances the immunogenicity of the immunogen. Specifically, in certain embodiments, immunogenicity of the inventive gp120 compounds can be significantly improved if the immunizing agent(s) (e.g., gp120 glycan(s) and/or construct(s) thereof) and/or composition thereof is, regardless of administration format, co-immunized with an adjuvant. Commonly, adjuvants are used as an 0.05 to 1.0 percent solution in phosphate-buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses. As such, embodiments of this invention encompass compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgGl isotype in the mouse, which may not be optimal for protection by some vaccinal agents. In addition to adjuvants used for therapeutic purposes (e.g., vaccines), other adjuvants may be used for raising antibodies in animals, which antibodies may be used, for example, in diagnostic and immunoassays. Examples of such adjuvants include, but are not limited to, bacteria or liposomes. For example, suitable adjuvants include but are not limited to, saponin adjuvants (e.g., GPI-0100), *Salmonella minnesota* cells, bacille Calmette-Guerin or QS21.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

The term "natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids. This includes, for example, $\alpha$-, $\beta$-, D-, L-amino acid residues, and compounds of the general formula

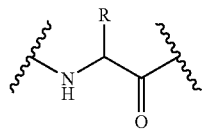

wherein the side chain R is other than the amino acid side chains occurring in nature.

More generally, the term "amino acid", as used herein, encompasses natural amino acids and unnatural amino acids.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. In certain embodiments, the biological sample is obtained from the prostate epithelium. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques. In certain emboidments, the biological sample is taken from a male human subject. In certain exemplary embodiment, the biological sample has been processed so that the gp120 glycan concentration out of the total glycan concentration in the original sample is increased. In certain exemplary embodiments, the sample may be purified serum gp120, purified gp120 glycoprotein, purified gp120 glycoprotein that has undergone sialidase digestion, purified gp120 glycans obtained from deglycosylated gp120 glycoprotein, or any combination thereof. It will be appreciated that the term "biological sample", as used herein, encompasses any combination of gp120 materials obtained from any biological sources (e.g., as detailed above) or by any processes that may be used to obtain gp120 glycan from the original sample (e.g., extraction, purification, glycoprotein deglycosylation, sialidase digestion, etc.).

As used herein, the term "isolated" when applied to the compounds of the present invention, refers to such compounds that are (i) separated from at least some components with which they are associated in nature or when they are made and/or (ii) produced, prepared or manufactured by the hand of man. In certain embodiments, isolated compounds of the invention are not substantially contaminated with, or otherwise in contact with any other compound. Accordingly, the present invention provides compounds of formula (I) and/or (II) in substantially pure form, i.e., in a purity of greater than about 95% by weight (not including $H_2O$ or salt content, which is to be expected, for example, from lyophilized peptides and glycopeptides), preferably greater than about 98%, and more preferably greater than about 99% by weight. In one aspect, the impurity in contact with a compound of formula (I) and/or (II) of the invention is an organic chemical, e.g., an organic solvent. In another aspect, the impurity in contact with a compound of formula (I) and/or (II) is another compound of formula (I) and/or (II). Thus, in one aspect, the present invention provides a compound of formula (I) and/or (II) that is pure in that it is not in contact with another compound of formula (I) and/or (II).

As used herein, the term "glycoconjugate" refers to one or more glycans covalently linked to a peptidic or non-peptidic backbone.

As used herein, the term "gp120 glycan" refers to a carbohydrate domain present on gp120. More specifically, gp120 glycan designates the carbohydrate portion of compounds of formula (I), (II) and/or (III) described herein. In certain embodiments, the term refers to compounds of formula (I), (II) and/or (III) where $R^4$ is a moiety other than a peptide, protein or other polymeric construct.

As used herein, the term "gp120 glycopeptide" refers to compounds of formula (I), (II) and/or (III) where $R^4$ comprises a peptide moiety covalently linked to the rest of the construct either directly (e.g., through N or O) or through a crosslinker.

As used herein, the term "eliciting an immune response" is defined as initiating, triggering, causing, enhancing, improving or augmenting any response of the immune system, for example, of either a humoral or cellular nature. The initiation or enhancement of an immune response can be assessed using assays known to those skilled in the art including, but not limited to, antibody assays (for example ELISA assays). In certain exemplary embodiments, the inventive gp120 glycans and/or glycoconjugates thereof, and the methods of the present invention essentially trigger or enhance primarily a humoral immune response.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF CERTAIN PREFERRED EMBODIMENTS OF THE INVENTION

As discussed above, the desire to develop improved methods for the preparation of synthetic vaccines has led to increased research efforts directed toward the synthesis of naturally occurring complex carbohydrate antigens, as well as novel complex structures (e.g., glycopeptides or other glycoconjugates) incorporating these antigenic structures. As is often the case during the course of any such large synthetic undertaking, improved synthetic methods are often developed that can be applied universally. In particular, synthetic studies of naturally occurring antigenic structures has led to the development of novel methodologies enabling the development of heretofore unavailable synthetic carbohydrate-based vaccines. For a review, see Danishefsky, S. J.; Allen, J. R., *Angew. Chem. Int. Ed. Engl.* 2000, 39, 836-863, and references cited therein.

Significantly, the present invention provides novel methodologies for the synthesis of complex carbohydrates and related therapeutic compounds (e.g., glycans and/or glycoconjugates thereof). In particular, in the context of synthetic studies developed for the total synthesis of glycosylated fragments of gp120 and conjugates thereof, generalized methodologies were developed for the improved synthesis of complex carbohydrate structures. This general synthetic method encompasses the realization that the incorporation of an amino group at the reducing end of a carbohydrate acceptor allows for accessibility to complex N-linked carbohydrate conjugates. In yet another aspect, the present invention also provides the recognition that for certain protected carbohydrates, the amino carbohydrate moieties can serve as useful precursors that can be utilized ultimately for the synthesis of complex N-linked glycopeptides or other glycoconjugates.

Specific examples, particularly with respect to the total synthesis of N-acetyllactosamine-type glycans and their incorporation into gp120 glycopeptide fragments and other non-peptidic glycoconjugates are described in more detail below, along with certain general methodologies developed during the course of these syntheses. It will be appreciated by one of ordinary skill in the art that these examples are not intended to be limiting; rather all equivalents are intended to be incorporated into the scope of the present invention.

1) Inventive Compounds

Figure 1:
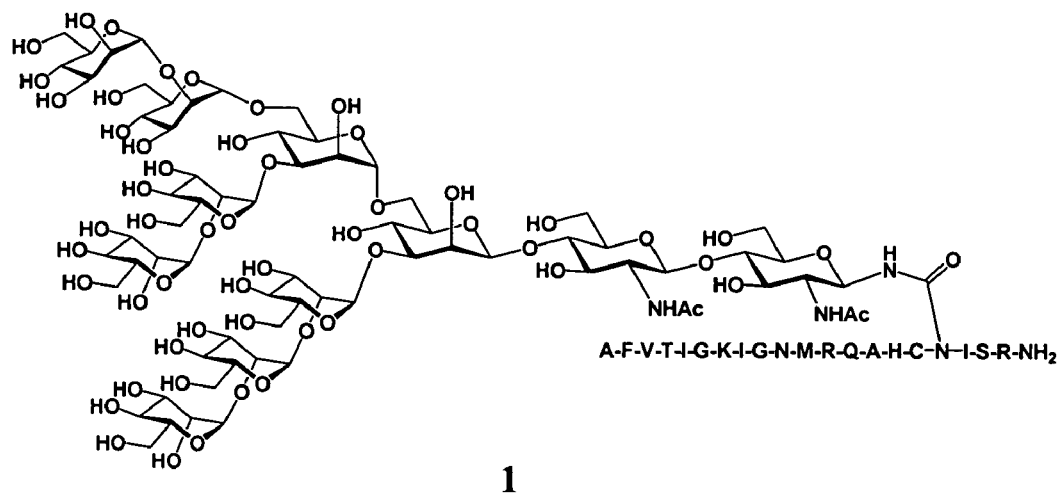
FIG. 1 depicts structures of gp120 glycopeptides 1-2.
Figure 1:
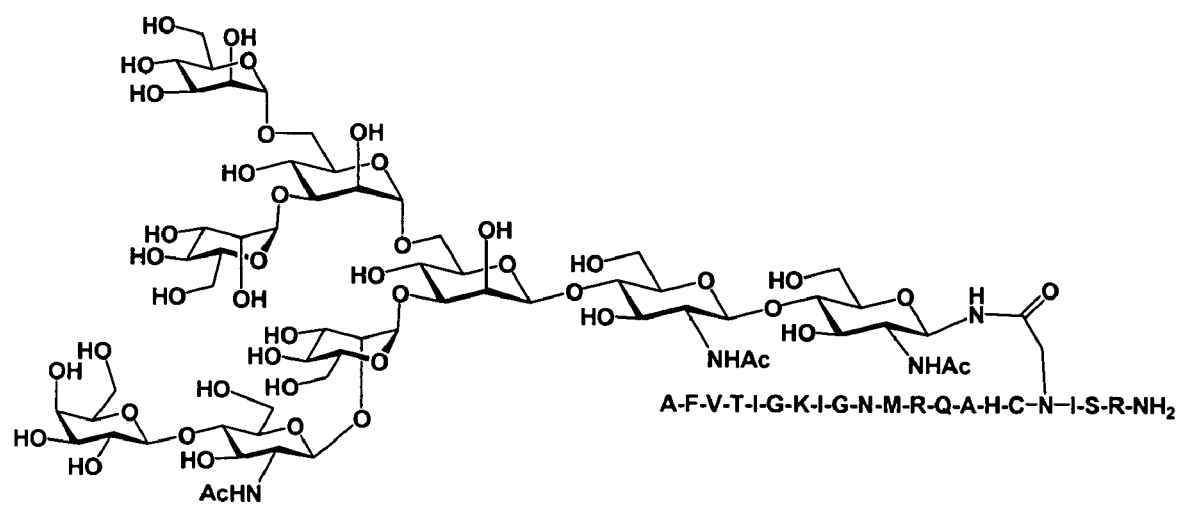

As mentioned above, the total synthesis of complex antigenic structures has led to significant development in methodologies for complex carbohydrate synthesis. Of particular recent interest is the naturally occurring antigenic gp120 glycans; e.g., "high-mannose"- and "hybrid"-type glycoforms thereof (See constructs 1-2 in FIG. 1) which heretofore had not yet been synthesized.

Thus, in one aspect of the present invention, the synthesis of the complex gp120 carbohydrate domains has been achieved and an isolated compound of formula (I) having the structure as shown below is provided:

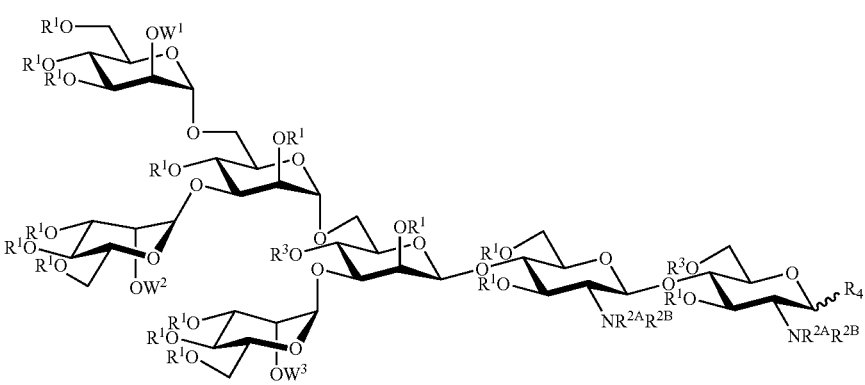

(I)

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

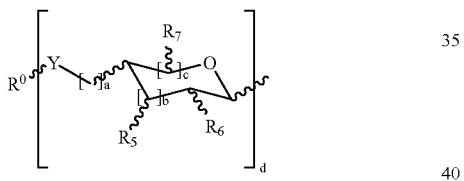

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently optionally substituted mannose, galactose or lactosamine moieties;

and wherein $R^4$ is $-OR^{4A}$ or $-NHR^{4A}$; wherein $R^{4A}$ is hydrogen, aliphatic, heteroaliphatic, aryl, heteroaryl, an amino acyl moiety, an amino acyl residue of a peptide, an amino acyl residue of a protein, or $R^{4A}$ comprises a protein, protein complex, peptide or lipid moiety covalently linked to the rest of the construct, or to the N or O atom to which it is attached, either directly or through a crosslinker.

In certain embodiments, $W^3$ is $R^1$, $R^3$, as defined above, or a moiety having the structure:

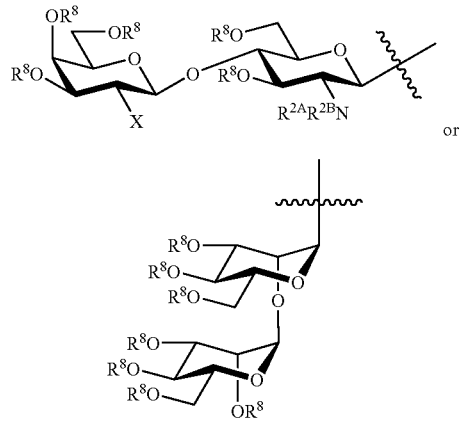

wherein X is $-OR^1$ or $-NR^{2A}R^{2B}$; and each occurrence of $R^8$ is independently $R^1$ or a sialic acid moiety.

In certain embodiments, $W^1$ and $W^2$ are independently $R^1$, $R^3$ or a moiety having the structure:

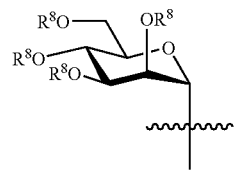

wherein each occurrence of $R^8$ is independently $R^1$ or a sialic acid moiety.

In certain embodiments, a compound of formula (II) having the structure as shown below is provided:

(II)

[structure of formula (II)]

wherein $R^1$, $R^{2A}$, $R^{2B}$, $R^3$ and $R^4$ are as defined above.

In certain embodiments, a compound of formula (III) having the structure as shown below is provided:

(III)

[structure of formula (III)]

wherein $R^1$, $R^{2A}$, $R^{2B}$, $R^3$ and $R^4$ are as defined above and X is $OR^1$ or $NR^{2A}R^{2B}$.

In certain embodiments, compounds of formula (I), (II) or (III) exclude naturally occurring gp120 (e.g., a glycan domain found on naturally occurring gp120 glycoprotein).

In certain embodiments, when $R^4$ comprises a peptide, the peptide is either identical to or closely related to that of gp120 near an N-glycosylation site. In certain exemplary embodiments, the peptide has the structure:

(SEQ ID NO: 3)

Cys-Asn-Ile-Ser-Arg;    or

-continued (SEQ ID NO: 4)

Lys-Ile-Gly-Asn-Met-Arg-Gln-Ala-His-Cys-Asn-Ile-Ser-Arg
|
Gly-Ile-Thr-Val-Phe-Ala or truncated, elongated or derivatized version thereof; wherein any one or more of the amino acid residues may bear one or more protecting groups. For the purpose of the invention, "truncated", refers to a peptide fragment comprising no fewer than about 6 amino acid residues; "elongated", refers to a peptide comprising no more than about 60 amino acid residues; and "derivatized" refers to a peptide in which at least one, but not more than about 2 out of every 10, amino acid residues have been added and/or deleted; and/or in which at least one amino acid residue has been substituted with a natural or non-natural amino acid residue so that the resulting peptide has a sequence identity equal or greater to about 70% with the original peptide.

In certain exemplary embodiments, for compounds of formula (I), (II) and (III) above, each occurrence of $R^1$ is independently an oxygen protecting group. In certain other exemplary embodiments, each occurrence of $R^1$ is independently hydrogen, alkyl, alkenyl, alkynyl, heteroalkyl, heteroalkenyl, heteroalkynyl, aryl, heteroaryl, alkylaryl, alkylheteroaryl, —Si($R^{1A}$)$_3$, —C(=O)$R^{1A}$, —C(=S)$R^{1A}$, —C(=N$R^{1A}$)$R^{1B}$, —SO$_2$$R^{1A}$, wherein $R^{1A}$ and $R^{1B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{1C}$ or —Z$R^{1C}$, wherein Z is —O—, —S—, —N$R^{1D}$, wherein each occurrence of $R^{1C}$ and $R^{1D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In yet other exemplary embodiments, each occurrence of $R^1$ is independently hydrogen, alkylaryl, —Si($R^{1A}$)$_3$ or —C(=O)$R^{1A}$, wherein $R^{1A}$ is as defined above. In yet other exemplary embodiments, each occurrence of $R^1$ is independently hydrogen, Bn or Bz. In certain other exemplary embodiments, each occurrence of $R^1$ is independently hydrogen.

In certain other exemplary embodiments, for compounds of formula (I), (II) and (III) above, for each occurrence of —N$R^{2A}$$R^{2B}$, at least one occurrence of $R^{2A}$ or $R^{2B}$ is independently a nitrogen protecting group. In certain other exemplary embodiments, each occurrence of —N$R^{2A}$$R^{2B}$, $R^{2A}$ and $R^{2B}$ is independently hydrogen, alkyl, alkenyl, —C(=O)$R^{2C}$, —C(=O)O$R^{2C}$, —S$R^{2C}$, SO$_2$$R^{2C}$, or $R^{2A}$ and $R^{2B}$, taken together with the nitrogen atom to which they are attached, form a substituted or unsubstituted heterocyclic or heteroaryl moiety; wherein each occurrence of $R^{2C}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{2D}$ or —Z$R^{2D}$, wherein Z is —O—, —S—, —N$R^{2E}$, wherein each occurrence of $R^{2D}$ and $R^{2E}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, for each occurrence of —N$R^{2A}$$R^{2B}$, at least one occurrence of $R^{2A}$ or $R^{2B}$ is independently —C(=O)$R^{2A}$ or SO$_2$$R^{2A}$; or $R^{2A}$ and $R^{2B}$, taken together with the nitrogen atom to which they are attached, form a substituted or unsubstituted heterocyclic or heteroaryl moiety. In yet other exemplary embodiments, for each occurrence of —N$R^{2A}$$R^{2B}$, at least one occurrence of $R^{2A}$ or $R^{2B}$ is independently —C(=O)$R^{2C}$ or SO$_2$$R^{2C}$ wherein $R^{2C}$ is as defined above, or $R^{2A}$ and $R^{2B}$, taken together with the nitrogen atom to which they are attached, form an azide or a substituted or unsubstituted phthalimide moiety. In yet other exemplary embodiments, for each occurrence of —N$R^{2A}$$R^{2B}$, at least one occurrence of $R^{2A}$ or $R^{2B}$ is independently acyl, —SO$_2$Ph or $R^{2A}$ and $R^{2B}$, taken together with the nitrogen atom to which they are attached, form an azide or a substituted or unsubstituted phthalimide moiety. In certain other exemplary embodiments, each occurrence of —N$R^{2A}$$R^{2B}$ is —NHAc.

In certain other exemplary embodiments, for compounds of formula (III) above, X is —O$R^1$, wherein $R^1$ is as defined generally above and in classes and subclasses herein.

In certain other exemplary embodiments, for compounds of formula (I), (II) and (III) above, each occurrence of $R^3$ is independently $R^1$, wherein $R^1$ is as defined generally above and in classes and subclasses herein. In certain embodiments, each occurrence of $R^3$ is independently hydrogen, alkylaryl, —Si($R^{3A}$)$_3$ or —C(=O)$R^{3A}$, wherein $R^{3A}$ is hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3B}$ or —Z$R^{3B}$, wherein Z is —O—, —S—, —N$R^{3C}$, wherein each occurrence of $R^{3B}$ and $R^{3C}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In yet other exemplary embodiments, each occurrence of $R^3$ is independently hydrogen, Bn or Bz. In certain other exemplary embodiments, each occurrence of $R^3$ is independently hydrogen.

In certain other exemplary embodiments, for compounds of formula (I), (II) and (III) above, each occurrence of $R^1$ and $R^3$ is independently hydrogen, alkylaryl, —Si($R^{3A}$)$_3$ or —C(=O)$R^{3A}$, wherein $R^{3A}$ is as defined above. In yet other exemplary embodiments, each occurrence of $R^1$ and $R^3$ is independently hydrogen, Bn or Bz. In certain other exemplary embodiments, each occurrence of $R^1$ is Bn and each occurrence of $R^3$ is Bz. In certain other exemplary embodiments, each occurrence of $R^1$ and $R^3$ is independently hydrogen.

In certain embodiments, for compounds of formula (I), (II) and (III) above, $R^4$ is —O$R^{4A}$ and the saccharide unit bearing $R^4$ has the structure:

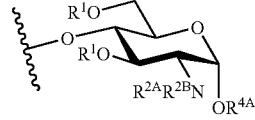

wherein $R^1$, $R^{2A}$ and $R^{2B}$ are as defined generally above and in classes and subclasses herein; $R^{4A}$ is hydrogen, alkyl, alkenyl, alkynyl, heteroalkyl, heteroalkenyl, heteroalkynyl, aryl, heteroaryl, alkylaryl, alkylheteroaryl, an amino acyl moiety, an amino acyl residue of a peptide, an amino acyl residue of a protein, —Si($R^{4B}$)$_3$, —C(=O)$R^{4B}$, —C(=S)$R^{4B}$, —C(=N$R^{4B}$)$R^{4C}$, —SO$_2$$R^{4B}$, wherein $R^{4B}$ and $R^{4C}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{4D}$ or —Z$R^{4D}$, wherein Z is —O—, —S—, —N$R^{4E}$, wherein each occurrence of $R^{4D}$ and $R^{4E}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; or $R^{4A}$ comprises a protein, protein complex, peptide or lipid moiety covalently linked to the O atom to which it is attached, either directly or through a crosslinker. In yet other exemplary embodiments, $R^{4A}$ is —Si($R^{4B}$)$_3$, wherein $R^{4B}$ is as defined above. In yet other exemplary embodiments, $R^{4A}$ is TBS. In yet other exemplary embodiments $R^{4A}$ comprises a serine (ser) amino acyl residue. In yet other exemplary embodiments $R^{4A}$ comprises a threonine (Thr) amino acyl residue. In yet other exemplary embodiments $R^{4A}$ comprises a peptide attached to O through a serine (Ser) residue. In yet other exemplary embodiments $R^{4A}$ comprises a peptide attached to O through a Threonine (Thr) residue.

In certain embodiments, for compounds of formula (I), (II) and (III) above, $R^4$ is —NHR$^{4A}$ and the saccharide unit bearing $R^4$ has the structure:

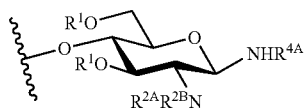

wherein $R^1$, $R^{2A}$ and $R^{2B}$ are as defined generally above and in classes and subclasses herein; and $R^{4A}$ is hydrogen, aliphatic, heteroaliphatic, aryl, heteroaryl, an amino acyl moiety, an amino acyl residue of a peptide, an amino acyl residue of a protein, or $R^{4A}$ comprises a protein, protein complex, peptide or lipid moiety covalently linked to the rest of the construct, or to the N atom to which it is attached, either directly or through a crosslinker.

In certain exemplary embodiments, $R^{4A}$ is hydrogen.

In certain other exemplary embodiments, $R^{4A}$ comprises an amino acyl residue of a peptide whose structure is either identical or closely related to that of gp120 near an N-glycosylation site.

In certain other exemplary embodiments, $R^{4A}$ comprises an Asparagine residue (Asn) of a peptide whose structure is either identical or closely related to that of gp120 near an N-glycosylation site.

For the purpose of the invention, a peptide whose structure is "closely related to that of gp120 near an N-glycosylation site" designates a gp120 peptide fragment, or truncated, elongated or derivatized version thereof, comprising≦about 60 amino acid residues, wherein one amino acid residue bears an N-glycosylation site, at least one amino acid residue has been added, deleted and/or substituted with a natural or non-natural amino acid residue, so that the resulting peptide has a sequence identity greater or equal to about 70% with the original gp120 peptide fragment. In certain embodiments, the peptide comprises≦about 55 amino acid residues. In certain embodiments, the peptide comprises≦about 50 amino acid residues. In certain embodiments, the peptide comprises≦about 45 amino acid residues. In certain embodiments, the peptide comprises≦about 40 amino acid residues. In certain embodiments, the peptide comprises≦about 35 amino acid residues. In certain embodiments, the peptide comprises≦about 30 amino acid residues. In certain embodiments, the peptide comprises≦about 25 amino acid residues. In certain embodiments, the peptide comprises≦about 20 amino acid residues. In certain embodiments, the peptide has a sequence identity greater or equal to about 75% with the original gp120 peptide fragment. In certain other embodiments, the peptide has a sequence identity greater or equal to about 80% with the original gp120 peptide fragment. In certain other embodiments, the peptide has a sequence identity greater or equal to about 85% with the original gp120 peptide fragment. In certain other embodiments, the peptide has a sequence identity greater or equal to about 90% with the original gp120 peptide fragment. In certain other embodiments, the peptide has a sequence identity greater or equal to about 95% with the original gp120 peptide fragment.

A peptide whose structure is "identical to that of gp120 near an N-glycosylation site" designates a gp120 peptide fragment of a naturally occurring gp120 glycoprotein, comprising≦about 60 amino acid residues, wherein one amino acid residue bears an N-glycosylation site. In certain embodiments, the peptide comprises≦about 55 amino acid residues. In certain embodiments, the peptide comprises≦about 50 amino acid residues. In certain embodiments, the peptide comprises≦about 45 amino acid residues. In certain embodiments, the peptide comprises≦about 40 amino acid residues. In certain embodiments, the peptide comprises≦about 35 amino acid residues. In certain embodiments, the peptide comprises≦about 30 amino acid residues. In certain embodiments, the peptide comprises≦about 25 amino acid residues. In certain embodiments, the peptide comprises≦about 20 amino acid residues.

In certain embodiments, for compounds of formula (I), (II) and (III) above, $R^4$ is —NHR$^{4A}$ wherein $R^{4A}$ comprises an Asparagine residue (Asn) of a peptide whose structure is either identical or closely related to that of gp120 near an N-glycosylation site and the saccharide unit bearing $R^4$ has the structure:

(SEQ ID NO: 3)

Cys-Asn-Ile-Ser-Arg; or (SEQ ID NO: 4)

Lys-Ile-Gly-Asn-Met-Arg-Gln-Ala-His-Cys-Asn-Ile-Ser-Arg
|
Gly-Ile-Thr-Val-Phe-Ala wherein $R^1$, $R^{2A}$ and $R^{2B}$ are as defined generally above and in classes and subclasses herein and wherein any of the amino acid residues may bear one or more protecting groups.

In certain exemplary embodiments, the saccharide unit bearing $R^4$ has the structure:

(SEQ ID NO: 3)

Fmoc-Cys-Asn-Ile-Ser-Arg-NH$_2$; or
|
tBuS (SEQ ID NO 4)

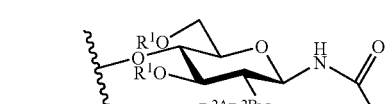

ivDde       Lys-Ile-Gly-Asn-Met-Arg-Gln-Ala-His-Cys-Asn-Ile-Ser-Arg-NH$_2$
|                  |
Gly-Ile-Thr-Val-Phe-Ala-Fmoc        tBuS wherein $R^1$, $R^{2A}$ and $R^{2B}$ are as defined generally above and in classes and subclasses herein.

In certain other exemplary embodiments, the saccharide unit bearing R⁴ has the structure:

(SEQ ID NO: 4)

[Chemical structure showing saccharide unit with R¹O, R²ᴬR²ᴮN substituents connected to:]

Lys-Ile-Gly-Asn-Met-Arg-Gln-Ala-His-Cys-Asn-Ile-Ser-Arg-NH₂
|
Gly-Ile-Thr-Val-Phe-Ala-NH₂ wherein R¹, R²ᴬ and R²ᴮ are as defined generally above and in classes and subclasses herein.

In certain embodiments, any of the isolated compounds, glycopeptides and/or glycoconjugates described herein may be further conjugated to an immunogenic carrier. In certain exemplary embodiments, the carrier is a protein, protein complex, a peptide or a lipid. In certain other exemplary embodiments, the carrier is Bovine Serum Albumin (BSA), Keyhole Limpet Hemocyanin (KLH) or polylysine. In certain other embodiments, the carrier is is a lipid carrier having the structure:

[Chemical structure of lipid carrier with Rᵥ, OH groups and (  )ₘ, (  )ₙ, (  )ₚ chains]

wherein m, n and p are each independently integers between about 8 and 20; and Rᵥ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., Pam-Cys).

It will be appreciated that the carrier can be linked to the rest of the construct either directly or through a crosslinker, and thus R⁴ encompasses proteins, protein complexes, peptides, and lipids, as well as (crosslinker-protein), (crosslinker-peptide) and (crosslinker-lipid) moieties.

Crosslinkers suited to the invention are widely known in the art (see, for example, 1994 Pierce Technical Handbook: cross-linking (See Appendix A in WO 04/50711), which is also available at http://www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain preferred embodiments, the crosslinker is MMCCH (4-(maleimidomethyl) cyclohexane-1-carboxyl hydrazide). In certain other preferred embodiments, the crosslinker is MBS (m-maleimidobenzoyl acid N-Hydroxysuccinimidyl ester). In certain embodiments, the crosslinker is a fragment having the structure:

[Chemical structure of maleimidobenzoyl fragment]

whereby said structure is generated upon conjugation of a maleimidobenzoic acid N-hydroxy succinimide ester with a suitable functionality on R⁴.

Recently, crystallographic studies revealed that the broadly neutralizing human antibody 2G12, which binds with nanomolar affinity to gp120, contains multiple, distinct binding sites for carbohydrates (e.g., glycans expressed on gp120) [see, Calarese et al., "Antibody domain exchange is an immunological solution to carbohydrate cluster recognition", *Science*, 300:2065-2071, 2003; which is incorporated herein by reference in its entirety]. It was proposed that these multiple binding sites of 2G12 were important for high-affinity interaction of the antibody with the dense array of oligomannose sugars on the surface of gp120.

Therefore, without wishing to be bound to any particular theory, Applicant proposes that constructs comprising several carbohydrate domains present on the surface of gp120, or analogs or derivatives thereof, could therefore elicit a humoral immune response comprising antibodies with enhanced binding affinity for gp120, and therefore have greater potential in the development of HIV vaccines.

Thus, in certain embodiments, there is provided an antigenic construct comprising one or more carbohydrate domains having the structure:

(I^det)

[Large chemical structure of carbohydrate domain with multiple saccharide units bearing R¹O, OW¹, OW², OW³, OR¹, R³O, NR²ᴬR²ᴮ substituents]

wherein each occurrence of $R^1$ is independently hydrogen or an oxygen protecting group;
each occurrence of $R^{2A}$ and $R^{2B}$ is independently hydrogen or a nitrogen protecting group;
each occurrence of $R^3$ is independently hydrogen, a protecting group or a carbohydrate domain comprising a saccharide moiety having the structure:

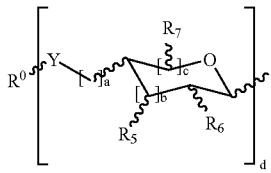

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently optionally substituted mannose, galactose or lactosamine moieties;

wherein each carbohydrate domain is independently covalently bound to a linker system, said linker system being a peptide or non-peptide nature, and wherein the linker system may be cyclic or acyclic.

In certain embodiments, $W^3$ is $R^1$, $R^3$, as defined above, or a moiety having the structure:

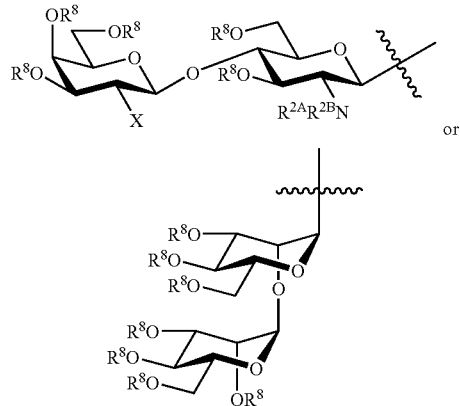

wherein X is $-OR^1$ or $-NR^{2A}R^{2B}$; and each occurrence of $R^8$ is independently $R^1$ or a sialic acid moiety.

In certain other embodiments, $W^1$ and $W^2$ are independently $R^1$, $R^3$ or a moiety having the structure:

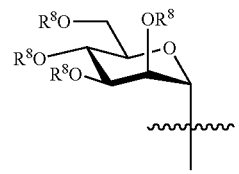

wherein each occurrence of $R^8$ is independently $R^1$ or a sialic acid moiety.

In yet other embodiments, inventive constructs comprise one or more carbohydrate domains having the structure:

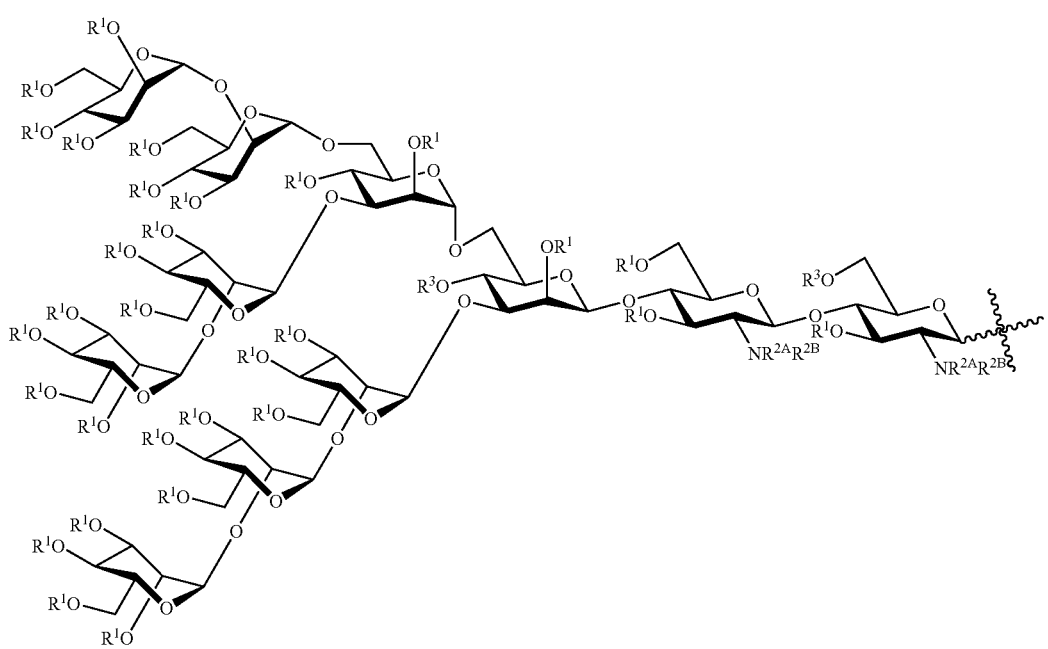

(II$^{det}$)

wherein $R^1$, $R^3$, $R^{2A}$ and $R^{2B}$ are as defined above for ($I^{det}$).

In yet other embodiments, inventive constructs comprise one or more carbohydrate domains having the structure:

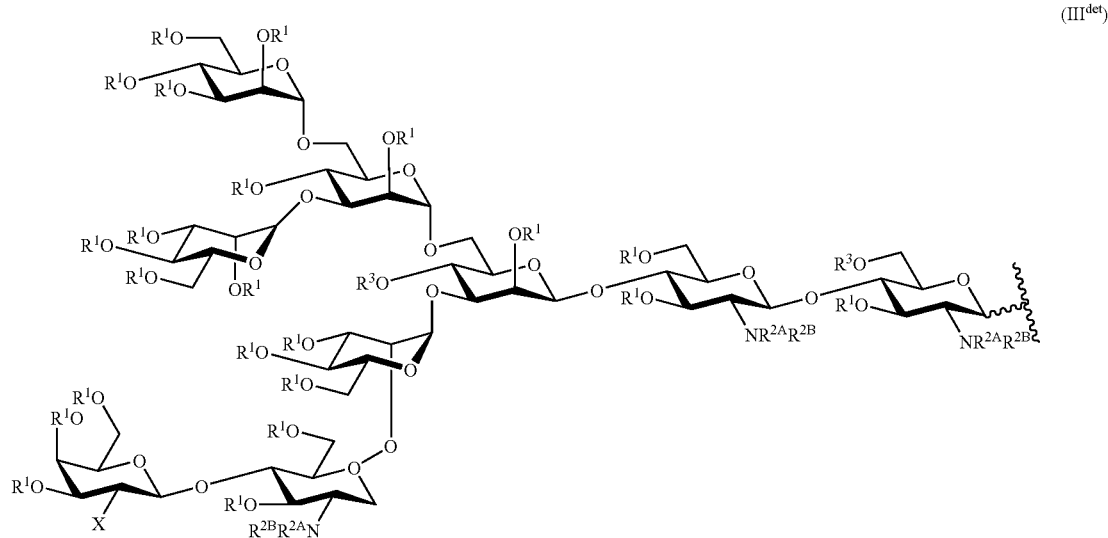

($III^{det}$)

wherein $R^1$, $R^3$, $R^{2A}$ and $R^{2B}$ are as defined above for ($I^{det}$).

In certain embodiments, some or all of carbohydrate domains are O-linked to the linker system. In certain other embodiments, some or all of carbohydrate domains are N-linked to the linker system. In yet other embodiments, the linker system is a peptide. In certain embodiments, the linker system is a cyclic peptide. In certain other embodiments, the linker system is cyclodextrin. In certain embodiments, the linker system is a peptide and comprises two or more carbohydrate domains covalently attached thereto, wherein the peptide sequence between each point of attachment of the carbohydrate domains comprises a cysteine residue. In certain embodiments, the multi-glycan construct is prepared by Native Chemical Ligation. In certain embodiments, the inventive constructs are symmetrical, nonsymmetrical and mixed (N-linked and O-linked carbohydrates). In certain embodiments, the linker system is designed to approximate the spatial position(s) of carbohydrate(s) in gp120. In yet other embodiments, the linker system is further attached to a carrier immunostimulant.

In certain embodiments, the linker system is a cyclic peptide having the structure:

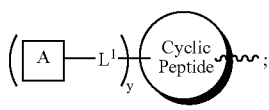

where y is an integer from 1-50; and each occurrence of A is independently a carbohydrate domain of formula ($I^{det}$), ($II^{det}$) or ($III^{det}$);

wherein ∿∿∿ denotes an optional attachment point to an immunogenic carrier, either directly or through a crosslinker or -linker-(crosslinker)$_q$-moiety, as defined herein.

In certain embodiments, the linker system is a cyclic peptide having the structure:

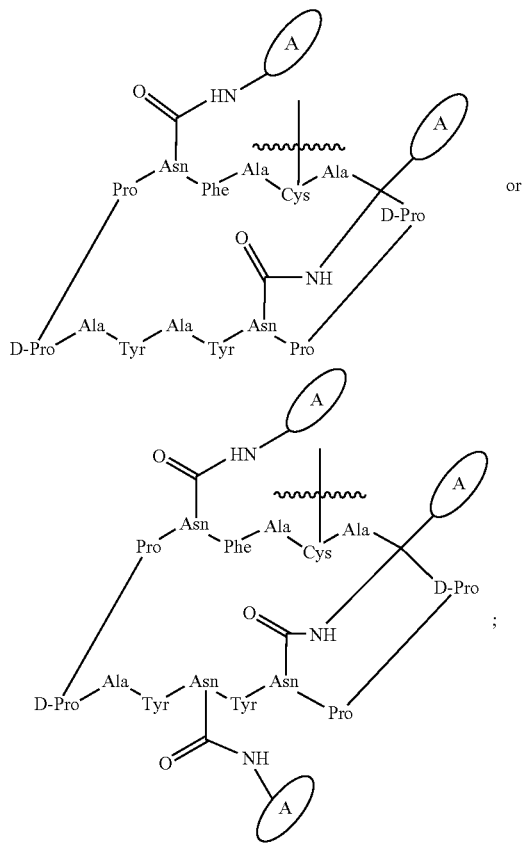

where each occurrence of A is independently a carbohydrate domain of formula ($I^{det}$), ($II^{det}$) or ($III^{det}$);

wherein ∿∿∿ denotes an optional attachment point to an immunogenic carrier, either directly or through a crosslinker or -linker-(crosslinker)$_q$-moiety, as defined herein.

In certain embodiments, each occurrence of A has the structure:

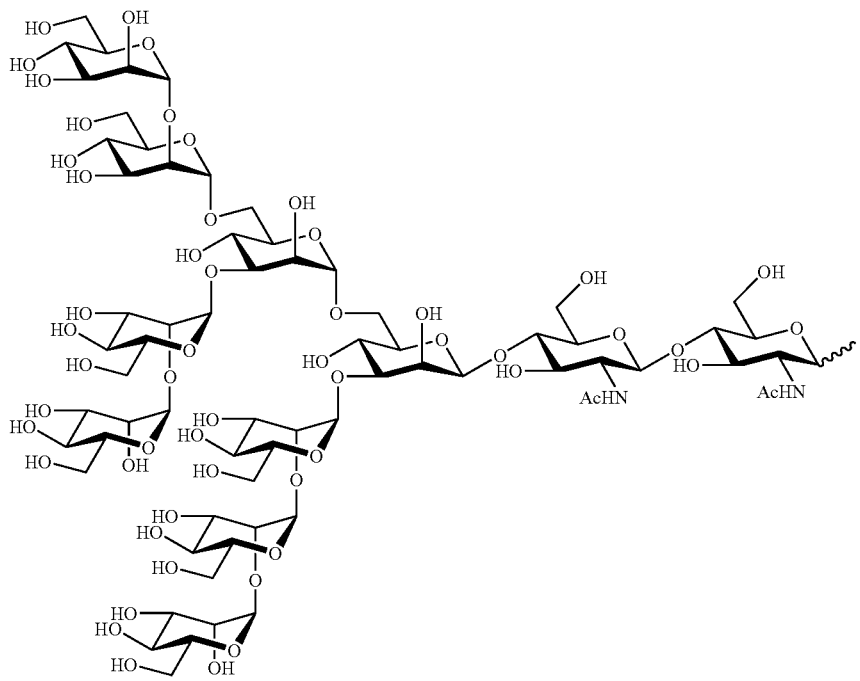

In certain embodiments, inventive constructs comprising one or more carbohydrate domains of the formula ($I^{det}$), ($II^{det}$) or ($III^{det}$) are similar to multi-antigenic constructs described in U.S. Ser. Nos. 09/083,776 filed Mar. 25, 1998, 09/276,595 filed Mar. 25, 1999, 10/600,012 filed Jun. 19, 2003, 09/641,742 filed Aug. 18, 2000, 10/209,618 filed Jul. 31, 2002 and 10/430,822, filed Dec. 3, 2003 and entitled "Clustered Multi-Antigenic Carbohydrate Constructs, Methods for their Preparation, and Uses Thereof"; each of the above applications is hereby incorporated by reference in its entirety. Guidance for preparing such constructs can be found, inter alia, in the above-cited applications.

For example, the present invention encompasses clustered glycoconjugates comprising a cyclic or acyclic backbone made up of two or more amino acids or other structural units, wherein one or more of said amino acids or structural units is/are independently substituted with a glycosidic moiety having the structure:

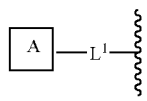

wherein each occurrence of $L^1$ is independently a substituted or unsubstituted, linear or branched, cyclic or acyclic, saturated or unsaturated aliphatic or heteroaliphatic moiety; and each occurrence of A is independently a carbohydrate domain of formula ($I^{det}$), ($II^{det}$) or ($III^{det}$).

In certain embodiments, the invention encompasses clustered multi-antigenic constructs having the structure:

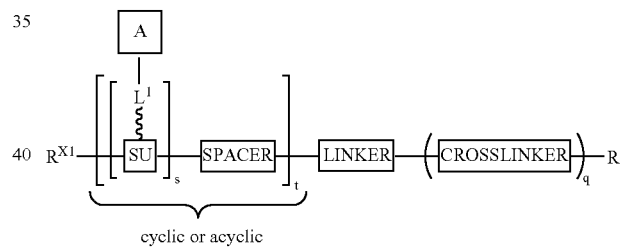

wherein q is 0 or 1;
each occurrence of s is independently an integer from 1-20;
t is an integer from 1-6;
wherein t+s>2;
$R^{X1}$ is hydrogen, alkyl, acyl, aryl, heteroaryl, -alkyl(aryl), -alkyl(heteroaryl) or a nitrogen protecting group; or $R^{X1}$ is covalently bound to a substituent on the last occurrence of the spacer, thereby forming a cyclic backbone;
R is hydrogen or an immunogenic carrier;
each occurrence of the structural unit SU is independently a substituted or unsubstituted aliphatic, heteroaliphatic, aryl, heteroaryl or peptidic moiety;
each occurrence of the spacer is independently a substituted or unsubstituted aliphatic, heteroaliphatic, aryl, heteroaryl or peptidic moiety;
the linker is absent, or is —O—, —$NR_G$—, —$NR_G$($CR_HR_J$)$_k NR_K$—, $NR_G(CR_HR_J)_k NR_K$(C=O)($CR_H R_J$)$_k$S—, —($CR_H R_J$)$_k NR_K$—, —O($CR_H R_J$)$_k NR_K$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5;

wherein each occurrence of $R_G$, $R_H$, $R_J$ or $R_K$ is independently hydrogen, a linear or branched, substituted or unsubstituted, cyclic or acyclic alkyl moiety, or a substituted or unsubstituted aryl moiety;

the crosslinker is a moiety derived from a crosslinking reagent capable of conjugating the carrier with the linker, or when the linker is absent, with the t braketed structure;

the carrier is a peptide, protein, protein complex or lipid;

each occurrence of $L^1$ is independently a substituted or unsubstituted aliphatic or heteroaliphatic moiety; and each occurrence of A is independently a carbohydrate domain of formula ($I^{det}$), ($II^{det}$) or ($III^{det}$).

In certain other embodiments, for the clustered multi-antigenic construct described directly above, each occurrence of $L^1$ is independently —O(CHR$^{aa}$)$_n$— or —NHC(=O)(CHR$^{aa}$)$_n$— wherein each occurrence of n is independently an integer from 1-10; and each occurrence of $R^{aa}$ is hydrogen, lower alkyl, aryl, heteroaryl, -alkyl(aryl) or -alkyl(heteroaryl). In certain exemplary embodiments, each occurrence of n is 1 and each occurrence of $R^{aa}$ is hydrogen or methyl. In certain embodiments, each occurrence of $L^1$ is independently a moiety having the structure —O(CH$_2$)$_n$— wherein n is an integer from 1-10 and each occurrence of A is O-linked to the construct backbone. In certain embodiments, each occurrence of $L^1$ is independently a moiety having the structure —NHC(=O)(CH$_2$)$_n$— wherein n is an integer from 1-10 and each occurrence of A is N-linked to the construct backbone.

In certain embodiments, for the clustered multi-antigenic constructs described directly above, the structural unit SU, for each occurrence, is independently an amino acid residue, a peptidyl moiety, a bivalent aryl or heteroaryl moiety or a substituted or unsubstituted $C_{1-6}$alkylidene or $C_{2-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of $R^{Z1}$ and $RZ^2$ is independently hydrogen, alkyl, heteroalkyl, aryl, heteroaryl or acyl. In certain embodiments, each occurrence of the structural unit SU is an amino acid residue, and the clustered multi-antigenic construct has the structure:

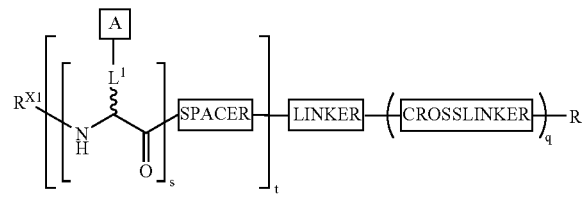

wherein q is 0 or 1;

each occurrence of s is independently an integer from 1-20;

t is an integer from 1-6;

wherein t+s>2;

$R^{X1}$ is hydrogen, alkyl, acyl, aryl, heteroaryl, -alkyl(aryl), -alkyl(heteroaryl) or a nitrogen protecting group; or $R^{X1}$ is covalently bound to a substituent on the last occurrence of the spacer, thereby forming a cyclic backbone;

R is hydrogen or an immunogenic carrier;

each occurrence of the structural unit SU is independently a substituted or unsubstituted aliphatic, heteroaliphatic, aryl, heteroaryl or peptidic moiety;

each occurrence of the spacer is independently a substituted or unsubstituted aliphatic, heteroaliphatic, aryl, heteroaryl or peptidic moiety;

the linker is absent, or is —O—, —NR$_G$—, —NR$_G$(CR$_H$R$_J$)$_k$NR$_K$—, NR$_G$(CR$_H$R$_J$)$_k$NR$_K$(C=O)(CR$_H$R$_J$)$_k$S—, —(CR$_H$R$_J$)$_k$NR$_K$—, —O(CR$_H$R$_J$)$_k$NR$_K$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5;

wherein each occurrence of $R_G$, $R_H$, $R_J$ or $R_K$ is independently hydrogen, a linear or branched, substituted or unsubstituted, cyclic or acyclic alkyl moiety, or a substituted or unsubstituted aryl moiety;

the crosslinker is a moiety derived from a crosslinking reagent capable of conjugating the carrier with the linker, or when the linker is absent, with the t braketed structure;

the carrier is a peptide, protein, protein complex or lipid;

each occurrence of $L^1$ is independently a substituted or unsubstituted aliphatic or heteroaliphatic moiety; and each occurrence of A is independently a carbohydrate domain of formula ($I^{det}$), ($II^{det}$) or ($III^{det}$).

In certain other embodiments, for the two clustered multi-antigenic constructs described directly above, t is ≧2 and within each bracketed structure s, independently, each occurrence of A is the same. In certain embodiments, occurrences of A from one bracketed structure s to the next may be the same or different. In certain embodiments, occurrences of A from one bracketed structure s to the next are different. In certain other embodiments, each occurrence of A is independently O or N-linked to the construct backbone. In certain other embodiments, each occurrence of A is independently α- or β-linked to the construct backbone.

In certain embodiments, for the clustered multi-antigenic construct described directly above, $R^{X1}$ is an acyl moiety. In certain exemplary embodiments, $R^{X1}$ is an amino acid residue.

In certain embodiments, for the two clustered multi-antigenic constructs described directly above, the spacer, for each occurrence, is independently a substituted or unsubstituted $C_{1-6}$alkylidene or $C_{2-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of $R^{Z1}$ and $R^{Z2}$ is independently hydrogen, alkyl, heteroalkyl, aryl, heteroaryl or acyl; a peptidyl moiety or a bivalent aryl or heteroaryl moiety. In certain exemplary embodiments, the spacer, for each occurrence, is independently —CHR$^{sp}$)$_n$—, where n is 1-8 and each occurrence of $R^{sp}$ is independently hydrogen, alkyl, cycloalkyl, aryl, heteroaryl, -alkyl(aryl), -alkyl(heteroaryl), —OR$^{sp1}$, —SR$^{sp}$1 or —NR$^{sp1}$R$^{sp2}$ where $R^{sp1}$ and $R^{sp1}$ are independently hydrogen or lower alkyl; a peptidyl moiety comprising one or more α-amino acid residues, or a bivalent aryl moiety having the structure:

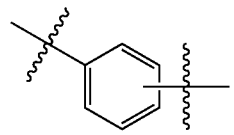

In certain exemplary embodiments, each occurrence of the spacer is independently a dipeptidyl moiety.

In certain other embodiments, for the clustered multi-antigenic constructs described directly above, each occurrence of $L^1$ is independently a natural amino acid side chain. In certain embodiments, each occurrence of $L^1$ is independently an unnatural amino acid side chain. In certain embodiments, each occurrence of $L^1$ is independently —O(CHR$^{aa}$)$_n$— or —NHC(=O)(CHR$^{aa}$)$_n$— wherein each occurrence of n is independently an integer from 1-10; and each occurrence of R$^{aa}$ is hydrogen, lower alkyl, aryl, heteroaryl, -alkyl(aryl) or -alkyl(heteroaryl). In certain exemplary embodiments, each occurrence of n is 1 and each occurrence of R$^{aa}$ is hydrogen or methyl. In certain embodiments, each occurrence of $L^1$ is independently a moiety having the structure —O(CH$_2$)$_n$— wherein n is an integer from 1-10 and each occurrence of A is O-linked to the construct backbone. In certain embodiments, each occurrence of $L^1$ is independently a moiety having the structure —NHC(=O)(CH$_2$)$_n$— wherein n is an integer from 1-10 and each occurrence of A is N-linked to the construct backbone.

In certain embodiments, the clustered multi-antigenic constructs described directly above have the following structure:

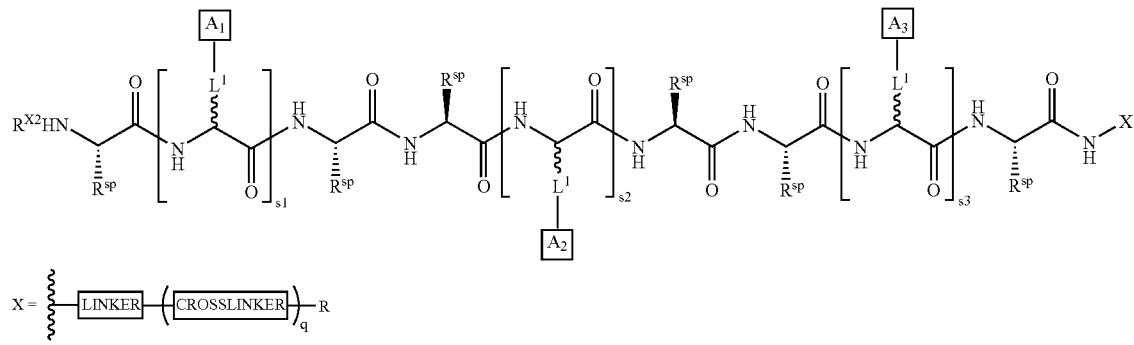

where the peptide backbone may be linear, as shown, above, or cyclic (e.g., the two occurrences of Rsp at the N- and C-termini, taken together, form a cyclic moiety);

wherein $L^1$ and $R^{sp}$ are as defined above; s1, s2 and s3 are independently integers from 2-5; $A_1$-$A_3$ are independently a carbohydrate domain of formula ($I^{det}$), ($II^{det}$) or ($III^{det}$), and are different from each other; and $R^{X2}$ is hydrogen, alkyl, acyl, aryl, heteroaryl, -alkyl(aryl), -alkyl(heteroaryl) or a nitrogen protecting group. In certain exemplary embodiments, each occurrence of $L^1$ is independently a natural amino acid side chain. In certain embodiments, each occurrence of $L^1$ is independently an unnatural amino acid side chain. In certain other embodiments, each occurrence of $L^1$ is independently —NHC(=O)(CHR$^{aa}$)$_n$— and the glycopeptide has the structure:

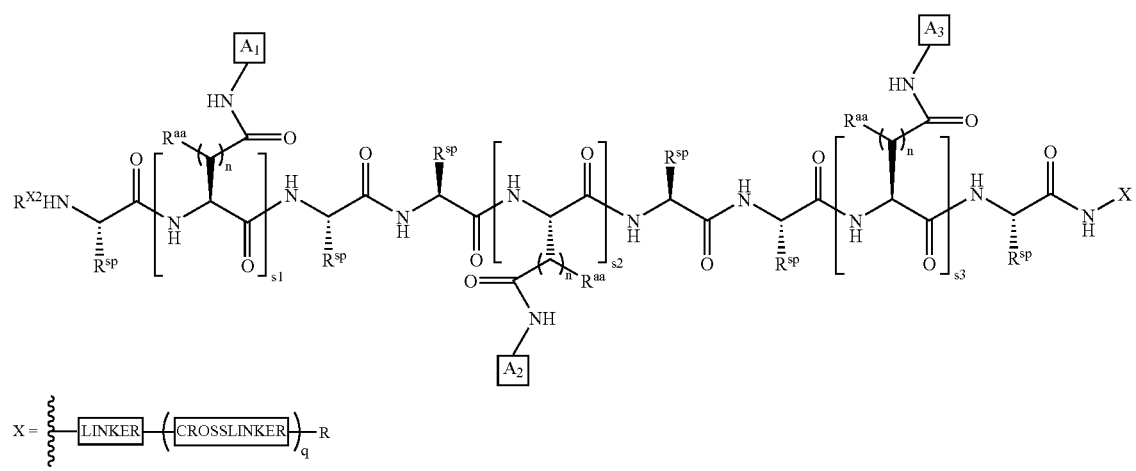

wherein R, $R^{X2}$, $R^{sp}$, s1, s2 and s3 and $A_1$-$A_3$ are as defined above; each occurrence of n is independently an integer from 1-10; and each occurrence of $R^{aa}$ is hydrogen, lower alkyl, aryl, heteroaryl, -alkyl(aryl) or -alkyl(heteroaryl). In certain exemplary embodiments, each occurrence of n is 1 and each occurrence of $R^{aa}$ is hydrogen. In certain embodiments, each occurrence of $R^{sp}$ is independently a natural amino acid side chain. In certain exemplary embodiments, each occurrence of $R^{sp}$ is hydrogen.

In certain embodiments, the clustered multi-antigenic construct is attached to a suitable immunogenic carrier via a linker and the construct has the structure:

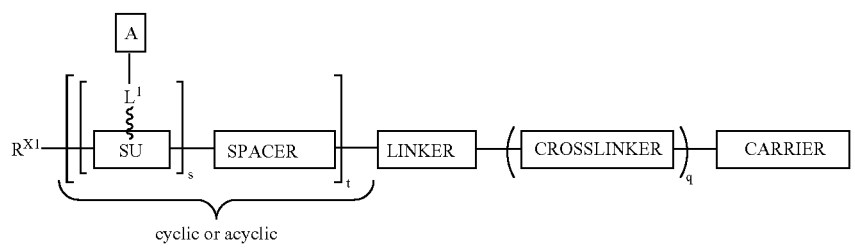

In certain embodiments, each occurrence of SU is an amino acid residue and the clustered multi-antigenic construct a glycopeptide having the structure:

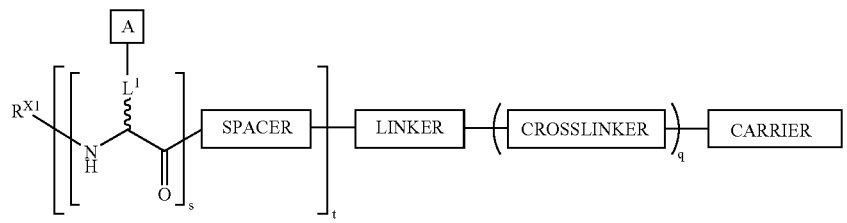

In certain embodiments, for the clusters glycopeptides described above and herein, R is a protein, protein complex, peptide or lipid immunogenic carrier.

In certain embodiments, the t bracketed structure is a cyclic peptide having the structure:

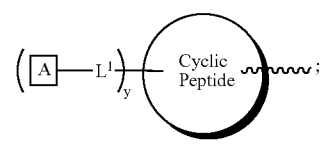

where y is an integer from 1-50; and
each occurrence of A is independently a carbohydrate domain of formula ($I^{det}$), ($II^{det}$) or ($III^{det}$).

In certain embodiments, the t bracketed structure is a cyclic peptide having the structure:

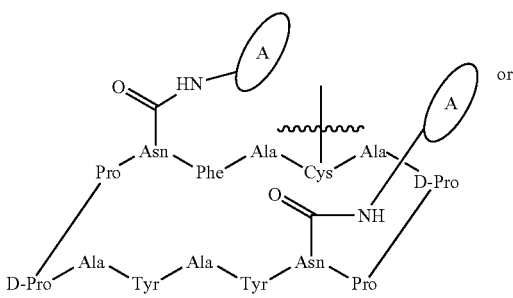

-continued

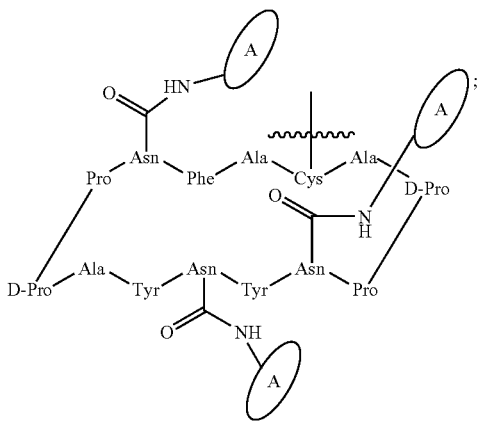

where each occurrence of A is independently a carbohydrate domain of formula ($I^{det}$), ($II^{det}$) or ($III^{det}$).

In certain embodiments, each occurrence of A has the structure:

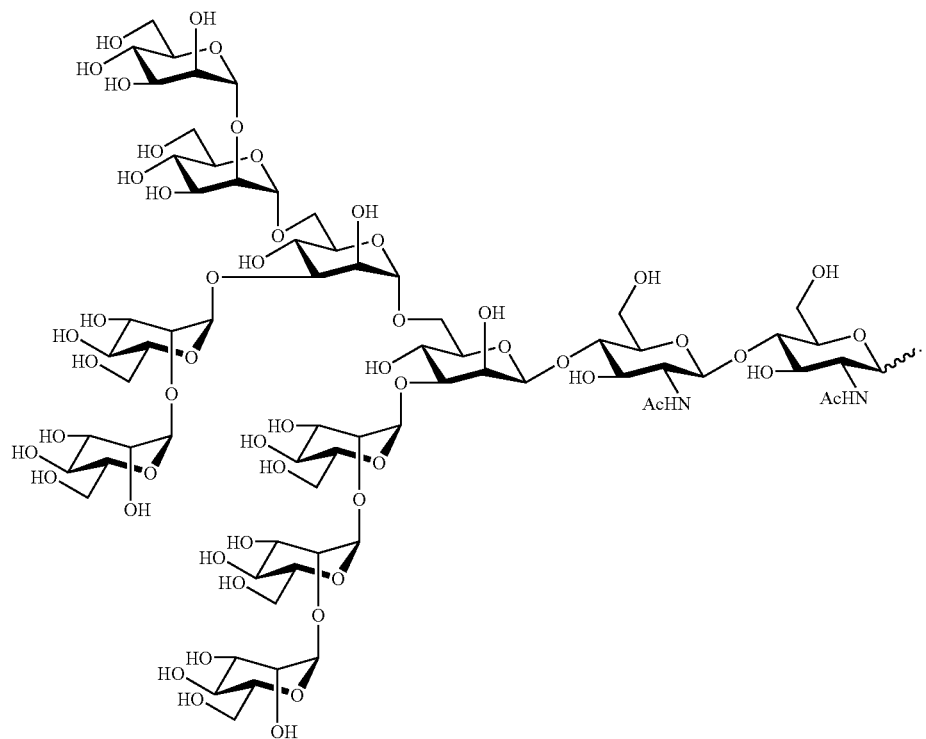
In certain embodiments, for the clustered multi-antigenic constructs described above and herein, each occurrence of A, $A^1$, $A^2$ and $A^3$ is independently a carbohydrate domain having one of the following structures:
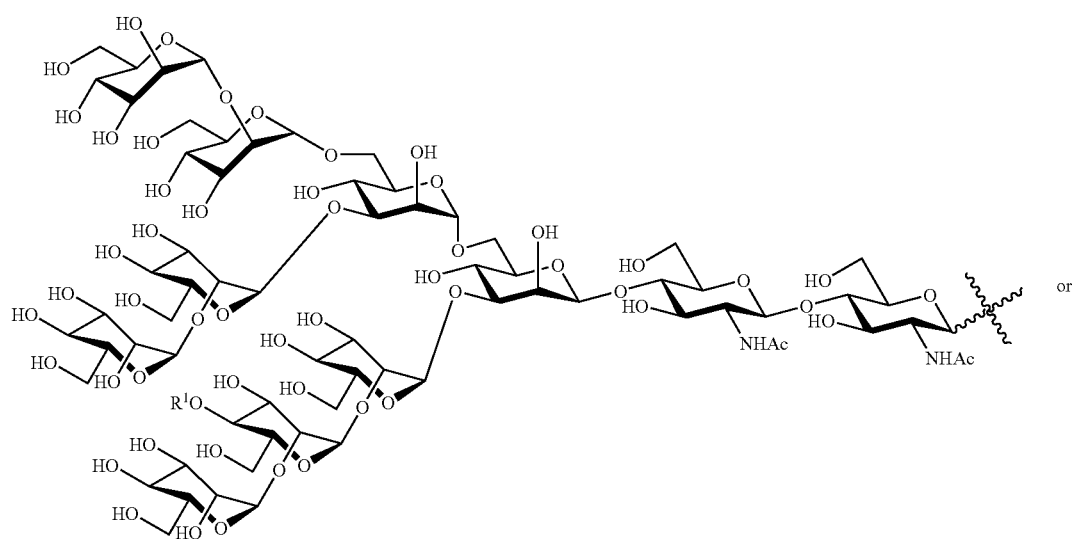

-continued

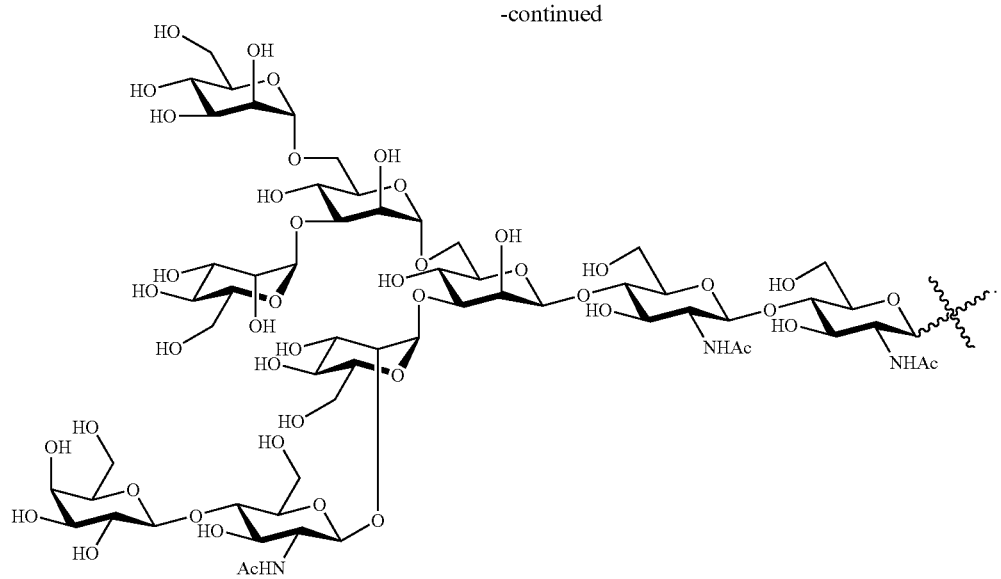

In certain embodiments, for the clustered multi-antigenic constructs described above and herein, R is a protein, protein complex, peptide or lipid immunogenic carrier. In certain other embodiments of the present invention, R is NHR''', and the carrier R''' is KLH or Bovine Serum Albumin. In still other embodiments of the present invention, R is NHR''', and the carrier R''' is a lipid having the structure:

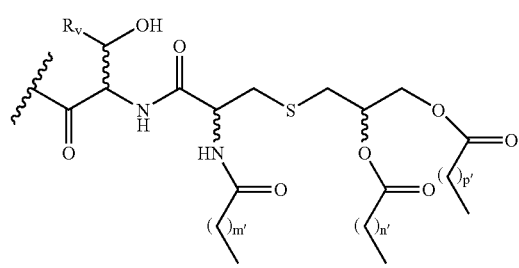

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., Pam-Cys). It will be appreciated that the protein, protein complex or lipid can be linked to N or the rest of the construct either directly or through a crosslinker and thus R''' incorporates proteins, protein complexes, peptides and lipids, as well as (crosslinker-protein), (crosslinker-peptide) and (crosslinker-lipid) moieties. In certain preferred embodiments, the crosslinker is MMCCH (4-(maleimidomethyl) cyclohexane-1-carboxyl hydrazide).

In certain embodiments, the invention encompasses multi-antigenic constructs having the structure:

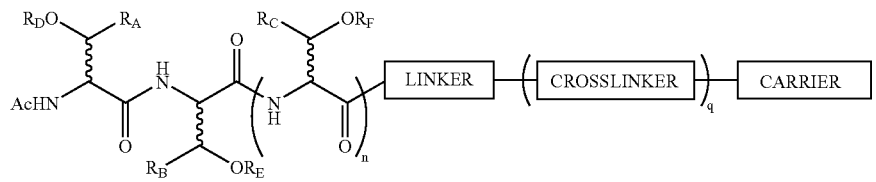

wherein the linker is —O—, —$NR_G$—, —$NR_G(CR_H R_J)_k NR_K$—, $NR_G(CR_H R_J)_k NR_K(C=O)(CR_H R_J)_k S$—, —$(CR_H R_J)_k NR_K$—, —$O(CR_H R_J)_k NR_K$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5;

wherein each occurrence of $R_G$, $R_H$, $R_J$ or $R_K$ is independently hydrogen, a linear or branched, substituted or unsubstituted, cyclic or acyclic alkyl moiety, or a substituted or unsubstituted aryl moiety;

wherein the crosslinker is a moiety derived from a crosslinking reagent capable of conjugating the carrier with the linker;

wherein the carrier is a peptide, protein, protein complex or lipid;

wherein n is 1, 2, 3 or 4;

wherein q is 0 or 1;

wherein each occurrence of $R_A$, $R_B$ and $R_C$ is independently hydrogen, substituted or unsubstituted linear or branched chain lower alkyl or substituted or unsubstituted phenyl; and wherein each occurrence of $R_D$, $R_E$ and $R_F$ are each independently a carbohydrate domain of formula ($I^{det}$), ($II^{det}$) or ($III^{det}$).

In certain embodiments, for the multi-antigenic constructs described herein, the linker is —O—, —NR$_G$—, —NR$_G$(aliphatic)NR$_J$—, —NR$_G$(heteroaliphatic)NR$_J$—, -(aliphatic)NR$_J$—, -(heteroaliphatic)NR$_J$—, —O(aliphatic)NR$_J$—, —O(heteroaliphatic)NR$_J$—, NR$_G$(aliphatic)NR$_J$(C=O)(CR$_H$R$_I$)$_k$S—, —NR$_G$(heteroaliphatic)NR$_J$(C=O)(CR$_H$R$_I$)$_k$S—, -(aliphatic)NR$_J$(C=O)(CR$_H$R$_I$)$_k$S—, -(heteroaliphatic)NR$_J$(C=O)(CR$_H$R$_I$)$_k$S—, —O(aliphatic)NR$_J$(C=O)(CR$_H$R$_I$)$_k$S—, —O(heteroaliphatic)NR$_J$(C=O)(CR$_H$R$_I$)$_k$S—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5; wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety, and wherein each aliphatic or heteroaliphatic moiety is independently substituted or unsubstituted, linear or branched, cyclic or acyclic.

In certain embodiments, for the multi-antigenic constructs described herein, the linker is —O—, —NR$_G$(CR$_H$R$_I$)$_k$NR$_J$—, —NR$_G$(CR$_H$R$_I$)$_k$NR$_J$(C=O)(CR$_H$R$_I$)$_k$S—, —NR$_G$—, —(CR$_H$R$_I$)$_k$NR$_J$—, —O(CR$_H$R$_I$)$_k$NR$_J$—, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5, wherein each occurrence of $R_G$, $R_H$, $R_I$ or $R_J$ is independently hydrogen, a linear or branched, substituted or unsubstituted, cyclic or acyclic moiety, or a substituted or unsubstituted aryl moiety.

In certain embodiments, for the multi-antigenic constructs described herein, the linker is a moiety having the structure —NH(CH$_2$)$_t$NHC(=O)(CH$_2$)$_v$S— wherein t and v are each integers from 1-6. In certain exemplary embodiments, t is 3 and v is 1.

In certain embodiments, for the multi-antigenic constructs described above, the carrier is a protein, protein complex, peptide or lipid immunogenic carrier. In certain other embodiments of the present invention, the carrier is NHR''', and R''' is KLH or Bovine Serum Albumin. In still other embodiments of the present invention, the carrier is NHR''', and R''' is a lipid having the structure:

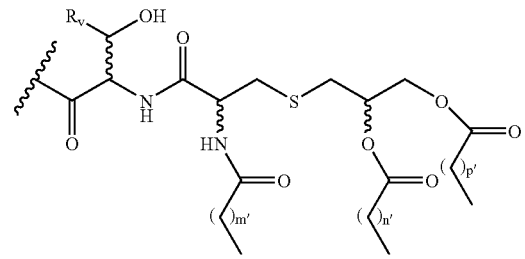

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., Pam-Cys). It will be appreciated that the protein, protein complex or lipid can be linked to N or the rest of the construct either directly or through a crosslinker and thus R''' incorporates protein, proteins complexes, peptides and lipids, as well as (crosslinker-protein), (crosslinker-peptide) and (crosslinker-lipid) moieties. In certain preferred embodiments, the crosslinker is MMCCH (4-(maleimidomethyl) cyclohexane-1-carboxyl hydrazide).

Crosslinkers suited to the invention are widely known in the art (see, for example, Appendix A in WO 04/50711: 1994 Pierce Technical Handbook: cross-linking, also available at www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain preferred embodiments, the crosslinker is MMCCH (4-(maleimidomethyl) cyclohexane-1-carboxyl hydrazide). In certain other preferred embodiments, the crosslinker is MBS (m-maleimidobenzoyl acid N-Hydroxysuccinimidyl ester).

In certain embodiments, for the multi-antigenic constructs described herein, q is 1 and the crosslinker is a fragment having the structure:

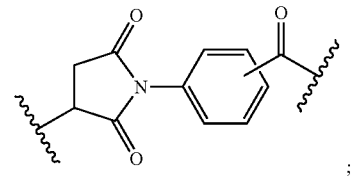

whereby said structure is generated upon conjugation of a maleimidobenzoic acid N-hydroxy succinimide ester with a linker.

In certain other embodiments, the invention encompasses multi-antigenic constructs having the structure:

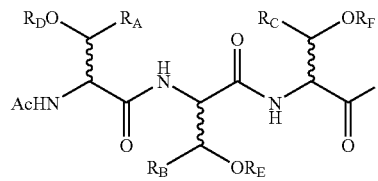
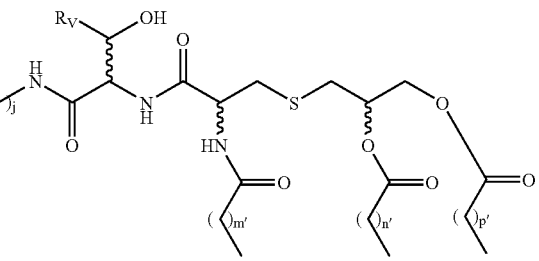

wherein m', n' and p' are integers between about 8 and 20;
j is an integer between 1 and about 8;
$R_V$, $R_A$, $R_B$ and $R_C$ are independently hydrogen, substituted or unsubstituted linear or branched chain lower alkyl or substituted or unsubstituted phenyl; and
$R_D$, $R_E$ and $R_F$ are each independently a carbohydrate domain of formula ($I^{det}$), ($II^{det}$) or ($III^{det}$). In certain exemplary embodiments, j is 3.

In certain other embodiments, the invention encompasses multi-antigenic constructs having the structure:

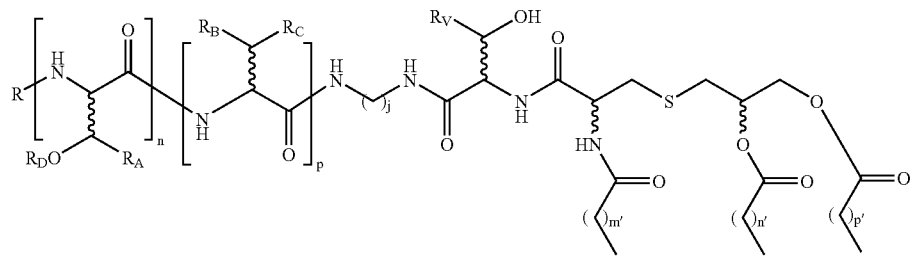

wherein n and p are each independently an integer from 1-6;
m', n' and p' are independently integers between about 8 and 20;
j is an integer between 1 and about 8;
R is a nitrogen protecting group;
$R_V$, and $R_A$, $R_B$, $R_C$, $R_E$ and $R_F$, for each occurrence, are independently hydrogen, substituted or unsubstituted linear or branched lower alkyl or substituted or unsubstituted phenyl;

each occurrence of $R_D$ is independently a carbohydrate domain of formula ($I^{det}$), ($II^{det}$) or ($III^{det}$). In certain exemplary embodiments, j is 3.

In certain embodiments, for the clustered multi-antigenic constructs described above and herein, each occurrence of $R_D$, $R_E$ and $R_F$ is independently a carbohydrate domain having one of the following structures:

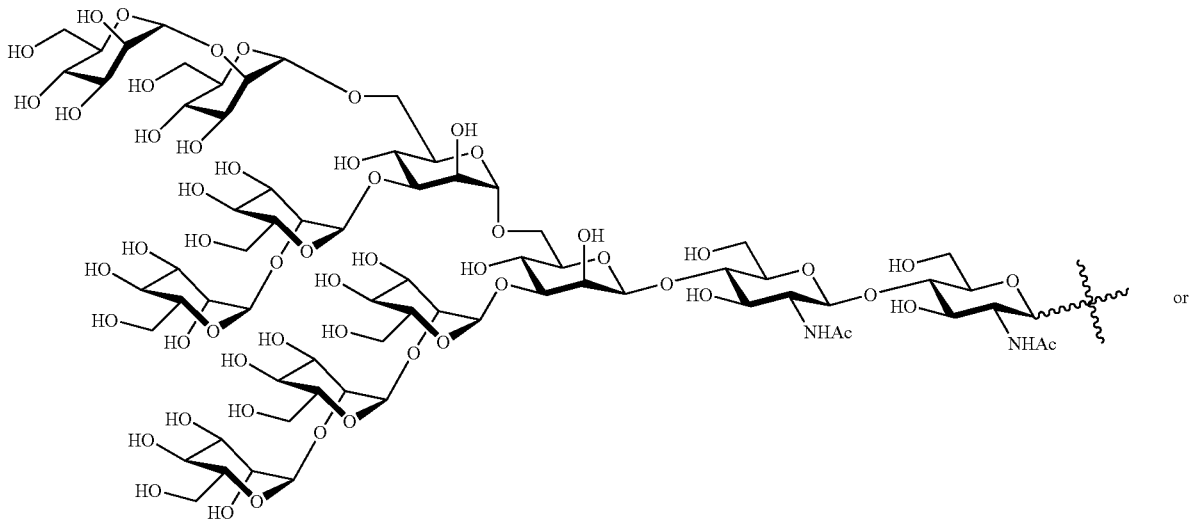

-continued

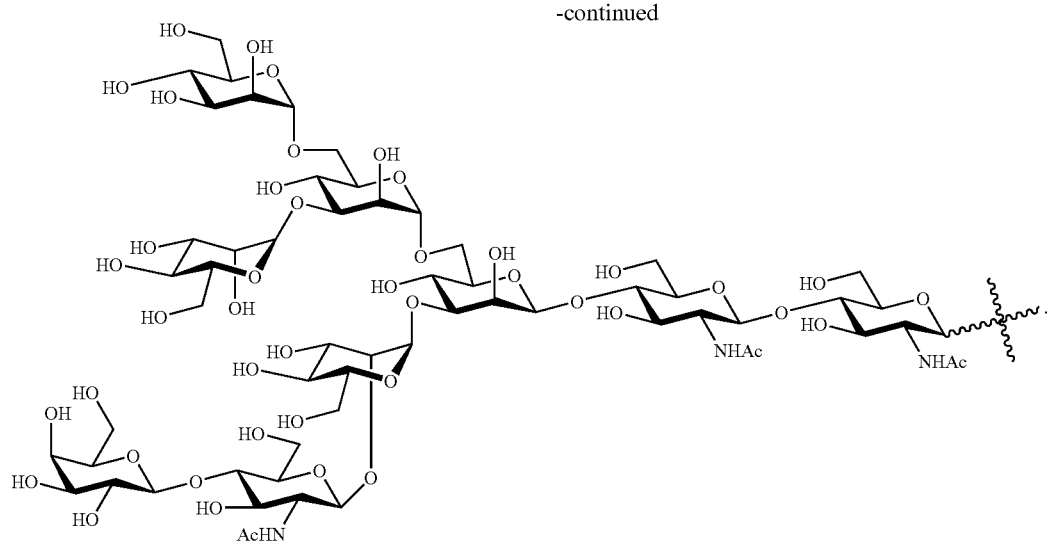

In certain embodiments, the invention provides glycopeptides comprising one occurrence of a carbohydrate domain of the formula ($I^{det}$), ($II^{det}$) or ($III^{det}$), whereby the glycopeptide structure allows for dimerization. In certain exemplary embodiments, the glycopeptide comprises one cysteine residue and the glycopeptide has the structure:

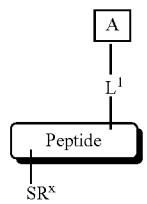

wherein $L^1$ is as defined above; A is a carbohydrate domain of the formula ($I^{det}$), ($II^{det}$) or ($III^{det}$); $R^x$ is hydrogen or a thiol protecting group.

The skilled practitioner will know how to select a thiol protecting group to allow protection/deprotection of the cysteine thiol without negatively affecting other protecting groups that might be present on the construct (e.g., on carbohydrate A). Guidance can be found, for example, in "Protective Groups in Organic Synthesis", Chapter 6, Third Ed. Greene, T. W. and Wuts, P. G., Eds., John Wiley & Sons, New York: 1999, the entire contents of which are hereby incorporated by reference. In certain exemplary embodiments, $R_x$ is —StBu.

In certain embodiments, inventive constructs comprising one or more carbohydrate domains of the formula ($I^{det}$), ($II^{det}$) or ($III^{det}$) are dimers of the above glycopeptides, and the constructs have the structure:

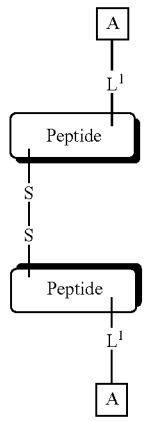

wherein each peptide may be the same or different; and each occurrence of A is independently a carbohydrate domain of the formula ($I^{det}$), ($II^{det}$) or ($III^{det}$).

In certain other embodiments, for the two glycopeptidic constructs described above, each occurrence of $L^1$ is independently a natural amino acid side chain. In certain embodiments, each occurrence of $L^1$ is independently an unnatural amino acid side chain. In certain embodiments, each occurrence of $L^1$ is independently —O(CHR$^{aa}$)$_n$— or —NHC(=O)(CHR$^{aa}$)$_n$— wherein each occurrence of n is independently an integer from 1-10; and each occurrence of $R^{aa}$ is hydrogen, lower alkyl, aryl, heteroaryl, -alkyl(aryl) or -alkyl(heteroaryl). In certain exemplary embodiments, each occurrence of n is 1 and each occurrence of $R^{aa}$ is hydrogen or methyl. In certain embodiments, each occurrence of $L^1$ is independently a moiety having the structure —O(CH$_2$)$_n$— wherein n is an integer from 1-10 and each occurrence of A is O-linked to the construct backbone. In certain embodiments, each occurrence of $L^1$ is independently a moiety having the structure —NHC(=O)(CH$_2$)$_n$— wherein n is an integer from 1-10 and each occurrence of A is N-linked to the construct backbone. In certain embodiments, each occurrence of $L^1$ is an aspartyl side chain.

In certain embodiments, for the two glycopeptidic constructs described above, the peptide has a structure that is either identical or closely related to that of gp120 near an N-glycosylation site. In certain embodiments, for the two glycopeptidic constructs described above, the peptide comprises the amino acid sequence: Cys-Asn-Ile-Ser-Arg, wherein any one or more of the amino acid residues may bear one or more protecting groups. In certain embodiments, for the two glycopeptidic constructs described above, the peptide comprises the amino acid sequence: Ala-Phe-Val-Thr-Ile-Gly-Lys-Ile-Gly-Asn-Met-Arg-Gln-Ala-His-Cys-Asn-Ile-Ser-Arg(SEQ ID NO: 4), wherein any one or more of the amino acid residues may bear one or more protecting groups.

In certain embodiments, the invention provides dimeric constructs having the structure:

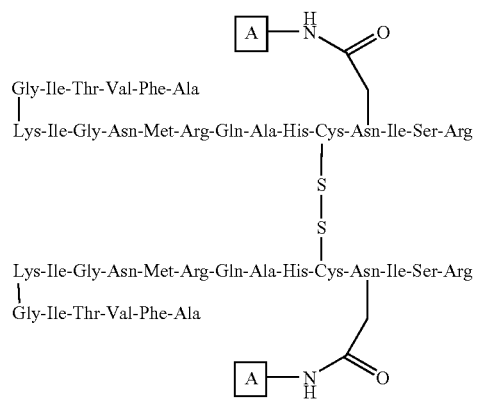
(SEQ ID NO: 4)

wherein each occurrence of A is independently a carbohydrate domain having one of the structures:

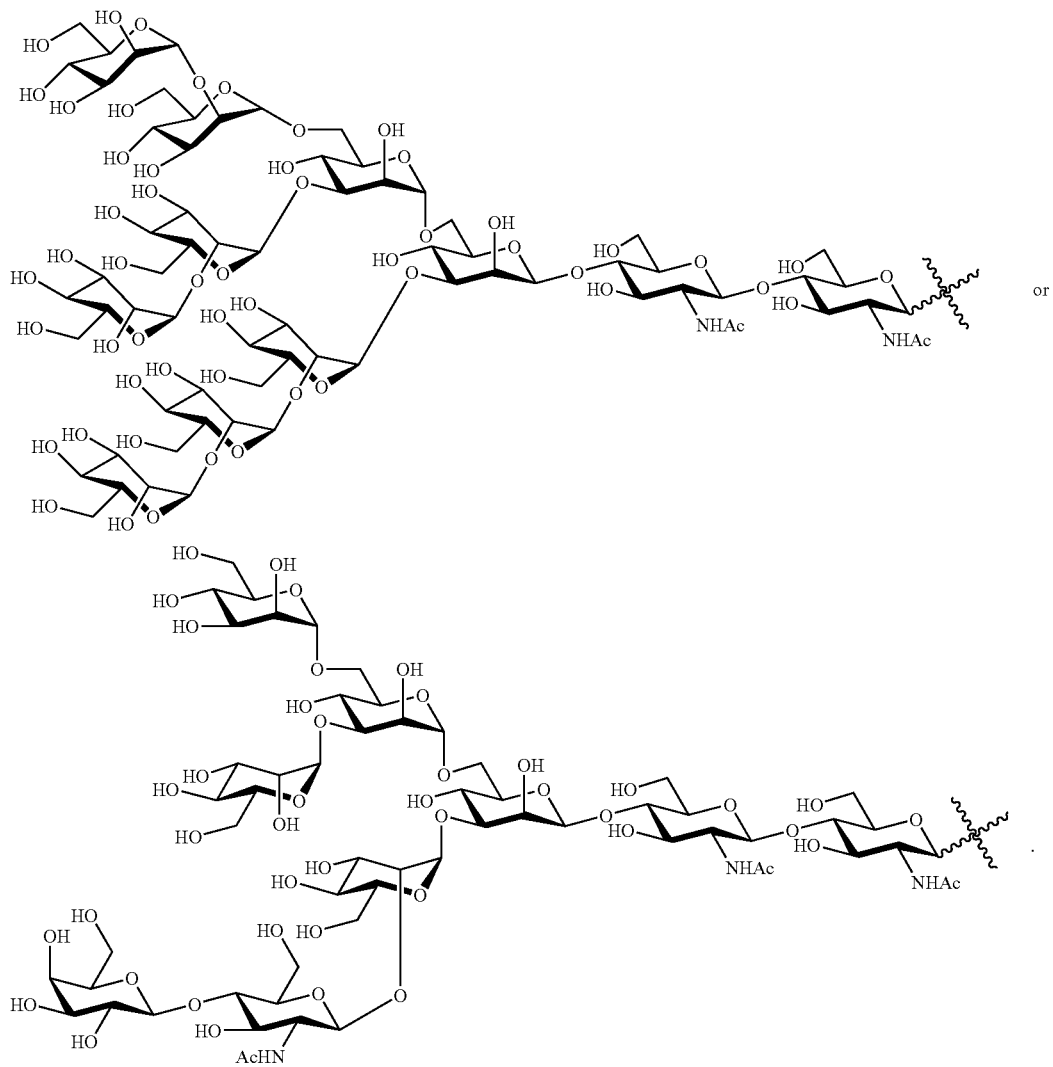

In certain embodiments, dimeric constructs having the following structure are provided:

(SEQ ID NO: 3)

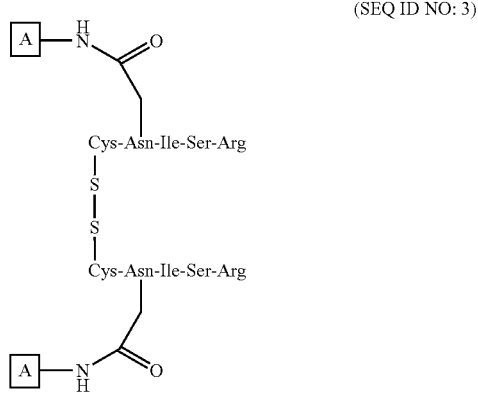

wherein A is as defined above.

In certain embodiments, the invention provides glycopeptides comprising one occurrence of a carbohydrate domain of the formula ($I^{det}$), ($II^{det}$) or ($III^{det}$), whereby the peptide structure is cyclic. In certain exemplary embodiments, the glycopeptide comprises one cysteine residue and the glycopeptide has the structure:

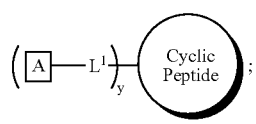

where y is an integer from about 1-50;
each occurrence of A is independently a carbohydrate domain of formula ($I^{det}$), ($I^{det}$) or ($III^{det}$); and any one or more of the peptide amino acids may be protected or unprotected.

In certain embodiments, the cyclic peptide comprises about 8-100 amino acid residues. In certain embodiments, the cyclic peptide comprises about 8-50 amino acid residues. In certain embodiments, the cyclic peptide comprises about 8-40 amino acid residues. In certain embodiments, the cyclic peptide comprises about 8-30 amino acid residues. In certain embodiments, the cyclic peptide comprises about 8-20 amino acid residues. In certain exemplary embodiments, the cyclic peptide comprises about 14 amino acid residues. In certain embodiments, the cyclic peptide comprises about 2-40 sites for carbohydrate attachment. In certain embodiments, the cyclic peptide comprises about 2-30 sites for carbohydrate attachment. In certain embodiments, the cyclic peptide comprises about 2-20 sites for carbohydrate attachment. In certain embodiments, the cyclic peptide comprises about 2-15 sites for carbohydrate attachment. In certain embodiments, the cyclic peptide comprises about 2-10 sites for carbohydrate attachment. In certain embodiments, the cyclic peptide comprises about 2-8 sites for carbohydrate attachment. In certain embodiments, the cyclic peptide comprises about 2-5 sites for carbohydrate attachment. In certain embodiments, the cyclic peptide comprises about 2-3 sites for carbohydrate attachment.

In certain embodiments, the cyclic peptide comprises about 10+4 n amino acid residues where n is an integer from 0-20. Thus, in certain exemplary embodiments, the cyclic peptides of the invention comprise about 10, 14, 18, 22, 26, 30, etc. amino acid residues. In certain embodiments, the cyclic peptides of the invention having about 10+4 n amino acid residues comprise about 4+2 n sites of carbohydrate attachment. Thus, in certain exemplary embodiments, the cyclic peptides of the invention comprise about 10, 14, 18, 22, 26, 30, etc. amino acid residues, and comprise about 4, 6, 8, 10, 12, 14 sites of carbohydrate attachment, respectively.

In certain embodiments, not all of the available carbohydrate attachment sites on the cyclic peptide bear a carbohydrate contruct. In certain embodiments, all of the available carbohydrate attachment sites on the cyclic peptide bear a carbohydrate contruct.

In certain embodiments, the cyclic peptide is modified to allow for linkage with a linker, crosslinker and/or carrier.

In certain embodiments, the cyclic peptide comprises a cysteine residue. In certain embodiments, the thiol group of the cysteine residue is protected. The skilled practitioner will know how to select a thiol protecting group to allow protection/deprotection of the cysteine thiol without negatively affecting other protecting groups that might be present on the construct (e.g., on carbohydrate A). Guidance can be found, for example, in "Protective Groups in Organic Synthesis", Chapter 6, Third Ed. Greene, T. W. and Wuts, P. G., Eds., John Wiley & Sons, New York: 1999, the entire contents of which are hereby incorporated by reference. In certain exemplary embodiments, the thiol group of the cysteine residue is protected with —StBu.

In certain embodiments, A-$L^1$-groups are covalently attached to aspartic acid residues of the cyclic peptide. In certain embodiments, covalent binding is effected through an amide linkage.

In certain embodiments, the cyclic peptide has the structure:

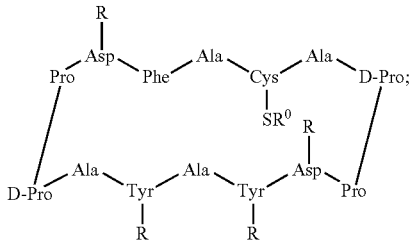

wherein $R^0$ is H or a thiol protecting group; and each occurrence of R represents the terminal group on the corresponding aspartic acid carboxyl group, and may be independently hydrogen or a carboxyl protecting group. In certain exemplary embodiments, each occurrence of R is independently hydrogen or tBu.

In certain embodiments, the cyclic peptide has the structure:

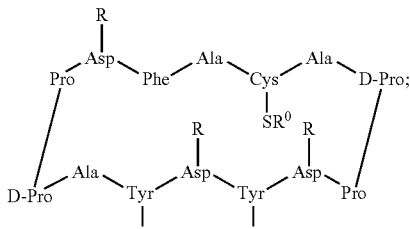

wherein $R^0$ is H or a thiol protecting group; and each occurrence of R represents the terminal group on the corresponding aspartic acid carboxyl group, and may be independently hydrogen or a carboxyl protecting group. In certain exemplary embodiments, each occurrence of R is independently hydrogen or tBu.

In certain embodiments, the cyclic peptide has the structure:

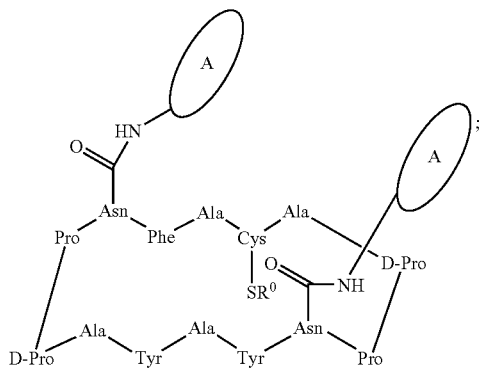

wherein $R^0$ is H or a thiol protecting group; and each occurrence of A is independently a carbohydrate domain of formula ($I^{det}$), ($II^{det}$) or ($III^{det}$).

In certain embodiments, the cyclic peptide has the structure:

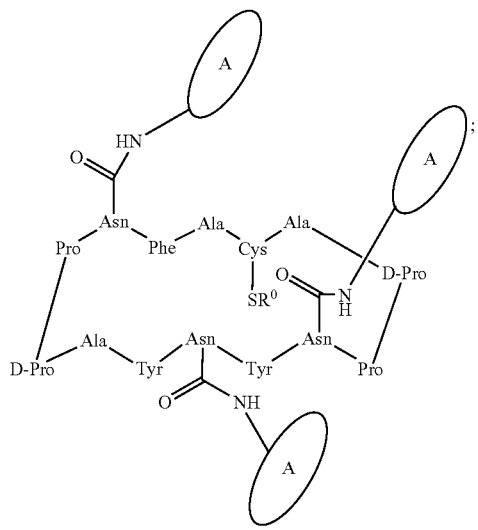

wherein $R^0$ is H or a thiol protecting group; and each occurrence A is independently a carbohydrate domain of formula ($I^{det}$), ($II^{det}$) or ($III^{det}$).

In certain exemplary embodiments, $R^0$ is H or —StBu.

In certain exemplary embodiments, for the cyclic glycopeptide described above, each occurrence of A has the structure:

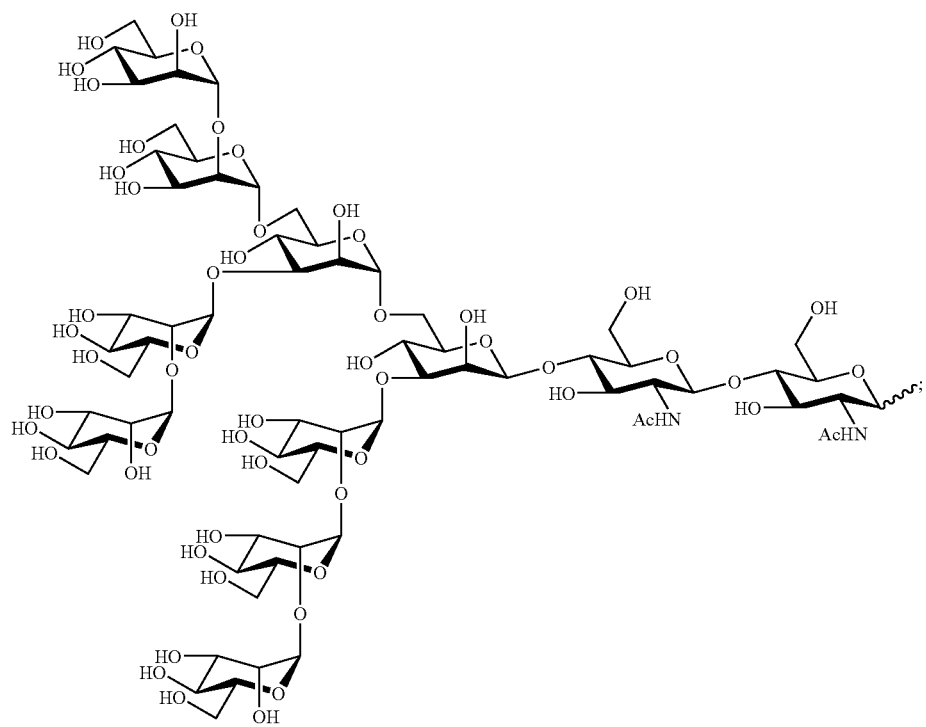

wherein the carbohydrate moiety is N-linked to the asparagine residue.

In certain embodiments, the cyclic glycopeptides described herein are conjugated to an immunogenic carrier (for example, a carrier protein, protein complex, peptide or lipid) either directly or indirectly through a -linker (crosslinker)$_q$-moiety, where the linker, crosslinker and q are as defined herein. In certain embodiments, the carrier is Bovine Serum Albumin (BSA), Keyhole Limpet Hemocyanin (KLH) or polylysine. In certain embodiments, the carrier may be an Outer Membrane Protein Complex (OMPC) of Neisseria meningitidis.

2) Synthetic Methodology

The practitioner has a a well-established literature of carbohydrate chemistry to draw upon, in combination with the information contained herein, for guidance on synthetic strategies, protecting groups, and other materials and methods useful for the synthesis of the compounds of this invention, and conjugates thereof.

The various patent documents and other references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

In one aspect of the invention, there is provided a method for preparing isolated an compound of formula (I):

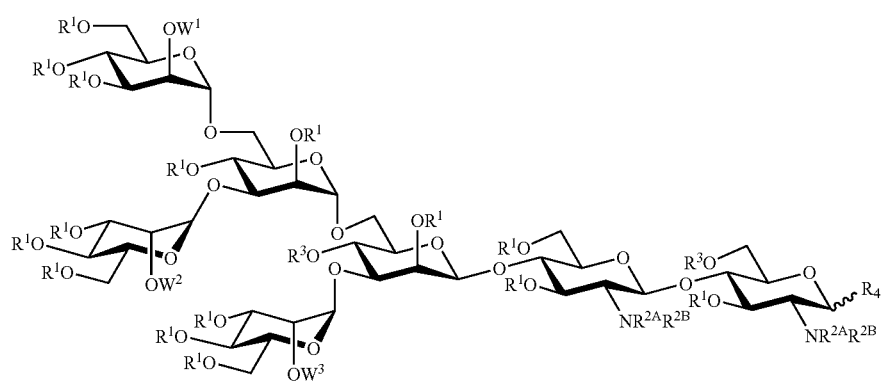

(I)

wherein $R^1$, $R^{2A}$, $R^{2B}$, $R^3$, $R^4$ and $W^1$-$W^3$ are as defined generally above and in classes and subclasses herein.

In one aspect of the invention, there is provided a method for preparing an isolated compound of formula (II):

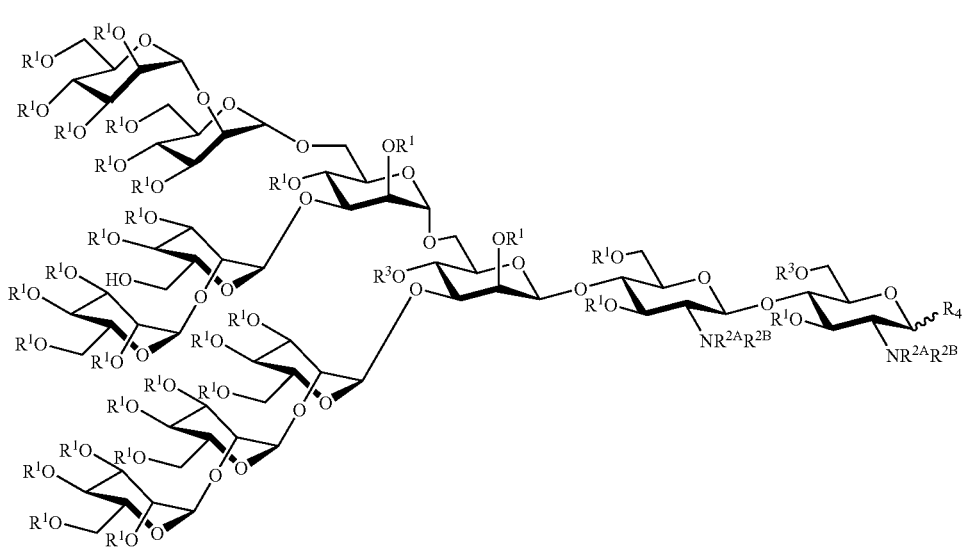

(II)

wherein $R^1$, $R^{2A}$, $R^{2B}$, $R^3$ and $R^4$ are as defined generally above and in classes and subclasses herein.

In another aspect of the invention, there is provided a method for preparing isolated an compound of formula (III):

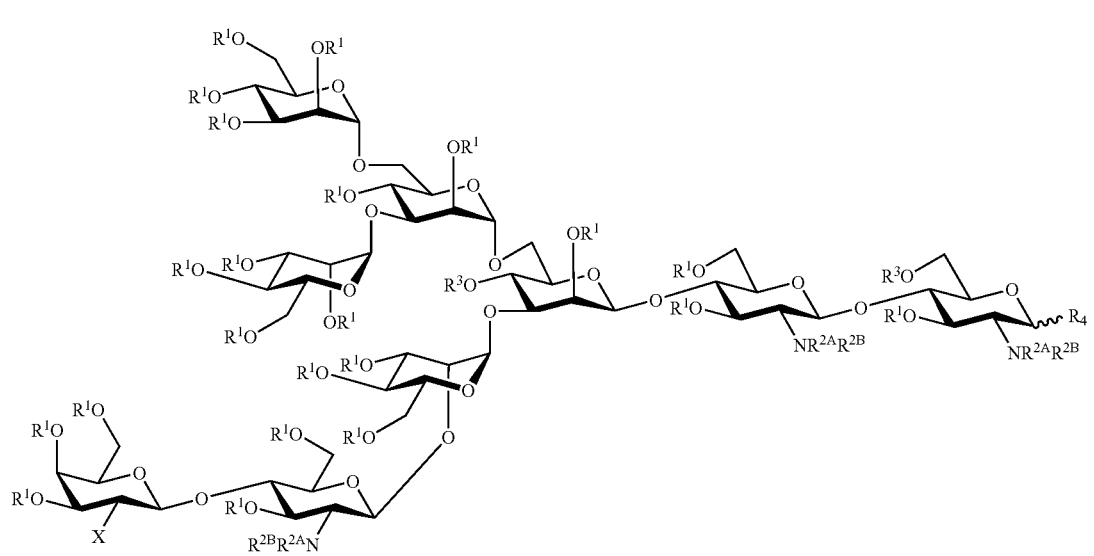

(III)

wherein X, $R^1$, $R^{2A}$, $R^{2B}$, $R^3$ and $R^4$ are as defined generally above and in classes and subclasses herein.

In certain exemplary embodiments, $R^4$ is $-NHR^{4A}$; wherein $R^{4A}$ is an amino acyl residue of a peptide and the invention provides a method for preparing homogeneous N-linked gp120-derived glycopeptides.

Glycan Synthesis

Glycan synthesis generally suffers from the stereochemical diversity of its targets and therefore of its building blocks, as well. The advent of a new target often requires a reworked, if not entirely different synthetic plan, based on varying protecting groups, coupling strategies, and starting materials. The present invention provides a method allowing access to a number of gp120-derived saccharides using only a small set of building blocks and the same general procedure for each glycan.

In certain embodiments, trisaccharide 3 in Scheme 1 embodies the protected core structure reported for the glycoforms expressed in gp 120.

In certain exemplary embodiments, trisaccharide 3 may be elaborated to give a pentasaccharide either by deprotection of the 6-position followed by simultaneous α-mannosylation at the free 3- and 6-positions or by sequential mannosylation at the 3-and 6-positions with an intermediate deprotection step. Simultaneous mannosylation with equivalently protected mannosyl donors would yield a "symmetrically" substituted pentasaccharide; further deprotections and glycosylations could be achieved in a synchronous fashion at both nonreducing termini. Sequential mannosylation would allow the inclusion of differentially protected mannose building blocks, permitting independent elaboration of the 3- and 6-substituted antennae. Thus the high-mannose pentasaccharide core (which is conserved in most natural N-linked glycans) may be synthesized in large quantities and used as a starting point for all of the gp120 targets. Moreover, because hybrid-type gp120 differs from high-mannose type gp120 in its degree of branching beyond the core pentasaccharide, this synthetic scheme would provide easy access to the multi-antennary glycoforms expressed in gp120.

Scheme 1. Proposed methodolgy for glycan synthesis.

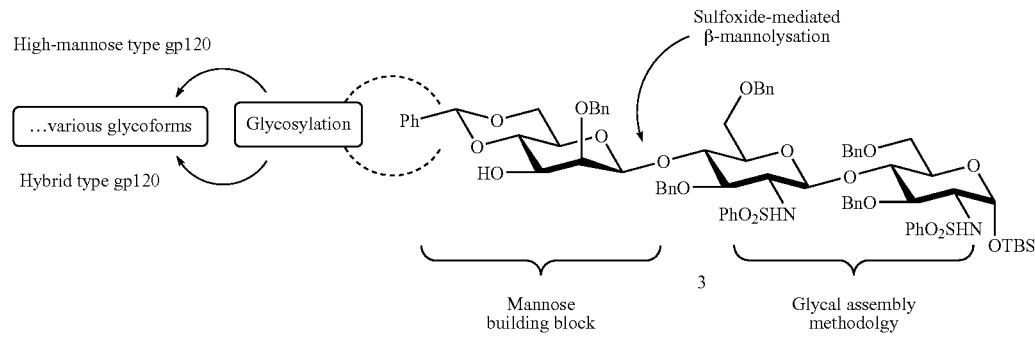

In certain embodiments, the synthetic approach includes: synthesis of protected oligasaccaride (undecassaccharide), global deprotection to prepare free glycan, amination, coupling with peptide acid and deprotection (Scheme 2).

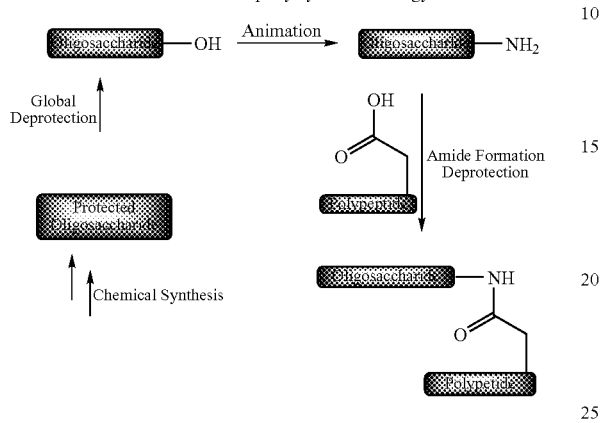

In certain embodiments, a synthesis for the high-mannose type glycopeptide having the structure:

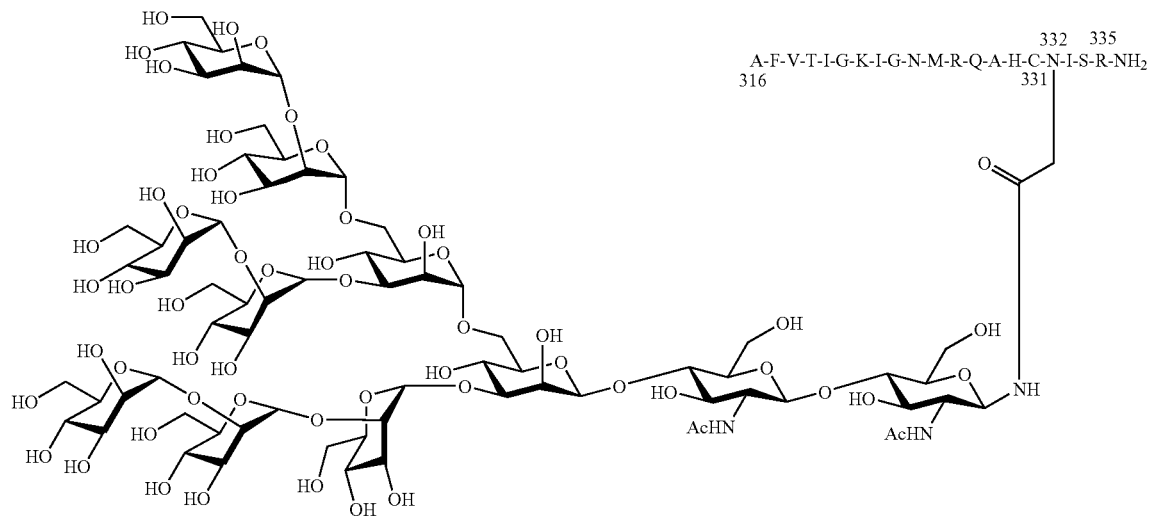

is provided. In certain embodiments, a synthetic plan for the preparation of the undecasaccharide is shown in Scheme 3. For example, starting from a trisaccharide intermediate (e.g., trisacchraide 3),[1] two successive glycosylations will give pentasaccharide, then two consecutive triple glycosylation would furnish the undecasaccharide.

Scheme 3. Exemplary synthetic strategy

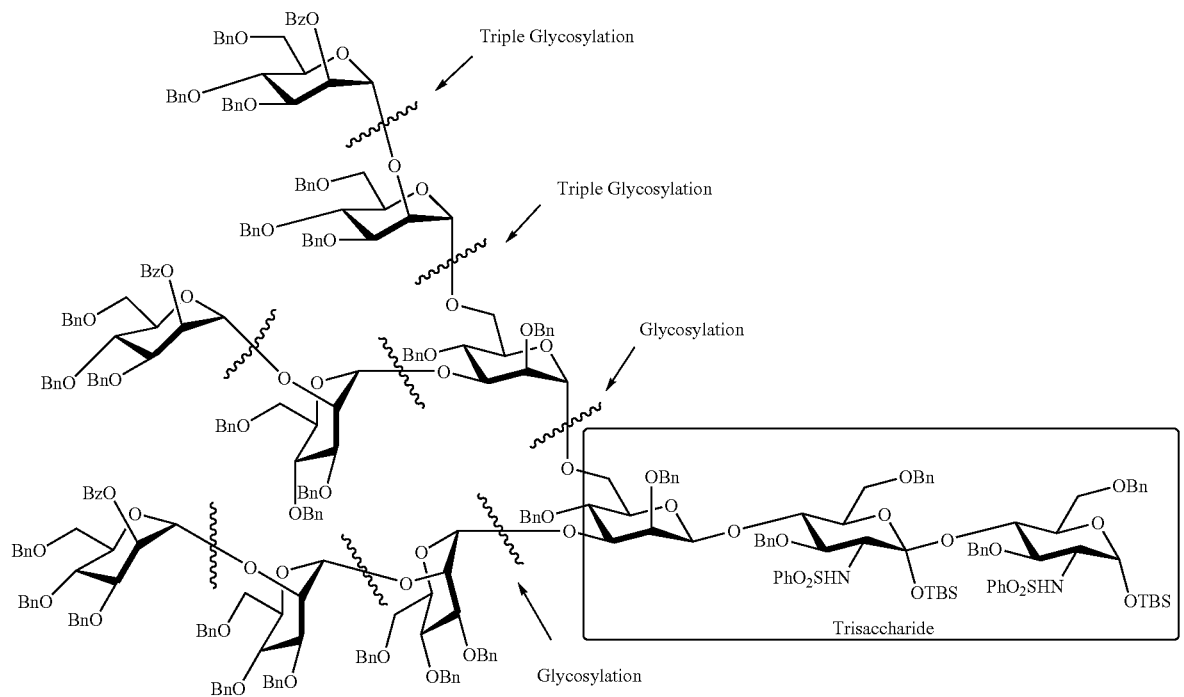

An exemplary synthesis using this route is shown in Scheme 4. For example, mannosylation of trisaccharide 3 using thiomannoside 4 and Sinaÿ radical cation activation[2,3] gave tetresaccharide in 78% yield. The benzylidene ring was reductively opened by borane and the resulting free alcohol 5 underwent mannosylation to give pentasaccharide 8 in 74% yield. After Zemplen reaction, the newly generated three free OH were mannosylated to afford octasaccharide 10 using same Sinaÿ conditions[2,3]. The same triple-glycosylation sequence was repeated to synthesize the undecsaccharide 12a in 55% yield (Scheme 5).

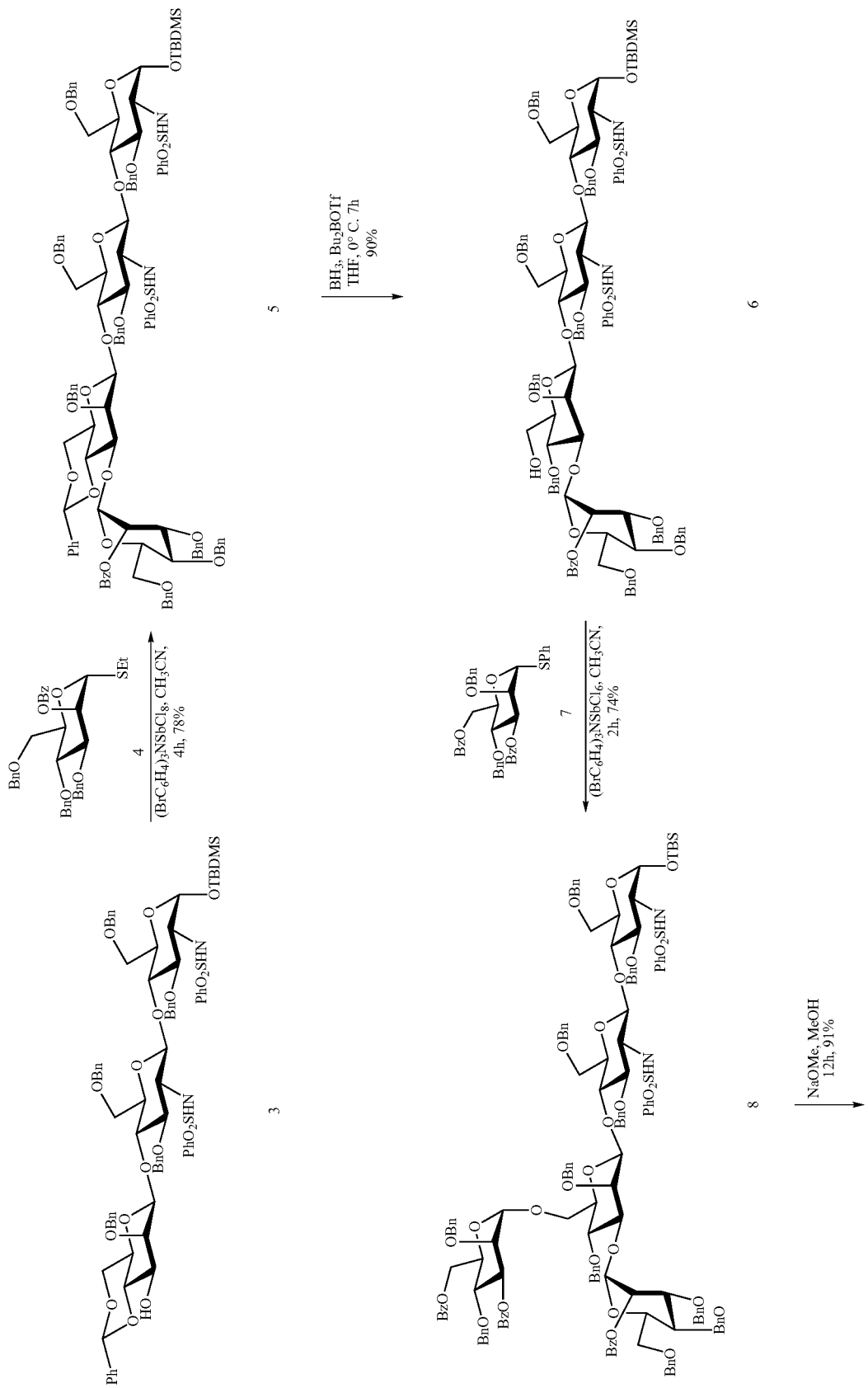

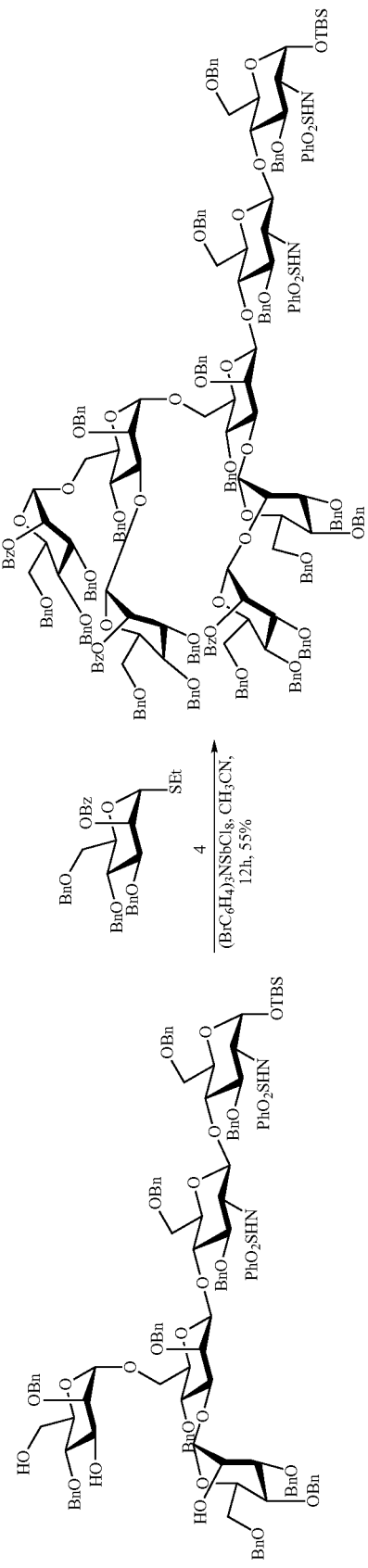

Scheme 5
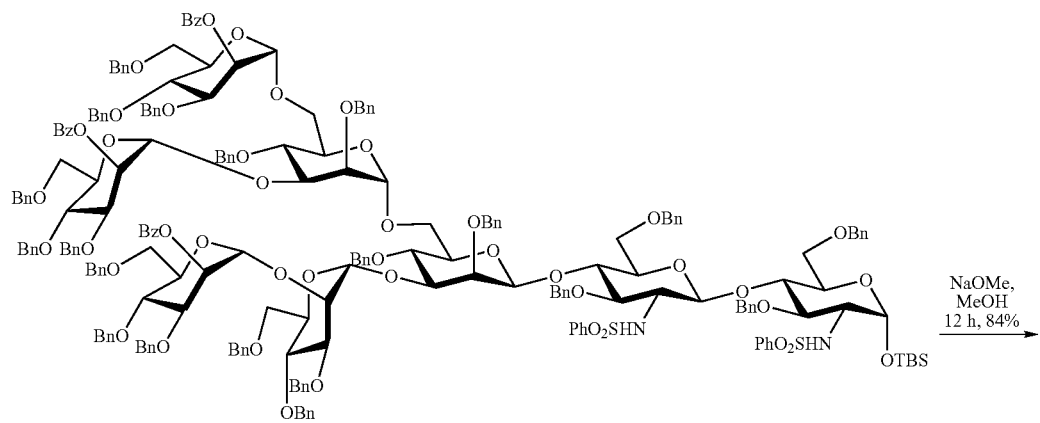
10
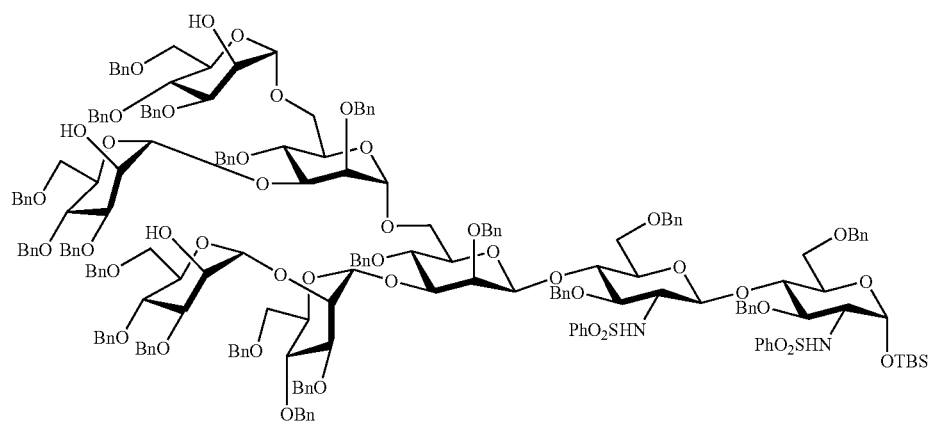
11
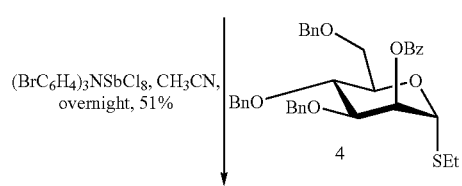

-continued
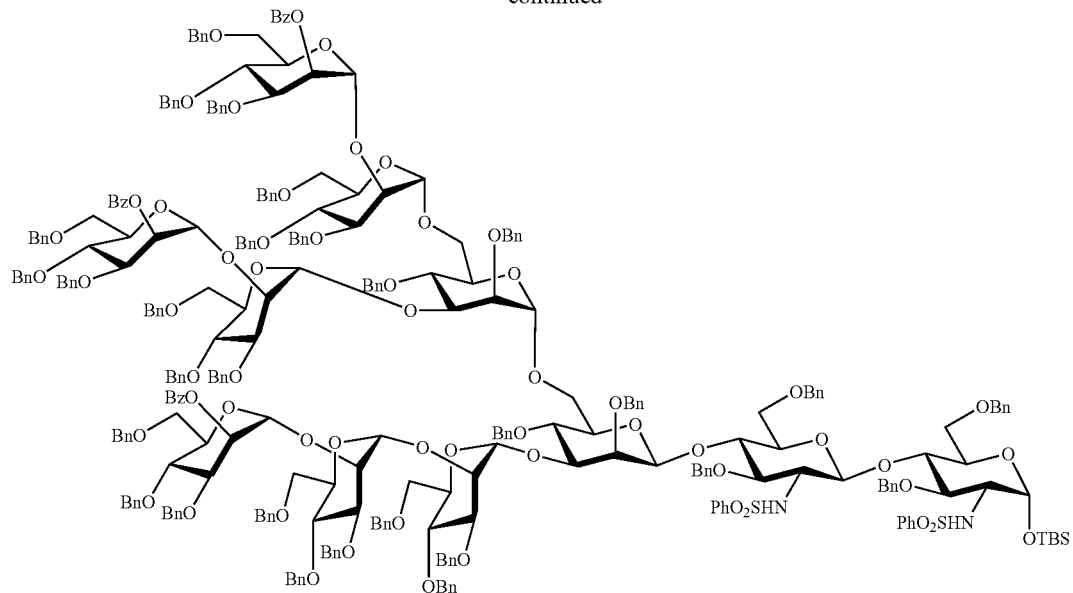
12a
For example, as shown in Scheme 6, the desired undecasaccharide could be synthesized by a 3+3 glycosylation (trisaccharide couples with another trisaccharide) followed by a 6+5 coupling. This synthetic plan is much shorter and more convergent than the first strategy.
Scheme 6
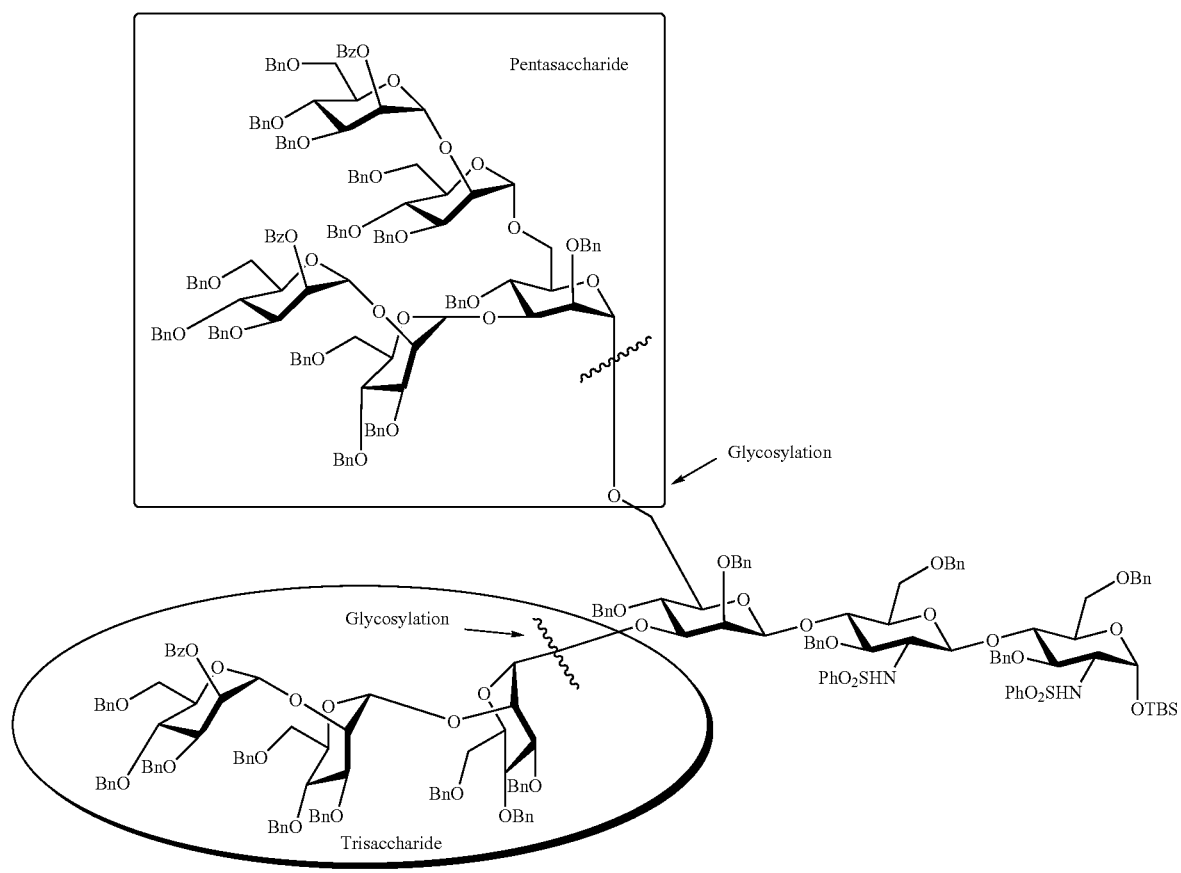

In certain embodiments, as shown in scheme 7, trisaccharide 3 first underwent glycosylation with trisaccharide donor 13 using MeOTf as promoter to afford hexasaccharide in 70% yield. Then reductive ring-opening of the benzylidene ring gave saccharide 15 in 87% yield.

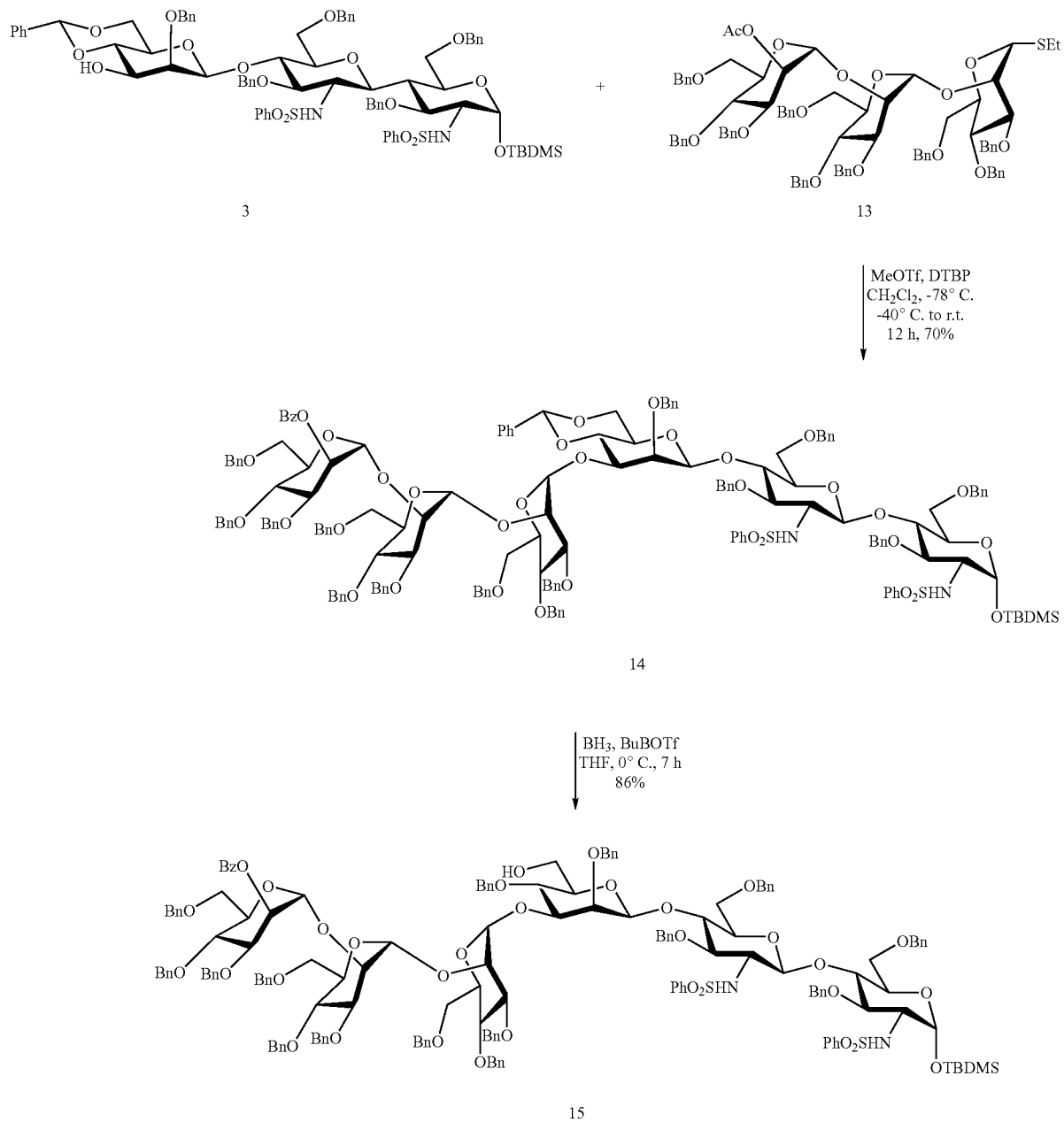

Scheme 7

In certain embodiments, the pentasaccharide which is the precursor for the upper-left portion of the final compound (1) was synthesized as shown in scheme 8. For example, double-glycosylation of mannose derivative 16 using chloro donor 17 and promoter silver triflate gave trisaccharide 18. After cleavage of the two acetyl groups, another double-glycosylation provided pentasaccharide 20 in 87% yield.

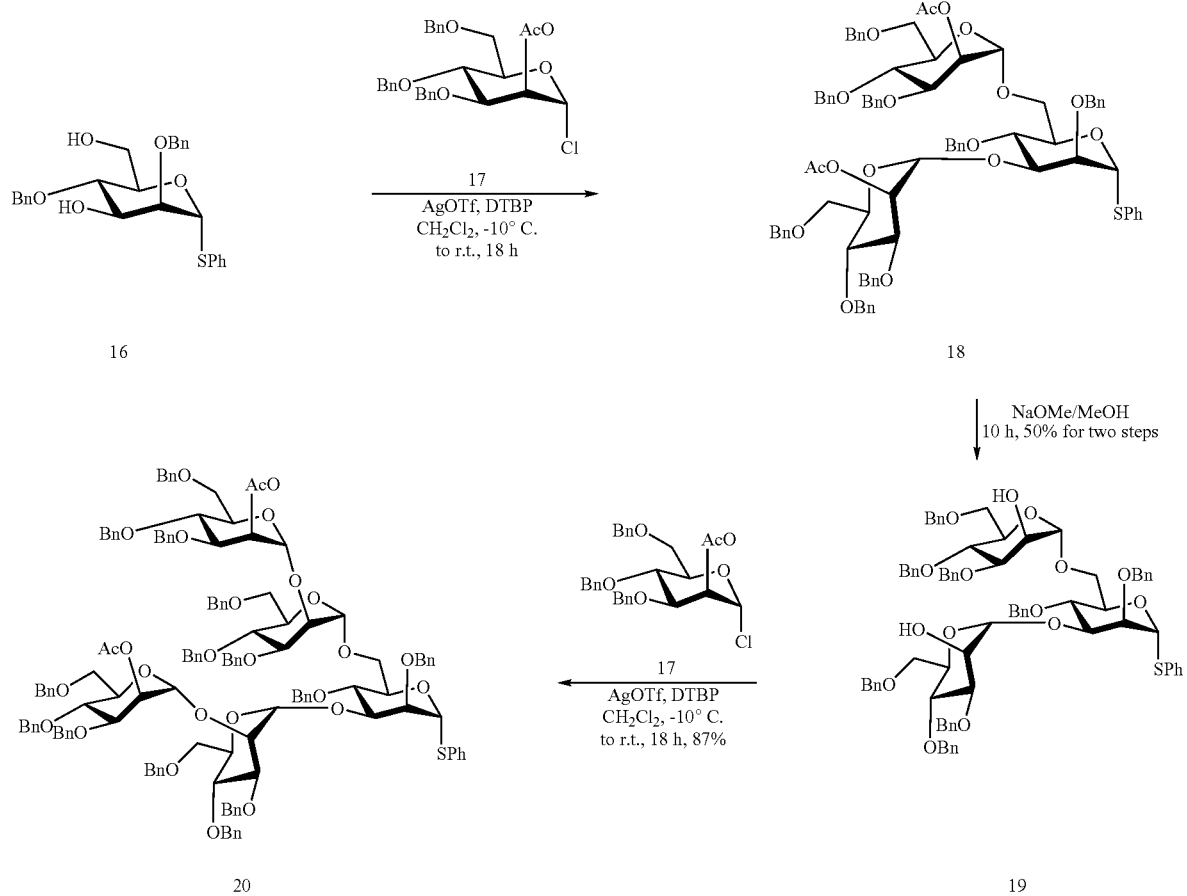
In certain embodiments, the 6+5 glycosylation using Sinaÿ radical cation activation[2,3] proceeded smoothly giving the desired undecasaccharide 12b in 85% yield (Scheme 9).
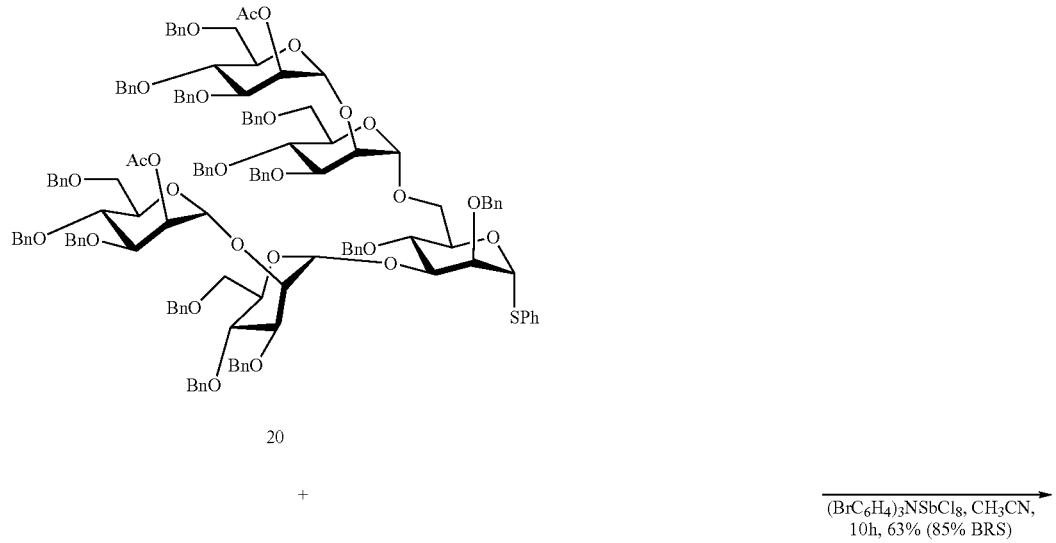

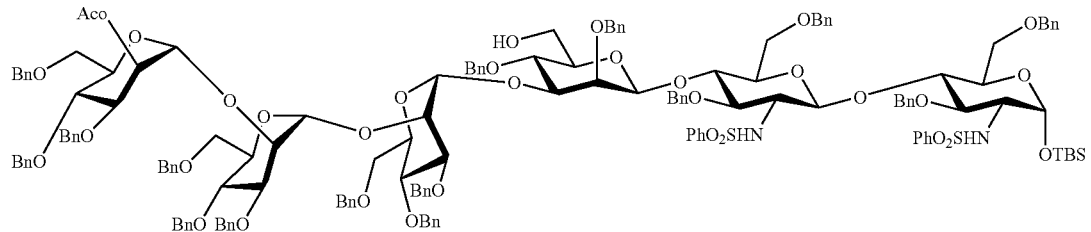

15

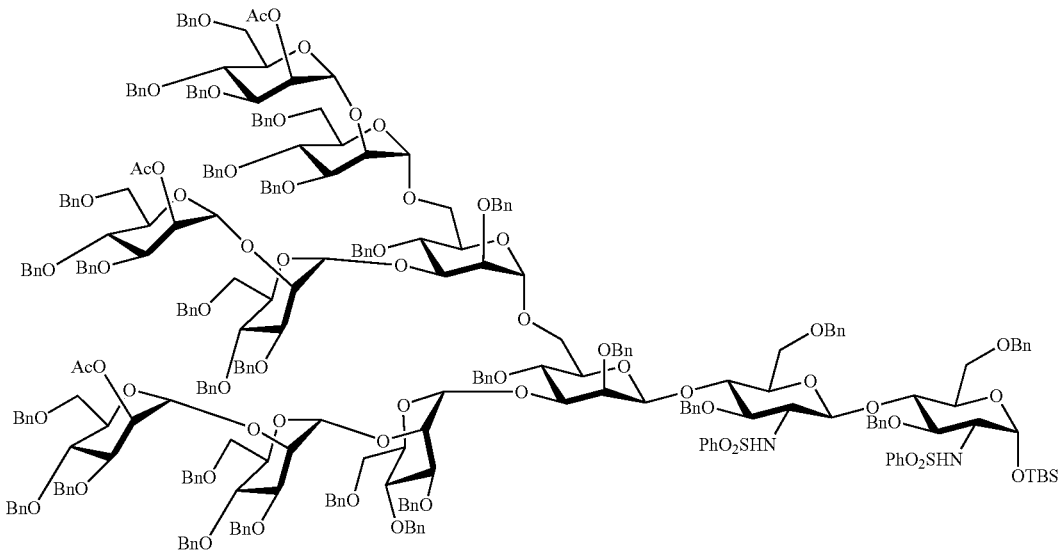

12b

In certain embodiments, protected undecasaccharide 12b was treated with sodium methoxide and HF-pyridine to remove the acetyl groups and TBS group, respectively. The resulting oligosaccharide 21 was then subjected to global Birch deprotection followed by selective acetylation using acetyl anhydride in saturated sodium bicarbonate solution to give free glycan in high yield.[5] Following Kochetkov amination[6] furnished free glycosylamine (Scheme 10).

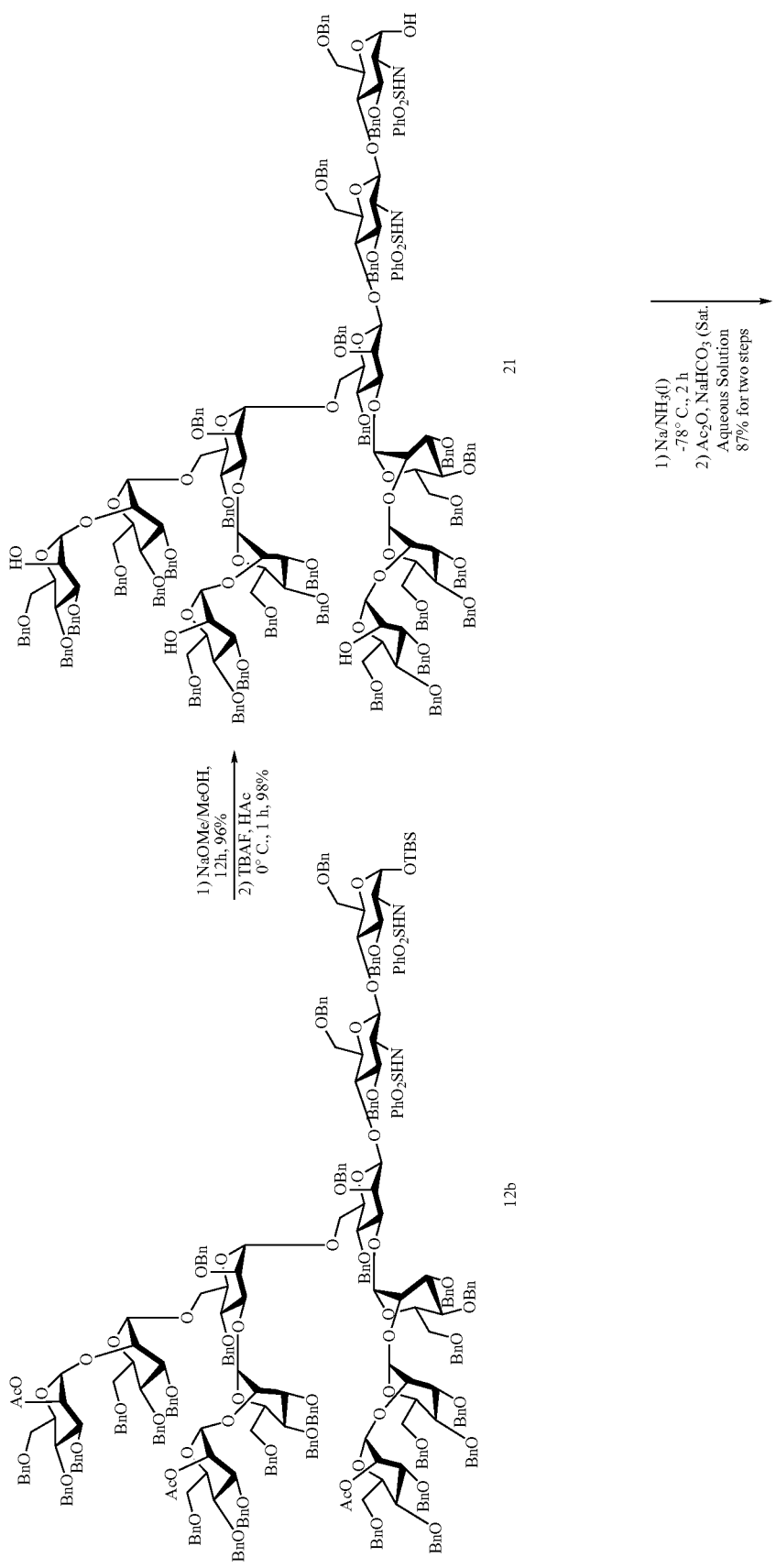

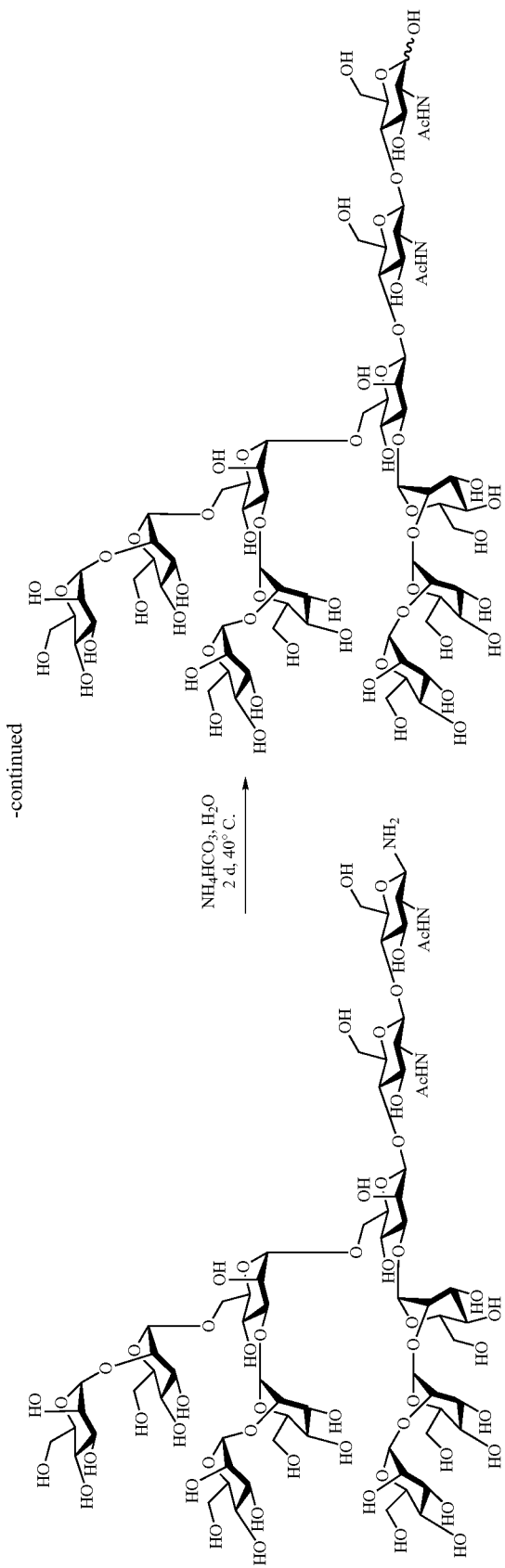

In certain embodiments, 20-mer peptide acid 34, which was made through applied biosynthesis synthesizer, was activate using HATU and coupled directly with glycosylamine 23. The Fmoc and ivDde protecting groups were removed by treatment with hydrazine and piperidine to give glycopeptide fragment 25 in 16% two steps yield (Scheme 11).

References ("Glycan Synthesis" Section)

1. Dudkin, V. Y.; Miller, J. S.; Danishefsky, S. J. *Tetrahedron Letters* 2003, 44, 1791-1793.

2. Zhang, Y.-M.; Mallet, J.-M.; Sinay, P. *Carbohydrate Research* 1992, 236, 73-88.

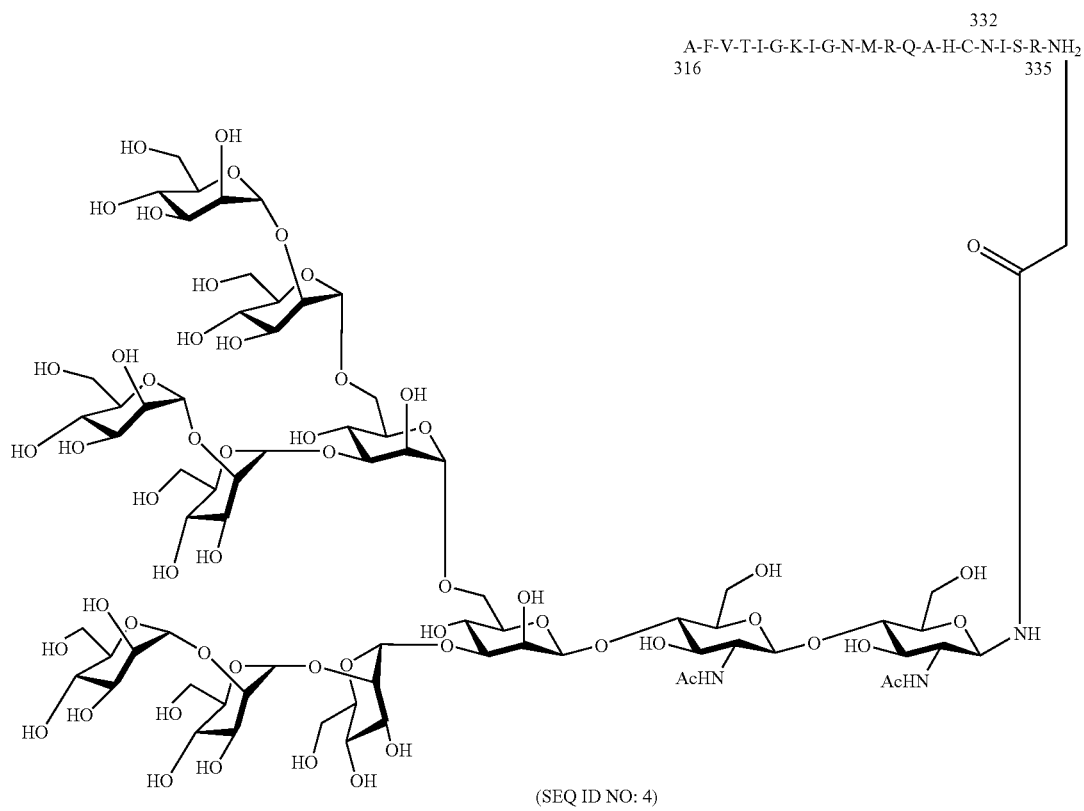

(SEQ ID NO: 4)

25

Methods of preparing trisaccharide 3 are known in the art. For example, guidance may be found in U.S. Provisional Patent Application No. 60/500,161 filed Sep. 4, 2003; and International Application No. PCT/US03/38453, filed Dec. 3, 2003 entitled "Prostate Specific Antigens, Conjugates Thereof, Methods for their Preparation and Uses Thereof"; the entire contents of each of the above applications are hereby incorporated by reference herein.

3. Marra, A.; Mallet, J. M.; Amatore, C.; Sinay, P. *Synlett* 1990, 572-574.

4. Matsuo, I.; Wada, M.; Manabe, S.; Yamaguchi, Y.; Otake, K.; Kato, K.; Ito, Y. *Journal of the American Chemical Society* 2003, 125, 3402-3403.

5. Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H.; Kelly, J. W.; Rudd, P. M.; Dwek, R. A.; Katinger, H.; Burton, D. R.; Wilson, I. A. *Science* (Washington, DC, United States) 2003, 300, 2065-2071.

6. Likhosherstov, L. M.; Novikova, O. S.; Derevitskaya, V. A.; Kochetkov, N. K. *Carbohydrate Research* 1986, 146, C1-C5.

Glycopeptides

Automated peptide synthesis is reliable for sequences up to about 60 amino acid residues in length, but saccharide moieties contained in glycopeptides render their solid phase synthesis less practical. Unlike peptide synthesis, complex glycan and glycoconjugate synthesis remains readily accessible only to a few select laboratories (See, for example, Hang, H. C.; Bertozzi, C. R. "Chemoselective approaches to glycoprotein assembly." *Acc. Chem. Res.* 2001, 34, 727-736). Syntheses of several natural O-linked glycopeptides containing simple glycans have been reported (See, for example, (1) Arsequell, G.; Haurum, J. S.; Elliott, T.; Dwek, R. A.; Lellouch, A. C. "Synthesis of Major Histocompatibility Complex Class-I Binding Glycopeptides." *J. Chem. Soc.-Perkin Trans.* 1 1995, 1739-1745, (2) Chen, X. T.; Sames, D.; Danishefsky, S. J. "Exploration of modalities in building alpha-O-linked systems through glycal assembly: A total synthesis of the mucin-related F1 alpha antigen." *J. Am. Chem. Soc.* 1998, 120, 7760-7769; (3) Macmillan, D.; Bertozzi, C. R. "New directions in glycoprotein engineering." *Tetrahedron* 2000, 56, 9515-9525; (4) Koeller, K. M.; Smith, M. E. B.; Huang, R. F.; Wong, C. H. "Chemoenzymatic synthesis of a PSGL-1 N-terminal glycopeptide containing tyrosine sulfate and alpha-O-linked sialyl Lewis X." *J. Am. Chem. Soc.* 2000, 122, 4241-4242; (5) Ajisaka, K.; Miyasato, M.; Ishii-Karakasa, I. "Efficient synthesis of O-linked glycopeptide by a transglycosylation using endo alpha-N-acetylgalactosaminidase from Streptomyces sp." *Biosci. Biotechnol. Biochem.* 2001, 65, 1240-1243; and (6) Marcaurelle, L. A.; Mizoue, L. S.; Wilken, J.; Oldham, L.; Kent, S. B. H.; Handel, T. M.; Bertozzi, C. R. "Chemical synthesis of lymphotactin: A glycosylated chemokine with a C-terminal mucin-like domain." *Chem. Eur. J.* 2001, 7, 1129-1132), as have examples of mimetics for N-linked glycopeptides (See, for example, Hang, H. C.; Bertozzi, C. R. "Chemoselective approaches to glycoprotein assembly." *Acc. Chem. Res.* 2001, 34, 727-736), and a chemoenzymatic synthesis of an N-linked glycopeptide (See, for example, Inazu, T.; Haneda, K.; Mizuno, M. "Synthetic study on N-glycopeptides." *J. Syn. Org. Chem. Jpn.* 1998, 56, 210-220), but no chemical synthesis has been reported for a natural N-linked glycopeptide with complex glycan and peptide structure. The state of the art for chemically synthesized N-linked glycopeptides is exemplified by the pentadecasaccharide N-linked to a pentapeptide reported by Wang and coworkers, which was recognized by appropriate antibodies to the H-type blood group antigens present at the glycan nonreducing termini (See, for example, Wang, Z. G.; Zhang, X. F.; Visser, M.; Live, D.; Zatorski, A.; Iserloh, U.; Lloyd, K. O.; Danishefsky, S. J. "Toward filly synthetic homogeneous glycoproteins: A high mannose core containing glycopeptide carrying full H-type2 human flood group specificity." Angew. Chem. Int. Ed. 2001, 40, 1728-1732).

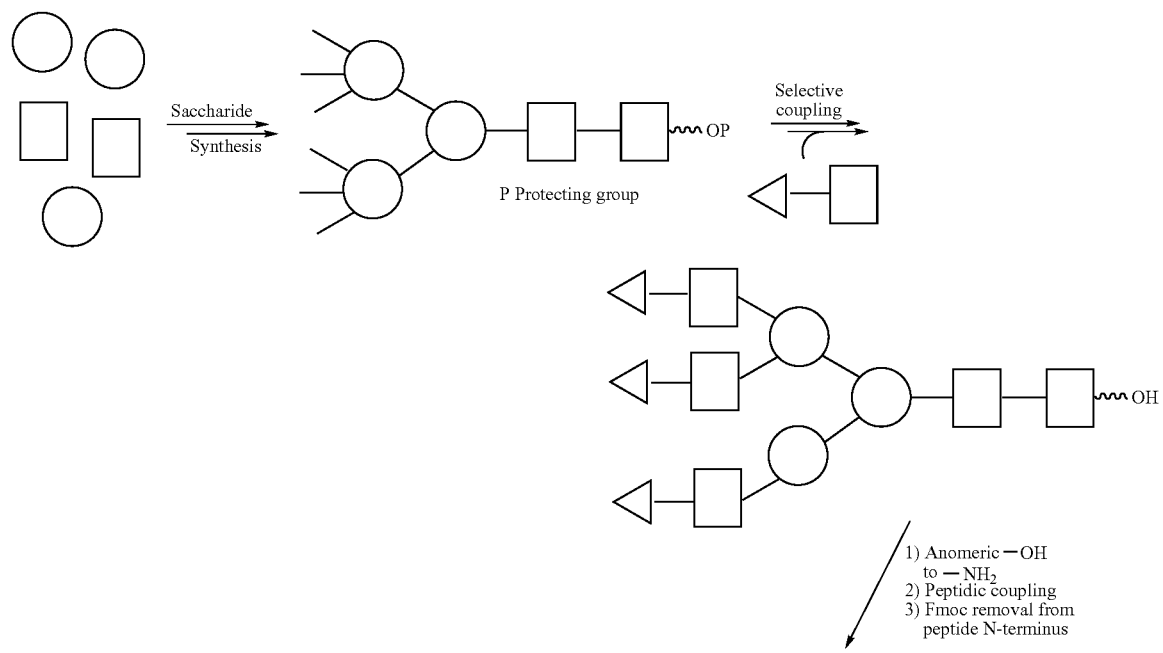

Scheme 12. Exemplary synthetic approach for the prepation of gp120 glycopeptides.

-continued

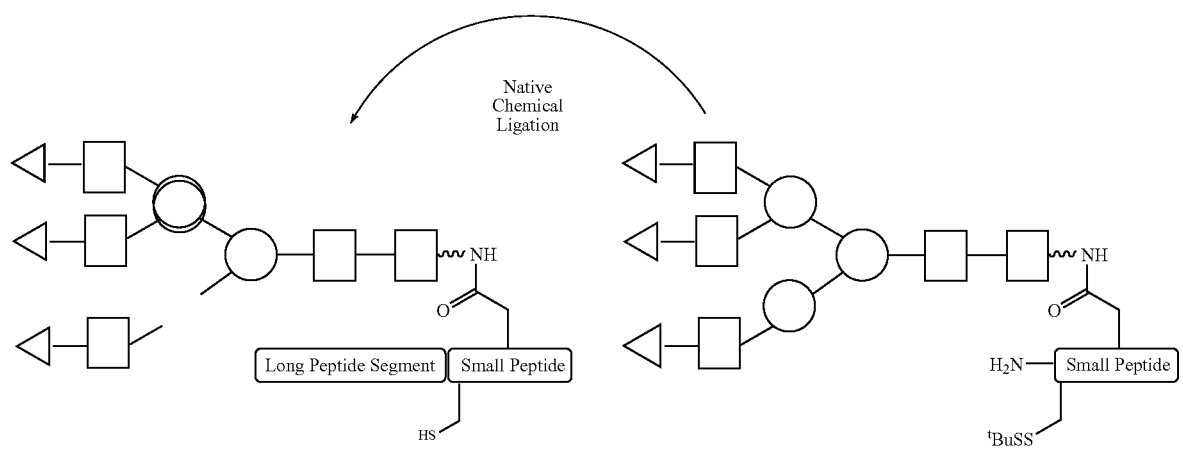

In certain embodiments, as shown in Scheme 12, the chemical synthesis of inventive glycopeptides may be divided logically into two sections: glycan synthesis (top) and glycopeptide assembly (bottom). At its core, the inventive method would extend the method of Wang, et al. (Wang, Z. G.; Zhang, X. F.; Visser, M.; Live, D.; Zatorski, A.; Iserloh, U.; Lloyd, K. O.; Danishefsky, S. J. "Toward fully synthetic homogeneous glycoproteins: A high mannose core containing glycopeptide carrying full H-type2 human flood group specificity." *Angew. Chem. Int. Ed.* 2001, 40, 1728-1732) to include one or more peptide elongation steps after synthesis of a short glycopeptide, allowing entry into the realm of fully elaborated, naturally derived glycoproteins (See, for example, Dawson, P. E.; Kent, S. B. H. "Synthesis of native proteins by chemical ligation." *Annu. Rev. Biochem.* 2000, 69, 923-960). In an inventive and important improvement, the glycan is fashioned here in a more convergent manner than previously realized, allowing the strategy to be adjusted in its late stage to accommodate the synthesis of various glycoforms, as illustrated in the next section.

Glycopeptide Assembly

Guidance for glycopeptide assembly may be found, inter alia, in U.S. Provisional Patent Application No.: 60/500,161 entitled "Prostate Specific Antigens, Conjugates Thereof, Methods for their Preparation and Uses Thereof", filed Sep. 4, 2003; the entire contents of which are hereby incorporated by reference herein. For example, a glycopeptide assembly strategy, as outlined in Scheme 12, involves peptide glycosylation followed by elongation of the peptide backbone, was examined, as illustrated in Scheme 13, using a model peptide and glycan (Miller, J. S. et al., *Angew. Chemie Int. Ed.,* 2003, 42, 431). To prepare free glycan 38 for coupling, its anomeric hydroxyl was first aminated to give β-aminoglycoside 39 as described by Kochetkov (See, for example, Likhosherstov, L. M.; Novikova, O. S.; Derevitskaja, V. A.; Kochetkov, N. K. "A New Simple Synthesis of Amino Sugar Beta-D-Glycosylamines." *Carbohydr. Res.* 1986, 146, C1-C5). Glycosylamine 39 and the aspartate free acid of peptide 40 were coupled in peptidic fashion according to the procedure of Lansbury and coworkers ((1) Cohen-Anisfeld, S. T.; Lansbury, P. T. "A Practical, Convergent Method for Glycopeptide Synthesis." *J. Am. Chem. Soc.* 1993, 115, 10531-10537; and (2) Anisfeld, S. T.; Lansbury, P. T. "A Convergent Approach to the Chemical Synthesis of Asparagine-Linked Glycopeptides." *J. Org. Chem.* 1990, 55, 5560-5562) with certain modifications: the reported peptide glycosylations involved excess or equimolar amounts of glycosylamine relative to peptide, and their isolated yields (50-60%) are reported based on peptide starting material (Cohen-Anisfeld, S. T.; Lansbury, P. T. "A Practical, Convergent Method for Glycopeptide Synthesis." *J. Am. Chem. Soc.* 1993, 115, 10531-10537). As is often the case, however, the saccharide here is the more precious material entering glycosylation because its preparation involves multistep, solution phase synthesis in relatively low overall yield compared to that of the peptide. A trial glycosylation of model pentapeptide 40 with pentasaccharide 39 indicates that under the appropriate reaction conditions, an excess of peptide produces a significantly greater yield of coupled product (over 70% based on valuable glycosylamine) [Miller, J. S. et al., *Angew. Chemie Int. Ed.,* 2003, 42, 431. Subsequent Fmoc (Fmoc=9-fluorenylmethyloxy-carbonyl) removal with piperidine afforded glycopeptide 41.

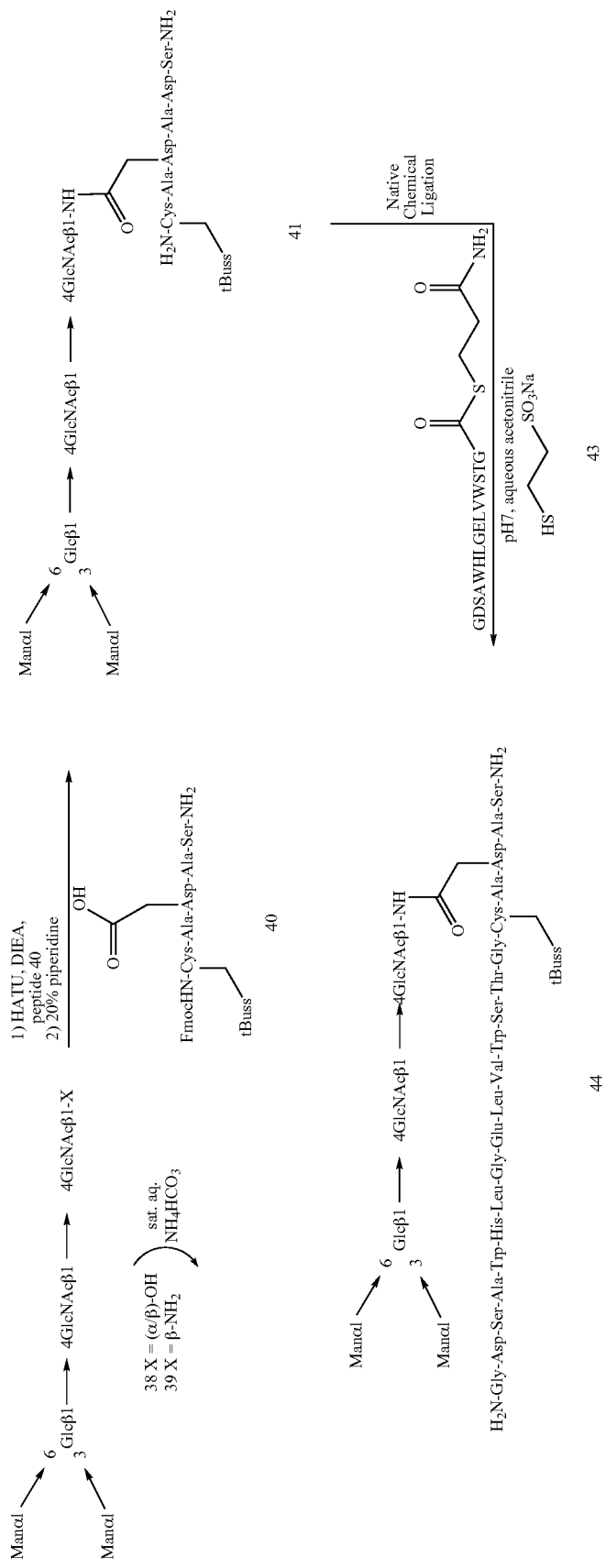

The final step toward completion of a model glycopeptide involved native chemical ligation (NCL) [See, for example, Dawson, P. E.; Muir, T. W.; Clark-Lewis, I.; Kent, S. B. H. "Synthesis of Proteins by Native Chemical Ligation." *Science* 1994, 266, 776-779], as indicated in Scheme 13. In situ deprotection of cysteine disulfide 41 and transthioesterification (See, for example, Dawson, P. E.; Churchill, M. J.; Ghadiri, M. R.; Kent, S. B. H. "Modulation of reactivity in native chemical ligation through the use of thiol additives." *J. Am. Chem. Soc.* 1997, 119, 4325-4329) of peptide thioester 42 with sodium 2-mercaptoethanesulfonate (43) in phosphate-buffered saline (PBS) at neutral pH led to a second thioester exchange with the (now free) cysteine thiol and subsequent rearrangement to give fully unprotected glycopeptide 44. gp120-derived glycopeptides obtained using the strategy detailed in Scheme 13 will require no additional manipulation other than purification before they can be examined for the generation of antibodies. The synthetic strategy thus requires only four assembly steps starting from free glycans to obtain homogeneous glycopeptides.

In certain embodiments, the lysine residue is differentially protected with respect to Fmoc removal during peptide synthesis, and remains protected through the peptide glycosylation step (due to its free amine side chain). Suitably protected Lys derivatives have been designed (See, for example, Chhabra, S. R.; Hothi, B.; Evans, D. J.; White, P. D.; Bycroft, B. W.; Chan, W. C. "An appraisal of new variants of Dde amine protecting group for solid phase peptide synthesis." *Tetrahedron Lett.* 1998, 39, 1603-1606), and can be deprotected in the presence of N-linked saccharides along with the N-terminal Fmoc amine in minutes using hydrazine at room temperature.

Peptide Thioester Synthesis

Several methods have been developed for peptide thioester synthesis, including the original "Boc chemistry" (Boc=tert-butyloxycarbonyl) method (See, for example, (1) Canne, L. E.; Walker, S. M.; Kent, S. B. H. "A General Method for the Synthesis of Thioester Resin Linkers for Use in the Solid-Phase Synthesis of Peptide Alpha-Thioacids." *Tetrahedron Lett.* 1995, 36, 1217-1220; and (2) Hojo, H.; Aimoto, S. "Polypeptide Synthesis Using the S-Alkyl Thioester of a Partially Protected Peptide Segment—Synthesis of the DNA-Binding Domain of C-Myb Protein (142-193)-NH2." *Bull. Chem. Soc. Jpn.* 1991, 64, 111-117) and several Fmoc-compatible systems (See, for example, (1) Shin, Y.; Winans, K. A.; Backes, B. J.; Kent, S. B. H.; Ellman, J. A.; Bertozzi, C. R. "Fmoc-based synthesis of peptide-(alpha)thioesters: Application to the total chemical synthesis of a glycoprotein by native chemical ligation." *J. Am. Chem. Soc.* 1999, 121, 11684-11689; (2) Ingenito, R.; Bianchi, E.; Fattori, D.; Pessi, A. "Solid phase synthesis of peptide C-terminal thioesters by Fmoc/t-Bu chemistry." *J. Am. Chem. Soc.* 1999, 121, 11369-11374; (3) Li, X. Q.; Kawakami, T.; Aimoto, S. "Direct preparation of peptide thioesters using an Fmoc solidphase method." *Tetrahedron Lett.* 1998, 39, 8669-8672; (4) Clippingdale, A. B.; Barrow, C. J.; Wade, J. D. "Peptide thioester preparation by Fmoc solid phase peptide synthesis for use in native chemical ligation." *J. Pept. Sci.* 2000, 6, 225-234; and (5) Bu, X. Z.; Xie, G. Y.; Law, C. W.; Guo, Z. H. "An improved deblocking agent for direct Fmoc solidphase synthesis of peptide thioesters." *Tetrahedron Lett.* 2002, 43, 2419-2422). In ceratin embodiments, the model thioester is a C-terminal glycine thioester, which is locally achiral and cannot be epimerized, and is therefore easy to synthesize. Though the desired gp120 thioester contains an epimerization-prone C-terminal histidine (His) residue, such thioesters have been synthesized previously and have in fact been shown to modulate favorably the rate of NCL (See, for example, Hackeng, T. M.; Griffin, J. H.; Dawson, P. E. "Protein synthesis by native chemical ligation: Expanded scope by using straightforward methodology." *Proc. Natl. Acad. Sci. U. S. A.* 1999, 96, 10068-10073).

Cyclic Peptidic Construct

Despite the partial success of HIV treatment via antiviral drug combination therapy, the worldwide epidemic of HIV infection has made ever more pressing the need for development of an effective vaccine. Vaccine strategies attempted thus far have met with limited success.[47] Nevertheless, several antibodies capable of neutralizing a broad range of HIV isolates have been obtained from immune individuals and found to confer various degrees of protection against infection in primate models.[48-53]

Scheme 14

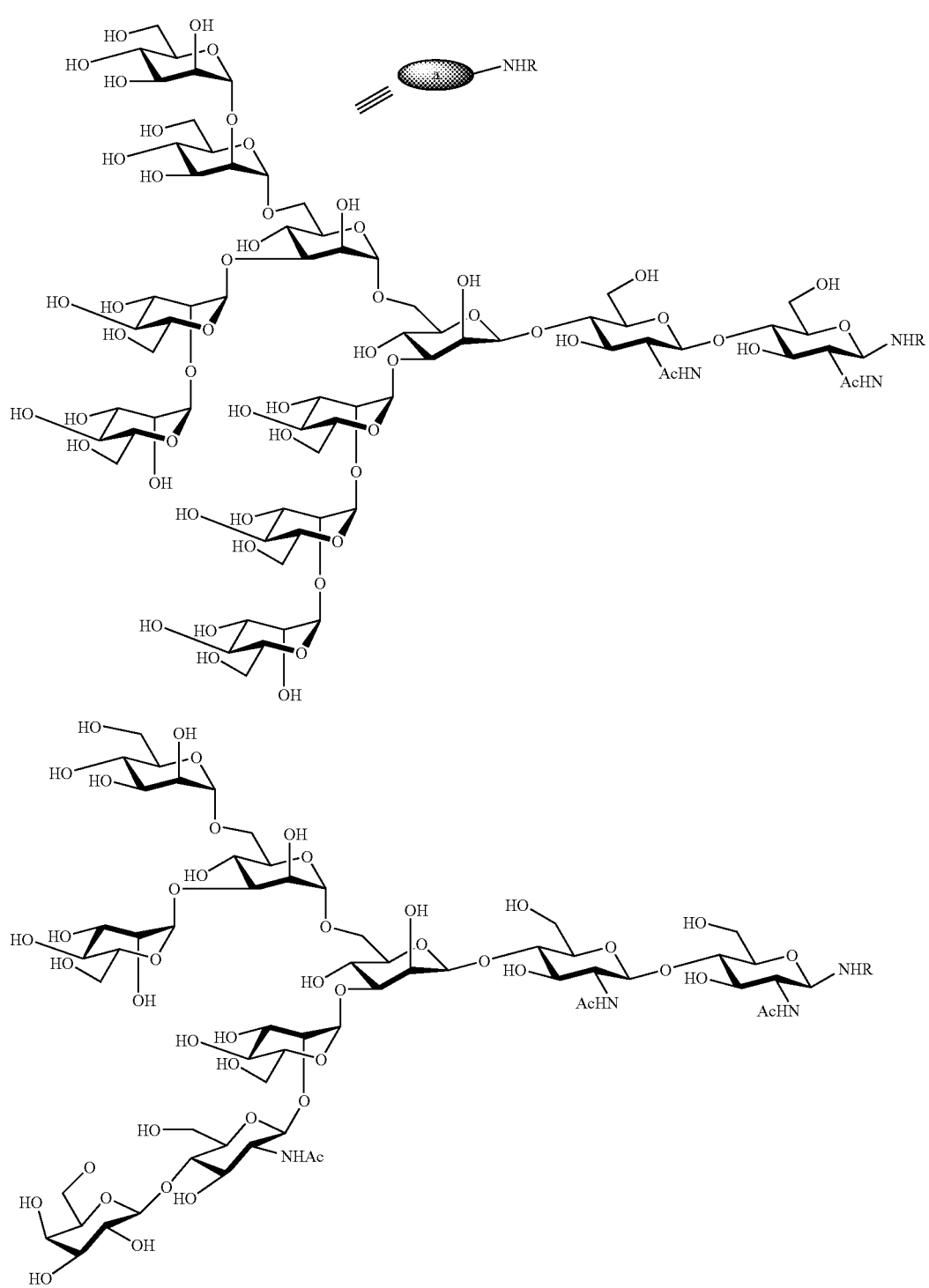

As discussed herein, our interest in carbohydrate synthesis called our attention to one such broadly-neutralizing antibody, 2G12. The 2G12 epitope on HIV protein gp120 is known to consist largely or exclusively of a cluster of oligosaccharides such as a and b (Scheme 14), both of which have been synthesized in these laboratories.[54] An X-ray diffraction study of 2G12 and 2G12-a cocrystals from the labs of Burton and Wilson[55] shows that 2G12 binds to a cluster of as many as three copies of a. Thus, the carbohydrate cluster effect may be responsible for the observed strength of the 2G12-gp120 binding interaction. We have demonstrated this principle in binding studies which show that divalent glycopeptide 40a$_2$ (Scheme 15) binds to 2G12 but the monovalent 40a does not.[56]

Scheme 15

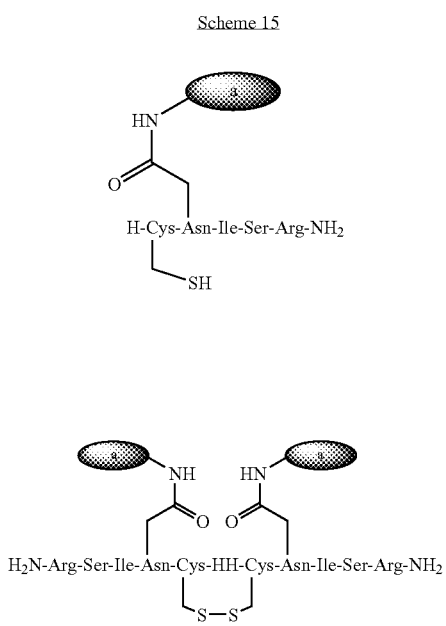

D-Pro-L-Pro sequences in two positions are employed impose a β-sheet conformation in which alternating residues (blue and red, as depicted) point their side chains above and below the macrocycle. The top (blue) positions provide up to six possible points of attachment for glycans such as a, through an N-linked glycosyl-asparagine linkage. As depicted in 41 and 41', two and three of these positions, respectively, have been selected for glycan linkage. Crude molecular models show that inter-side-chain distances among the six top residues range from 7-17 Å, providing us with the opportunity to vary the spacing of the glycans. We placed a cysteine residue in one of the four bottom (red) positions as a handle for eventual conjugation to a carrier (e.g., protein or protein complex); and hydrophobic residues were chosen for the other three bottom positions in recognition of the principle that transannular hydrophobic/aromatic stacking interactions may also help to stabilize a β-sheet conformation.[58] As an additional point of flexibility in this design, we have the option of changing the linkage of the glycan to our scaffold by using glutamate or some entirely different type of amino acid side chain as our handle for glycan attachment.

Scheme 16

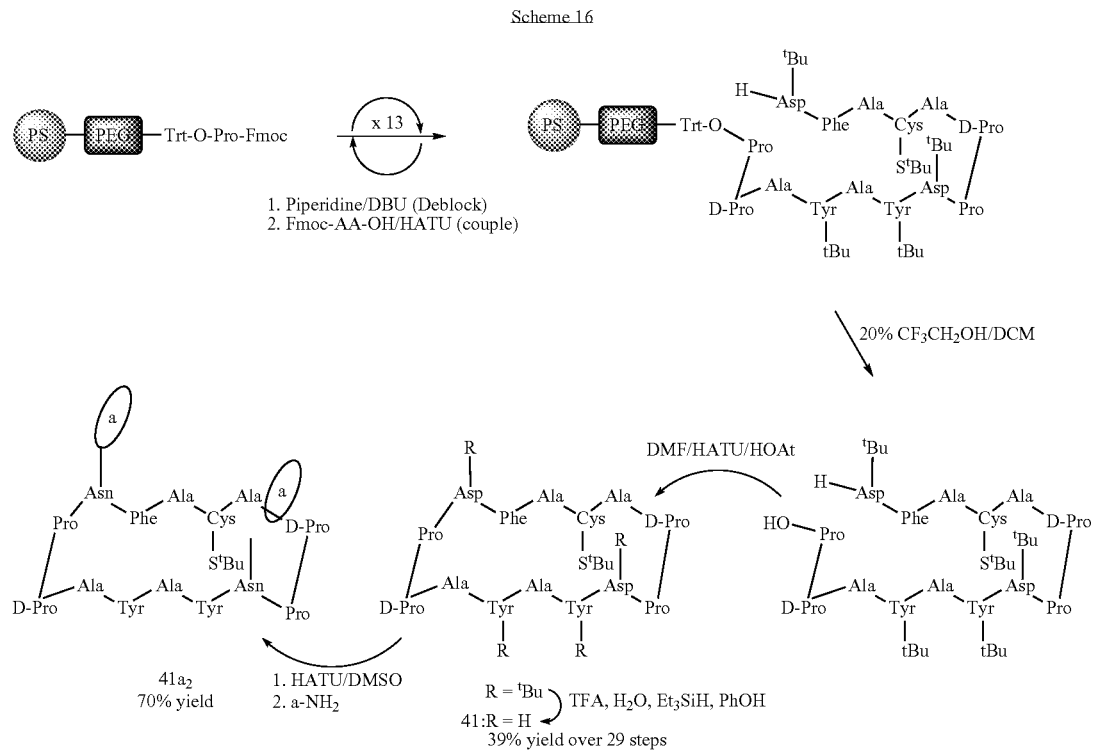

Figure 2:
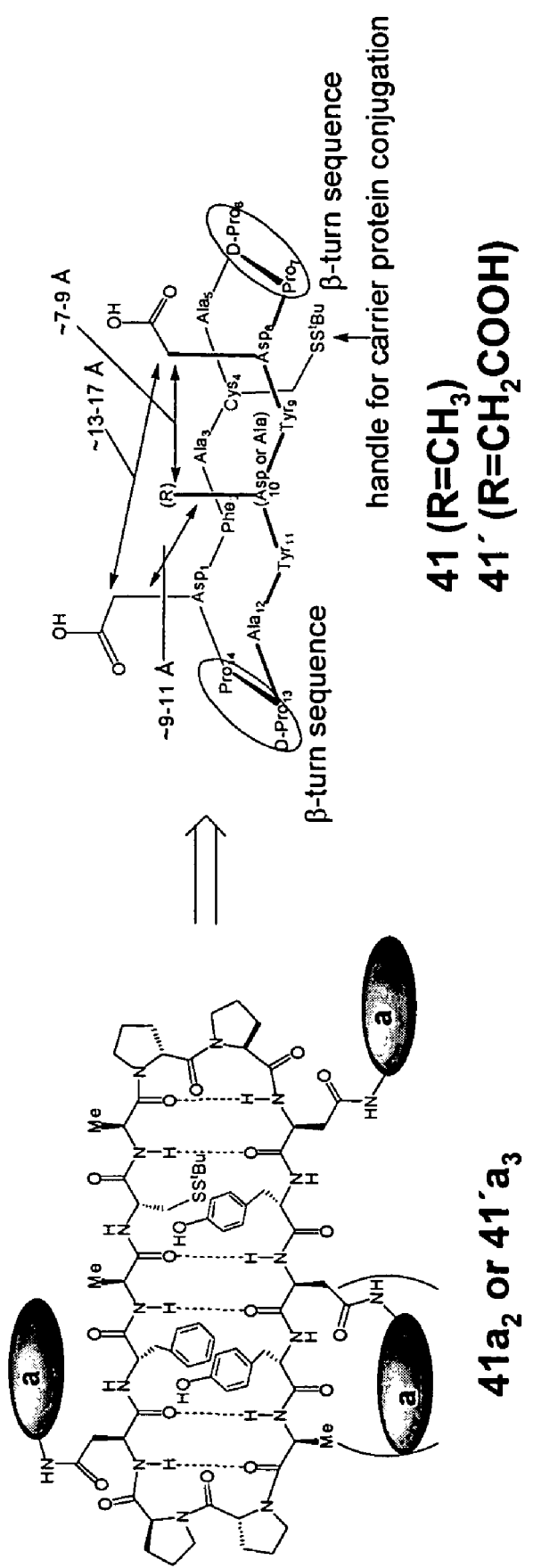
FIG. 2 depicts exemplary di- and tri glycosylated cyclic peptides of the invention.

With a view towards creating synthetic epitopes which could be used as vaccines to induce the production of antibodies similar to 2G12, we embarked on the design and synthesis of compound 41a$_2$ (FIG. 2). 41, the cyclic tetradecapeptide backbone of 41a$_2$, was designed in analogy to work of Dumy and Robinson.[57] In this construct, β-turn-inducing Our synthesis of this initial design was accomplished as represented in Scheme 16. The side-chain-protected linear precursor of peptide 41 was prepared by automated Fmoc solid-phase synthesis starting with L-Proline-loaded PEGylated trityl resin. The resulting peptide chain was cleaved with 20% trifluoroethanol/DCM and cyclized in solution with HATU/HOAt. t-butyl groups were then removed with 87% aqueous trifluoroacetic acid in the presence of phenol and triethylsilane to afford peptide 41 in 39% overall yield from the resin (See Examples 34-36). Glycosyl amine a was then obtained by previously described protocols.[54] A double Lansbury aspartylation[59] then proceeded smoothly to afford bis-glycosylated product 41a$_2$ in 70% yield.

This bis-glycosylated product 41a$_2$ could be conjugated to a variety of carriers, for example KLH or BSA. Guidance for conjugation methods may be found, for example, in WO04/60915. The bis-glycosylated product 41a$_2$ could be conjugated to OMPC, a strong immunogenic carrier protein. OMPC and methods for its conjugation are known in the art (See, for example, U.S. Pat. Nos. 5,606,030 and 5,623,057; and references cited therein).

In another aspect of the present invention, a method of preparing an isolated compound having the structure:

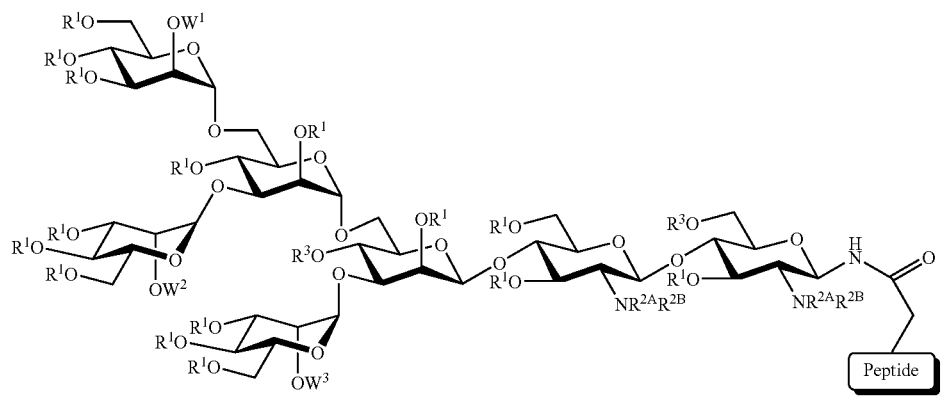

wherein each occurrence of $R^1$ is independently hydrogen or an oxygen protecting group;
each occurrence of $R^{2A}$ and $R^{2B}$ is independently hydrogen or a nitrogen protecting group;
each occurrence of $R^3$ is independently hydrogen, a protecting group or a carbohydrate domain comprising a saccharide moiety having the structure:

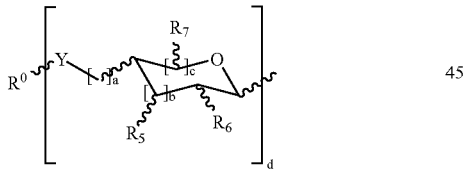

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently optionally substituted mannose, galactose or lactosamine moieties;

said method comprising steps of:

(a) providing an α-O-protected carbohydrate construct having the structure:

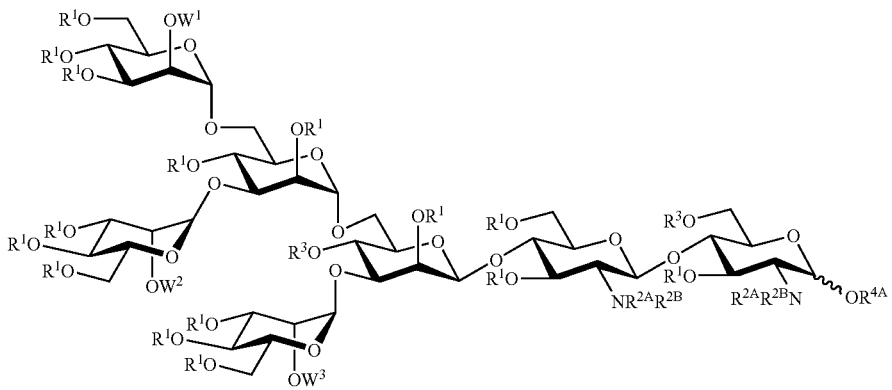

wherein $R^{4A}$ is hydrogen or a suitable oxygen protecting group;

(b) reacting the construct of step (a) under suitable conditions to form a β-amino carbohydrate construct having the structure:

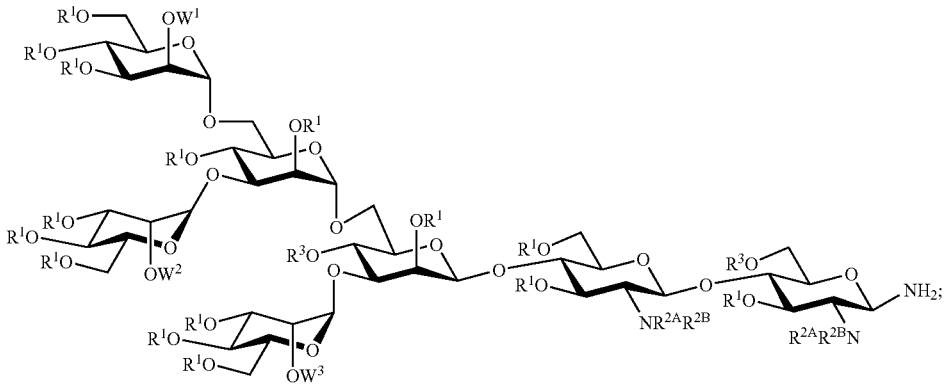

(c) reacting said β-amino carbohydrate construct under suitable conditions with a peptide whose structure is either identical or closely related to that of gp120 near an N-glycosylation site and which comprises a —$CH_2CO_2H$ moiety, to form a glycopeptide having the structure:

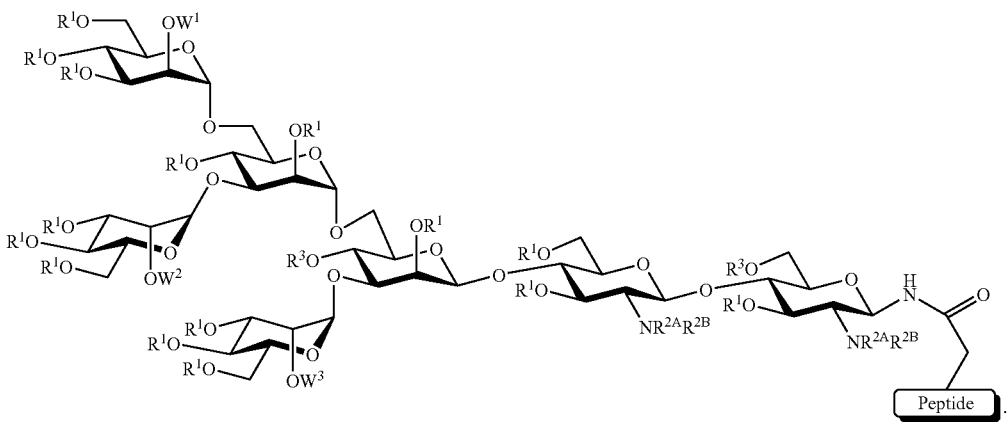

In certain embodiments, the peptide comprises a cysteine residue and thus, the peptide may be dimerized under suitable oxidization conditions to form the corresponding disulfide dimer. In certain exemplary embodiments, the disulfide dimer has the structure:

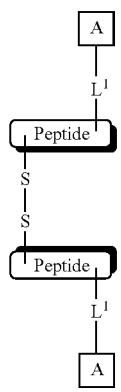

wherein each peptide may be the same or different; each occurrence of L¹ may be the same or different and is as defined above; and each occurrence of A is independently a carbohydrate domain as defined above.

In certain exemplary embodiments, in the step of reacting the carbohydrate construct of step (a) under suitable conditions to form the β-amino carbohydrate construct, Kochetkov amination conditions are used. In certain exemplary embodiments, in the step of reacting the carbohydrate construct of step (a) under suitable conditions to form the β-amino carbohydrate construct, $NH_4HCO_3/H_2O$ is used. In certain exemplary embodiments, in the β-amino carbohydrate construct of step (b), each occurrence of $R^1$ and $R^3$ is hydrogen and each occurrence of —$NR^{2A}R^{2B}$ is —NHAc.

In certain other exemplary embodiments, in the step of reacting the β-amino carbohydrate construct under suitable conditions with a peptide whose structure is either identical or closely related to that of gp120 near an N-glycosylation site, the reaction conditions comprise HATU and Hünig's base in a suitable solvent. In certain embodiments, the solvent is DMSO. In certain embodiments, the peptide has the following structure:

(SEQ ID NO: 6)

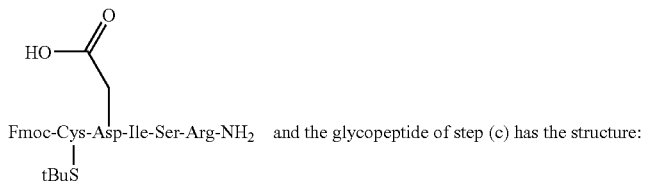

and the glycopeptide of step (c) has the structure:

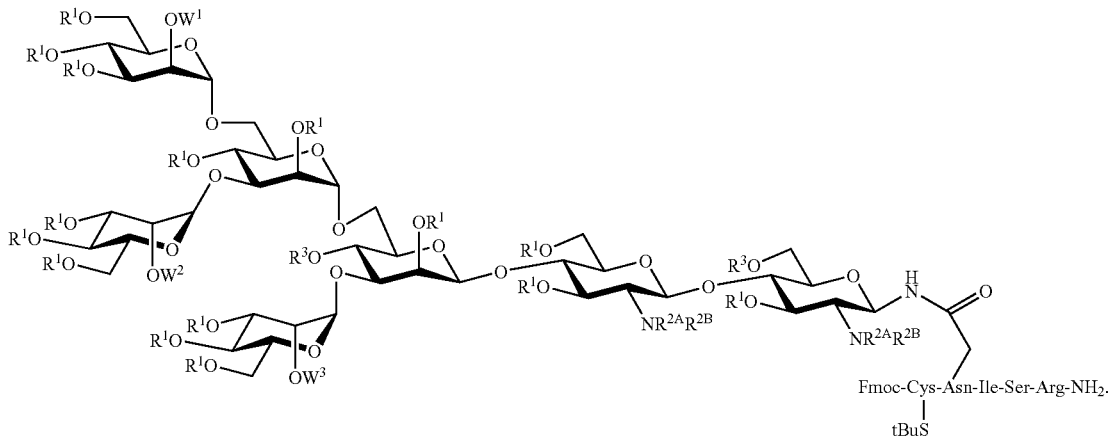

In certain exemplary embodiments, in the step of reacting the β-amino carbohydrate construct formed in step (b), each occurrence of $R^1$ and $R^3$ is hydrogen, each occurrence of —$NR^{2A}R^{2B}$ is —NHAc.

In certain other exemplary embodiments, the α-O-protected carbohydrate construct of step (a) has the structure:

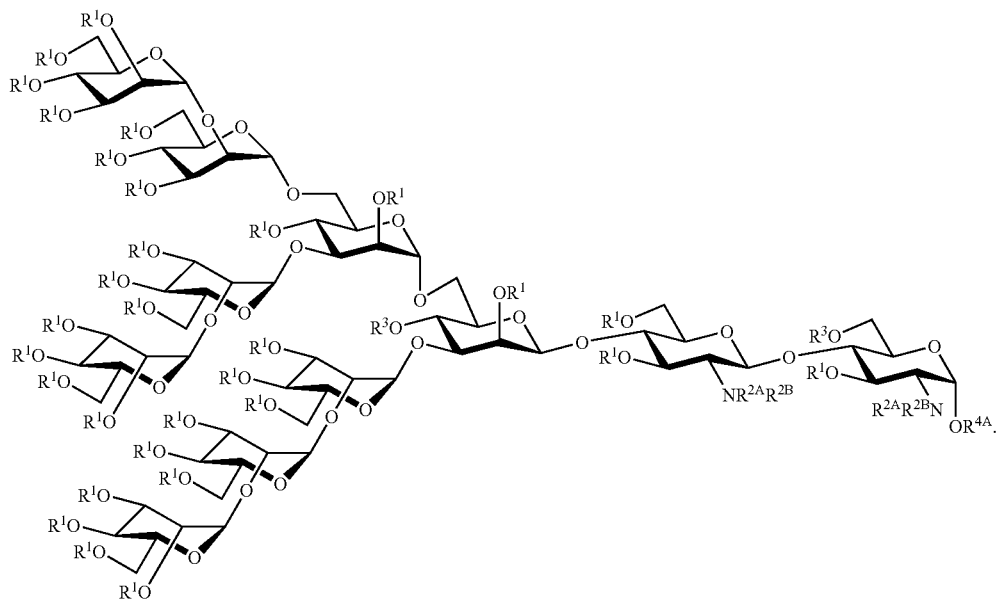
In certain other exemplary embodiments, the glycopeptide 30 formed in step (c) has the structure:
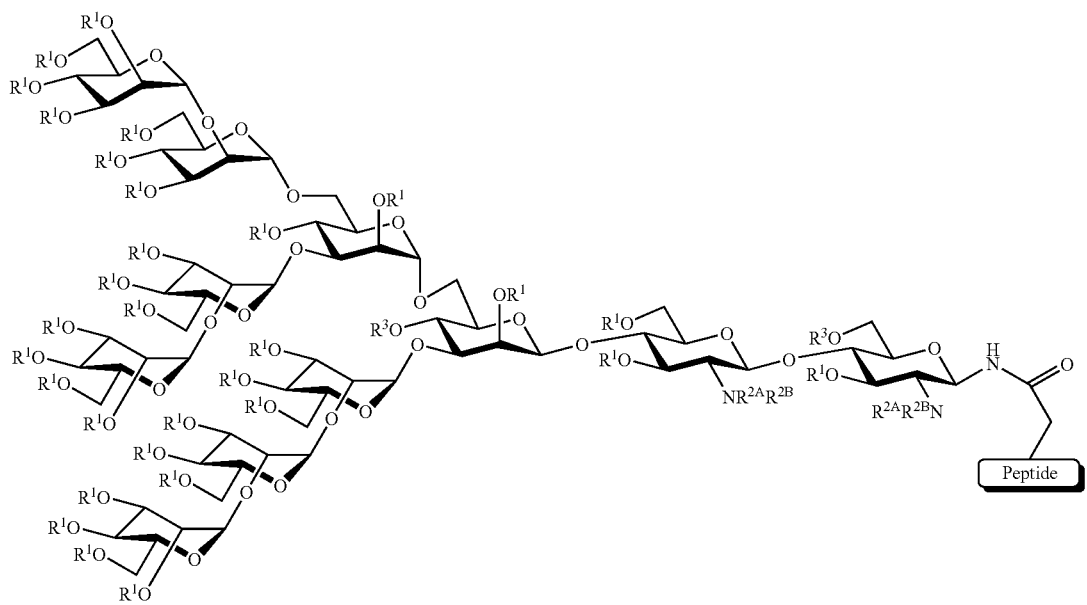
In certain other exemplary embodiments, the α-O-protected carbohydrate construct of step (a) has the structure:

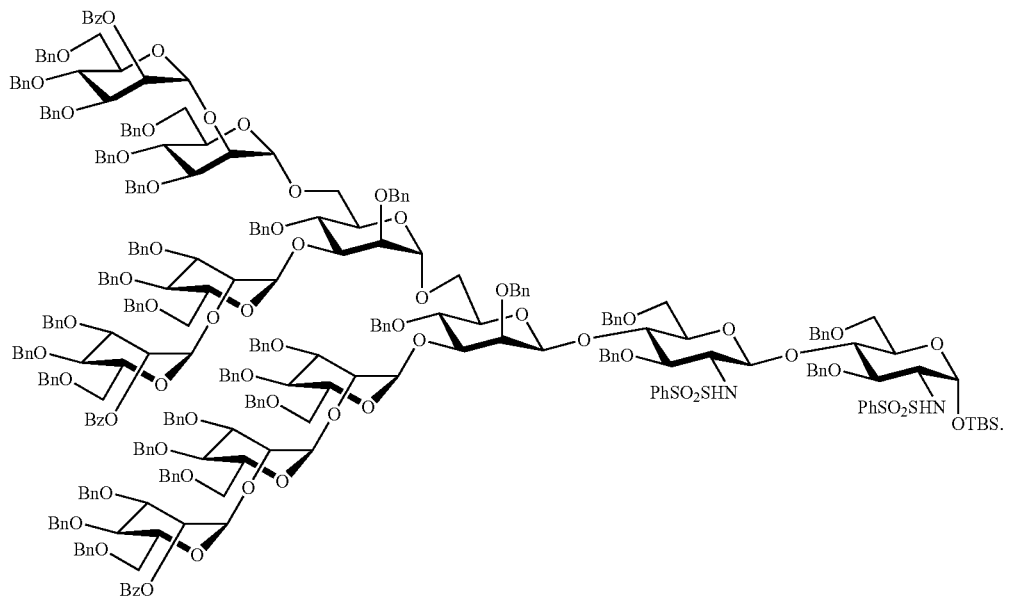
30
In certain other exemplary embodiments, the glycopeptide formed in step (c) has the structure:
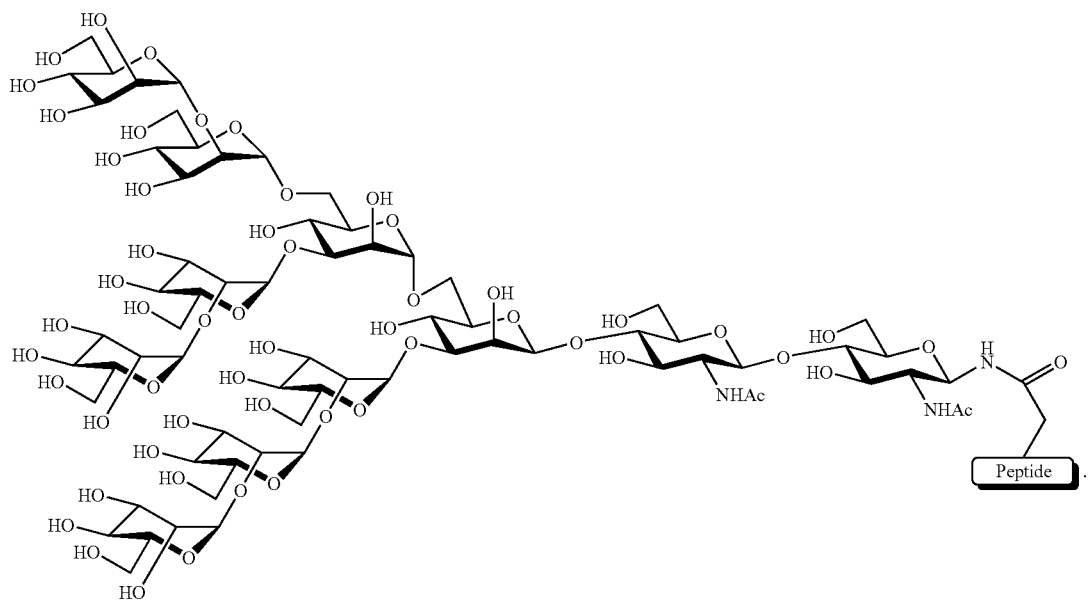
In certain other exemplary embodiments, the α-O-protected carbohydrate construct of step (a) has the structure:

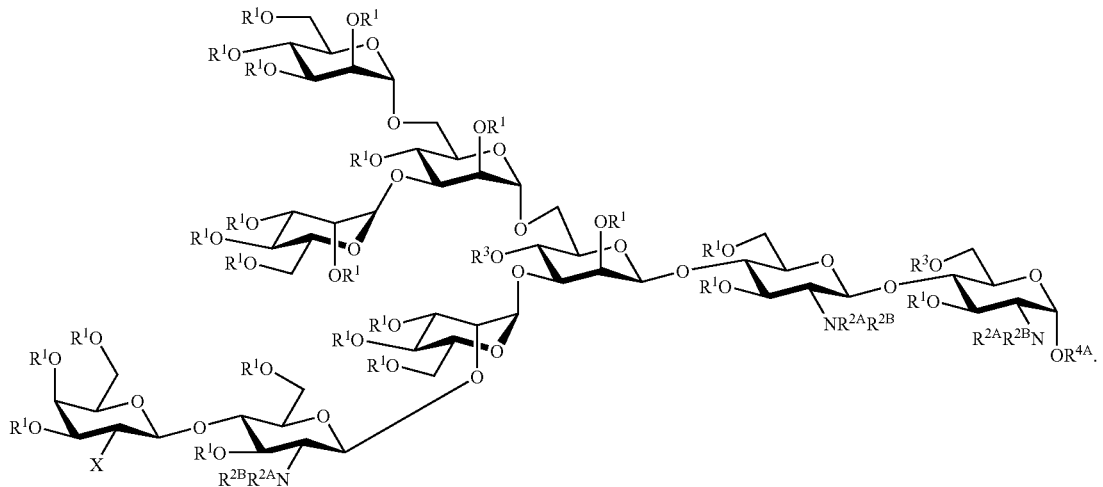
In certain other exemplary embodiments, the glycopeptide formed in step (c) has the structure:
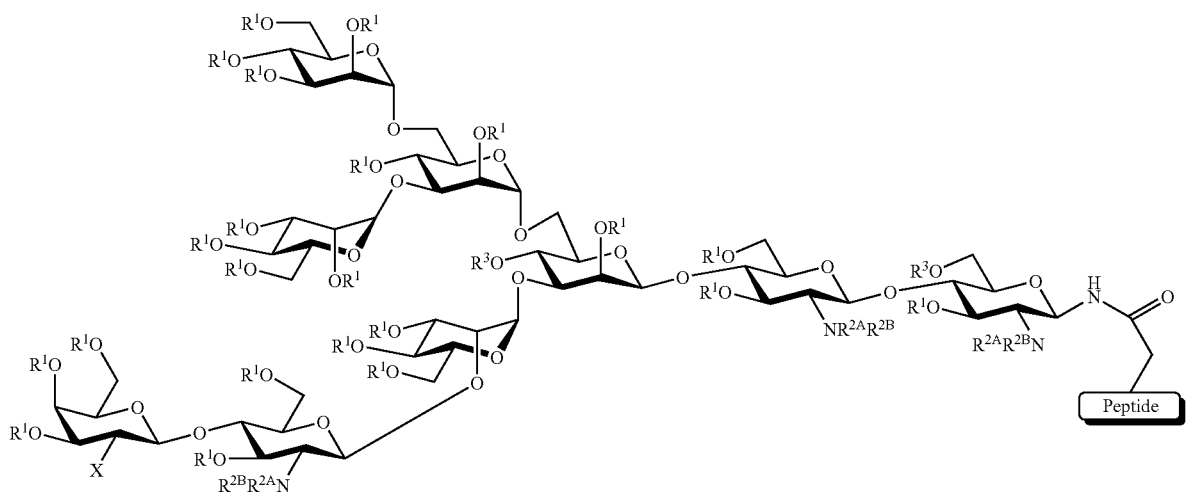
In certain other exemplary embodiments, the α-O-protected carbohydrate construct of step (a) has the structure:

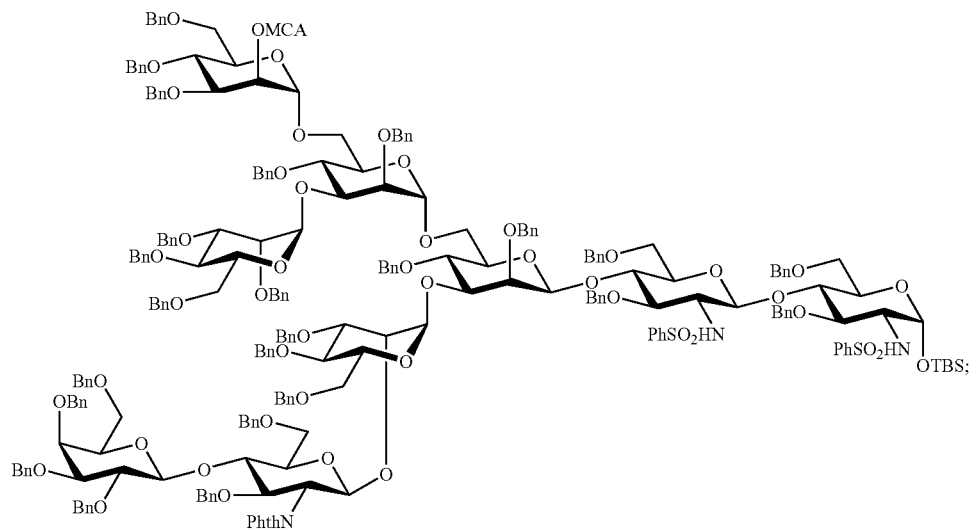

wherein MCA represent monochloroacetate.

In certain other exemplary embodiments, the glycopeptide formed in step (c) has the structure:

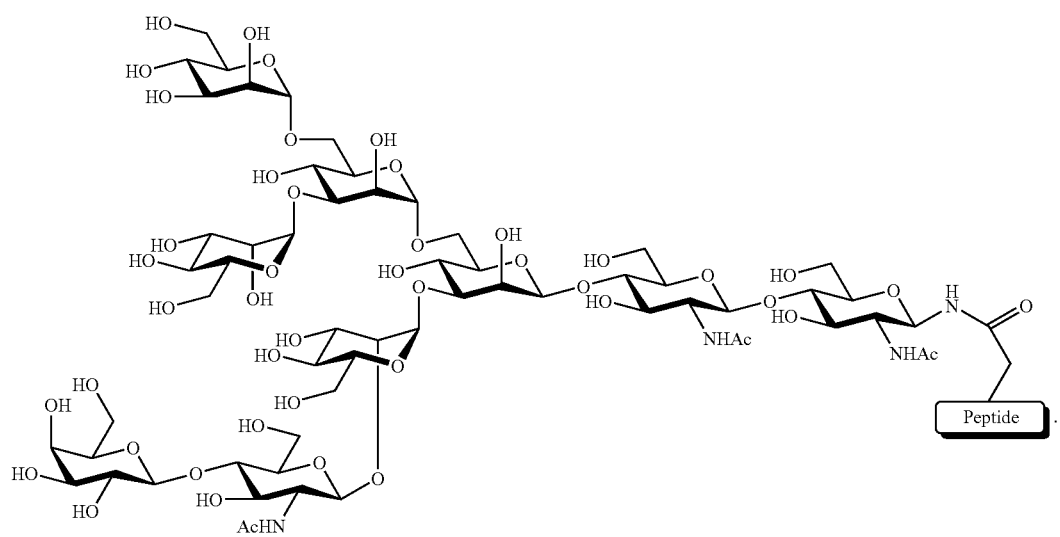

In certain other embodiments, the method further comprises a step of subjecting the glycopeptide formed in step (c) to Native Chemical Ligation conditions in the presence of a suitable polypeptide to form a glycopolypeptide having the structure:

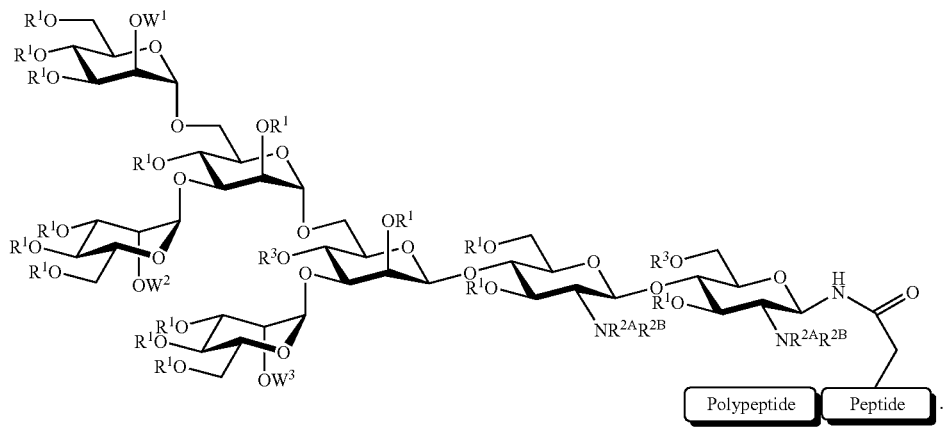

In certain embodiments, the peptide is either identical to or closely related to that of gp120 near an N-glycosylation site and comprises the amino acid sequence: Cys-Asn-Ile-Ser-Arg wherein any one or more of the amino acid residues may bear one or more protecting groups. In certain exemplary embodiments, the carbohydrate construct is attached to an Asparagine residue (Asn) on the peptide via an amide linkage. In certain other exemplary embodiments, the peptide is either identical to or closely related to that of gp120 near an N-glycosylation site and comprises the amino acid sequence:

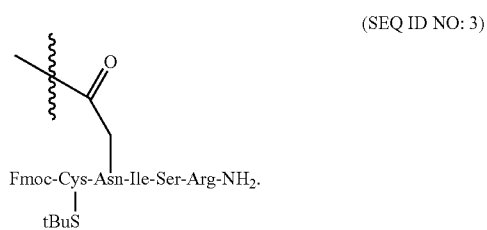

(SEQ ID NO: 3)

Fmoc-Cys-Asn-Ile-Ser-Arg-NH$_2$.
|
tBuS

In certain other embodiments, when the glycopeptide formed in step (c) is further subjected to Native Chemical Ligation, the polypeptide comprises the amino acid sequence: Ala-Phe-Val-Thr-Ile-Gly-Lys-Ile-Gly-Asn-Met-Arg-Gln-Ala-His-Cys-Asn-Ile-Ser-Arg(SEQ ID NO: 4), wherein any one or more of the amino acid residues may bear one or more protecting groups or a moiety suitable for Native Chemical Ligation. In certain embodiments, the polypeptide comprises a moiety suitable for Native Chemical Ligation, wherein the NCL moiety comprises a thioester.

The synthetic methodology is easily applicable to the generation of significantly longer (or shorter) segments of gp120. Both the peptide to be glycosylated and the thioester utilized for NCL can more closely approach the ~60 residue limit for linear synthesis; the resulting peptide can thus extend entirely to the N-terminus of gp120. If the peptide to be glycosylated is extended significantly towards the C-terminus of gp120 the glycosylation yield might suffer due to secondary structure formation of the longer peptide (See, for example, (1) Kent, S. B. H. "Chemical Synthesis of Peptides and Proteins." *Annu. Rev. Biochem.* 1988, 57, 957-989; and (2) Tam, J. P.; Lu, Y. A. "Coupling Difficulty Associated with Interchain Clustering and Phase-Transition in Solid-Phase Peptide-Synthesis." *J. Am. Chem. Soc.* 1995, 117, 12058-12063), but reaction conditions involving chaotropic salts have been devised to overcome issues of aggregation (See, for example, Thaler, A.; Seebach, D.; Cardinaux, F. "Lithium Salt Effects in Peptide Synthesis. 2. Improvement of Degree of Resin Swelling and of Efficiency of Coupling in Solid-Phase Synthesis." *Helv. Chim. Acta* 1991, 74, 628-643).

In certain exemplary embodiments, the polypeptide has the structure: Ala-Phe-Val-Thr-Ile-Gly-Lys-Ile-Gly-Asn-Met-Arg-Gln-Ala-His-SR; (SEQ ID NO: 5); where R is a functional group suitable for effecting chemical ligation; and the resulting glycopeptide has the structure:

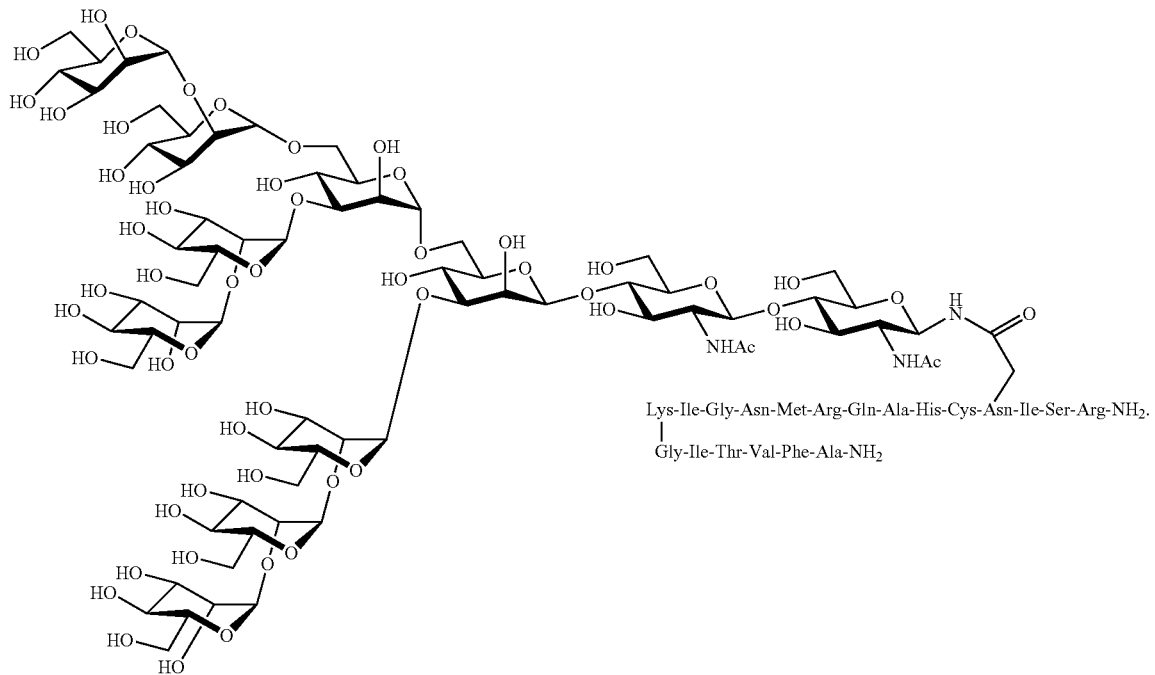

(SEQ ID NO: 4)

In certain embodiments, R, in the polypeptide used for native chemical ligation, is —(CH$_2$)$_2$C(=O)NH$_2$.

In certain exemplary embodiments, the polypeptide has the structure: Ala-Phe-Val-Thr-Ile-Gly-Lys-Ile-Gly-Asn-Met-Arg-Gln-Ala-His-SR (SEQ ID NO: 5); where R is a functional group suitable for effecting chemical ligation; and the resulting glycopeptide has the structure:

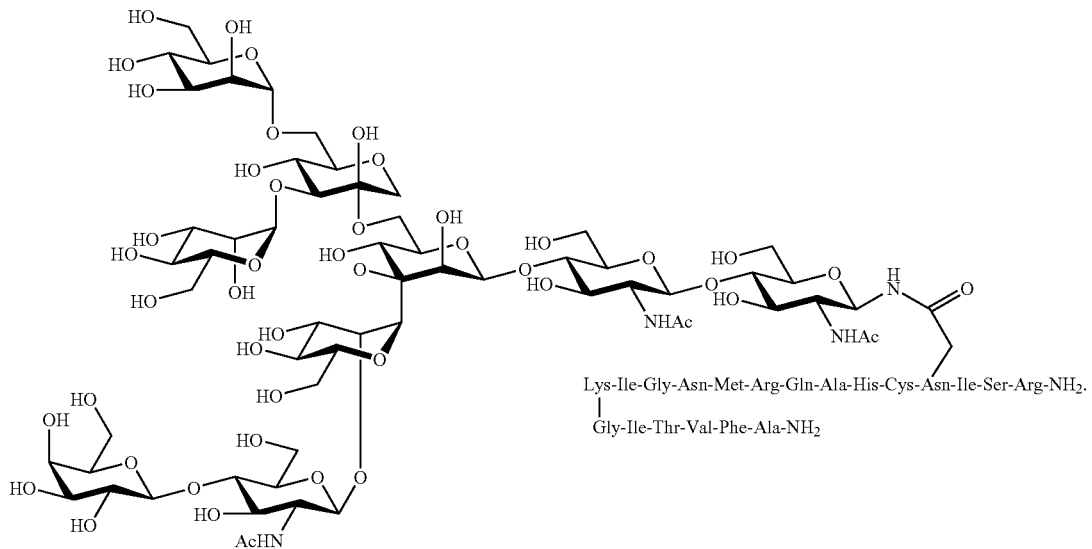

(SEQ ID NO: 4)

In certain embodiments, R, in the polypeptide used for native chemical ligation, is —(CH$_2$)$_2$C(=O)NH$_2$.

In another aspect, the invention provides a method of preparing an α-O-protected carbohydrate construct having the structure:

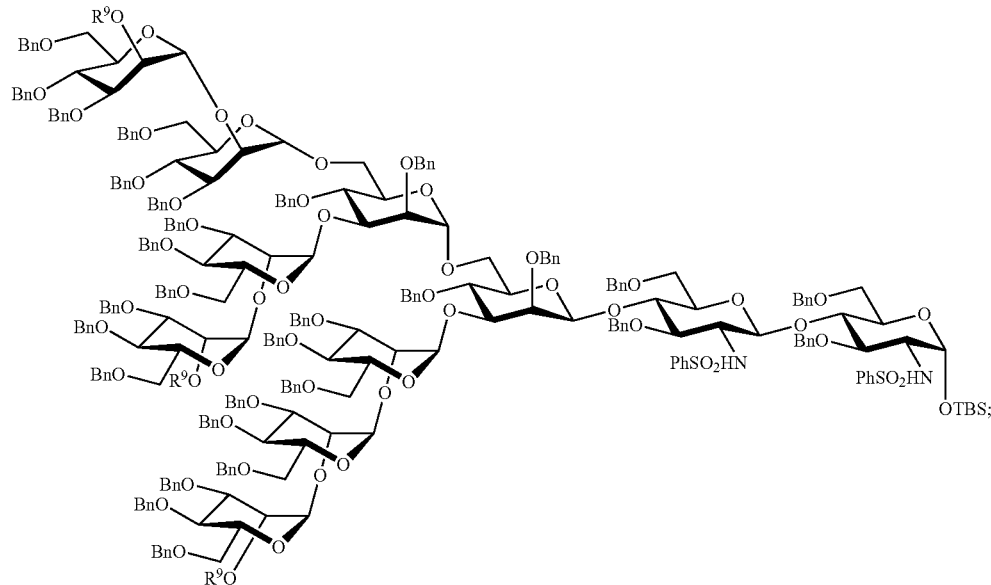

wherein each occurrence of R$^9$ is independently Bz or Ac; said method comprising steps of:
(a) coupling a trisaccharide having the structure:

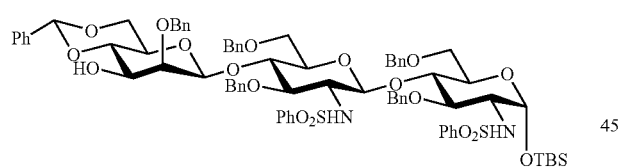

with a monosaccharide having the structure:

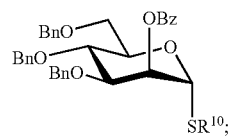

wherein R$^{10}$ is lower alkyl or aryl;

in the presence of an activating agent under suitable conditions to form a protected tetrasaccharide having the structure:

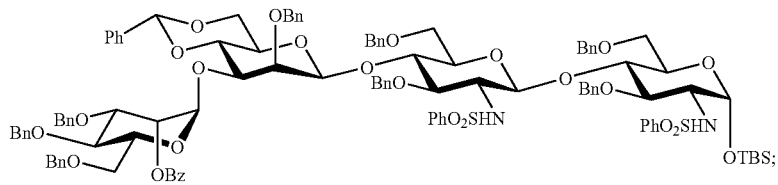

(b) partially deprotecting the protected tetrasaccharide formed in step (a) under suitable conditions to form a partially deprotected tetrasaccharide having the structure:

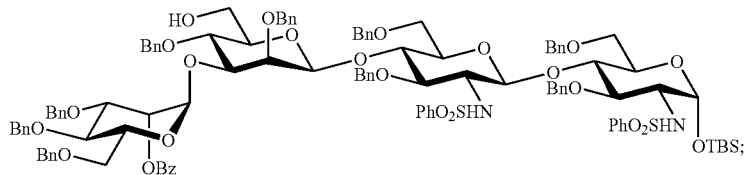

(c) coupling the partially deprotected tetrasaccharide formed in step (b) with a monosaccharide having the structure:

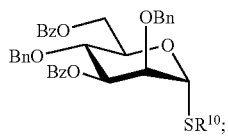

wherein $R^{10}$ is lower alkyl or aryl;
in the presence of an activating agent under suitable conditions to form a protected pentasaccharide having the structure:

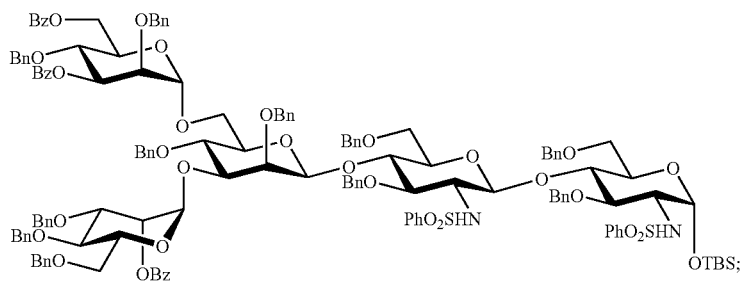

(d) partially deprotecting the pentasaccharide formed in step (c) under suitable conditions to form a partially deprotected pentasaccharide having the structure:

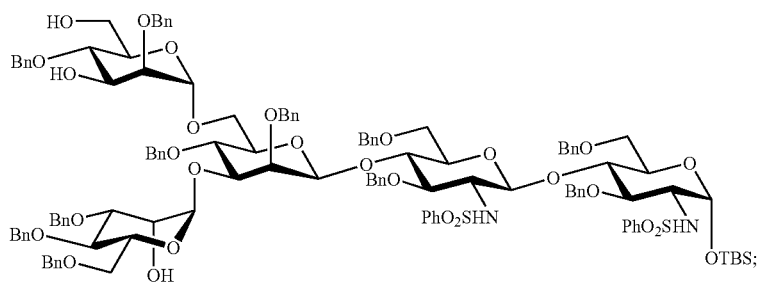

(e) coupling the partially deprotected pentasaccharide formed in step (d) with a monosaccharide having the structure:

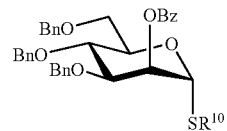

wherein $R^{10}$ is lower alkyl or aryl;
in the presence of an activating agent under suitable conditions to form an octasaccharide having the structure:

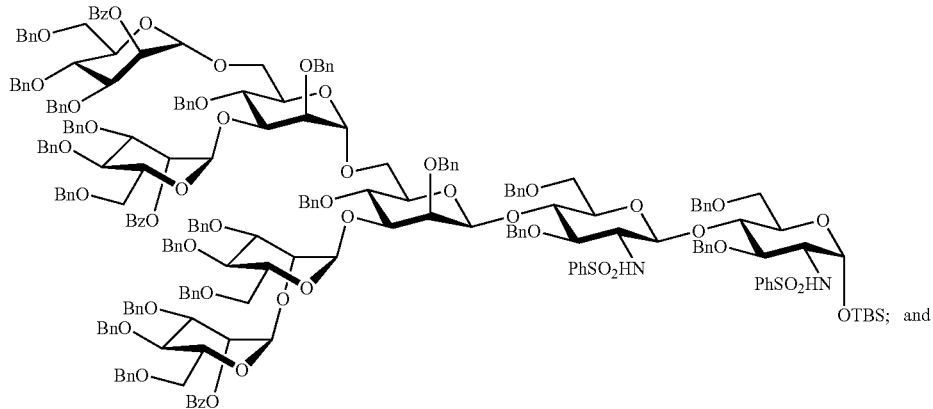

(f) partially deprotecting the octasaccharide formed in step (e) under suitable conditions to form a partially deprotected octasaccharide having the structure:

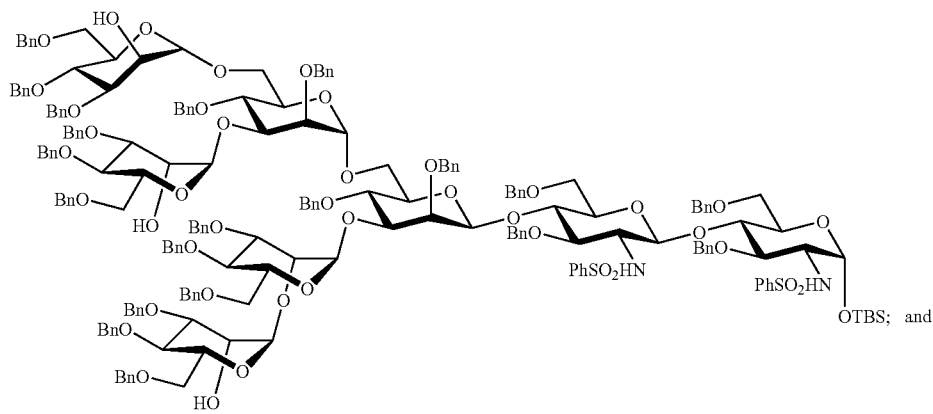

(g) coupling the partially deprotected octasaccharide formed in step (f) with a monosaccharide having the structure:

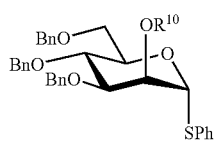

in the presence of an activating agent under suitable conditions to the α-O-protected carbohydrate construct.

In certain exemplary embodiments, the activating agent used in steps (a), (c), (e) and (g) comprises $(BrC_6H_4)_3NSbCl_6$. In certain other exemplary embodiments, in the step of partially deprotecting the protected tetrasaccharide (step (b)), the protected tetrasaccharide formed in step (a) is subjected to reductive reaction conditions comprising $Bu_2BOTf$, $BH_3$. In certain other exemplary embodiments, in the step of partially deprotecting the protected pentasaccharide (step (d)), the protected pentasaccharide formed in step (c) is subjected to reaction conditions comprising NaOMe. In certain other exemplary embodiments, in the step of partially deprotecting the protected octasaccharide (step (f)), the protected octasaccharide formed in step (e) is subjected to reaction conditions comprising NaOMe.

In another aspect, the invention provides a method of preparing an α-O-protected carbohydrate construct having the structure:

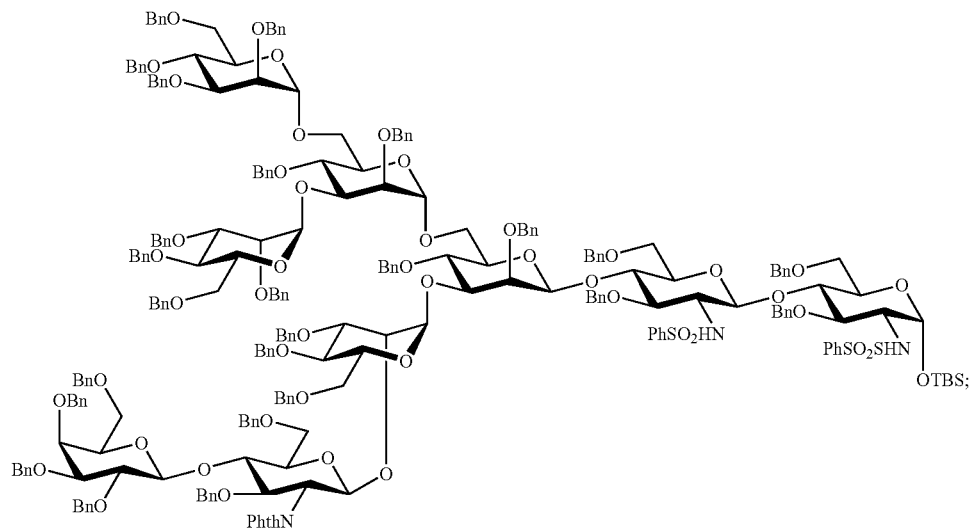

said method comprising steps of:
(a) coupling a trisaccharide having the structure:

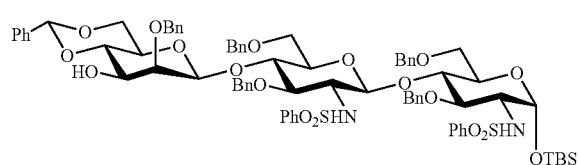

with a monosaccharide having the structure:

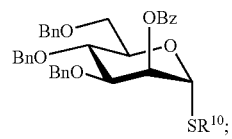

wherein $R^{10}$ is lower alkyl or aryl;
in the presence of an activating agent under suitable conditions to form a protected tetrasaccharide having the structure:

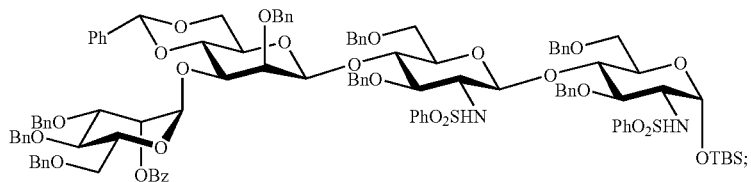

(b) partially deprotecting the protected tetrasaccharide formed in step (a) under suitable conditions to form a partially deprotected tetrasaccharide having the structure:

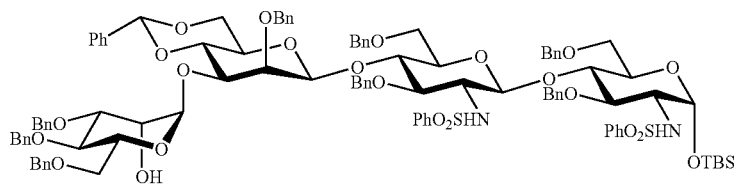

(c) coupling the partially deprotected tetrasaccharide formed in step (b) with an ethylthioglycoside having the structure:

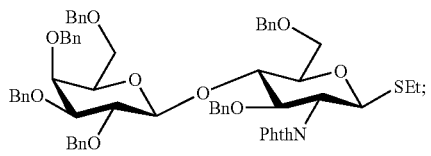

under suitable conditions to form a protected hexasaccharide having the structure:

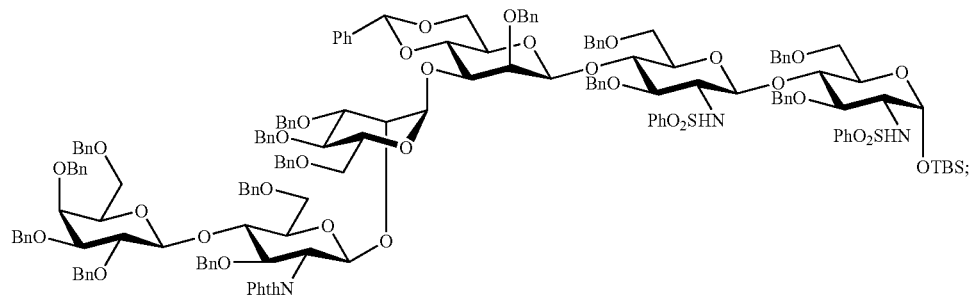

(d) partially deprotecting the hexasaccharide formed in step (c) under suitable conditions to form a partially deprotected hexasaccharide having the structure:

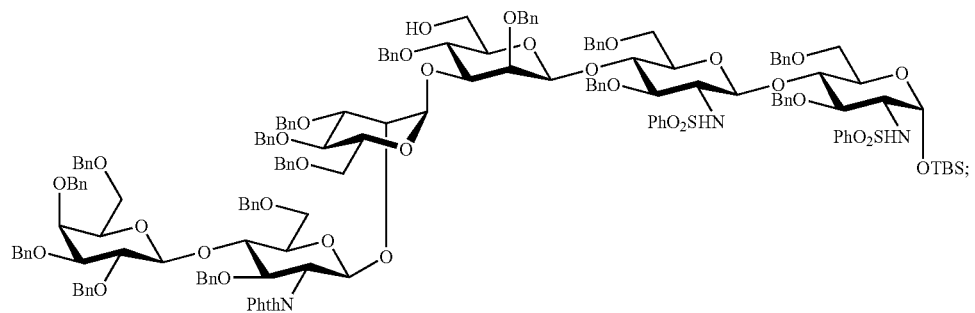

(e) coupling the partially deprotected hexasaccharide formed in step (d) with a monosaccharide having the structure:

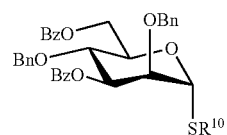

wherein $R^{10}$ is lower alkyl or aryl;

in the presence of an activating agent under suitable conditions to form an heptasaccharide having the structure:

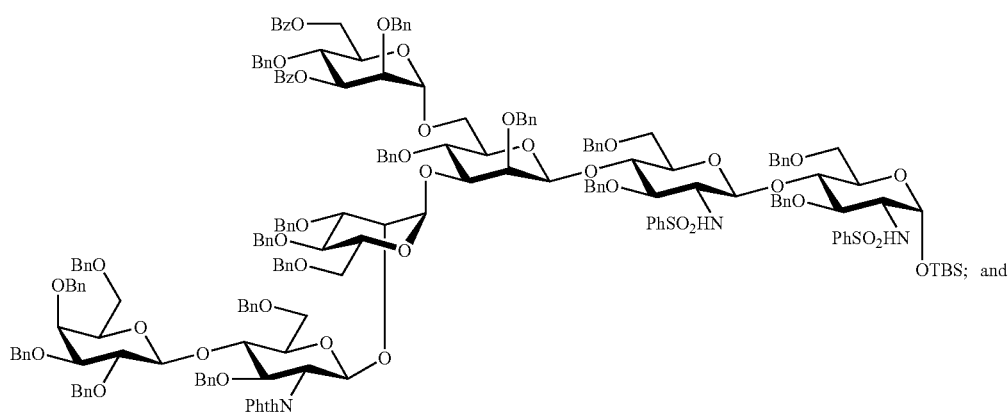

(f) partially deprotecting the heptasaccharide formed in step (e) under suitable conditions to form a partially deprotected heptasaccharide having the structure:

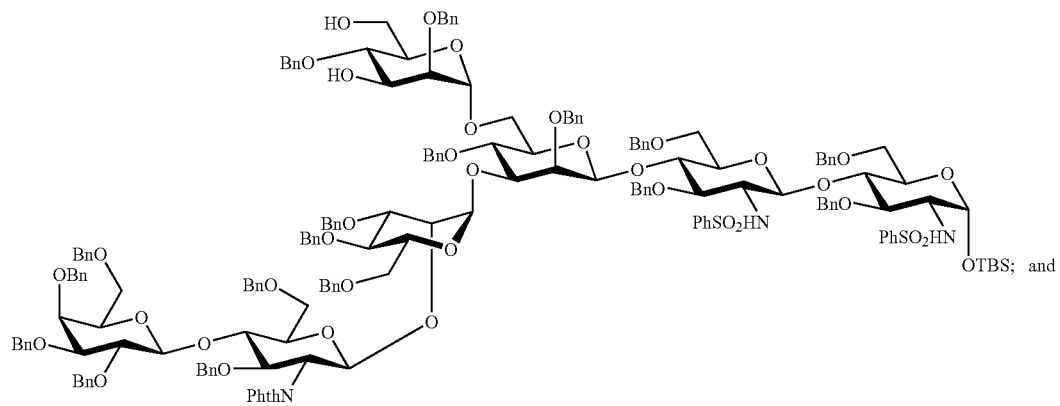

(g) coupling the partially deprotected heptasaccharide formed in step (f) with a monosaccharide having the structure:

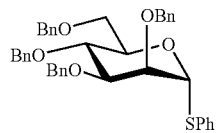

in the presence of an activating agent under suitable conditions to the α-O-protected carbohydrate construct.

In certain embodiments, $R^{10}$ is ethyl or phenyl.

In certain exemplary embodiments, the activating agent used in steps (a), (e) and (g) comprises $(BrC_6H_4)_3NSbCl_6$. In certain other exemplary embodiments, in the step of partially deprotecting the protected hexasaccharide (step (d)), the protected hexasaccharide formed in step (c) is subjected to reductive reaction conditions comprising $Bu_2BOTf$, $BH_3$. In certain other exemplary embodiments, in the step of partially deprotecting the protected tetrasaccharide (step (b)), the protected tetrasaccharide formed in step (a) is subjected to reaction conditions comprising NaOMe. In certain other exemplary embodiments, in the step of partially deprotecting the protected heptasaccharide (step (f)), the protected heptasaccharide formed in step (e) is subjected to reaction conditions comprising NaOMe.

It will be appreciated that for each of the methods as detailed herein, the full arsenal of protecting groups known in the art of organic synthesis can be utilized, for example, as set forth in "Activating Agents and Protecting Groups: Handbook of Reagents for Organic Synthesis" Roush, W. R. and Pearson, A. J., Eds., John Wiley & Sons: 1999; and "Protective Groups in Organic Synthesis" Greene, T. W. and Wuts, P. G., John Wiley & Sons, New York: 1999, the entire contents of which are hereby incorporated by reference. In but a few examples, suitable protecting groups utilized herein include, but are not limited to, Bn (benzyl), TIPS (triisopropylsilyl), and Ac (acetate). In a certain exemplary embodiments of the present invention, coupling of glycoside moieties are effected under MeOTf promotion, as described herein. It will be appreciated by one of ordinary skill in the art however, that a variety of conditions known in the art of organic synthesis can be utilized to effect coupling of glycoside moieties.

The skilled practitioner will know how to adapt the synthetic methods detailed in the present invention to access a variety of other multi-branched gp120 glycans and constucts thereof.

In certain other exemplary embodiments, the construct should be so functionalized as to anticipate the need for its conjugation to an immunogenic carrier (e.g., protein or lipid) in anticipation of the need to stimulate an immune response. As discussed above, such constructs may be used to generate antibodies for use in HIV vaccine. The present invention provides improvements in total synthesis and HIV therapy. For example, as discussed extensively herein, the present invention provides novel glycopeptide synthetic methodology that allows access to complex glycans linked to various backbones.

As discussed above, in one embodiment of the present invention, the inventive compounds can be conjugated either directly or through a crosslinker to an appropriate carrier (e.g., KLH) to generate a synthetic tumor antigen. Methods of conjugation are well known in the art. For example, a conjugation strategy may be employed that involves a reductive coupling of an aldehyde (CHO) functionality on the antigenic compound, with the intended protein carrier, or lipid, presumably at the E-amino acid residues of exposed lysines. (M. A. Bernstein; L. D. Hall, *Carbohydr. Res.* 1980, 78, C1; R. V. Lemieux *Chem. Soc. Rev.* 1978, 7, 423). Thus, in another aspect, the present invention provides synthetic constructs, whereby novel antigenic structures, as described herein, are conjugated to immunogenic carriers (e.g., proteins, peptides or lipids).

In summary, there is provided a method for gp120 glycan synthesis that is easily modified to incorporate higher degrees of carbohydrate branching. In addition, the inventive synthetic method allows the incorporation of synthetic glycans into relatively long gp120 peptides using a fast, high-yielding strategy that remains synthetically flexible. Accordingly, the glycopeptide structures may be optimized based on their abilities to generate antibodies for use in an HIV vaccine.

3) Compositions

In another aspect, the present invention provides compositions comprising any one or more of the inventive gp120 glycans and/or constructs thereof.

In certain embodiments, the inventive compositions may comprise an adjuvant. In certain embodiments, the adjuvant is a saponin adjuvant (see, e.g., Marciani et al., *Vaccine*, 2000, 18, 3141, U.S. Pat. Nos.: 6,080,725 and 5,977,081, the entire contents of which are hereby incorporated by reference). One example of a preferred saponin adjuvant includes, but is not limited to, GPI-0100, (Galenica Pharmaceuticals, Inc., Frederick, Md.) which is a semi-synthetic adjuvant derived by modifying selected natural saponins.

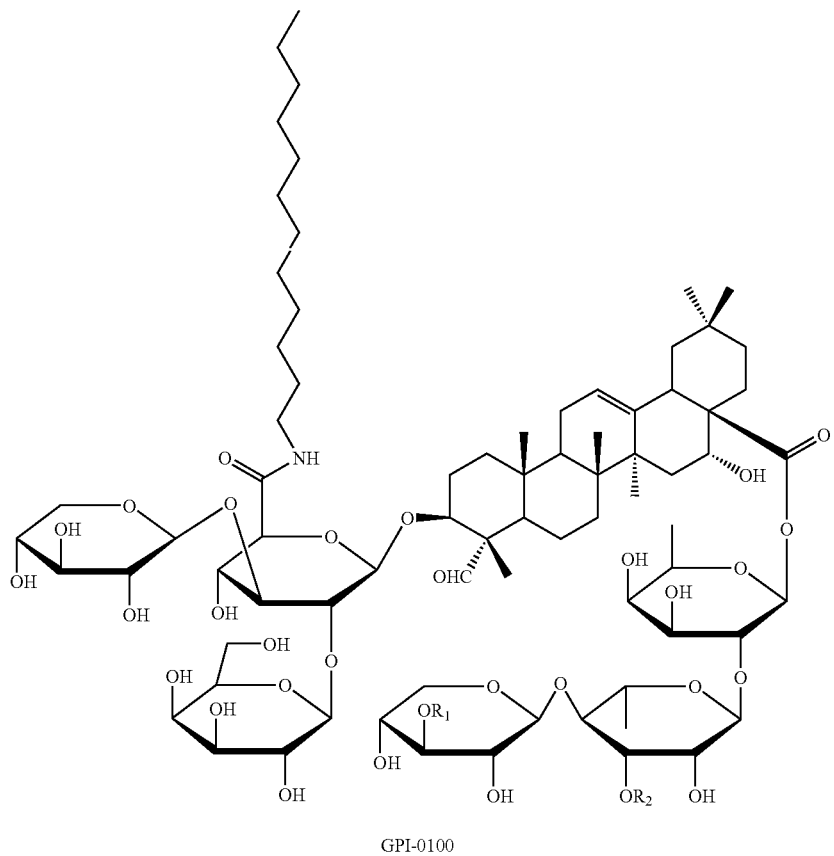

GPI-0100

Saponins isolated from *Quillaja soponaria Molina* contain two acyl moieties, a normonoterpene carboxylic acid and a normonoterpene carboxylic acid glycoside, which are linked linearly to a fucosyl residue attached at position C-28. It has been hypothesized that these lipophilic acyl groups may be responsible for these saponins' toxicity and their ability to stimulate cytotoxic T cells against exogenous antigens. The linkage between the fucosyl residue and the acyl group is unstable and hydrolyzes under mild conditions (pH≧6) with concomittant loss of saponins capability to stimulate cell-mediated immune response. Unlike their saponin precursors, GPI-0100 adjuvants comprise a stable non-toxic lipophilic moiety in the saponin's glucuronic residue. Methods for preparing these semi-synthetic adjuvants are well-known in the art. For example, GPI-0100 adjuvants may be prepared by hydrolizing *quillaja saponins* (which are commercially available) under basic conditions to yield the corresponding deacylated product. The deacylated intermediate may then be reacted with a suitable amine reagent using standard carboxylic acid moiety activation methodology to give the desired compounds. A wide variety of procedures are effective for extrating saponin compounds. They are generalized as follows: (i) defatting of the organic matter with a hydrophobic organic solvent such as petroleum ether; (ii) extraction with a suitable alcohol (e.g., methanol or ethanol) or alcohol-water mixture; (iii) evaporation of the carinol solvent; and (iv) partitioning of the dried alcohol extract between water and n-butanol saturated with water, followed by precipitation of the crude saponins from the n-butanol/water with a suitable organic solvent (e.g., diethyl ether). Purification of the saponin extract may require multiple separation steps. For example, preliminary fractionation may be carried out using conventional open column chromatography or flash chromatography on silica gel, in combination with a more sophisticated chromatographic technique such as High Pressure Liquid Chromatography (HPLC), droplet counter-current liquid chromatography (DCCC) or centrifugal Liquid Chromatography (RLCC). The integration of these techniques with preparative TLC typically affords separated and purified saponins.

In certain other preferred embodiments, the adjuvant is bacteria or liposomes. In certain examples, the adjuvant includes but is not limited to, *Salmonella minnesota* cells, bacille Calmette-Guerin or QS21.

As described above, the present invention provides compounds and synthetic methodologies useful in the development of novel therapeutic agents, particularly for fully synthetic HIV vaccines and/or therapeutics. In general, the compounds (e.g., gp120 glycans, glycopeptides thereof and other constructs thereof) prepared as disclosed herein can be conjugated to a protein carrier or a lipid to generate useful glycoconjugates for the treatment and/or prevention of HIV in a subject suffering therefrom. In addition, glycoconjugates prepared by processes disclosed herein are useful in adjuvant therapies as vaccines capable of inducing a potent and broad neutralizing antibody response. Such adjuvant therapies may reduce the rate of progression of HIV and/or prevent the onset of HIV.

Thus, the present invention provides pharmaceutical compositions for treating HIV, and for preventing the onset or progression of HIV, comprising any of the compounds of the present invention disclosed herein, as an active ingredient, optionally, though typically in combination with a pharmaceutically acceptable carrier. The pharmaceutical compositions of the present invention may further comprise other therapeutically active ingredients (e.g., anti-HIV and/or palliative agents). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

The inventive compositions include those suitable for oral, rectal, topical (including transdermal devices, aerosols, creams, ointments, lotions and dusting powders), parenteral (including subcutaneous, intramuscular, and intravenous), ocular (opthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy. In certain embodiments, the compositions are suitable for parenteral administration. In certain exemplary embodiments, the compositions are suitable for intravenous administration.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disinterating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as a powder or granule optionally mixed with a binder, lubricant, inert diluent or surface active or dispersing agent. Molded tablets may be made by molding in a suitable machine, a mixture of the powdered compound moistened with an inert liquid diluent.

4) Pharmaceutical Uses and Methods of Treatment
Pharmaceutical Uses

In one aspect, the present invention provides gp120 glycans and constructs thereof for use as active pharmaceutical agent useful for preventing or reducing the rate of infection with HIV in subjects.

In another aspect, the inventive gp120 glycans and constructs thereof may be used to raise antibodies specific to HIV virus. In another aspect, the invention provides an antibody which is specific to one or more gp120 glycans and/or constructs thereof described herein.

Accordingly, in one aspect of the invention, there is provided an antibody or antibody fragment which is specific to one or more of the inventive gp120 glycans and/or glycoconjugates thereof described herein, said antibody being a purified polyclonal antibody or a monoclonal antibody. As used herein, the term "antibody fragment" is generally intended to mean any antibody fragment having conserved the specificity of the antibody of origin, and in particular fragments of the Fab and F(ab$^1$) type. Unless otherwise indicated, the term "antibody" also subsequently denotes antibody fragments when appropriate. The expression "antibody which binds specifically to gp120 antigen" or "antibody which is specific to gp120 antigen" is intended to denote, an antibody which binds to one or more gp120 glycans described herein, with high specificity. For example, in certain embodiments, the product which is bound to the antibody consists of at least 80% and preferably of at least 90%, of said gp 120 antigen.

Thus, in one aspect, the invention provides an antibody or antibody fragment which is specific to any one of the inventive antigens (independently of the others) present on a multiantigenic construct comprising one or more carbohydrate domains having the structure:

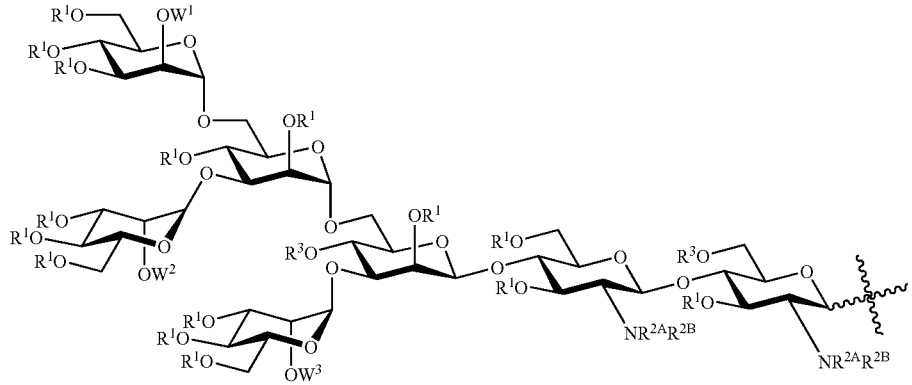

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

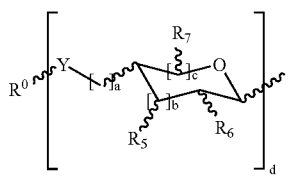

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently optionally substituted mannose, galactose or lactosamine moieties;

wherein each carbohydrate domain is independently covalently bound to a linker system, said linker system being a peptide or non-peptide nature; and wherein the linker system may be cyclic or acyclic; and and wherein said antibody is a purified polyclonal antibody or a monoclonal antibody. In certain embodiments, the antibody is a monoclonal antibody.

In certain embodiments, $W^3$ is $R^1$, $R^3$, as defined above, or a moiety having the structure:

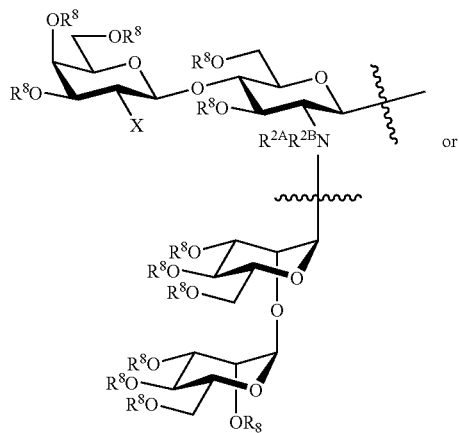

wherein X is $-OR^1$ or $-NR^{2A}R^{2B}$; and each occurrence of $R^8$ is independently $R^1$ or a sialic acid moiety.

In certain embodiments, $W^1$ and $W^2$ are independently $R^1$, $R^3$ or a moiety having the structure:

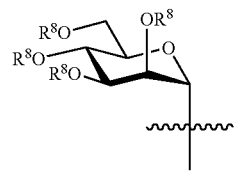

wherein each occurrence of $R^8$ is independently $R^1$ or a sialic acid moiety.

In certain other embodiments, the antigen comprises a carbohydrate domain having the structure:

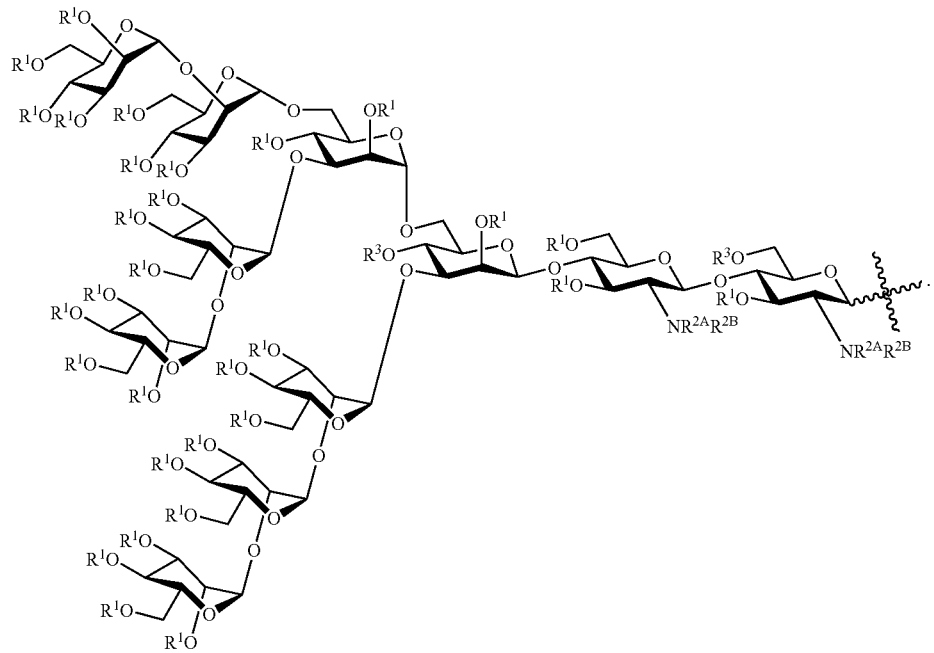

In certain other embodiments, the antigen comprises a carbohydrate domain having the structure:

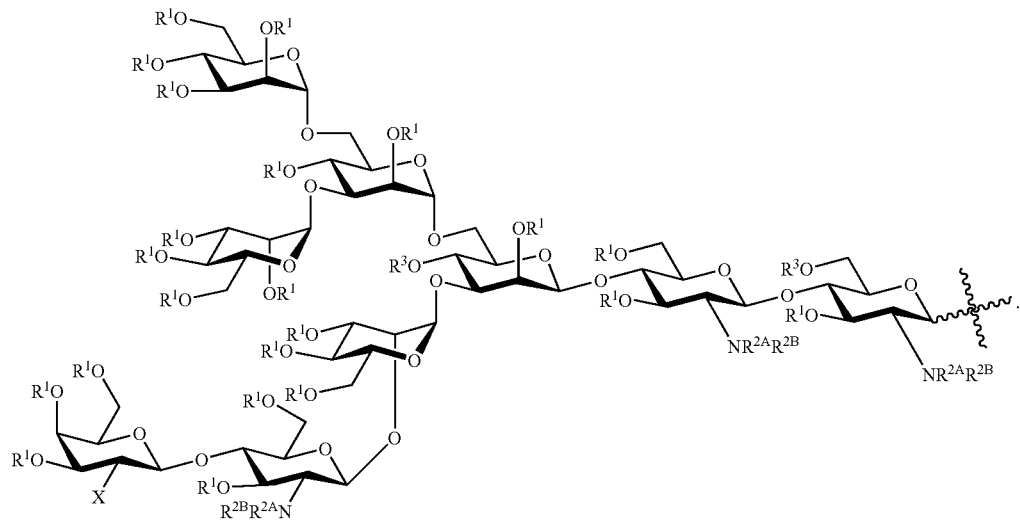

In certain embodiments, the invention provides an antibody or antibody fragment which is specific to any one or more of the inventive antigens present on a multi-antigenic construct comprising a cyclic or acyclic peptidic or non-peptidic backbone made up of two or more structural units, wherein one or more of said structural units is/are independently substituted with a glycosidic moiety having the structure:

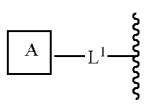

wherein each occurrence of $L^1$ is independently a substituted or unsubstituted, linear or branched, cyclic or acyclic, saturated or unsaturated aliphatic or heteroaliphatic moiety; and each occurrence of A is independently a carbohydrate domain of formula:

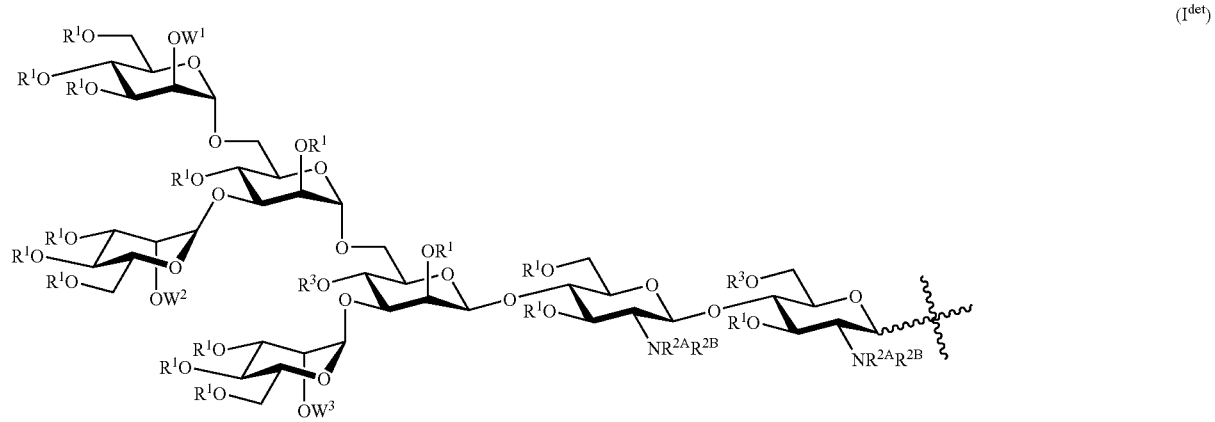

($I^{det}$)

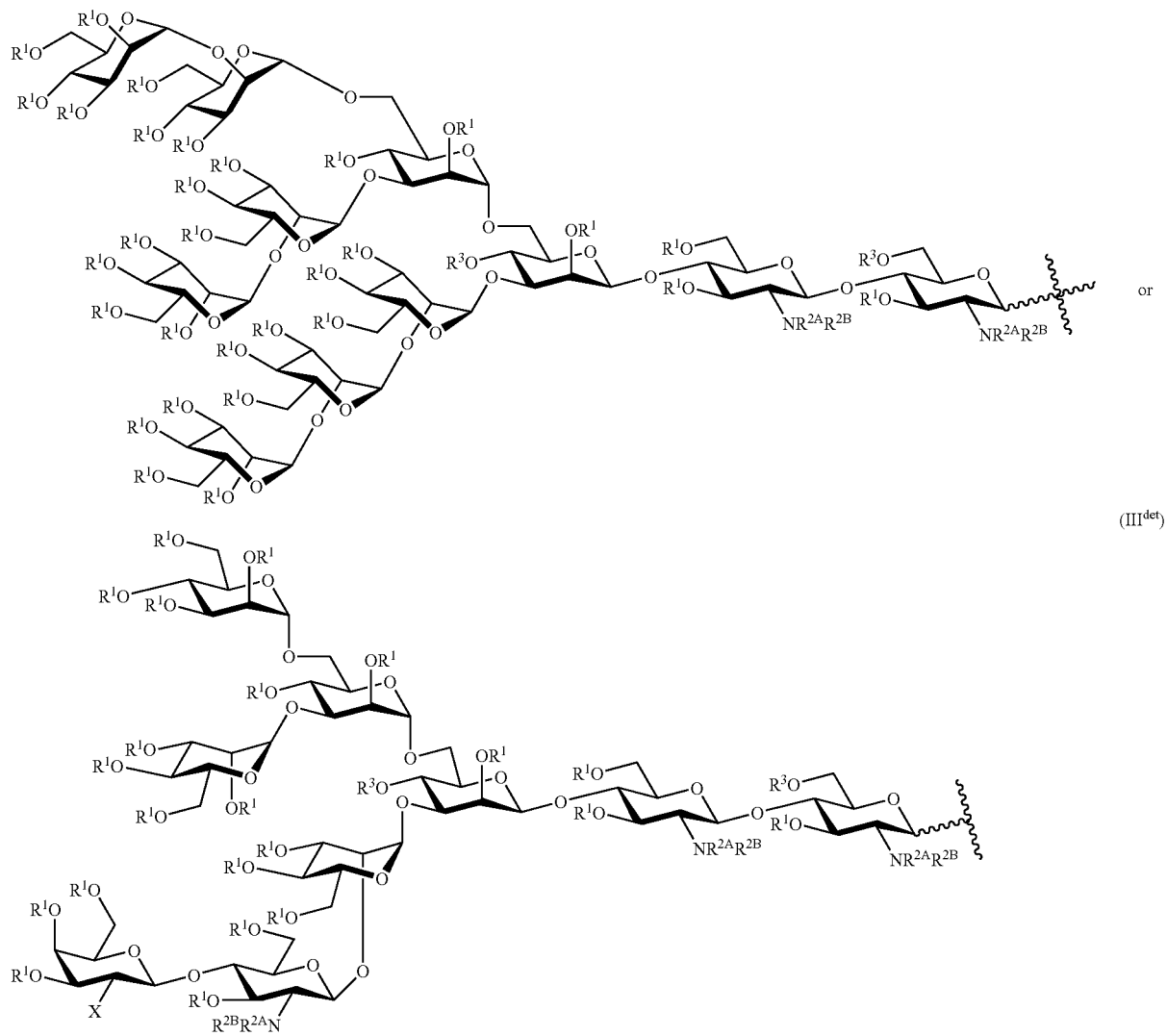

(II$^{det}$)

or (III$^{det}$)

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

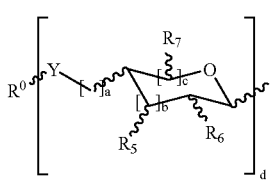

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, OR$^i$, NR$^{ii}$R$^{iii}$, NHCOR$^i$, F, CH$_2$OH, CH$_2$OR$^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$, R$^{ii}$ and R$^{iii}$ is independently hydrogen, a protecting group, a sialic acid moiety, CHO, COOR$^{iv}$, or a substituted or unsubstituted linear or branched chain alkyl, acyl, arylalkyl or aryl group, or R$^{ii}$ and R$^{iii}$, taken together with the nitrogen atom to which they are attached, form a substituted or unsubstituted heterocyclic or heteroaryl moiety; and wherein each occurrence of R$^{iv}$ is independently H, or a substituted or unsubstituted linear or branched chain alkyl, arylalkyl or aryl group; and $W^1$, $W^2$ and $W^3$ are independently optionally substituted mannose, galactose or lactosamine moieties.

In certain embodiments, the invention provides an antibody or antibody fragment which is specific to any one or more of the inventive antigens present on a dimeric glycopeptide having the structure:

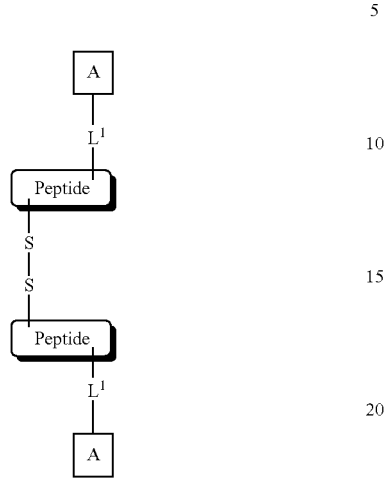

wherein each peptide may be the same or different; and each occurrence of A is independently a carbohydrate domain of formula ($I^{det}$), ($II^{det}$) or ($III^{det}$).

In certain embodiments, the antigen has the structure:

(SEQ ID NO: 4)

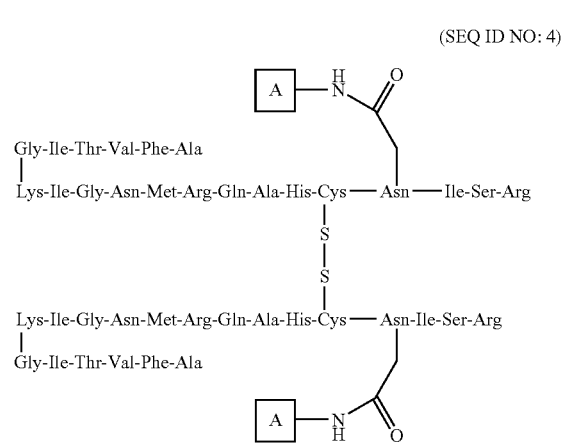

wherein each occurrence of A is independently a carbohydrate domain having one of the structures:

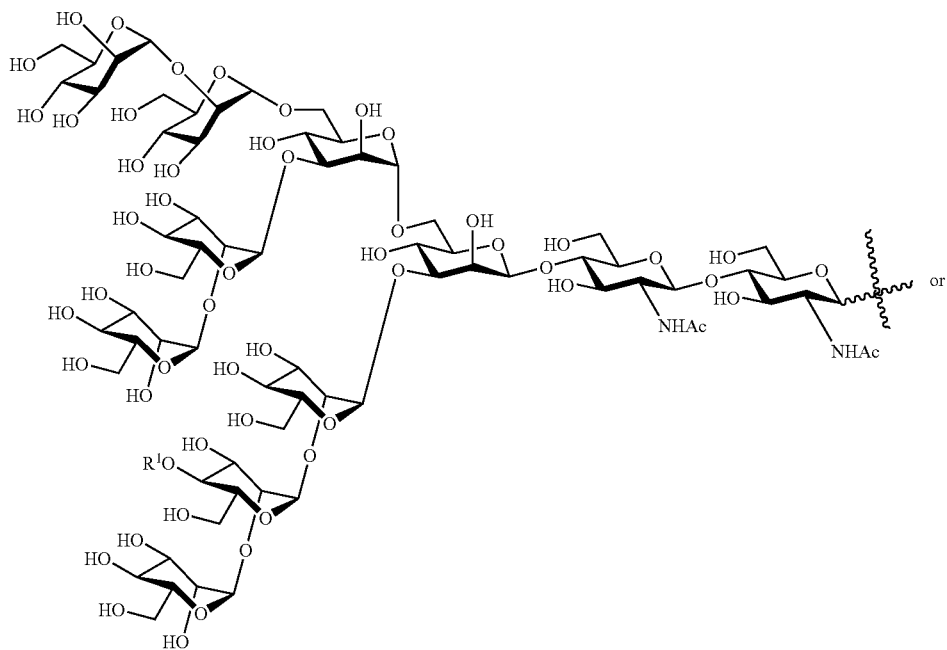

-continued
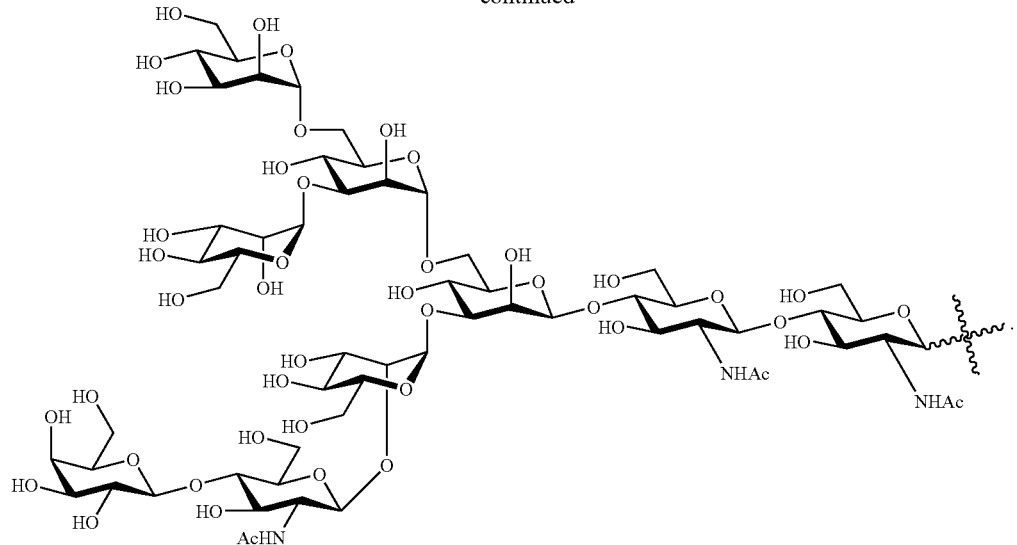
In certain embodiments, the antigen has the structure:
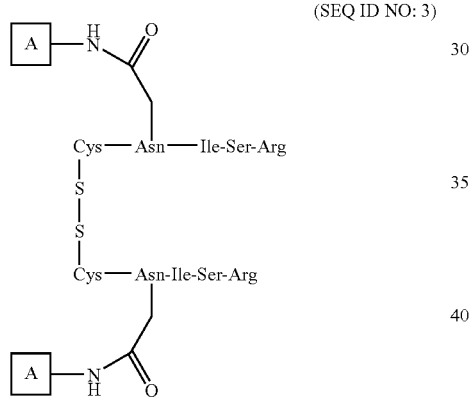
(SEQ ID NO: 3)
wherein A is as defined above.
In yet other embodiments, the antigen comprises a carbohydrate antigen having the structure:
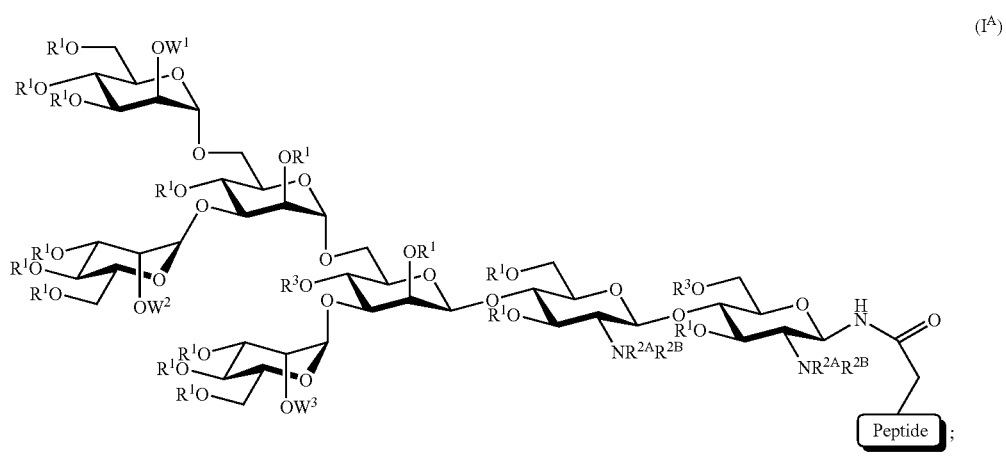
(I$^A$)

wherein the peptide has a structure either identical to or closely related to that of gp120 near an N-glycosylation site.

In certain embodiments, the invention provides an antibody or antibody fragment which is specific to a compound of formula (II$^A$) having the structure:

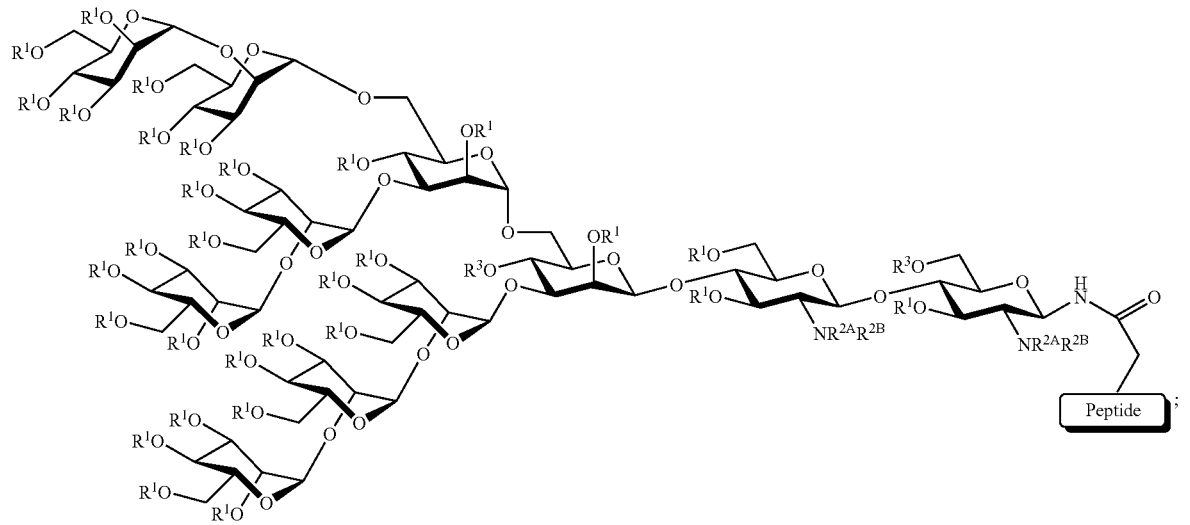

(II$^A$)

wherein each occurrence of $R^1$ is independently hydrogen or an oxygen protecting group; each occurrence of $R^{2A}$ and $R^{2B}$ is independently hydrogen or a nitrogen protecting group; and each occurrence of $R^3$ is independently hydrogen or a protecting group;
wherein the peptide has a structure either identical to or closely related to that of gp120 near an N-glycosylation site;
and wherein said antibody is a purified polyclonal antibody or a monoclonal antibody.

In certain embodiments, the invention provides an antibody or antibody fragment which is specific to a compound of formula (III$^A$) having the structure:

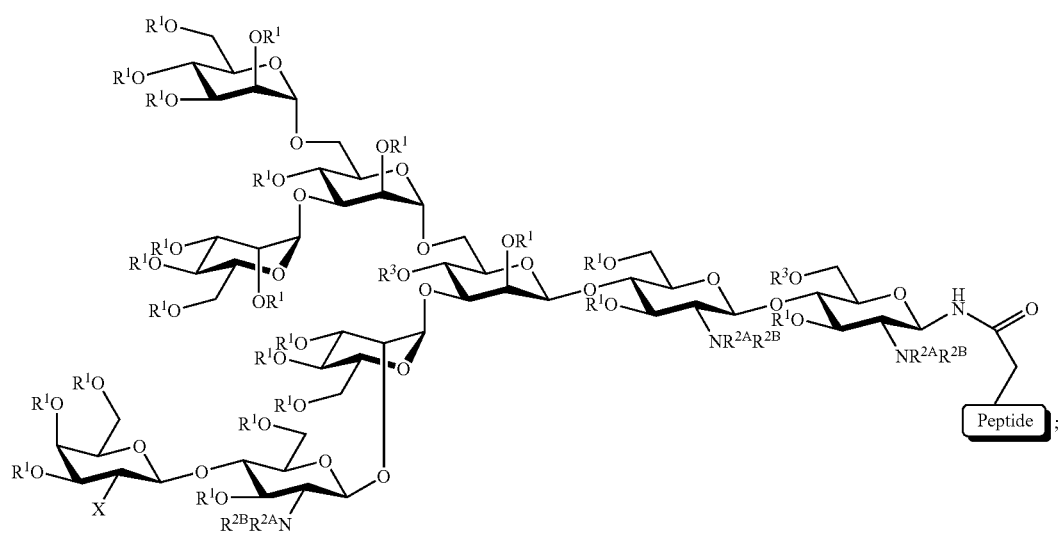

(III$^A$)

wherein each occurrence of $R^1$ is independently hydrogen or an oxygen protecting group; each occurrence of $R^{2A}$ and $R^{2B}$ is independently hydrogen or a nitrogen protecting group; and each occurrence of $R^3$ is independently hydrogen or a protecting group;
wherein the peptide has a structure either identical to or closely related to that of gp120 near an N-glycosylation site;
and wherein said antibody is a purified polyclonal antibody or a monoclonal antibody.

In certain exemplary embodiments, the antibody is a monoclonal antibody.

In certain embodiments, the antibody or antibody fragment is specific to the cyclic glycopeptides described herein, conjugated or unconjugated to a carrier.

The compounds of the invention may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986.

The compounds, as well as antibodies specific for the inventive gp120 glycans and/or constructs thereof may be labelled using conventional methods with various enzymes, fluorescent materials, luminescent materials and radioactive material. Linking an antibody or an antibody fragment to a label, whether it is a radioactive, enzymatic or colored label or any other type of label commonly used in immunological techniques, is well known and described in the literature. Suitable enzymes, fluorescent materials, luminescent materials, and radioactive material are well known to the skilled artisan.

It is presently unknown, however, how large a segment of gp120 is required to generate appropriate antibodies; e.g., the glycopeptide may not have enough native structure to develop appropriately specific antibodies. The glycopeptide might not itself be immunogenic, and could therefore require the use of an adjuvant to stimulate an immune response. Examples of suitable adjuvants include, but are not limited to, saponin adjuvants (e.g., GPI-0100), *Salmonella minnesota* cells, bacille Calmette-Guerin and/or QS21.

A lack of immune response with any length glycopeptide would call for the use of a carrier protein such as keyhole limpet hemocyanin (KLH), [34-36] an adjuvant [37] such as covalently bound Pam$_3$Cys, [38] or coadministered QS21. [39] Such immunostimulants have been used alone or in concert[40-42] to generate antibodies from small glycopeptide haptens, [43-45] and should prove effective here, as well. Though the first two systems require covalent conjugation, the synthetic design allows late-stage conjugation as demonstrated previously for other glycopeptides.[46]

REFERENCES

34. Ragupathi, G. "Carbohydrate antigens as targets for active specific immunotherapy." *Cancer Immunol. Immun.* 1996, 43, 152-157.
35. Helling, F.; Shang, A.; Calves, M.; Zhang, S. L.; Ren, S. L.; Yu, R. K.; Oettgen, H. F.; Livingston, P. O. "G(D3) Vaccines for Melanoma—Superior Immunogenicity of Keyhole Limpet Hemocyanin Conjugate Vaccines." *Cancer Res.* 1994, 54, 197-203.
36. Harris, J. R.; Markl, J. "Keyhole limpet hemocyanin (KLH): A biomedical review." *Micron* 1999, 30, 597-623.
37. Kellner, J.; Erhard, M.; Schranner, I.; Losch, U. "The Influence of Various Adjuvants on Antibody Synthesis Following Immunization with an Hapten." *Biol. Chem. Hoppe-Seyler* 1992, 373, 51-55.
38. Metzger, J.; Wiesmuller, K. H.; Schaude, R.; Bessler, W. G.; Jung, G. "Synthesis of Novel Immunologically Active Tripalmitoyl-S-Glycerylcysteinyl Lipopeptides as Useful Intermediates for Immunogen Preparations." *Int. J. Pept. Protein Res.* 1991, 37, 46-57.
39. Kensil, C. R.; Patel, U.; Lennick, M.; Marciani, D. "Separation and Characterization of Saponins with Adjuvant Activity from Quillaja-Saponaria Molina Cortex." *J. Immunol.* 1991, 146, 431-437.
40. Livingston, P. O.; Adluri, S.; Helling, F.; Yao, T. J.; Kensil, C. R.; Newman, M. J.; Marciani, D. "Phase-1 Trial of Immunological Adjuvant QS-21 with a GM2 Ganglioside-Keyhole Limpet Hemocyanin Conjugate Vaccine in Patients with Malignant-Melanoma." *Vaccine* 1994, 12, 1275-1280.
41. Zhang, S. L.; Graeber, L. A.; Helling, F.; Ragupathi, G.; Adluri, S.; Lloyd, K. O.; Livingston, P. O. "Augmenting the immunogenicity of synthetic MUC1 peptide vaccines in mice." *Cancer Res.* 1996, 56, 3315-3319.
42. Musselli, C.; Livingston, P. O.; Ragupathi, G. "Keyhole limpet hemocyanin conjugate vaccines against cancer: the Memorial Sloan Kettering experience." *J. Cancer Res. Clin. Oncol.* 2001, 127, R20-R26.
43. Adluri, S.; Helling, F.; Ogata, S.; Zhang, S. L.; Itzkowitz, S. H.; Lloyd, K. O.; Livingston, P. O. "Immunogenicity of Synthetic TF-KLH (Keyhole Limpet Hemocyanin) and STn-KLH Conjugates in Colorectal Carcinoma Patients." *Cancer Immunol. Immun.* 1995, 41, 185-192.
44. Kudryashov, V.; Glunz, P. W.; Williams, L. J.; Hintermann, S.; Danishefsky, S. J.; Lloyd, K. O. "Toward optimized carbohydrate-based anticancer vaccines: Epitope clustering, carrier structure, and adjuvant all influence antibody responses to Lewis(y) conjugates in mice." *Proc. Natl. Acad Sci. U. S. A.* 2001, 98, 3264-3269.
45. Ragupathi, G.; Howard, L.; Cappello, S.; Koganty, R. R.; Qiu, D. X.; Longenecker, B. M.; Reddish, M. A.; Lloyd, K. O.; Livingston, P. O. "Vaccines prepared with sialyl-Tn and sialyl-Tn trimers using the 4-(4-maleimidomethyl)cyclohexane-1-carboxyl hydrazide linker group result in optimal antibody titers against ovine submaxillary mucin and sialyl-Tn-positive tumor cells." *Cancer Immunol. Immun.* 1999, 48, 1-8.
46. Glunz, P. W.; Hintermann, S.; Williams, L. J.; Schwarz, J. B.; Kuduk, S. D.; Kudryashov, V.; Lloyd, K. O.; Danishefsky, S. J. "Design and synthesis of Le(y)-bearing glycopeptides that mimic cell surface Le(y) mucin glycoprotein architecture." *J. Am. Chem. Soc.* 2000, 122, 7273-7279.
47. Spearman, P. "HIV Vaccine Development: Lessons from the Past and Promise for the Future." *Curr. HIV Res.* 2003, 1, 101-20.
48. Trkola, A.; Purtscher, M.; Muster, T.; Ballaun, C.; Buchacher, A.; Sullivan, N. et al. "Human Monoclonal Antibody 2G12 Defines A Distinctive Neutralization Epitope On The Gp120 Glyco-Protein Of Human Immunodeficiency Virus Type 1." *J. Virol.* 1996, 70, 1100-8.
49. Stiegler, G.; Armbruster, C.; Vcelar, B.; Stoiber, H.; Kunert, R.; Michael, N. L. et al. "Antiviral Activity Of The Neutralizing Antibodies 2F5 And 2G12 In Asymptomatic HIV-1-Infected Humans: A Phase I Evaluation." *AIDS* 2002, 16, 2019-25.
50. Armbruster, C.; Stiegler, G. M.; Vcelar, B. A.; Jäger, W.; Michael, N. L.; Vetter, N. et al. "A Phase I Trial With Two Human Monoclonal Antibodies (Hmab 2F5, 2G12) Against HIV-1." *AIDS* 2002, 16, 227-33.
51. Mascola, J. R.; Lewis, M. G.; Stiegler, G.; Harris, D.; VanCott, T. C.; Hayes, D. et al. "Protection Of Macaques Against Pathogenic Simian/Human Immunodeficiency Virus 89.6PD By Passive Transfer Of Neutralizing Antibodies." *J. Virol.* 1999, 73, 4009-18.
52. Mascola, J. R.; Stiegler, G.; VanCott, T. C.; Katinger, H.; Carpenter, C. B.; Hanson, C. E. et al. "Protection Of Macaques Against Vaginal Transmission Of A Pathogenic HIV-1/SIV Chimeric Virus By Passive Infusion Of Neutralizing Antibodies." *Nature Med.* 2000, 6, 207-10.
53. Wolbank, S.; Kunert, R.; Stiegler, G. and Katinger, H. "Characterization of Class-Switched Polymeric (Immunoglobulin M [IgM] and IgA) Anti-Human Immunodeficiency Virus Type 1 Antibodies 2F5 and 2G12." *J. Virol.* 2003, 77, 4095-4103.
54. Mandal, M.; Dudkin, V. Y.; Geng, X.; and Danishefsky, S. J. "In Pursuit of Carbohydrate-based HIV vaccines. Part 1. The Total Synthesis of Hybrid type gp120 fragments." *Angew. Chem. Int. Ed. Engl.* 2004, 2557. Geng, X.; Dudkin, V. Y.; Mandal, M.; and Danishefsky, S. J. "In Pursuit of Carbohydrate-based HIV vaccines. Part 2. The Total Synthesis of High-mannose type gp120 fragments: Evaluation of Strategies Directed to Maximal Convergence." *Angew. Chem. Int. Ed. Engl.* 2004, 2562.
55. Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H. et al. "Antibody Domain Exchange Is An Immunological Solution To Carbohydrate Cluster Recognition." *Science* 2003, 300, 2065-2071.
56. Dudkin, V. Y., Orlova, M., Geng, X., Mandal, M., Olson, W. C., Danishefsky, S. J. "Toward Fully Synthetic Carbohydrate-based HIV Antigen Design: on the Critical Role of Bivalency." *J. Am. Chem. Soc.* 2004, 126, 9560-2. A similar concept was demonstrated by Wang, et. al.: Wang, L.-X.; Ni, J.; Singh, S.; and Li, H. "Binding of High-Mannose-Type Oligosaccharides and Synthetic oligomannose Clusters to Human Antiobody 2G12: Implications for HIV-1 Vaccine Design." *Chem. Bio.* 2004, 11, 127-134.
57. Dumy, P.; Eggleston, I. M.; Cervigni, S.; Sila, U.; Sun, X. and Mutter M. "A Convenient Synthesis of Cyclic Peptides as Regioselectively Addressable Functionalized Templates (RAFT)." *Tetrahedron Lett.* 1995, 36, 1225-58. Dumy, P.; Renaudet, O. "Chemoselectively Template-Assembled Glycoconjugates as Mimics for Multivalent Presentation of Carbohydrates." *Org. Lett.* 2003, 5, 243-246. Shankaramma, S. C.; Moehle, K.; James, S.; Vrijbloed, J. W.; Obrecht, D.; and Robinson, J. "A Family of Macrocyclic Antibiotics with a Mixed Peptide-Peptoid β-hairpin Backbone Conformation." *Chem. Commun.* 2003, 1842-1843. Renard, A.; Mueller, M.; Zurbriggen, R.; Pluschke, G. and Robinson, J. A. (2003) "Cyclic Peptidomimetics Derived from the Apical Membrane Antigen I of *Plasmodium falciparum* and Their Use in Malaria Vaccine Design." *Helv. Chim. Act.* 2003, 86, 3638-3647.
58. Espinosa J. F.; Syud, F. A. and Gellman, S. H. "Anaylsis of the Factors that Stabilize a Designed Two-Stranded Antiparallel β-sheet." *Protein Sci.* 2002, 11, 1492.
59. Cohen-Anisfeld, S. T. and Lansbury, P. T. "A Practical, Convergent Method for Glycopeptide Synthesis." *J. Am. Chem. Soc.* 1993, 115, 10531-7.

Methods of Treatment

As detailed above, a major drawback in using carbohydrate epitopes, is that they are generally not readily available by isolation from natural sources. For example, the immense difficulties associated with their purification from natural sources render them virtually nonavailable as homogeneous starting materials for a clinical program. Thus, the incorporation of these naturally occurring epitopes into carrier proteins/peptides or any favorable molecular context via conjugation for eliciting a therapeutically useful immunological response is inefficient at best, and often virtually impossible. Therefore, to effectively study vaccines as therapeutic agents, sufficient material can only be obtained by chemical synthesis. As discussed above, the present invention provides a variety of synthetic glycoforms of gp120 (glycans glycopeptide conjugates and/or other constructs thereof), and methods for preparing them.

Accordingly, in another aspect of the invention, a method of treatment is provided comprising administering to a subject in need thereof a therapeutically effective amount of any of the gp120 glycans and/or glycoconjugates thereof disclosed herein (e.g., cyclic or acyclcic glycopeptides, which may additionally be conjugated to a protein, peptide or lipid carrier, either directly or through a crosslinker or -linker (crosslinker)$_q$-moiety), optionally in combination with a pharmaceutically acceptable carrier. In certain embodiments, a method for preventing the infection with HIV is provided comprising administering to a subject in need thereof a therapeutically effective amount of any of the gp120 glycans and/or glycoconjugates thereof disclosed herein, optionally in combination with an adjuvant. In certain embodiments, a method for the treatment of HIV is provided comprising administering to a subject in need thereof a therapeutically effective amount of any of the gp120 glycans and/or glycoconjugates thereof disclosed herein, optionally in combination with an adjuvant. In certain embodiments, a method for inducing antibodies in a human subject, wherein the antibodies are specific to a carbohydrate antigen expressed on the surface of gp120, which comprises administering to the subject an amount of any of the glycans and/or glycoconjugates disclosed above effective to induce antibodies. In certain embodiments, the method utilized any one or more of the gp120 glycans and/or glycoconjugates thereof disclosed herein, where the glycan(s) and/or glycoconjugate(s) is/are linked to an immunogenic carrier either directly or through a crosslinker, which carrier is a protein, peptide or lipid. In certain embodiments, the carrier is Bovine Serum Albumin, polylysine or KLH. In certain other embodiments, the carrier is a lipid having the structure:

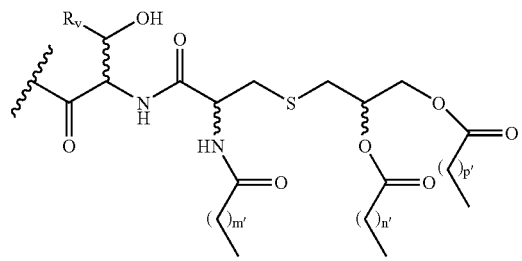

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., Pam-Cys).

In certain other embodiments, the method comprises administering to a subject in need thereof a therapeutically effective amount of any of the compounds and/or glycoconjugates disclosed herein, in combination with an immunogenic carrier, optionally in combination with a pharmaceutically acceptable carrier. Specifically, in certain exemplary embodiments, the method comprises administering a gp120 glycan and/or glycoconjugate thereof additionally conjugated to an immunogenic carrier. In certain embodiments, the method comprises administering to the subject a therapeutically effective amount of any one or more of the glycoconjugates disclosed herein (e.g., glycopeptides, which may additionally be conjugated to a protein, peptide or lipid carrier, either directly or through a crosslinker or -linker (crosslinker)$_q$- moiety), in combination with an immunogenic carrier, optionally in combination with a pharmaceutically acceptable carrier. In certain embodiments, the method comprises administering one or more gp120 glycans and/or glycoconjugates and an immunogenic carrier that have not been conjugated. Rather, they are administered concurrently, or successively, as separate entities. In certain other exemplary embodiments, the method comprises administering one or more gp120 glycans and/or glycoconjugates of the invention conjugated (i.e., covalently linked) to an immunogenic carrier. In certain embodiments, the method comprises administering any one or more inventive gp120 glycans and/or glycoconjugates thereof disclosed herein that have not been conjugated to an immunogenic carrier. Rather, the gp120 glycan(s) and/or glycoconjugate(s) thereof and the immunogenic carrier are administered concurrently, or successively, as separate entities. In certain embodiments, the immunogenic carrier is a protein, peptide or lipid. In certain exemplary embodiments, the carrier is Bovine Serum Albumin, polylysine or KLH. In certain other embodiments, the carrier is PamCys. In certain other embodiments, the carrier may be OMPC. For the purpose of the invention, a compound/glycoconjugate and a carrier are said to be administrered concurrently when they are administered (i) as a single composition containing the compound/glycoconjugate and the carrier, (ii) as two separate compositions or (iii) are delivered by separate routes within a short enough period of time that the effective result is equivalent to that obatined when both compound/glycoconjugate and carrier are administered as a single composition.

In still other embodiments, the present invention provides the related method of inducing antibodies which further comprises co-administering an immunological adjuvant, or a combination of immunological adjuvants.

In certain exemplary embodiments, the inventive gp120 glycans and glycoconjugates thereof comprise carbohydrate domains, or truncated or elongated versions thereof, that are found on the surface of gp120. In certain exemplary embodiments, the inventive glycoconjugates comprise peptidic domains, or truncated or elongated versions thereof, that are found near an N-glycosylation site of naturally occurring gp120.

Accordingly, embodiments of this invention encompass methods of eliciting immune responses in animals comprising administering effective amounts of inventive gp120 glycans and/or glycoconjugate(s) thereof and/or compositions of the invention wherein the immune response is directed against on eor more carbohydrates expressed on the surface of gp120.

A further embodiment of this invention encompasses a use of effective amounts of inventive gp120 glycans and/or glycoconjugate(s) thereof and/or a composition of the present invention to elicit an immune response in an animal preferably to treat and/or prevent HIV. The present invention further includes a use of effective amounts of inventive gp120 glycans and/or glycoconjugate(s) thereof and/or a composition of the present invention to prepare a medicament to elicit an immune response in animal, preferably to treat and/or prevent HIV.

It will be appreciated that the magnitude of the therapeutic dose of the compounds of the invention will vary with the nature and severity of the condition to be treated and with the particular compound and its route of administration. In general, the daily dose range for antiHIV activity lies in the range of 0.0001 to 1.0 mg/kg of body weight in a mammal, although the present invention is not intended to be limited by this range.

Any suitable route of administration may be employed for providing a mammal, especially a human, with an effective dosage of a compound disclosed herein. For example, oral, rectal, topical, parenteral, ocular, pulmonary, nasal, etc. routes may be employed. Dosage forms include tablets, troches, dispersions, suspensions, solutions, capsules, creams, ointments, aerosols, etc. In preferred embodiments, the effective dosage is employed using a syringe injection.

It will be appreciated by one of ordinary skill in the art, however, that the most suitable route for administration will depend largely on the nature and severity of the condition being treated and on the nature of the active ingredient. As discussed above, the inventive therapeutics may be conveniently presented in unit dosage form and prepared by any of the methods well known in the art of pharmacy.

Additionally, once a synthetic vaccine has been derivatized and characterized, mouse immunological studies can be performed to assess the potency and/or specificity of the novel HIV vaccines.

Kits of the Invention

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. In but one illustrative example, protecting groups play an important role in the synthesis of the carbohydrate domains and synthetic conjugates, as described herein; however it will be appreciated by one of ordinary skill in the art that the present invention encompasses the use of various alternate protecting groups known in the art. Those protecting groups used in the disclosure including the Examples below are merely illustrative.

It should further be appreciated that, uless otherwise indicated, the contents of those cited references are incorporated herein by reference to help illustrate the state of the art. The following examples contain important additional information, exemplification and guidance which can be adapted to the practice of this invention in its various embodiments and the equivalents thereof.

Exemplification

Gp120 Glycans and Glycopeptides

General Methods: Reagents obtained from commercial suppliers were used without further purification unless otherwise noted. THF, toluene, and methylene chloride was obtained from a dry solvent system (passed through a pre-packed column of alumina) and used without further drying. All air and water sensitive reactions were performed in flame-dried glassware under a positive pressure of prepurified argon gas. NMR ($^1$H and $^{13}$C) spectra were recorded on Bruker AMX-400 MHz or Bruker Advance DRX-500 MHz as noted individually, referenced to CDCl₃ (7.27 ppm for ¹H and 77.0 ppm for ¹³C) or CD₃COCD₃ (2.09 ppm for ¹H and 30.6 and 205.9 ppm for ¹³C). Optical rotations were obtained on a JASCO model DIP-370 digital polarimeter. Analytical thin-layer chromatography was performed on E. Merck silica gel 60 F254 plates. Compounds which were not UV active were visualized by dipping the plates in para-anisaldehyde solution and heating. Preparative thin layer chromatography was performed using the indicated solvent on Whatman® (LK6F Silica gel 60 Å 250 μM or Pk6F Silica Gel 60 Å 1000 μM) TLC plate.

EXAMPLE 1

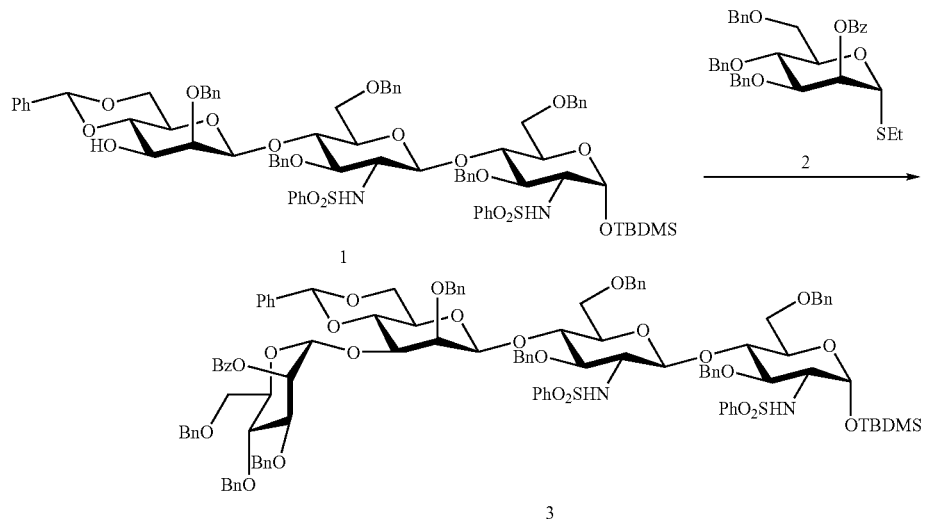

Tetrasaccharide 3: A mixture of trisacchride 1¹ (106 mg, 0.074 mmol), thiomannoside 2 (133 mg, 0.222 mmol) and molecular sieves in CH₃CN (2 mL) was stirred for 2 h at r.t. and tris(4-bromophenyl)aminium hexachloroantimonate (199 mg, 0.244 mmol) was added at 15° C. The solution was stirred for 4 h at r.t. and then quenched by triethylamine. The mixture was filtered through celite, concentrated, dissolved in EtOAc, filtered through silica gel and concentrated. The residue was purified by preparative TLC (PTLC) using pentane/ether (1/2) as the eluent to afford 3 as a white solid (113 mg, 78%). [α]$_D^{25}$ −205.0 (c 0.14, CHCl₃). ¹H NMR (400 MHz, CDCl₃) selected signals: δ 0.00 (s, 3H), 0.06 (s, 3H), 0.87 (s, 9H), 5.07 (s, 1H), 5.30 (s, 1H), 5.36 (s, 1H), 5.74 (s, 3H). ¹³C NMR (100 MHz, CDCl₃) δ −5.8, −4.6, 13.9, 17.8, 20.8, 25.6, 57.8, 58.6, 60.1, 66.8, 67.5, 67.8, 68.2, 68.4, 68.9, 69.5, 71.0, 72.3, 73.1, 73.3, 73.5, 73.9, 74.3, 74.9, 75.1, 75.3, 75.8, 77.3, 77.6, 77.9, 78.2, 79.9, 92.6, 98.4, 100.7, 100.9, 125.6, 126.7, (126.8–129.5), 129.6, 136.9, 137.4, 137.6, 138.0, 138.1, 138.2, 138.3, 140.4, 141.3, 165.1. LRMS (ESI) calcd for C₁₁₂H₁₂₂N₂O₂₄S₂SiNa⁺ [M+Na]⁺ 1994.76, found 1994.8.

EXAMPLE 2

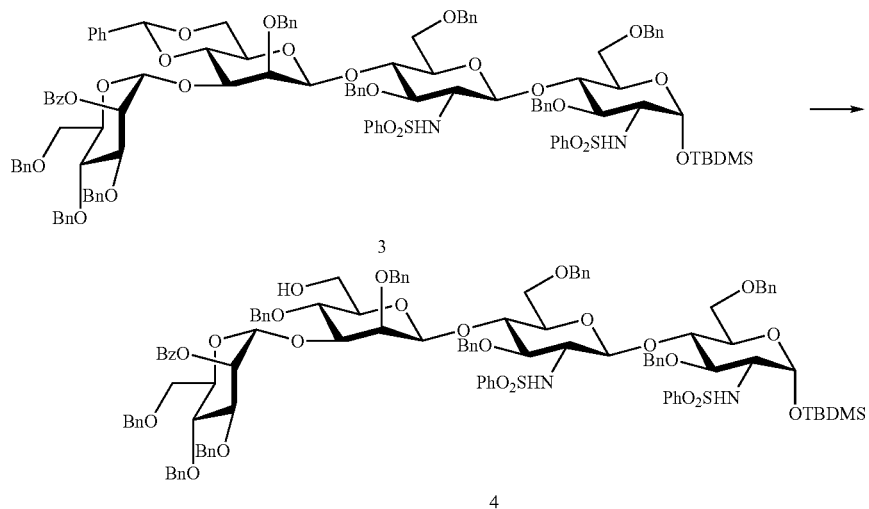

Tetrasaccharide 4: To a solution of 3 (200 mg, 0.101 mmol) in borane tetrahydrofuran etherate (1.1 mL, 1.0 M in THF, 1.01 mmol) was added dibutylboron triflate (0.334 mL, 1.0 M in CH$_2$Cl$_2$, 0.333 mmol) at 0° C. The reaction mixture was stirred for 7 h at 0° C. and quenched with triethylamine and methanol and concentrated. The residue was purified by PTLC using pentane/ether (1/2) as the eluent to afford 4 as a white solid (172 mg, 90%). $[\alpha]_D^{25}$ −187.0 (c 0.13, CHCl$_3$). $^1$H NMR (400 MHz, CDCl$_3$) selected signals: δ −0.08 (s, 3H), −0.04 (s, 3H), 0.80 (s, 9H), 4.96 (d, J=2.6 Hz, 1H), 5.15 (s, 1H), 5.55 (s, 1H). $^{13}$C NMR (100 MHz, CDCl$_3$) δ −5.7, −4.6, 17.9, 25.7, 57.9, 58.3, 67.6, 68.9, 69.8, 71.3, 72.4, 73.2, 73.4, 73.9, 74.3, 74.5, 75.0, 76.0, 77.3, 78.1, 79.6, 79.9, 92.7, 99.3, 100.6, 101.0, 126.8-128.7, 129.8, 137.6, 137.7, 138.2, 138.3, 138.4, 140.5, 141.0, 165.2. LRMS (ESI) calcd for C$_{112}$H$_{124}$N$_2$O$_{24}$S$_2$SiNa$^+$ [M+Na]$^+$ 1995.8, found 1995.8.

EXAMPLE 3

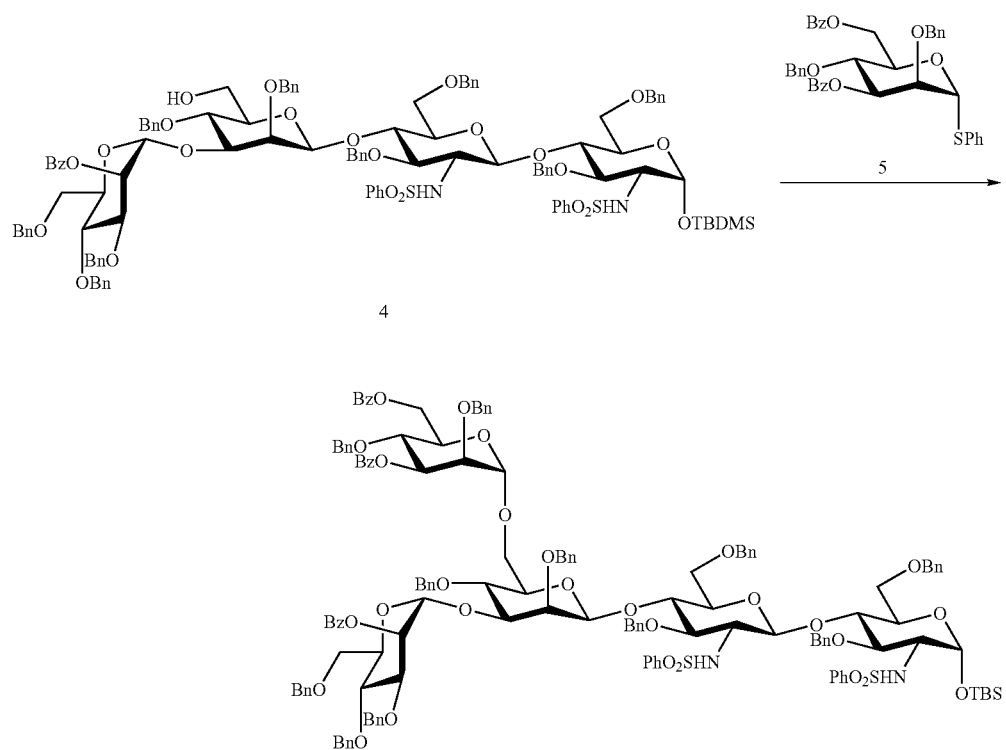

Pentasaccharide 6: 6 was prepared using same procedure as the synthesis of 3. White solid (80 mg, 74%). $[\alpha]_D^{25}$ 51.0 (c 0.13, CHCl$_3$). $^1$H NMR (400 MHz, CDCl$_3$) selected signals: δ −0.07 (s, 3H), −0.02 (s, 3H), 0.80 (s, 9H), 4.95 (s, 1H), 4.99 (s, 1H), 5.25 (s, 1H), 5.54 (dd, J=9.5, 2.5 Hz, 1H), 5.58 (s, 1H). $^{13}$C NMR (100 MHz, CDCl$_3$) δ −5.8, −4.6, 14.0, 17.9, 20.9, 22.5, 25.7, 31.4, 57.8, 58.6, 60.2, 67.7, 68.9, 69.6, 70.1, 71.5, 72.5, 72.9, 73.2, 73.9, 74.4, 74.8, 75.2, 75.9, 76.4, 77.3, 79.1, 92.7, 97.9, 99.4, 101.1, 126.9-129.5, 129.6, 137.3, 137.7, 138.2, 138.4, 141.1, 165.2, 165.5, 166.1. LRMS (ESI) calcd for C$_{146}$H$_{154}$N$_2$O$_{31}$S$_2$SiNa$^+$ [M+Na]$^+$ 2546.0, found 2545.9.

EXAMPLE 4

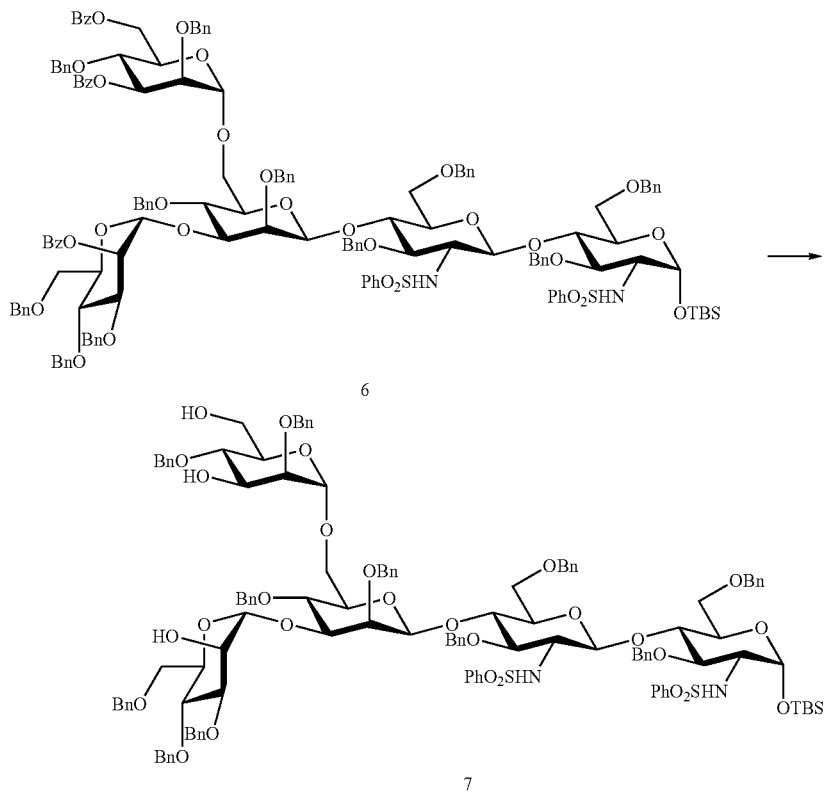

Pentasaccharide triol 7: To a solution of 6 (80 mg, 0.032 mmol) in MeOH (2 mL) was added sodium methoxide in MeOH (25%, 0.1 mL) and stirred for 12 h and quenched with NH$_4$Cl saturated aqueous solution and concentrated. The residue was dissolved in EtOAc and washed with water and brine. The organic layer was dried with anhydrous MgSO$_4$, filtered and concentrated. The residue was purified by PTLC using pentane/ether (1/3) as the eluent to afford 7 as a white solid (64 mg, 91%). [α]$_D^{25}$ 121.8 (c 0.16, CHCl$_3$). $^1$H NMR (400 MHz, CDCl$_3$) selected signals: δ 0.00 (s, 3H), 0.05 (s, 3H), 0.93 (s, 9H), 4.92 (s, 1H), 5.06 (d, J=1.8 Hz, 1H), 5.14 (s, 1H). $^{13}$C NMR (100 MHz, CDCl$_3$) δ −5.8, −4.6, 14.0, 17.9, 20.9, 25.7, 57.8, 58.4, 60.2, 65.9, 68.4, 69.6, 71.6, 71.9, 72.4, 72.6, 73.1, 73.2, 73.3, 73.9, 74.1, 74.4, 74.7, 74.8, 74.9, 75.3, 75.8, 76.1, 76.4, 77.3, 78.3, 79.1, 79.6, 80.6, 92.7, 97.2, 100.5, 101.2, 101.3, 126.8-128.6, 137.6, 137.8, 137.9, 138.2, 138.3, 138.6, 140.5, 141.1. LRMS (ESI) calcd for C$_{125}$H$_{142}$N$_2$O$_{28}$S$_2$SiNa$^+$ [M+Na$^+$] 2233.9, found 2233.9.

EXAMPLE 5

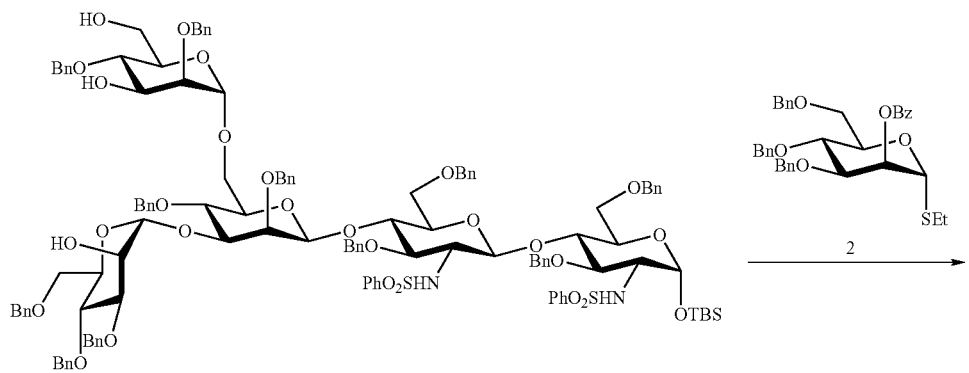

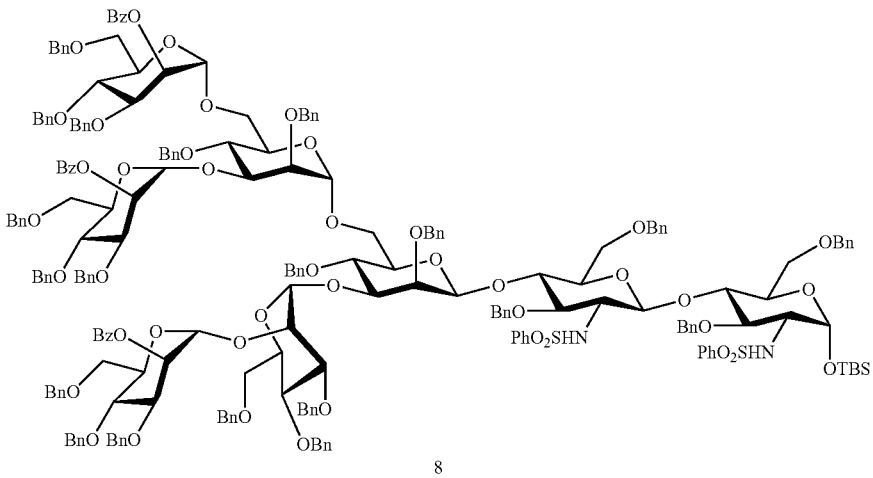
8
Octasaccharide 8: 8 was prepared following the same protocol as used for 3 using thiol mannoside donor 2 as excess (10 eq.) White solid: (61 mg, 55%). $[\alpha]_D^{25}$ 32.8 (c 0.15, CHCl$_3$). $^1$H NMR (400 MHz, CDCl$_3$) selected signals: δ 0.00 (s, 3H), 0.05 (s, 3H), 0.88 (s, 9H), 4.79 (s, 1H), 4.88 (s, 1H), 5.01 (s, 1H), 5.06 (s, 1H), 5.23 (s, 1H), 5.58 (s, 1H), 5.62 (s, 1H), 5.66 (s, 1H). $^{13}$C NMR (100 MHz, CDCl$_3$) δ −5.1, −3.9, 14.7, 18.5, 21.5, 26.3, 30.2, 58.4, 59.1, 60.9, 66.5, 69.0, 69.3, 69.4, 70.3, 71.3, 72.0, 72.2, 72.6, 72.8, 73.6, 73.7, 73.8, 74.0, 74.6, 75.1, 75.3, 75.5, 75.7, 78.4, 78.9, 80.4, 82.2, 93.3, 98.2, 98.9, 99.7, 101.2, 101.8, 102.8, 126.9-130.5, 138.5, 138.6, 138.8, 139.0, 139.1, 139.6, 141.2, 165.8, 165.9. LRMS (ESI) calcd for C$_{227}$H$_{238}$N$_2$O$_{46}$S$_2$SiNa$_2$ [M+2Na]$^{2+}$ 1932.8, found 1933.0.
EXAMPLE 6
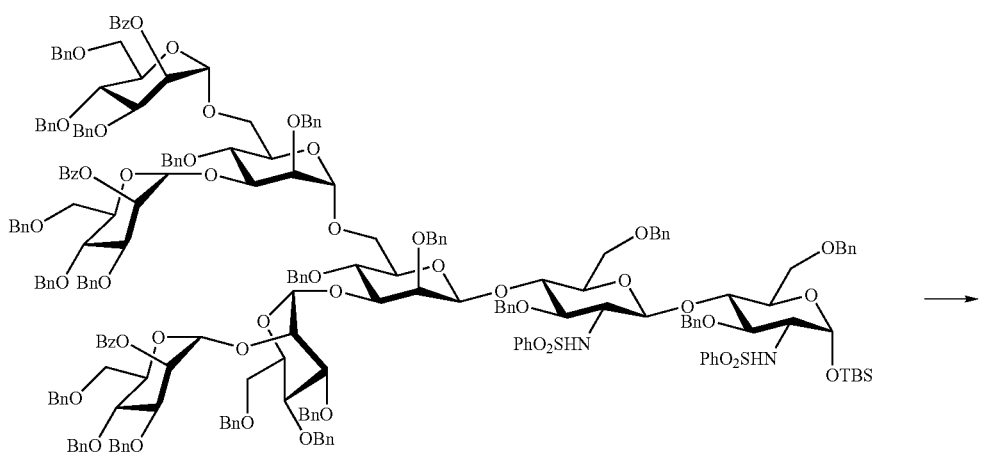
8

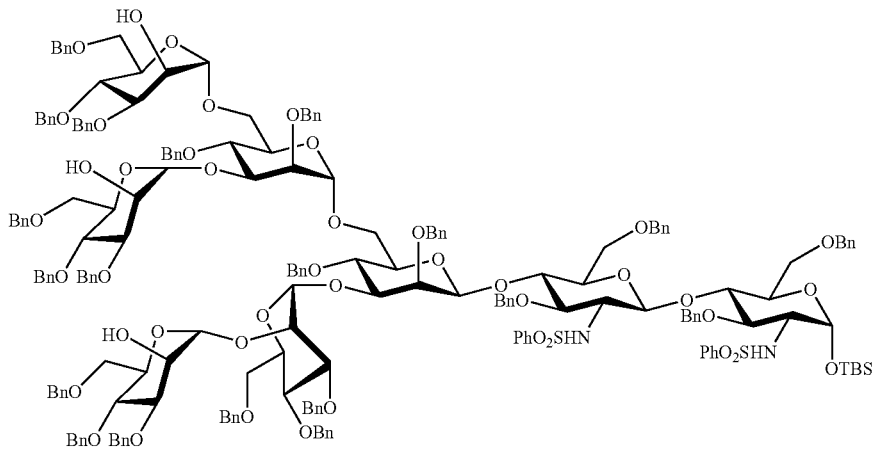
Octasaccharide triol 9: The synthesis of 9 follows the synthetic procedure of 7. White solid (46 mg, 87%). $[\alpha]_D^{25}$ 280.0 (c 0.12, CHCl$_3$). $^1$H NMR (400 MHz, CDCl$_3$) selected signals: δ −0.08 (s, 3H), −0.03 (s, 3H), 0.80 (s, 9H), 4.92 (s, 1H), 4.94 (s, 1H), 4.97 (s, 1H), 5.03 (s, 1H), 5.07 (s, 1H). $^{13}$C NMR (100 MHz, CDCl$_3$) δ −5.7, −4.4, 0.0, 14.1, 18.0, 22.7, 25.8, 29.3, 29.7, 31.9, 58.0, 58.6, 65.5, 66.3, 67.7, 68.4, 68.5, 68.8, 71.1, 71.2, 71.7, 71.8, 72.0, 72.3, 72.9, 73.2, 73.3, 73.5, 74.1, 74.2, 74.3, 74.5, 74.8, 74.9, 75.0, 79.4, 81.8, 92.8, 97.4, 100.0, 100.7, 100.9, 101.3, 102.9, 127.1-128.8, 138.0-138.5, 140.7, 141.3. LRMS (ESI) calcd for C$_{206}$H$_{226}$N$_2$O$_{43}$S$_2$SiNa$_2$ [M+2Na]$^{2+}$ 1776.7, found 1776.7.
EXAMPLE 7
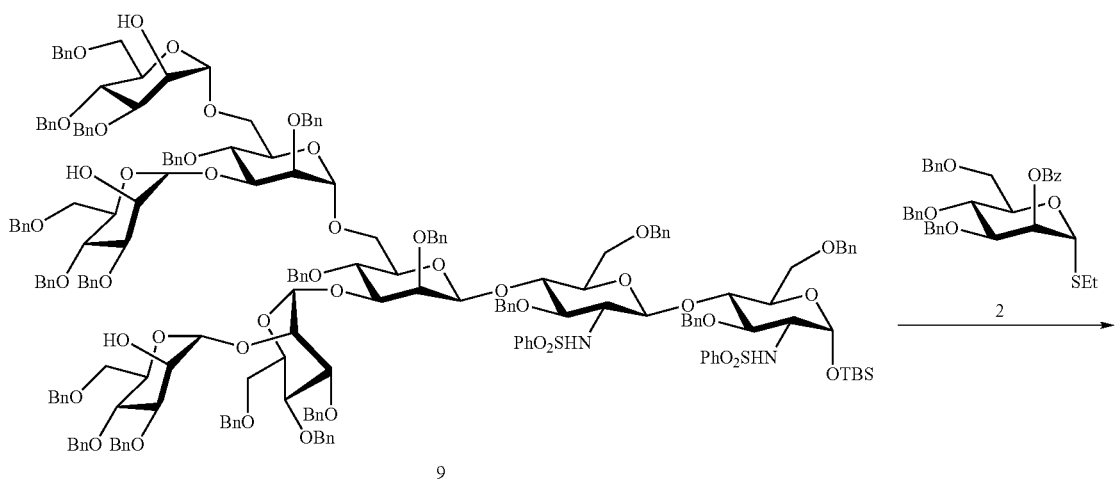

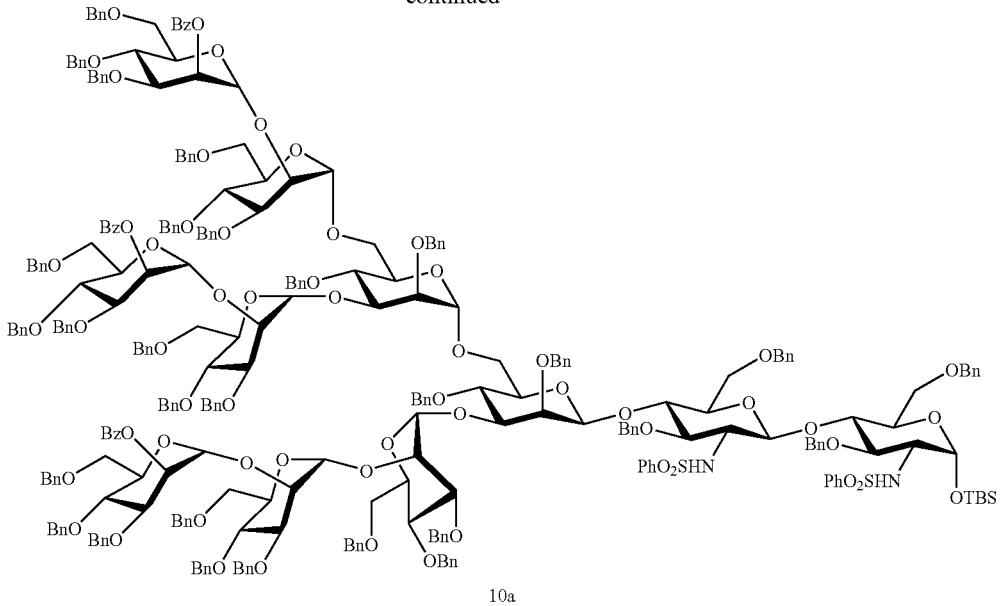

10a

Undecasaccharide 10a: The synthesis of 10a follows same synthetic procedure as 8. 10a, white solid (81 mg, 51%). $[\alpha]_D^{25}$ 73.8 (c 0.09, CHCl$_3$). $^1$H NMR (400 MHz, CDCl$_3$) selected signals: δ −0.05 (s, 3H), −0.00 (s, 3H), 0.82 (s, 9H), 5.00-5.20 (m, 7H), 5.65-5.68 (m, 3H). LRMS (ESI) calcd for C$_{308}$H$_{322}$N$_2$O$_{61}$S$_2$SiNa$_2$ [M+2Na]$^{2+}$ 2581.1, found 2581.3.

EXAMPLE 8

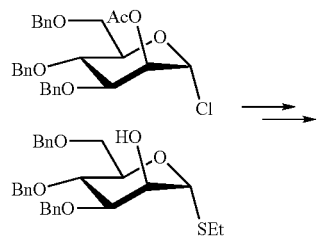

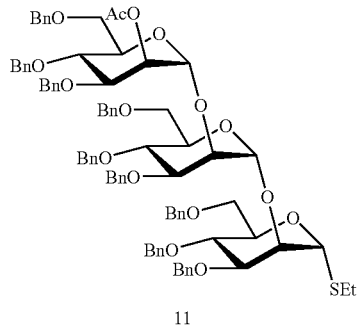

11

Trisaccharide donor 11: Trisaccharide donor 11 was prepared from the known chloride and thiomannoside monosaccharides according to standard coupling procedures. $^1$H NMR (CDCl$_3$, 400 MHz) δ: 1.21 (t, J=7.5 Hz, 3H), 2.16 (s, 3H), 2.47-2.57 (m, 2H), 3.57 (d, J=10.7 Hz, 1H), 3.67-3.75 (m, 4H), 3.78-3.85 (m, 4H), 3.89-3.97 (m, 3H), 3.99-4.04 (m, 2H), 4.08-4.12 (m, 3H), 4.36 (d, J=12.2 Hz, 1H), 4.43-4.73 (m, 14H), 4.82-4.88 (m, 3H), 5.08 (d, J=2.0 Hz, 1H), 5.20 (d, J=2.0 Hz, 1H), 5.46 (d, J=1.3 Hz, 1H), 5.56 (dd, J=3.0, 1.9 Hz, 1H), 7.14-7.38 (m, 45H).

EXAMPLE 9

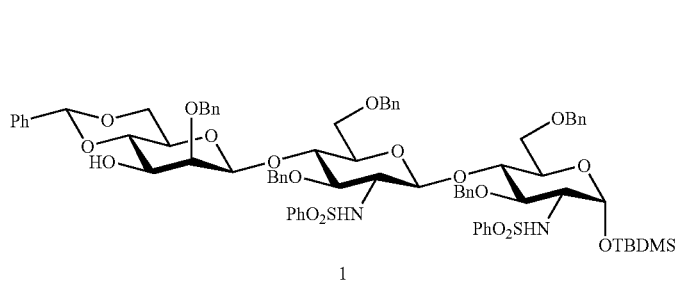

1

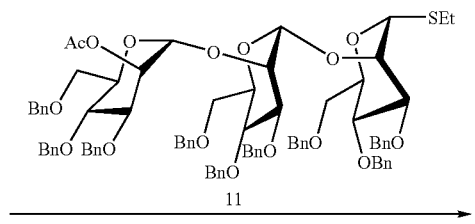

11

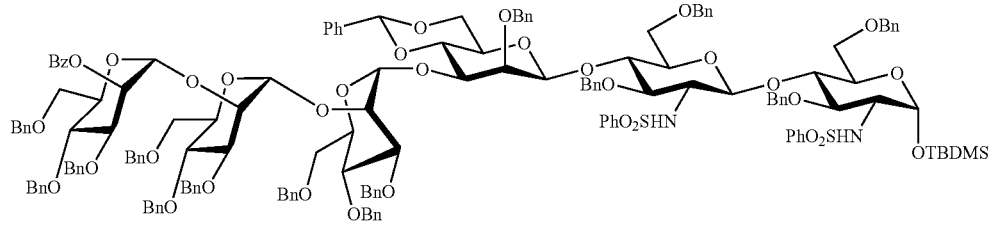

12

Hexasaccharide 12: To a mixture of 1 (35 mg, 0.024 mmol), 11 (51 mg, 0.037 mmol) and molecular sieves in CH$_2$Cl$_2$ (2 mL) was added di-tert-butylpyridine (DTBP) (0.019 mL, 0.085 mmol) at –40° C. and stirred for 1 h at –40° C. MeOTf (0.011 mL, 0.096 mmol) was added and the reaction mixture was warmed up to r.t. and stirred for 12 h before quenched with triethylamine, filtered through celite, washed with NaHCO$_3$ saturated aqueous solution, brine, dried over anhydrous MgSO$_4$ and filtered. The organic layer was concentrated and residue purified by PTLC using pentane/ether (1/1.3) as the eluent to afford 12 as a white solid (47 mg, 47%). [α]$_D^{25}$ 41.4 (c 0.65, CHCl$_3$). $^1$H NMR (400 MHz, CDCl$_3$) selected signals: δ 0.91 (s, 9H), 4.97 (s, 1H), 5.11 (s, 1H), 5.21 (s, 1H), 5.25 (s, 1H), 5.28 (s, 1H), 5.52 (s, 1H). $^{13}$C NMR (100 MHz, CDCl$_3$) δ –5.7, –4.4, 0.0, 14.2, 18.0, 21.0, 21.1, 25.8, 58.0, 58.8, 60.4, 67.0, 68.6, 68.7, 69.8, 71.6, 71.9, 72.1, 72.9, 73.3, 73.7, 73.8, 74.4, 74.6, 75.1, 75.4, 75.5, 76.0, 77.4, 78.3, 78.8, 80.2, 92.9, 99.5, 99.9, 100.2, 100.8, 101.0, 101.1, 125.9, 127.1-128.5, 137.9, 138.1, 138.4, 138.6, 138.8, 140.7, 170.0, 171.1. LRMS (ESI) calcd for C$_{161}$H$_{176}$N$_2$O$_{34}$S$_2$SiNa$_2$ [M+2Na]$^{2+}$ 1409.6, found 1409.4.

Hexasaccharide 13: 13 was prepared using the same procedure as the one for 4. 13, white solid (542 mg, 86%). [α]$_D^{25}$ 91.5 (c 0.54, CHCl$_3$). $^1$H NMR (400 MHz, CDCl$_3$) selected signals: δ 0.02 (s, 3H), 0.04 (s, 3H), 0.87 (s, 9H), 5.01 (s, 1H), 5.06 (s, 1H), 5.09 (s, 1H), 5.15 (s, 1H), 5.49 (s, 1H). $^{13}$C NMR (100 MHz, CDCl$_3$) δ –5.7, –4.4, 0.0, 14.2, 18.0, 21.0, 21.1, 21.4, 25.8, 58.0, 58.3, 60.4, 61.3, 67.6, 68.6, 69.9, 71.8, 72.0, 72.1, 73.1, 73.3, 73.5, 74.1, 74.5, 74.6, 74.8, 75.1, 76.1, 76.2, 78.2, 78.7, 79.8, 81.1, 92.8, 99.4, 100.5, 100.7, 101.0, 101.3, 125.3, 127.0-128.5, 137.9, 138.0, 138.4, 138.5, 138.6, 138.7, 140.7, 170.1. LRMS (ESI) calcd for C$_{161}$H$_{178}$N$_2$O$_{34}$S$_2$SiNa$_2$ [M+2Na]$^{2+}$ 1410.6, found 1410.4.

EXAMPLE 11

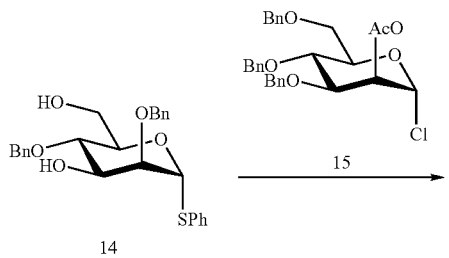

EXAMPLE 10

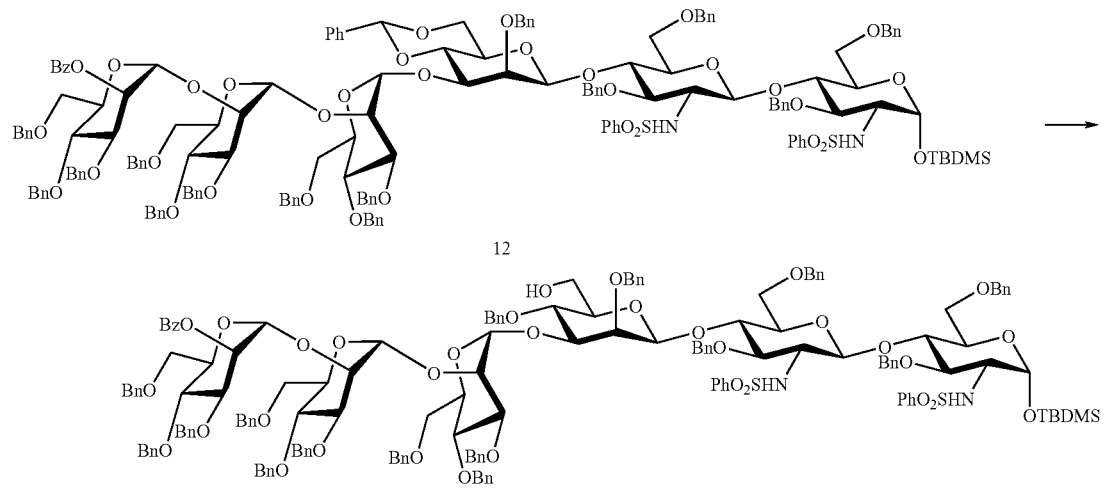

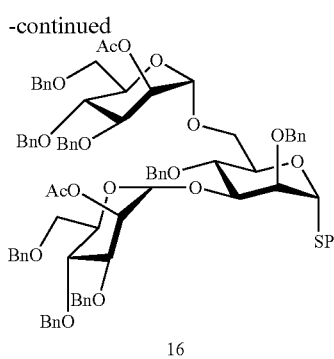

16

Trisaccharide 16: To a 25 mL flask containing donor 15 (169 mg, 0.332 mmol) and acceptors 14 (37 mg, 0.083 mmol) (dried azeotropically with toluene) in 1.5 mL dichloromethane was added activated MS 4 Å and the mixture was stirred for 1 h at room temperature. In a separate flask, AgOTf (0.087 gm, 0.332 mmol) and DTBP (0.078 mL, 0.347 mmol) in 1.5 mL dichloromethane were stirred with MS 4 Å. After one hour the flask containing the AgOTf/DTBP was cooled to −10° C. and the solution containing mixture of donor and acceptor was added over 5 minutes. The solution was stirred in dark with warming up to room temperature over 18 hr. The reaction mixture was diluted with ethyl acetate and was added aqueous saturated NaHCO$_3$ solution. After stirring for 10 minutes, the reaction mixture was filtered through bed of Celite and the filtrate was washed with water, brine, dried over MgSO$_4$ and evaporated in vacuo. The crude product was purified by silica gel column chromatography (10% ethyl acetate/toluene) to afford diacetate 16. This diacetate was used for next step without further purification.

EXAMPLE 12

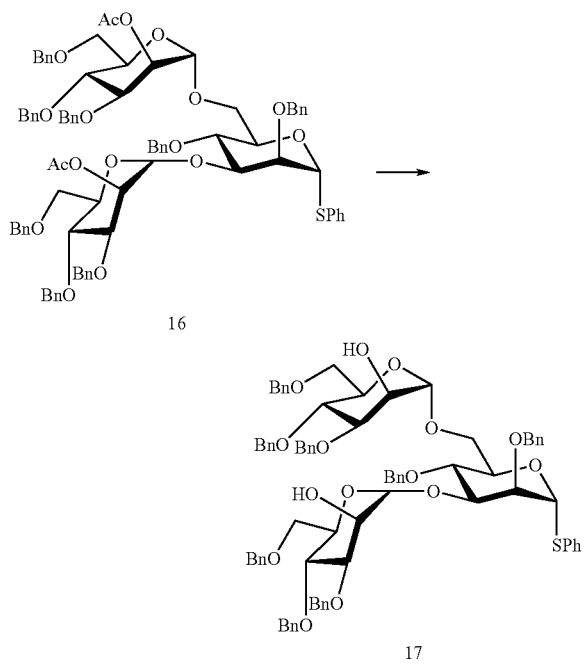

Trisaccharide diol 17: 16 was dried azeotropically with toluene and dissolved in 2 mL of anhydrous methanol under argon. Sodium methoxide (25% by weight in methanol, 100 µL) was added and the reaction mixture was stirred for 12 h. Solid ammonium chloride was added and the mixture was stirred for 20 min. The reaction mixture was carefully evaporated to solid residues, and the residues were dissolved in ethyl acetate and washed with brine. Evaporation of ethyl acetate layers provided crude products, which was purified by silica gel column chromatography (10% ethyl acetate/dichloromethane) to yield diol 17 in 50% over two steps. $[\alpha]_D^{25}$ +53.1 (c 1.0, CHCl$_3$); $^1$H NMR (CDCl$_3$, 400 MHz) δ 4.94 (bs, 1H), 5.17 (bs, 1H), 5.44 (bs, 1H). $^{13}$C NMR (CDCl$_3$, 125 MHz) δ 138.68, 138.66, 138.4, 138.1, 138.06, 138.03, 134.9, 131.0, 129.3, 128.72, 128.70, 128.67, 128.61, 128.49, 128.47, 128.16, 128.13, 128.10, 128.01, 127.96, 127.88, 127.86, 127.83, 127.82, 127.79, 127.76, 127.71, 127.35, 99.9, 85.3, 80.5, 80.2, 79.6, 75.3, 75.15, 75.07, 74.6, 74.4, 73.8, 73.5, 72.7, 72.3, 72.2, 71.8, 71.7, 71.3, 69.5, 68.94, 68.90, 68.2, 66.4. LRMS (ESI) calcd for C$_{80}$H$_{84}$O$_{15}$SNa$^+$ [M+Na]$^+$ 1339.6, found 1339.5.

EXAMPLE 13

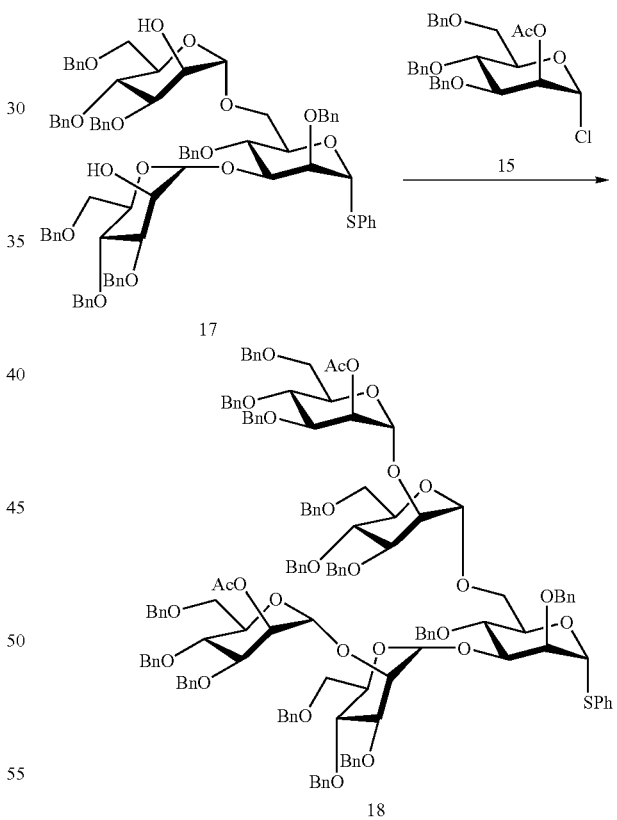

Pentasaccharide 18: To a mixture of 17 (208 mg, 0.158 mmol), 15 (332 mg, 0.631 mmol), molecular sieves, DTBP (0.088 mL, 0.347 mmol) in CH$_2$Cl$_2$ (13 mL) was added AgOTf (166 mg, 0.646 mmol) at 0° C. The mixture was stirred for 18 h at r.t. and quenched with triethylamine, filtered, diluted with EtOAc, washed with NaHCO$_3$ saturated aqueous solution, brine, dried over anhydrous MgSO$_4$ and filtered. The organic layer was concentrated and residue purified by PTLC using pentane/ether (2/1) as the eluent to afford 18 as a white solid (310 mg, 87%). $[\alpha]_D^{25}$ 443.4 (c 0.49, CHCl$_3$). $^1$H NMR (400 MHz, CDCl$_3$) selected signals: δ 2.10 (s, 3H), 2.11 (s, 3H), 4.88 (s, 1H), 5.02 (s, 1H), 5.04 (s, 1H), 5.21 (s, 1H), 5.51 (s, 1H). $^{13}$C NMR (100 MHz, CDCl$_3$) δ 14.2, 20.9, 21.0, 21.1, 29.6, 44.6, 60.3, 66.6, 68.7, 68.8, 71.5, 71.7, 71.8, 72.0, 72.1, 73.1, 73.3, 73.4, 74.1, 74.2, 74.4, 74.6, 74.7, 75.0, 75.2, 78.0, 78.1, 79.2, 80.3, 84.8, 89.8, 95.4, 99.0, 99.4, 99.5, 101.2, 116.9, 125.1, 127.1-128.4, 129.1, 130.8, 138.0-138.6, 146.8, 168.3, 170.0. LRMS (ESI) calcd for C$_{138}$H$_{144}$O$_{27}$SNa$^+$ [M+Na]$^+$ 2288.0, found 2287.9.
EXAMPLE 14
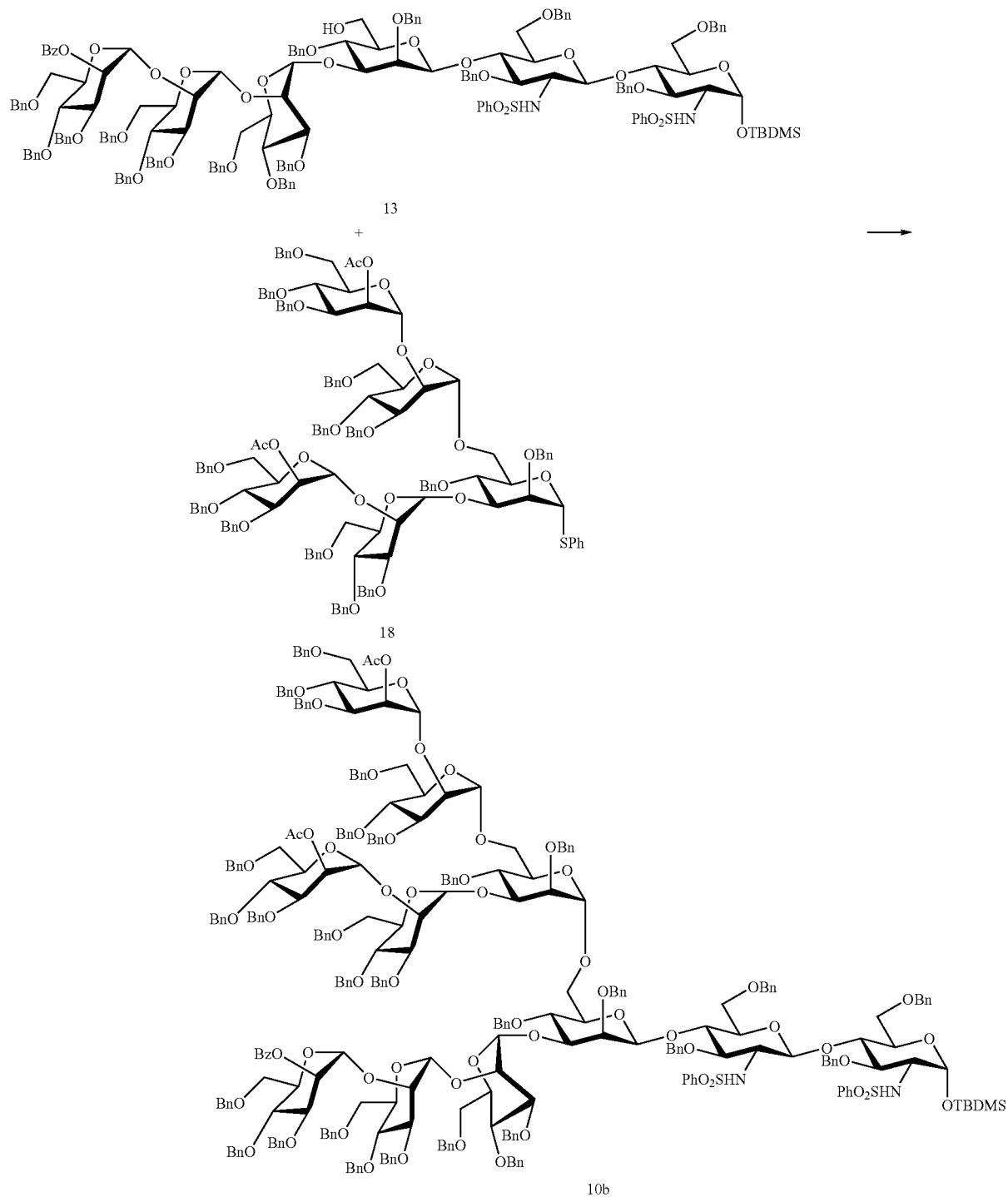
Undecasaccharide 10b: The preparation of 10b from 18 and 13 follows the same procedure as the one used for 3. 10b, white solid (529 mg, 63% yield, 85% based on recovered starting material). $[\alpha]_D^{25}$ 214.3 (c 0.23, CHCl$_3$). $^1$H NMR (400 MHz, CDCl$_3$) selected signals: δ 0.07 (s, 3H), 0.15 (s, 3H), 0.90 (s, 9H), 2.01 (s, 3H), 2.10 (bs, 6H), 5.05 (bs, 1H), 5.07 (bs, 1H), 5.10 (bs, 1H), 5.12 (bs, 1H), 5.13 (bs, 1H), 5.15 (bs, 1H), 5.23 (bs, 1H), 5.51 (bs, 1H), 5.54 (bs, 1H). $^{13}$C NMR (100 MHz, CDCl$_3$) δ −5.7, −4.4, 0.0, 1.0, 14.2, 18.0, 21.0, 21.1, 21.2, 25.8, 29.7, 58.0, 58.6, 60.4, 68.6, 68.7, 68.8, 71.8, 72.2, 72.3, 73.0, 73.1, 73.2, 73.3, 74.2, 74.5, 74.8, 75.0, 75.1, 78.2, 78.3, 78.4, 79.4, 92.8, 99.3, 99.5, 100.7, 101.6, 102.3, 127.3-128.4, 138.1-138.7, 140.7, 141.3, 170.0, 170.1, 170.15. LRMS (ESI) calcd for C$_{293}$H$_{316}$N$_2$O$_{61}$S$_2$SiNa$_2$ [M+2Na]$^{2+}$ 2488.0, found 2488.0.

EXAMPLE 15

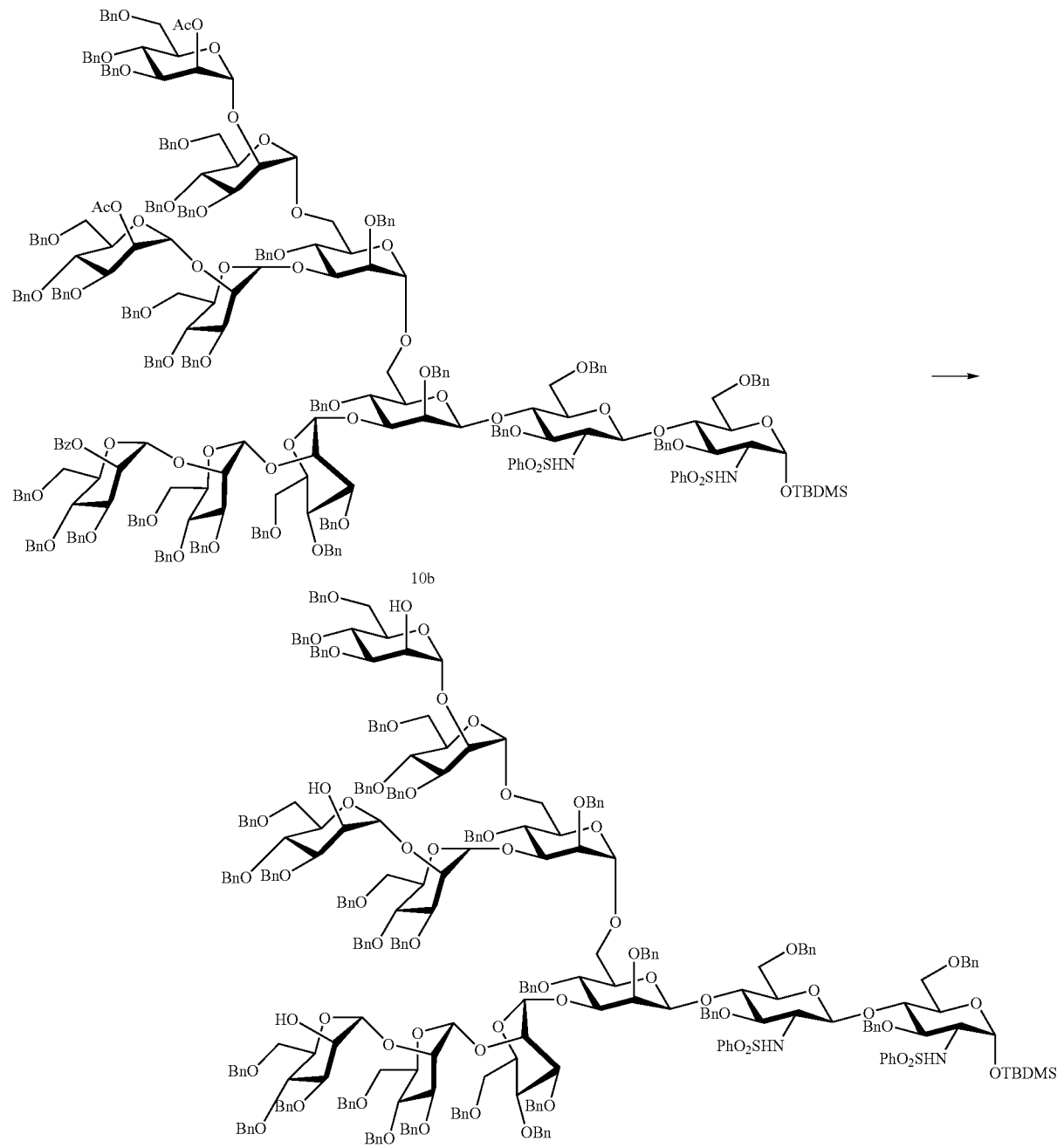

Undecasaccharide triol 24: 24 was prepared using the same procedure as described for 7. 24, white solide (468 mg, 96%). $[\alpha]_D^{25}$ 214.3 (c 0.23, CHCl$_3$). $^1$H NMR (400 MHz, CDCl$_3$) selected signals: δ 0.03 (s, 3H), 0.05 (s, 3H), 0.90 (s, 9H), 5.07 (s, 1H), 5.08 (s, 1H), 5.13 (s, 1H), 5.18 (s, 1H), 5.21 (s, 1H), 5.30 (s, 1H). $^{13}$C NMR (100 MHz, CDCl$_3$) δ −5.7, −4.5, 0.0, 14.1, 18.0, 21.0, 25.8, 29.6, 57.9, 58.6, 60.3, 67.6, 68.4, 68.6, 68.7, 68.9, 71.5, 71.9, 72.0, 72.3, 73.0, 73.1-73.5, 74.2, 74.5, 74.7, 74.9, 75.0, 75.2, 79.9, 80.0, 92.7, 99.4, 100.2, 100.7, 101.1, 101.5, 102.3, 126.7-128.7, 138.1-138.8, 140.7, 141.3. LRMS (ESI) calcd for $C_{287}H_{310}N_2O_{58}S_2SiNa_2$ $[M+2Na]^{2+}$ 2425.0, found 2425.2.

EXAMPLE 16

Undecasaceharide tetraol 19: To a solution of 24 (468 mg, 0.097 mmol) in HAc (1.0 M in THF, 2.5 mL) was added TBAF (1.0 M in THF, 2.5 mL) and the reaction mixture was stirred for 1 h before additional HAc (1.0 M in THF, 5.0 mL) was added. The mixture was concentrated and residue purified by column chromatography using 2.5% MeOH in $CH_2Cl_2$ as the eluent to afford 19 as a white solid (460 mg, 98%). $[\alpha]_D^{25}$ 121.7 (c 0.32, $CHCl_3$). $^1$H NMR (400 MHz,

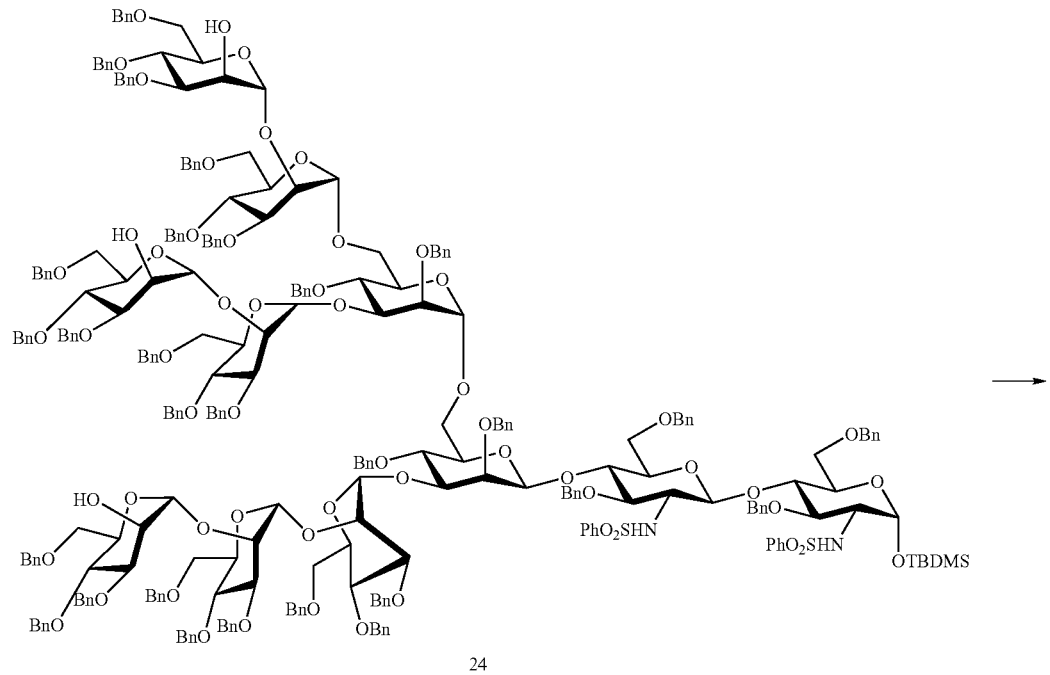

24

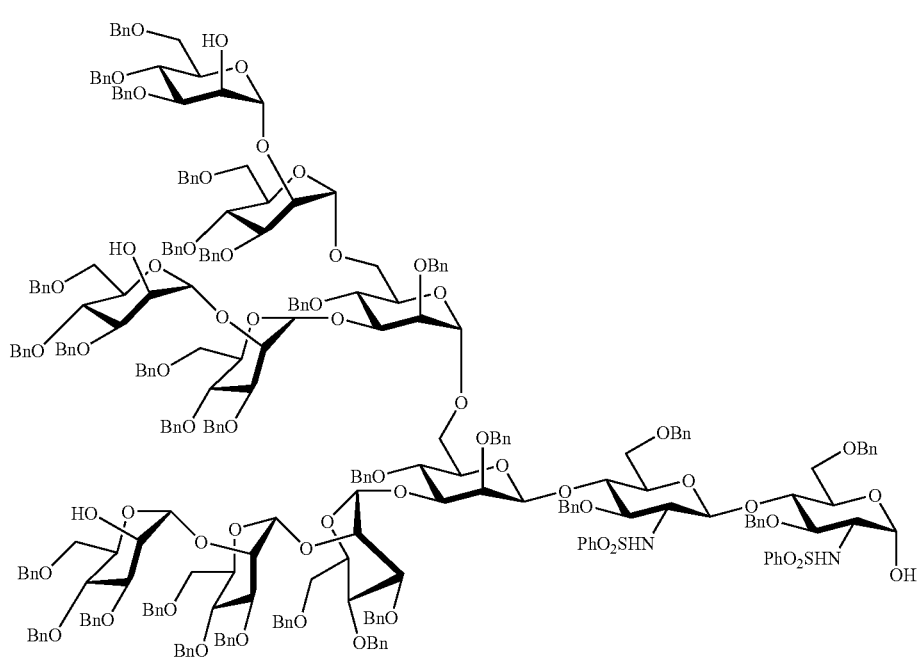

19

CDCl$_3$) selected signals: δ 4.95 (bs, 2H), 5.08 (s, 1H), 5.20 (bs, 2H), 5.24 (s, 1H), 5.27 (s, 1H). LRMS (ESI) calcd for C$_{281}$H$_{296}$N$_2$O$_{58}$S$_2$Na$_2$ [M+2Na]$^{2+}$ 2367.9, found 2367.6.

EXAMPLE 17

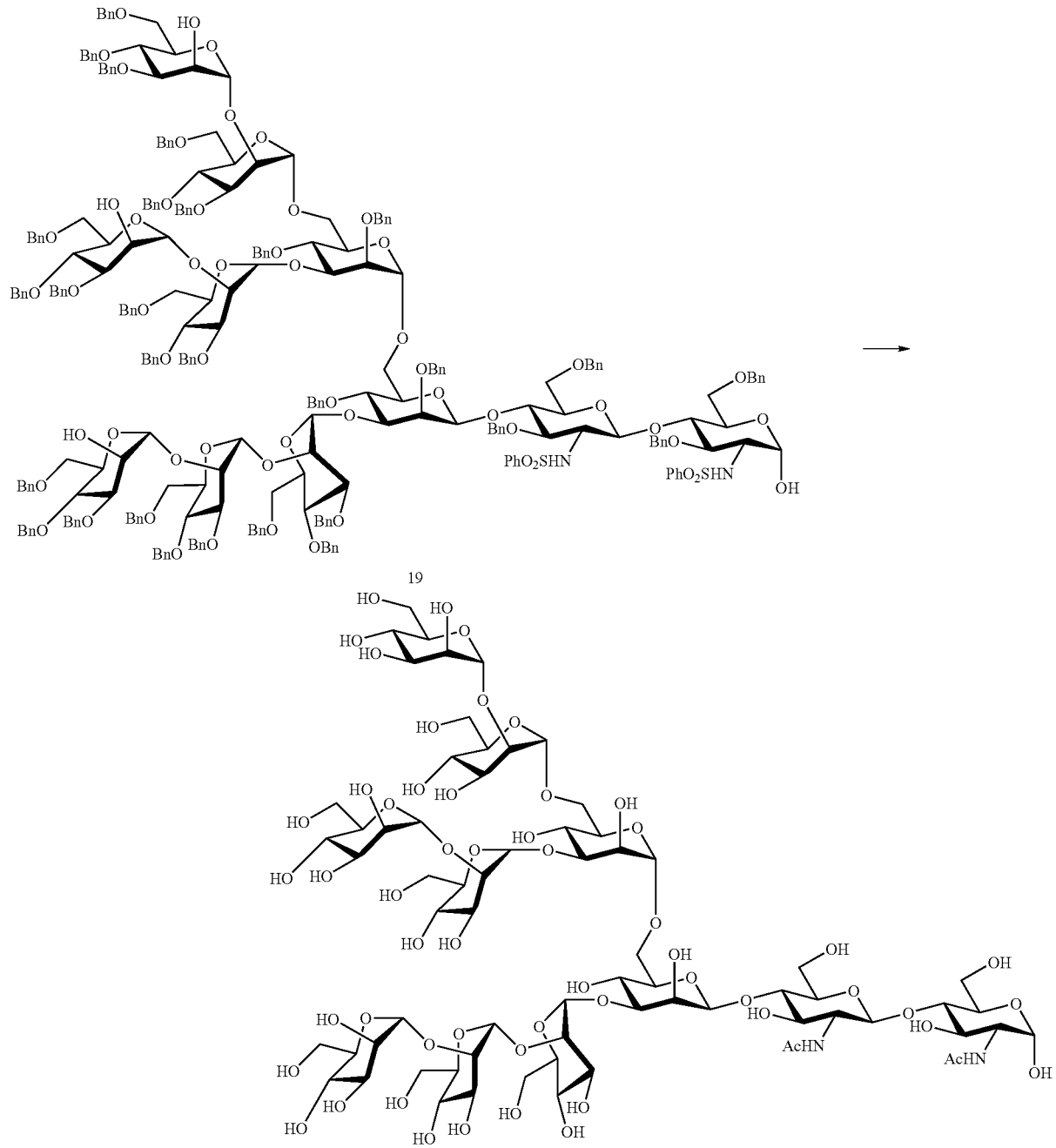

Glycan 20: To a solution of sodium (101 mg, 4.391 mmol) in 15 mL liquid ammonia was added 19 (95 mg, 0.020 mmol) in THF (4 mL) at −78° C. and the reaction mixture was stirred for 2 h at −78° C. The reaction was quenched with solid NH$_4$Cl at −78° C. and then warmed up to r.t. while argon was blowing through the reaction flask to evaporate all liquid. The residue was dried on vaccum for 2 h and dissolved in saturated NaHCO$_3$ aqueous solution (2 mL) and cooled to 0° C. Ac$_2$O (0.1 mL) was then added at 0° C. and the ice bath was then removed and 5 min later additional Ac$_2$O (0.05 mL) was added. 30 min later, low resolution mass spectrum showed reaction is complete. The reaction mixture was loaded on to a Bio-Gel P-2 column (BIO-RAD, catalog number 150-4134, molecular cutoff 2000) using water as the eluent to remove salt and small molecular weight compounds. The fraction containing desired material (illustrated by MassSpectrum) was conbined and lyophilized to afford glycan 20 as a white solid (33 mg, 87% from 19). $^1$H NMR (400 MHz, CDCl$_3$) selected signals: δ 5.07 (bs, 2H), 5.08 (s, 1H), 5.13 (s, 1H), 5.33 (s, 1H), 5.36 (s, 1H), 5.40 (s, 1H). LRMS (ESI) calcd for C$_{70}$H$_{118}$N$_2$O$_{56}$Na$^+$ [M+Na]$^+$ 1905.6, found 1905.6.

EXAMPLE 18

Glycosylamine 21: A solution of 20 (33 mg, 0.018 mmol), NH$_4$Cl (10 g) in 30 mL water was heated to 40° C. for 2 days and Mass spectrum indicated that reaction is complete. So the reaction mixture was frozen and lyophilized. The residue was dissolved in 20 mL water, frozen and lyophilized again. This process was repeated until the weight of the residue is constant (36 mg). LRMS (ESI) calcd for C$_{70}$H$_{119}$N$_3$O$_{55}$Na$^+$ [M+Na]$^+$ 1904.7, found 1904.8.

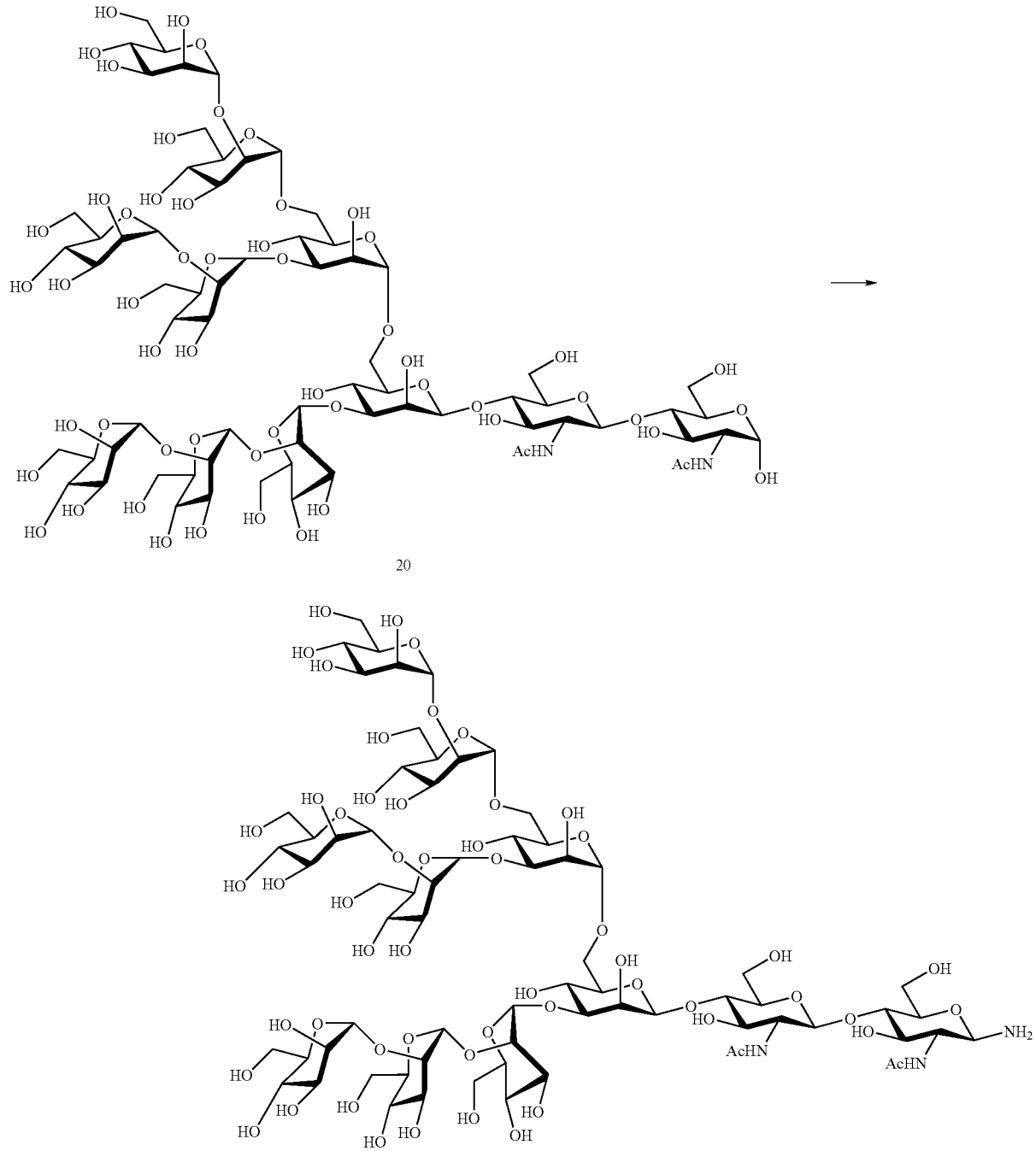

EXAMPLE 19

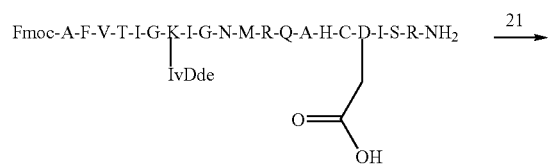

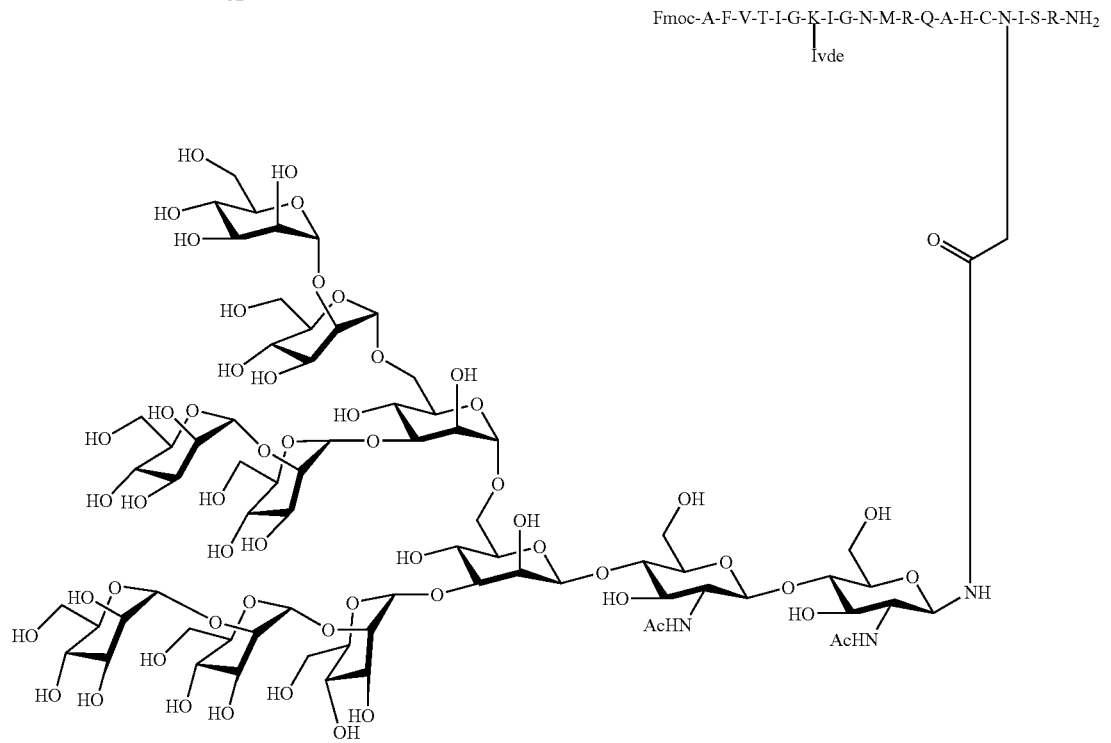

(SEQ ID NO: 4)

23

Gp120 glycopeptide 23: A solution of peptide acid 32 (21 mg, 0.008 mmol), HATU (6 mg, 0.016 mmol), diehtylpropylamine (DIEPA) (2 µL, 0.011 mmol) in DMSO (150 µL) was stirred for 5 min and transferred to the flask containing 21 (5 mg, 0.002 mmol) and the reaction mixture was stirred for 2 h. Additional DIEPA was added (0.6 µL at 4 h and 0.6 µL at 6H). At 7 h, a mixture of hydrazine, piperidine and DMF (volume ratio: 5:15:85, 0.2 mL) was added and the reaction mixture was stirred for 5 min and TFA in water (10%, 0.55 mL) was added and stirred for 30 min. The crude solution was purified by HPLC using a Varian C18-DYNAMAX-60 Å column. HPLC Conditions: 10%B to 50%B over 50 min, UV 214 nM (A: 0.05% TFA in water; B: 0.04% TFA in $CH_3CN$). Retention time: 19.8 min. The fraction containing 23 was lyophilized to give 23 as a white solid (1.7 mg, 16% from 20). $^1H$ NMR (400 MHz, $CDCl_3$) selected signals: δ 4.99 (s, 1H), 5.16 (s, 1H), 5.19 (s, 1H), 5.25 (s, 1H), 8.29 (s, 1H). LRMS (ESI) calcd for $C_{164}H_{275}N_{35}O_{80}S_2Na_3$ $[M+3Na]^{3+}$ 1360.6, found 1360.7; calcd for $C_{164}H_{275}N_{35}O_{80}S_2Na_4$ $[M+4Na]^{4+}$ 1020.7, found 1020.6.

REFERENCES (1) Dudkin, V. Y.; Miller, J. S.; Danishefsky, S. J. *Tetrahedron Letters* 2003, 44, 1791-1793.

(2) Zhang, Y.-M.; Mallet, J.-M.; Sinay, P. *Carbohydrate Research* 1992, 236, 73-88.

(3) Marra, A.; Mallet, J. M.; Amatore, C.; Sinay, P. *Synlett* 1990, 572-574.

(4) Matsuo, I.; Wada, M.; Manabe, S.; Yamaguchi, Y.; Otake, K.; Kato, K.; Ito, Y. *Journal of the American Chemical Society* 2003, 125, 3402-3403.

(5) Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H.; Kelly, J. W.; Rudd, P. M.; Dwek, R. A.; Katinger, H.; Burton, D. R.; Wilson, I. A. *Science (Washington, D.C., United States)* 2003, 300, 2065-2071.

(6) Likhosherstov, L. M.; Novikova, O. S.; Derevitskaya, V. A.; Kochetkov, N. K. *Carbohydrate Research* 1986, 146, C1-C5.

EXAMPLE 20

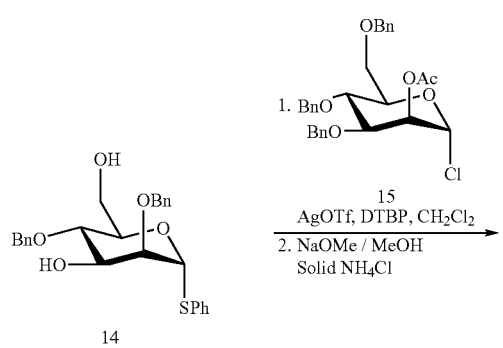

Into a 25 mL flask containing donor 15 (0.169 gm, 0.332 mmol) and acceptors 14 (0.037 gm, 0.083 mmol) (azeotropically dried with toluene) in 1.5 dichloromethane was added activated MS 4A and the mixture was stirred for 1 hr at room temperature. In a separate flask, AgOTf (0.087 gm, 0.332 mmol) and DTBP (0.078 mL, 0.347 mmol) in 1.5 mL of dichloromethane were stirred with MS 4A. After stirring for 1 hr, the flask containing the AgOTf/DTBP was cooled to −10° C. and the solution containing mixture of donor and acceptor was added over 5 minutes. The solution was stirred in dark with gradual warming up to room temperature over 24 hr. The reaction mixture was diluted with ethyl acetate and was added aqueous saturated NaHCO₃. After stirring for 10 minutes, the reaction mixture was filtered through bed of Celite and the filtrate was washed with water, then with brine, dried over MgSO₄ and evaporated in vacuo. The crude product was purified by silica gel column chromatography (10% ethyl acetate/toluene) to afford semi pure trimer diacetate. This diacetate was dried azeotropically with toluene and dissolved in 2 mL of anhydrous methanol under argon. Sodium methoxide, 25% by weight in methanol (100 μL) was added and the reaction mixture was stirred for 12 h. Solid ammonium chloride was added and the resulting solution was stirred for 20 min. The reaction mixture was carefully evaporated to solid residues, and the solid residues were washed with ethyl acetate. Evaporation of ethyl acetate layer provided crude product, which was purified by silica gel column chromatography (10% ethyl acetate/dichloromethane) to yield diol 17 in 65% yield (over two steps. [α]+53.1 (c 1, CHCl₃); ¹H-NMR (CDCl₃, 400 MHz) δ 7.33-7.03 (45H, m, aromatic), 5.44 (1H, br-s), 5.17 (1H, br-s), 4.94 (1H, br-s), ; ¹³C-NMR (CDCl₃, 125 MHz) δ 138.68, 138.66, 138.4, 138.1, 138.06, 138.03, 134.9, 131.0, 129.3, 128.72, 128.70, 128.67, 128.61, 128.49, 128.47, 128.16, 128.13, 128.10, 128.01, 127.96, 127.88, 127.86, 127.83, 127.82, 127.79, 127.76, 127.71, 127.35, 99.9, 85.3, 80.5, 80.2, 79.6, 75.3, 75.15, 75.07, 74.6, 74.4, 73.8, 73.5, 72.7, 72.3, 72.2, 71.8, 71.7, 71.3, 69.5, 68.94, 68.90, 68.2, 66.4. ESI-MS calcd for C₈₀H₈₄O₁₅S Na [M+Na]¹⁺ m/z=1339.5: found 1339.5

EXAMPLE 21

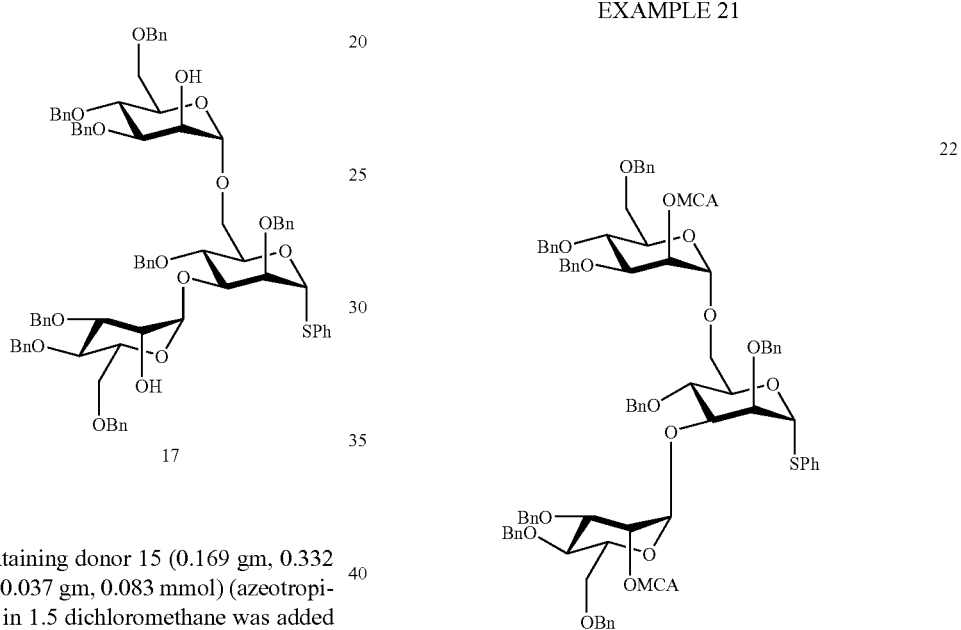

Into a 25 mL flask containing 17 (0.099 gm, 0.0689 mmol, azeotropically dried with toluene) in 0.4 mL mL of dry dichloromethane under argon and cooled to 0° C. Pyridine (55 μL, mmol, 6.8 mmol) and chloroacetic anhydride (0.047 gm, 0.0275 mmol), were added successively and resulting reaction mixture was stirred for 2 h at 0° C., and then diluted with ethyl acetate, washed two times with 0.5N HCl, water, sat NaHCO₃, brine, and dried with MgSO₄. Evaporation of ethyl acetate layer followed by silica gel column chromatography (20 ethyl acetate in hexanes) provided 0.166 gm (79% yield) of 22. R_f 0.33 (20% ethyl acetate in hexanes). [α]+58.2 (c 1, CHCl₃); ¹H-NMR (CDCl₃, 400 MHz) δ 7.30-7.03 (45H, m, aromatic), 5.47 (2H, m), 5.41 (1H, br-s), 5.15 (1H, s), 4.88 (1H, s), 4.75 (2H, t, J=10.5 Hz); ¹³C-NMR (CDCl₃, 125 MHz) δ 166.88, 166.78, 138.57, 138.51, 138.3, 137.79, 137.76, 137.74, 134.7, 130.9, 129.3, 128.7, 128.6, 128.59, 128.51, 128.48, 128.43, 128.30, 128.10, 128.0, 127.97, 128.86, 127.78, 127.75, 127.74, 127.7, 127.4, 99.5, 97.9, 84.9, 79.0, 78.1, 77.7, 75.4, 75.2, 75.1, 74.3, 74.1, 73.7, 73.5, 72.43, 72.37, 72.29, 71.78, 71.69, 70.7, 70.4, 69.0, 68.7, 66.8, 41.2, 41.0

EXAMPLE 22

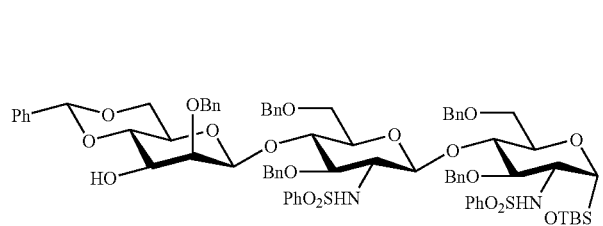 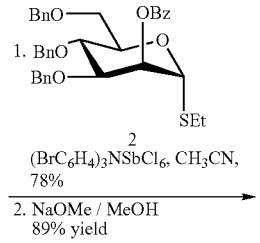

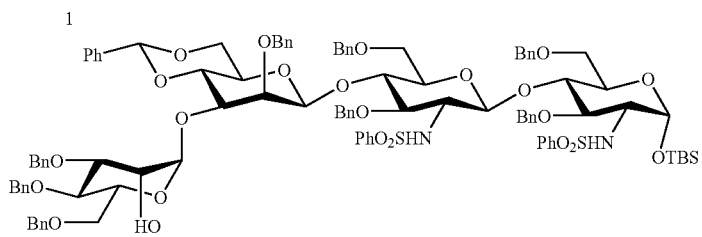

Into a 25 mL flask containing donor 2 (125 mg, 0.0696 mmol, azeotropically dried with toluene) and 4A molecular sieves in dry acetonitrile were stirred for 1 hr under argon. Tris (4-bromophenyl) aminium hexachloroantimonate [(BrC$_6$H$_4$)$_3$NSbCl$_6$] (140 mg, promoter) and then a solution of acceptor 1 (100 mg, 0.0696 mmol) were added slowly while cooling the flask at 15° C. After stirring for 15 min, another portion of tris (4-bromophenyl) aminium hexachloroantimonate [(BrC$_6$H$_4$)$_3$NSbCl$_6$] (46 mg) was added and the reaction mixture was warmed to room temperature and stirred for 3 hr. Freshly distilled triethyl amine (1.5 mL) was added to neutralize the reaction. The reaction mixture was filtered through a bed of Celite and concentrated. The crude product was purified by silica gel column chromatography to afford tetrasaccharide (0.110 gm). R$_f$0.65 (20% ethyl acetate in toluene). Under argon this material was dissolved in mixture of dry methanol (2 mL) and dichloromethane (1.5 mL). Sodium methoxide, 25% by weight in methanol (0.038 mL) was added and stirred for 12 hr. Solid ammonium chloride was added and the mixture was evaporated to dryness. The solid residue was washed several times with ethyl acetate and concentrated. Purification by silica gel column chromatography afforded the 0.092 gm (89% yield) of 23. R$_f$0.42 (40% ethyl acetate in hexanes). [α]–8.8 (c 1, CHCl$_3$); $^1$H-NMR (CDCl$_3$, 400 MHz) (selected signals) δ 7.75 (2H, d, J=7.6 Hz), 7.72 (2H, d, J=6.8 Hz), 5.41 (1H, br-s), 5.26 (1H, d, J=2.0 Hz), 5.11 (1H, d, J=2.4 Hz), 3.14 (1H, m), 3.0 (2H, m), 1.57 (1H, br-s), 0.908 (9H, s), 0.09 (3H, s), 0.03 (3H, s); $^{13}$C-NMR (CDCl$_3$, 100 MHz) δ 141.7, 140.9, 138.7, 138.65, 138.61, 138.4, 138.0, 137.9, 137.8, 137.5, 132.6, 132.4, 129.5, 129.1, 129.0, (128.9-127.6), 127.4, 127.3, 127.2, 126.2, 101.5, 101.3, 101.1, 100.4, 93.0, 80.3, 80.0, 76.2, 75.8, 75.6, 75.5, 75.2, 74.8, 74.4, 73.96, 73.87, 73.6, 72.2, 72.0, 69.9, 69.3, 68.8, 68.5, 68.2, 67.8, 67.2, 37.5, 33.8, 33.6, 32.1, 30.3, 30.2, 29.9, 29.5, 29.1, 27.3, 26.9, 26.0, 23.4, 22.9, 19.9, 18.2, 14.4, 14.3, 7.6, –4.2, –5.4.

EXAMPLE 23

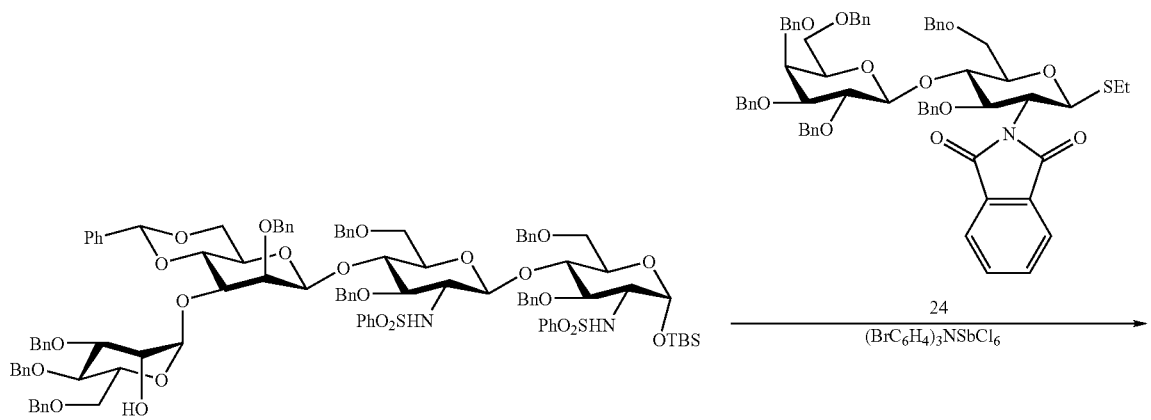

-continued

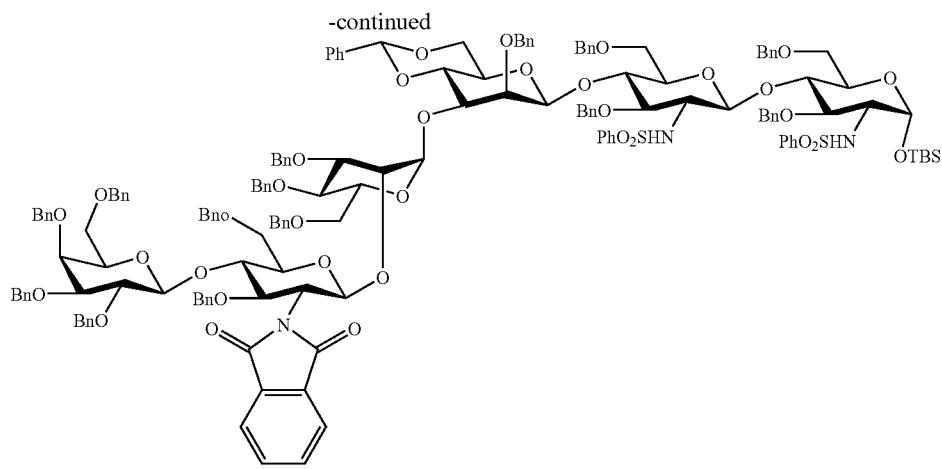

25

Into a 25 mL round-bottomed flask containing acceptor 23 (0.100 gm, 0.0535 mmol, azeotropically dried with toluene) in 1 mL dry acetonitrile was added 4A activated molecular sieves and was stirred at room temperature under argon for 1 hr. Similarly the donor 24 (0.1498 mmol, 0.158 gm) and 4A molecular sieves in 1 mL dry acetonitrile were stirred at room temperature for 1 hr. The flask containing donor was cooled to 15° C. and 0.091 gm of tris (4-bromophenyl) aminium hexachloroantimonate [$(BrC_6H_4)_3NSbCl_6$] (promoter) was added followed by the solution of acceptor. The reaction mixture was stirred at 15° C. for 20 min and then additional 0.031 gm of promoter was added. The cooling bath was removed and the reaction mixture was stirred for 3 hr. The reaction mixture was cooled to 0° C. and triethyl amine (1 mL) was added. After stirring 10 min at 0° C., the reaction mixture was warmed to room temperature and stirred for additional 10 min. Filtering through a pad of Celite and evaporation of the filtrate afforded the crude product, which was purified by preparative TLC (first using 5% ethyl acetate in dichloromethane, then 30% ethyl acetate in hexanes) to afford 0.091 gm of 25 (60% yield), [α]−16.6 (c 1, $CHCl_3$); $^1$H-NMR ($CDCl_3$, 400 MHz) (selected signals) δ 7.72 (2H, d, J=7.2 Hz), 7.67 (2H, d, J=7.2 Hz), 5.21 (1H, br-s), 5.07 (1H, br-s), 5.01 (1H, br-s), 4.98 (1H, d, J=8 Hz), 2.99 (1H, m), 2.89 (1H, t, J=8.4 Hz), 2.80 (1H, m), 2.64 (2H, m), 0.875 (9H, s), 0.07 (3H, s), 0.05 (3H, s); $^{13}$C-NMR ($CDCl_3$, 100 MHz) δ 140.5, 139.7, 138.04, 138.01, 137.7, 137.69, 137.63, 137.59, 137.56, 137.47, 137.41, 137.3, 137.0, 136.8, 136.5, 136.4, 132.4, 131.3, 131.1, 130.9, 128.4, 128.1, 127.8, (127.5-126.1), 125.8, 125.3, 122.4, 122.0, 102.3, 100.3, 99.9, 99.4, 96.5, 94.7, 91.8, 81.5, 78.9, 77.6, 77.36, 77.31, 75.1, 74.4, 74.2, 74.1, 73.9, 73.8, 73.6, 73.5, 73.1, 72.8, 72.7, 72.4, 72.2, 71.9, 71.8, 71.6, 71.5, 71.2, 57.8, 56.9, 51.3, 28.7, 24.8, 16.9, 7.6, −5.4, −6.6

EXAMPLE 24

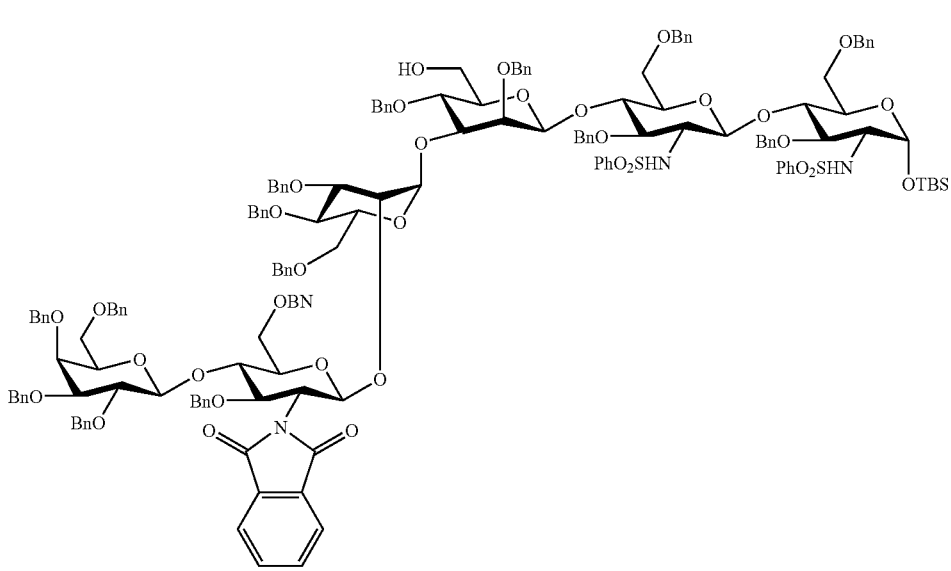

26

To the azeotropically dried 25 (0.307 gm, 0.107 mmol) in 25 mL round bottomed flask was added 8 mL of $BH_3 \cdot THF$ (1 molar) and stirred for 5 minutes at room temperature. The reaction mixture was cooled to 0° C. and 0.35 mL of $nBu_2OTf$ (1 molar in $CH_2Cl_2$) was added. The resulting reaction mixture was stirred at 0° C. for 9 hr. Freshly distilled triethyl amine (0.492 mL) was added and followed by careful addition of methanol until the evolution of $H_2$ had ceased. The reaction was evaporated to dryness, twice codistilled from methanol to afford the crude product as clear oil. Purification by silica gel column chromatography (30% ethyl acetate in hexanes) provided the 26 in 75% yield (0.231 gm).

[α]−7.0 (c 1, $CHCl_3$); $^1$H-NMR ($CDCl_3$, 400 MHz) (selected signals) δ 7.74 (2H, d, J=7.2 Hz), 7.69 (2H, d, J=6.8 Hz), 5.07 (2H, m), 2.96 (1H, m), 2.75 (2H, m), 0.90 (9H, s), 0.07 (3H, s), 0.02 (3H, s); $^{13}$C-NMR ($CDCl_3$, 100 MHz) δ 168.5, 167.7, 141.4, 140.9, 139.3, 139.2, 138.97, 138.91, 138.73, 138.66, 138.64, 138.58, 138.50, 138.45, 138.27, 138.1, 137.8, (129.2-126.9), 123.5, 123.4, 103.3, 101.0, 100.9, 99.2, 96.5, 92.9, 82.6, 80.1, 79.9, 78.7, 78.4, 76.5, 76.0, 75.9, 75.4, 75.1, 74.9, 74.8, 74.68, 74.63, 74.49, 74.34, 74.29, 74.24, 73.84, 73.77, 73.6, 73.45, 73.3, 73.2, 73.0, 72.8, 72.7, 61.4, 60.6, 58.6, 59.2, 55.8, 26.0, 21.3, 19.3, 18.2, 14.4, 14.1, −4.2, −5.4.

EXAMPLE 25

Into a 5 mL v vial were taken azeotropically dried donor 22 and acceptor in 26 mL anhydrous acetonitrile and activated 4A MS was added. The resulting reaction mixture was stirred under argon for 1 hour at room temperature and then was cooled to 15° C. At this point Tris (4-bromophenyl) aminium hexachloroantimonate [$(BrC_6H_4)_3NSbCl_6$] was added to the reaction mixture. The cooling bath was removed and the reaction mixture was stirred at room temperature for 12 h or TLC indicated the disappearance of the acceptor. The reaction mixture was cooled to 0° C. and 2 mL triethyl amine was added and stirred for 30 minutes with gradual warming up to room temperature. The reaction mixture was filtered through a pad of Celite and concentrated to provide crude material, which was purified by preparative TLC (20×20 cm×1 mm thickness PK6F plates) using 40% ethyl acetate in hexanes to yield 27. [α]+9.4 (c 1, $CHCl_3$); $^1$H-NMR ($CDCl_3$, 400 MHz) (selected protons) δ 5.41 (1H, br-s), 5.32 (1H, br-s), 5.09 (1H, br-s), 4.97 (2H, m), 0.83 (9H, s), 0.05 (s, 3H), 0.03 (s, 3H); $^{13}$C-NMR ($CDCl_3$, 100 MHz) 168.6, 167.6, 166.70, 166.67, 141.5, 140.9, 139.30, 139.23, 139.0, 138.9, (138.8-138.1), 137.89, 137.86, 137.6, 133.6, 132.5, 132.3, 132.0, (129.0-126.9), 126.7, 103.3, 101.7, 100.9, 99.3, 98.0, 97.8, 96.3, 92.9, 82.6, 81.3, (78.9-65.1), 58.6, 58.1, 55.8, 39.9, 39.8, 28.7, 24.8, 17.0, −5.4, −6.7.

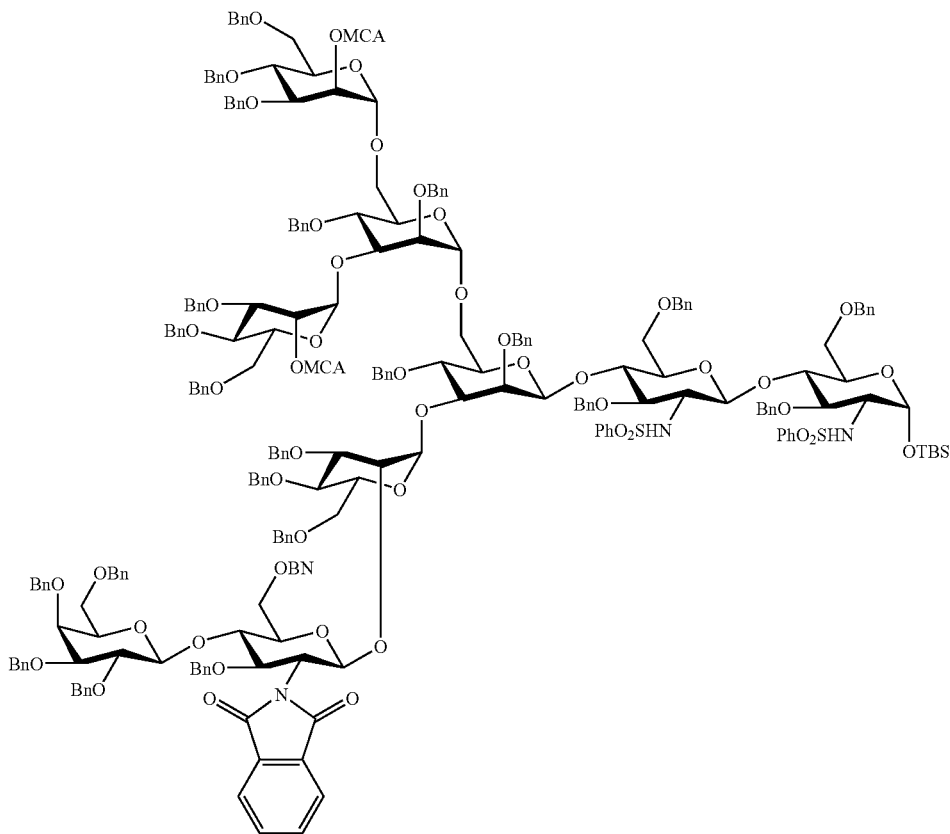

27

EXAMPLE 26

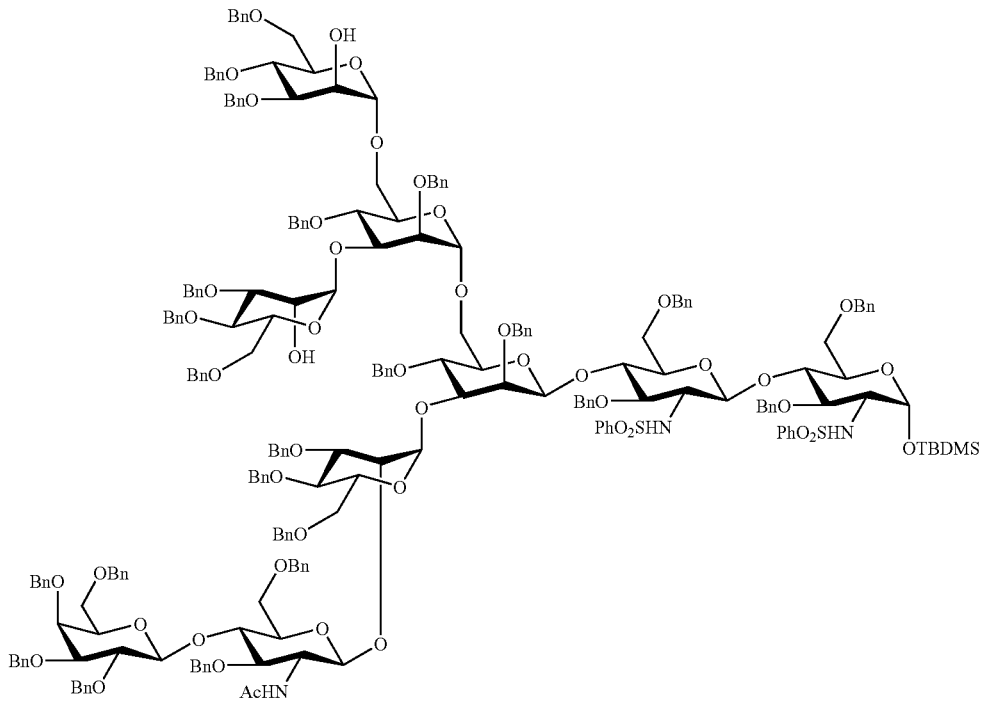

28

To azeotropically dried 27 (100 mg, 0.023 mmol) in a v 5 mL v vial equipped with spin bar were added fresh toluene (2 mL) and n-butanol (4 mL). Ethylenediamine was added and the reaction mixture was heated at 90° C. for 18 hr. After cooling to room temperature, the reaction mixture was concentrated under vacuo. The crude product was dissolved in 5 mL of toluene and evaporated to dryness. Pyridine and acetic anhydride were added and the reaction mixture was stirred for 16 hr at room temperature. The reaction mixture was evaporated to dryness, twice from toluene, yielding foam with some solid. This material was dissolved in 5 mL of methanol and 2 mL of THF under argon and 0.35 mL of 25% sodium methoxide in methanol was added and the reaction mixture was stirred for 12 hr. Solid ammonium chloride was added and stirred for 30 min. Careful evaporation of this biphasic reaction mixture provided white solid residue, which was washed three times by ethyl acetate. Concentration of ethyl acetate layer yielded the crude product, which was purified by preparative TLC (10% ethanol in toluene) to afford 28 in 69% yield (0.064 gm). $R_f$=0.67 (10 ethanol in toluene). $[\alpha]$+14.6 (c 1, $CHCl_3$); $^1$H-NMR ($CDCl_3$, 500 MHz) (selected protons) δ 7.65 (2H, d, J=9 Hz), 7.60 (2H, d, J=7.5 Hz), 5.22 (1H, d, J=8 Hz), 5.10 (1H, br-s), 5.07 (2H, br-s), 3.06 (1H, m), 2.96 (1H, m), 2.24 (2H, d, J=14.5 Hz), 1.68 (3H, s), 0.90 (9H, s), 0.07 (3H, s), 0.027 (3H, s). $^{13}$C-NMR ($CDCl_3$, 125 MHz)δ 169.6, 141.5, 140.9, 139.6, 139.3, 139.1, 138.97, 138.95, 138.89, 138.7, 138.6, 138.5, 138.39, 138.36, 138.3, 138.2, 138.0, 137.7, 132.6, 132.4, 129.0, 128.9, (128.7-127.3), 127.2, 126.7, 103.0, 102.0, 100.9, 100.0, 99.9, 98.3, 97.793.0, 82.5, 81.4, 80.2, 80.1, 79.7, 79.4, 78.8, 78.6, 78.1, 77.9, 77.8, 76.6, 76.0, 75.3, 75.2, 74.9, 74.8, 74.7, 74.4, 74.38, 74.35, 74.2, 73.9, 73.7, 73.6, 73.5, 73.49, 73.45, 73.37, 73.2, 73.1, 72.0, 71.9, 71.8, 71.4, 71.4, 71.3, 71.1, 70.0, 69.7, 69.1, 68.9, 68.7, 68.4, 67.9, 67.8, 66.7, 65.7, 58.8, 58.2, 57.2, 26.0, 23.6, 18.2, 1.2, −4.2, 5.4.

EXAMPLE 27

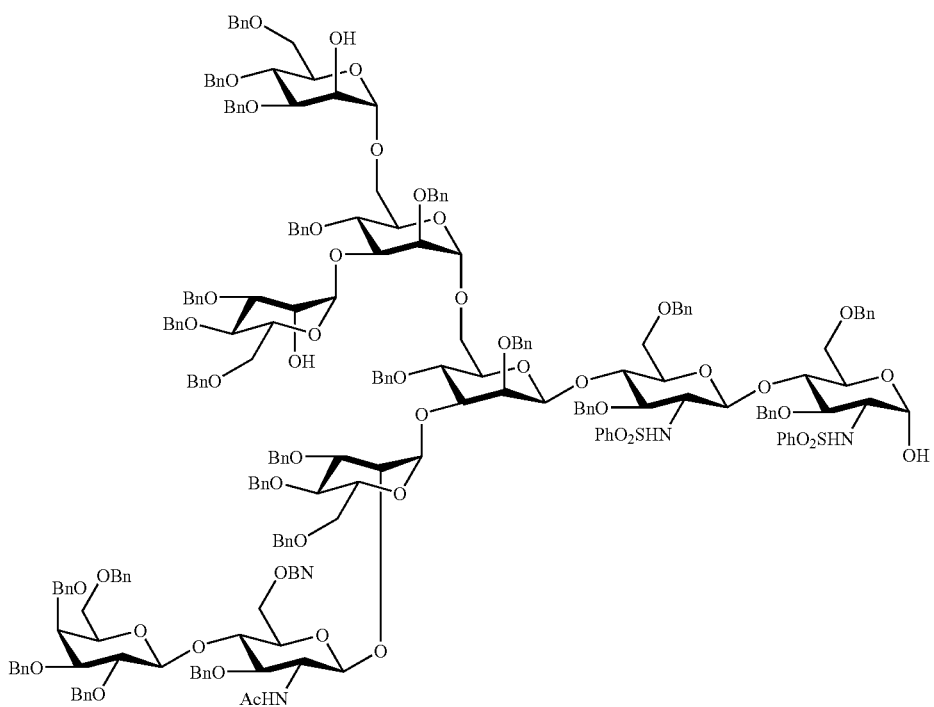

29

To the azeotropically dried 28 in a 25 mL round bottomed flask equipped with stir bar was added 0.5 mL 1M acetic acid in THF and the reaction mixture was cooled to 0° C. To this ice cooled reaction mixture was added 0.5 mL TBAF (1M in THF). The cooling bath was removed and the reaction mixture was stirred for 3 hr. Additional 2 mL 1M acetic acid in THF was added and the reaction mixture was stirred for 15 min. The reaction mixture was evaporated to dryness and the crude product was purified by preparative TLC (10% ethanol in toluene) to afford 0.055 gm (89% yield) of 29. $[\alpha]+9.40$ (c 1, CHCl$_3$); $^1$H-NMR (CDCl$_3$, 500 MHz) (selected protons) δ 7.66 (2H, d, J=8 Hz), 7.60 (2H, d, J=7.6 Hz), 5.17 (1H, d, J=7.2 Hz), 5.07 (1H, br-s), 5.01 (2H, m), 2.34 (1H, br), 2.18 (1H, br), 1.61 (s, 3H).

EXAMPLE 28

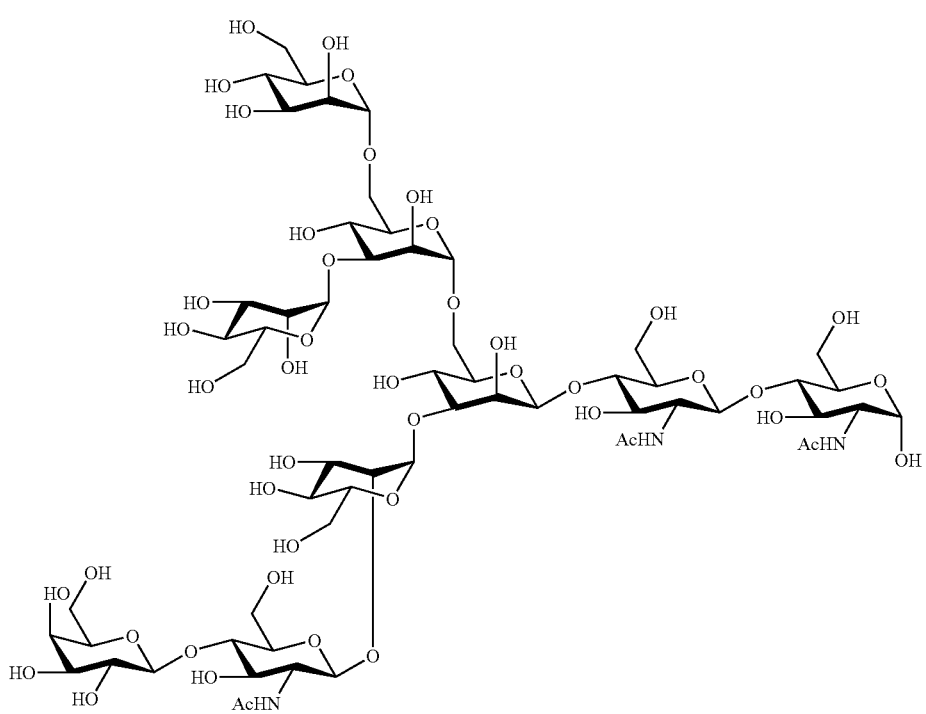

30

Into a three necked round bottomed flask, equipped with dry ice acetone condenser was condensed 15 mL ammonia under argon. Sodium metal (0.095 gm, 153 equiv.) was added in three portions. The resulting blue solution was stirred for 30 min at −78° C. The compound 29 (0.104 gm, 0.027 mmol) in 1.5 mL (3×0.5 mL) was added to the solution and the reaction mixture was stirred for 2 hr. Solid ammonium chloride (0.263 gm, 4.97 mmol) was added to quench the reaction and the reaction mixture was warmed to room temperature slowly. Evaporation of the residual liquid provided solid residue, which was dissolved in 5 mL pyridine. To this mixture was added acetic anhydride (3 mL) and DMAP (5 mg) and the resulting mixture was stirred with slowly warming to room temperature over 12 hr. The reaction mixture was evaporated to dryness and purified carefully by silica gel column chromatography to afford peracetate. The peracetate in 5 mL methanol was added solution of NaOMe, 25% by weight in methanol (0.4 mL) and was stirred for 24 hr. The resulting cloudy solution was treated with water at 0° C. and stirred for another 24 hr. The reaction mixture was neutralized using Amberlyst–15 acidic regin and evaporated to afford crude product, which was purified by size exclusion chromatography using Bio-Gel P2 regin yielding 30 mg of free glycan.

EXAMPLE 29

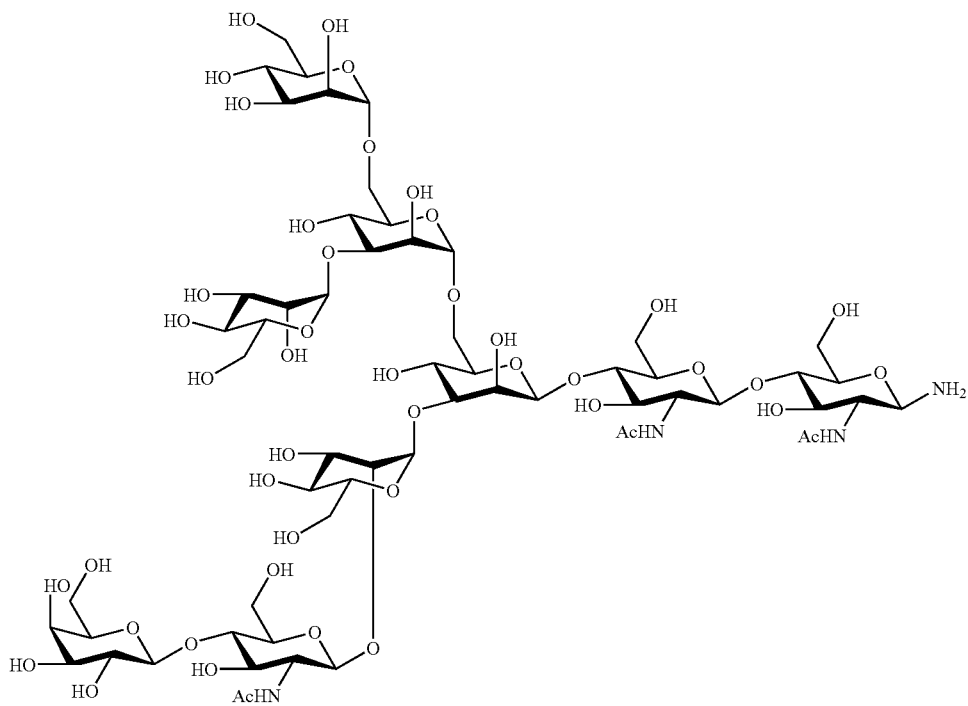

31

Free glycan (10 mg) in 15 mL of saturated ammonium bicarbonate was heated at 40° C. Additional ammoniumhydrogen carbonate was added time to time to keep the solution saturated. After two days of stirring the content of the flask was shell frozen, lyophilized, dissolved in water (10 mL), lyophilized; this process was repeated until the white solid residue reached constant mass of 10 mg, which was used directly in the next step.

EXAMPLE 30
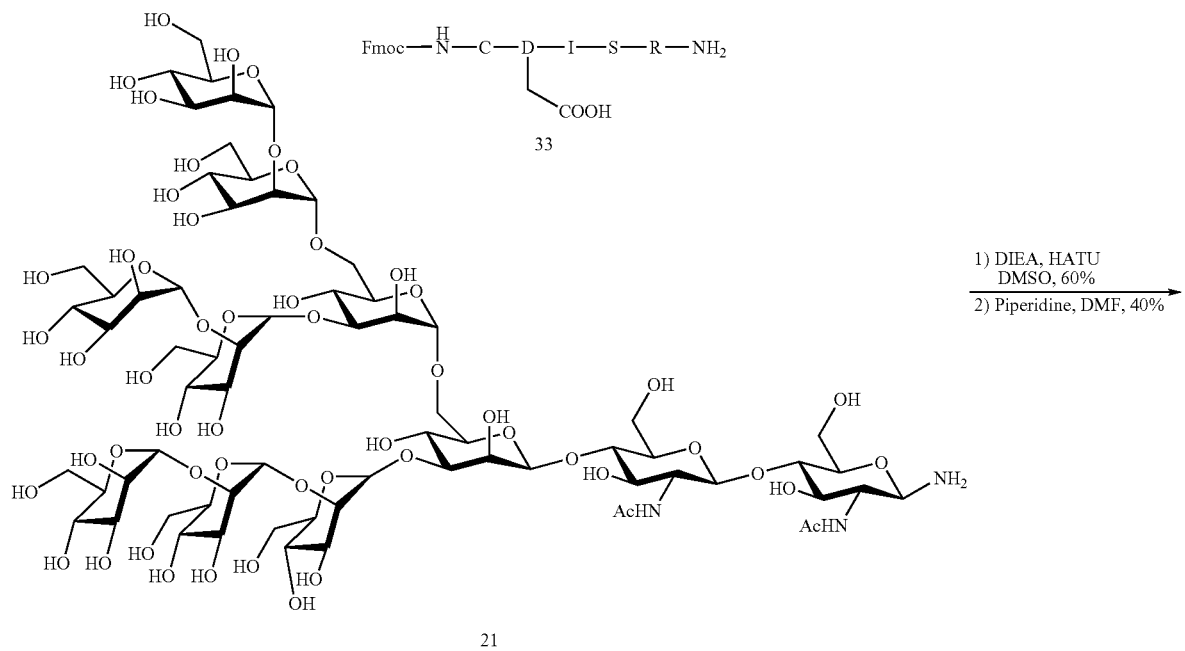
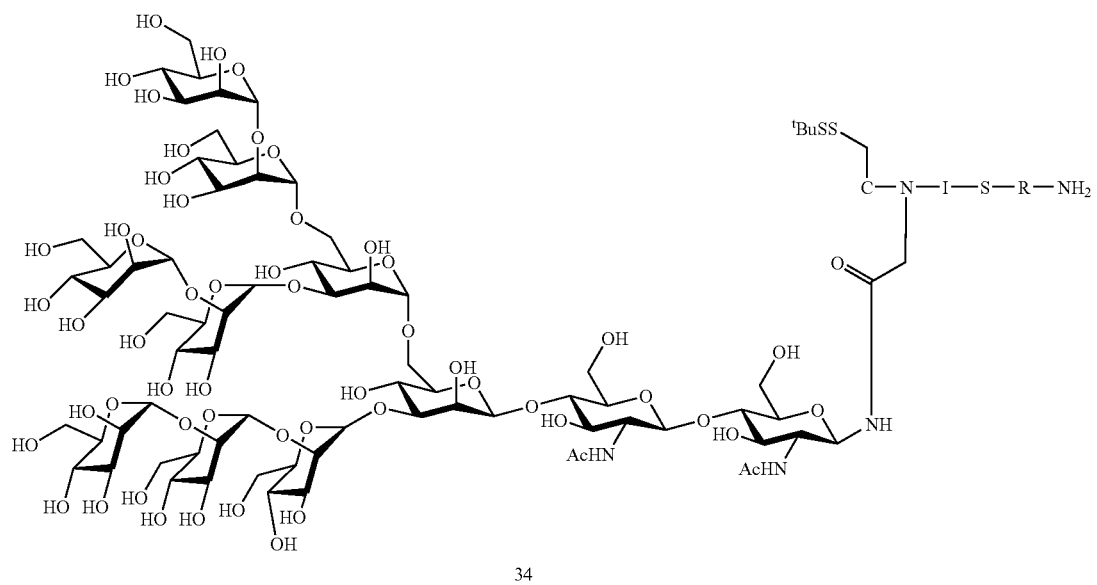

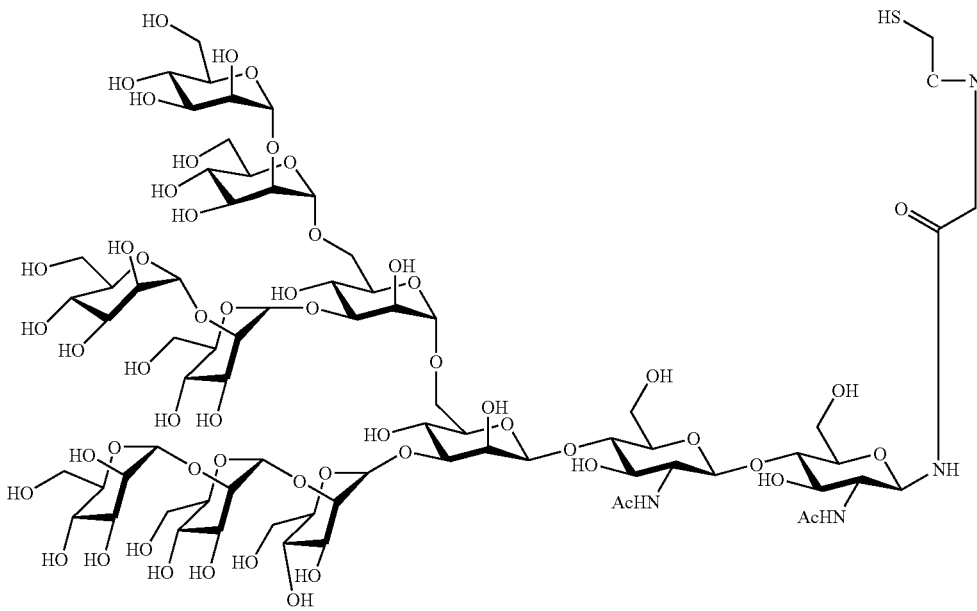

(SEQ ID NO: 3)
35

Glycopeptide 34:

A solution of acid 33 (6 mg, 0.007 mmol), HATU (5 mg, 0.013 mmol), DIEPA (1.7 µL, 0.012 mmol) in DMSO (0.1 mL) was stirred for 10 min and transferred to a falcon tube (25 mL) containing 4.2 mg of 21. The solution was stirred for 2 h and additional DIEPA (1.2 µL) was added. The reaction mixture was purified by semiprep HPLC column (30 to 50%B over 20 min) to afford Fmoc-protected glycopeptide (3.6 mg, 60%). LRMS (ESI) calcd for $C_{111}H_{177}N_{12}O_{64}S_2Na^{++}$ [M+H+Na]$^{++}$ 1394.5, found 1394.5. This Fmoc-protected glycopeptide was dissolved in 0.4 mL pipyridine/DMF (1:4) solution and stirred for 15 min and quenched by THF/H$_2$O (10%) until the pH=2~3. The crude mixture was purified on semiprep HPLC column (5 to 25%B over 20 min) to afford 34 (2 mg, 40%). LRMS (ESI) calcd for $C_{96}H_{167}N_{12}O_{62}S_2Na^{++}$ [M+H+Na]$^{++}$ 1283.5, found 1283.6. $^1$H NMR (400 MHz, CDCl$_3$) selected signals: δ 4.99 (s, 1H), 5.02 (s, 1H), 5.16 (s, 1H), 5.18 (s, 1H), 5.25 (s, 1H).

Glycopeptide 35:

To a solution of 34 (2 mg, 0.0008 mmol) in phosphorous buffer (NaH$_2$PO$_4$ and Na$_2$HPO$_4$, pH=7.4, 0.5 mL) was added HSCH$_2$CH$_2$SO$_3$Na (10 mg, 0.061 mmol) and stirred for 2 days. TCEP (30 mg, 0.104 mmol) was then added and the resulting solution was stirred for 1 h. The residue was purified on semiprep HPLC column (5 to 25% B over 20 min) to afford 35 (1.7 mg, 60%). LRMS (ESI) calcd for $C_{92}H_{160}N_{12}O_{62}S^{++}$ [M+2H]$^{++}$ 1228.5, found 1228.5. $^1$H NMR (400 MHz, CDCl$_3$) selected signals: δ 4.90 (s, 1H), 4.99 (s, 1H), 5.15 (s, 1H), 5.18 (s, 1H), 5.25 (s, 1H).

EXAMPLE 31

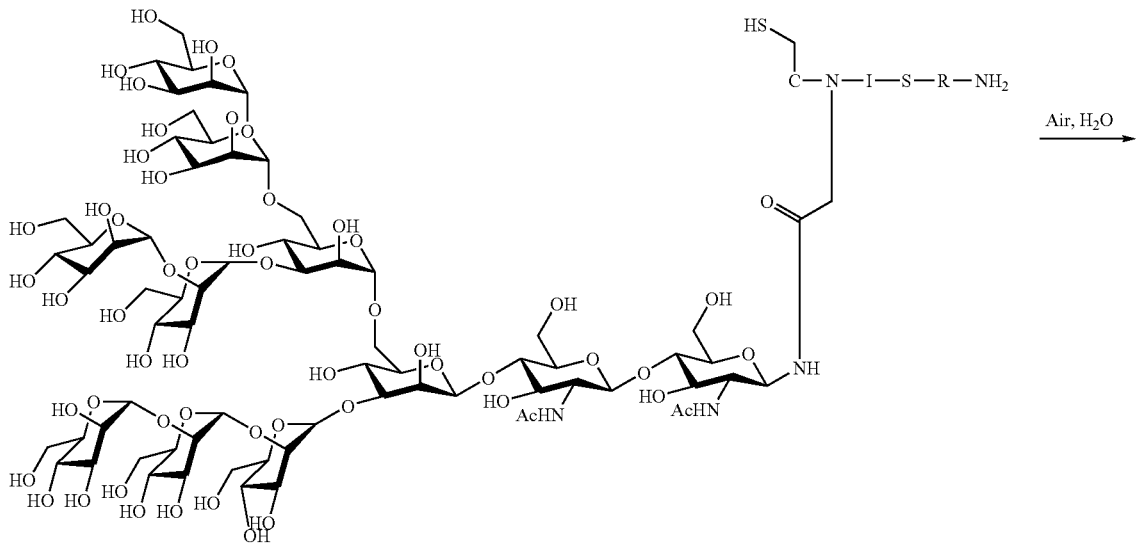

35

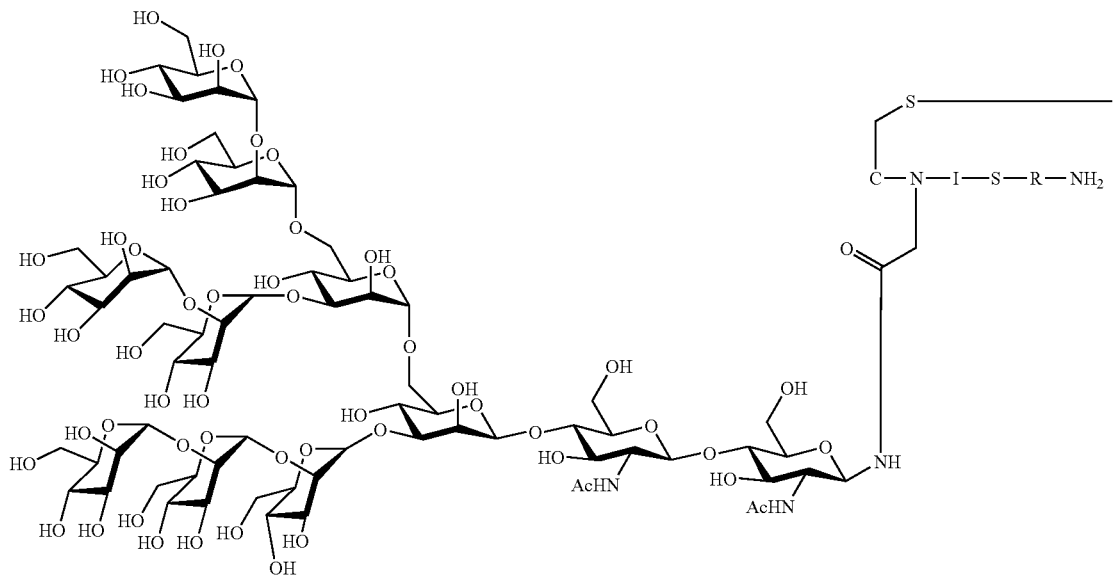
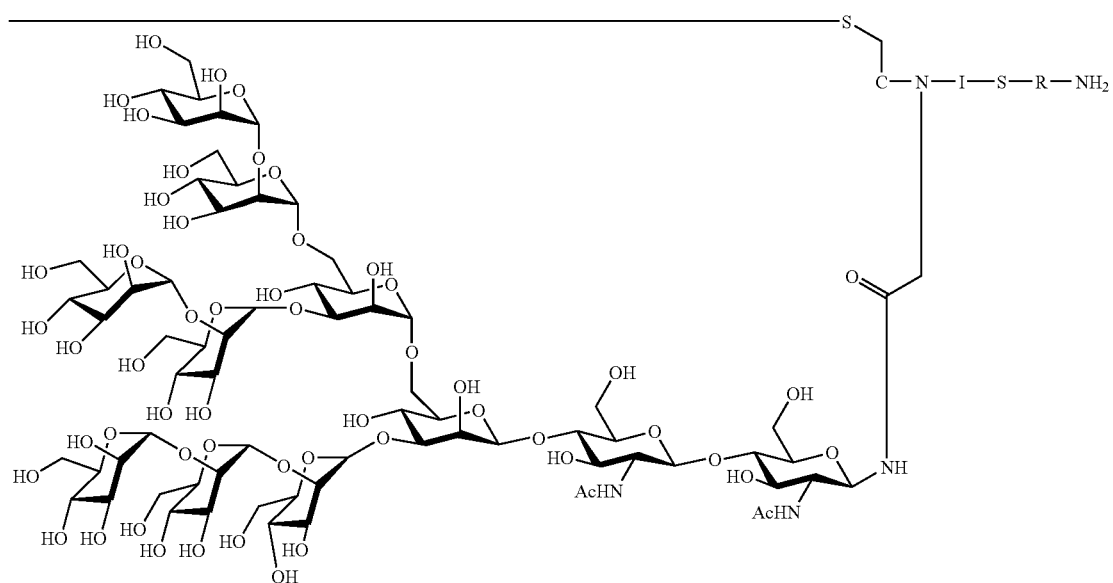
(SEQ ID NO: 3)
36
Glycopeptide, when dissolved in $H_2O$ and exposed to air, formed dimer 36. HPLC (Varian Microsorb 100-5-C18) retention time, 12.75 min (0% to 40% acetonitrile in water). LRMS: (ESI) $C_{184}H_{317}N_{24}O_{124}S_2$:$[M+3H]^{+++}$: calculated: 1636.95, found, 1636.99.

EXAMPLE 32
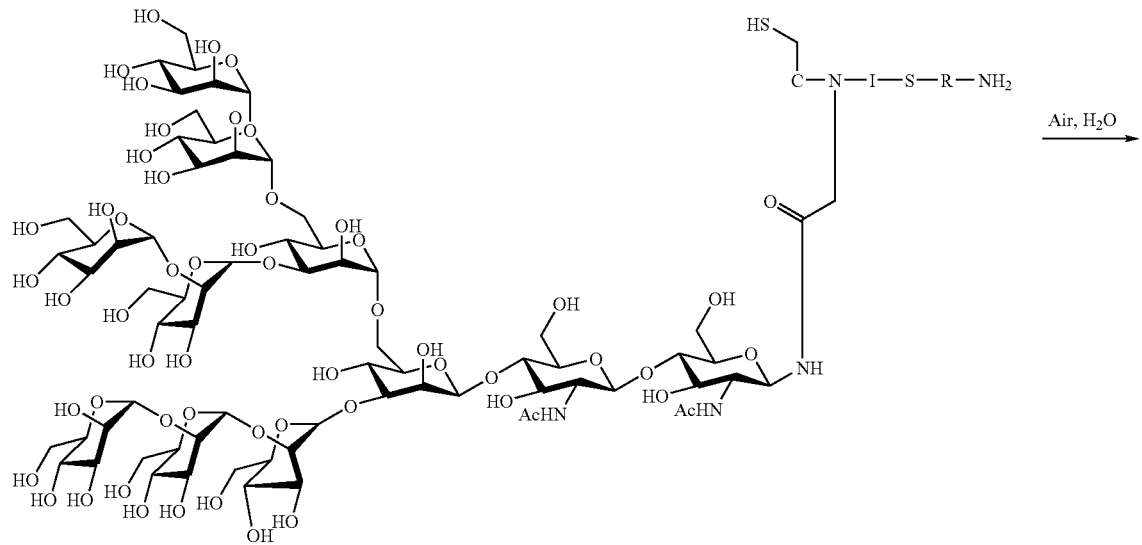
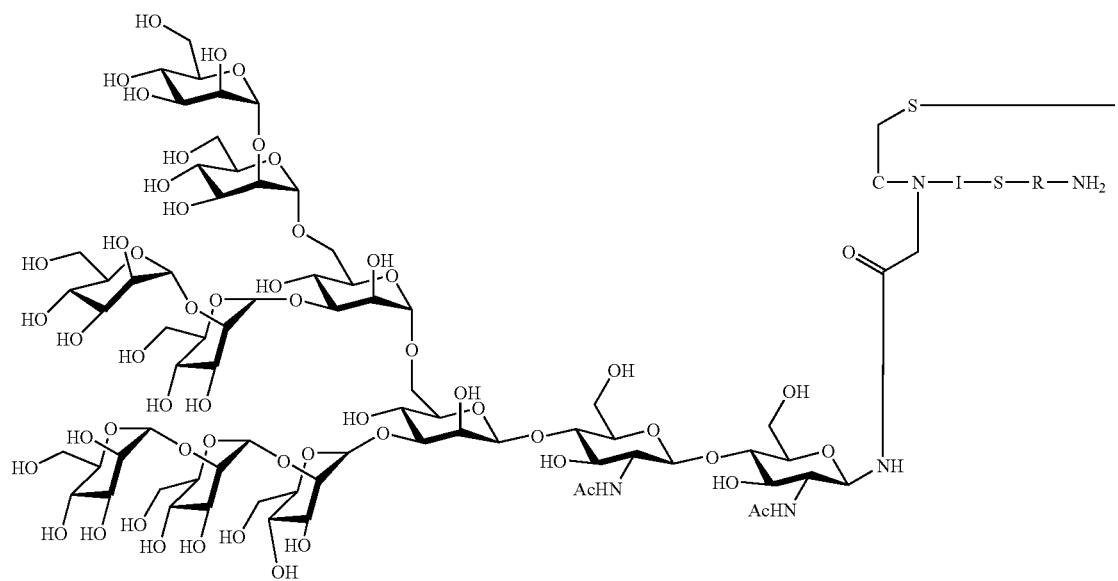

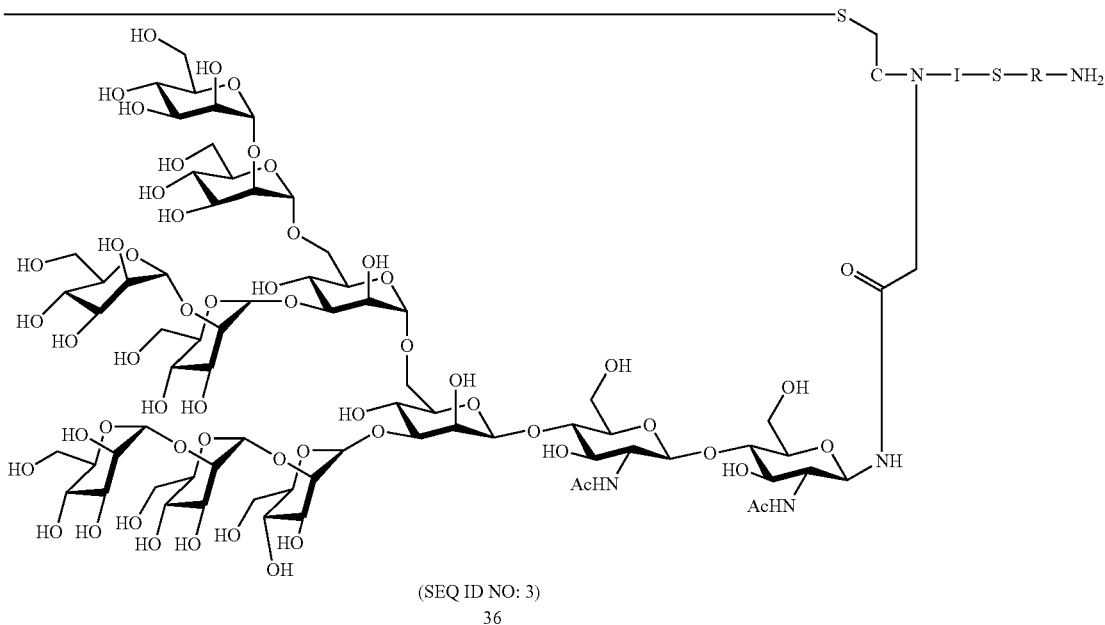

(SEQ ID NO: 3)
36

To a 15 mL polypropylene conical tube equipped with stir bar in 0.2 mL DMSO was added peptide 33 (11 mg, 3 equiv.) and HATU (15 mg, 5.9 equiv.). The solution was stirred for 1 min and was added diisopropyl ethyl amine (3.58 µL, 3 equiv.) and was stirred for another minute. This orange-yellow solution was transferred via 0.5 mL syringe to the flask containing glycosylamine 31 (11 mg). The conical tube was rinsed with additional 0.1 mL of DMSO and transferred to the flask containing glycosyl amine using the same 0.5 mL syringe. Monitoring by LCMS showed that no additional product formation after 6 hr. Purification of the reaction mixture by size exclusion chromatography provided the 37. To this Fmoc protected 38 was added a 1:3:16 mixture of hydrazine:piperidine:DMF (200 µL). The resulting yellowish solution was stirred for 30 min before addition of a solution of TFA to bring the pH to 3. The reaction mixture was purified by semiprep HPLC column (5 to 25%B over 25 min) to afford the Fmoc deprotected 38 in 30% yield. $^1$H-NMR (CDCl$_3$, 500 MHz) (selected protons) δ 4.78 (2H, d, J=12.4 Hz), 4.70 (1H, d, J=9.6 Hz), 4.57 (2H, d, J=13.2 Hz), 4.26 (4H, m), 4.14 (1H, d, J=7.2 Hz), 1.01 (9H, s), 0.575 (6H, m).

EXAMPLE 33

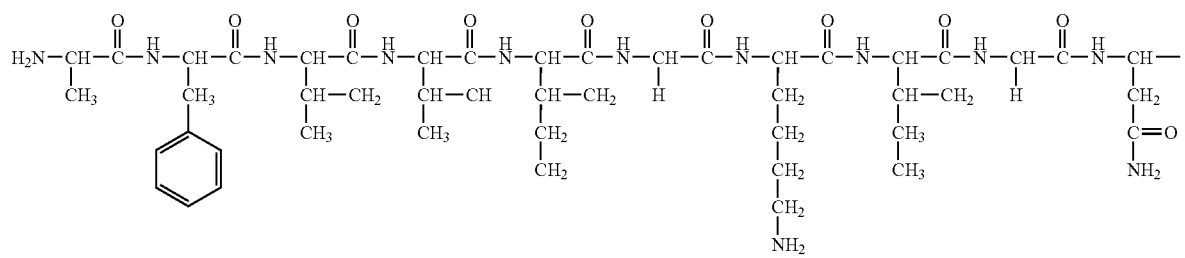

39

-continued

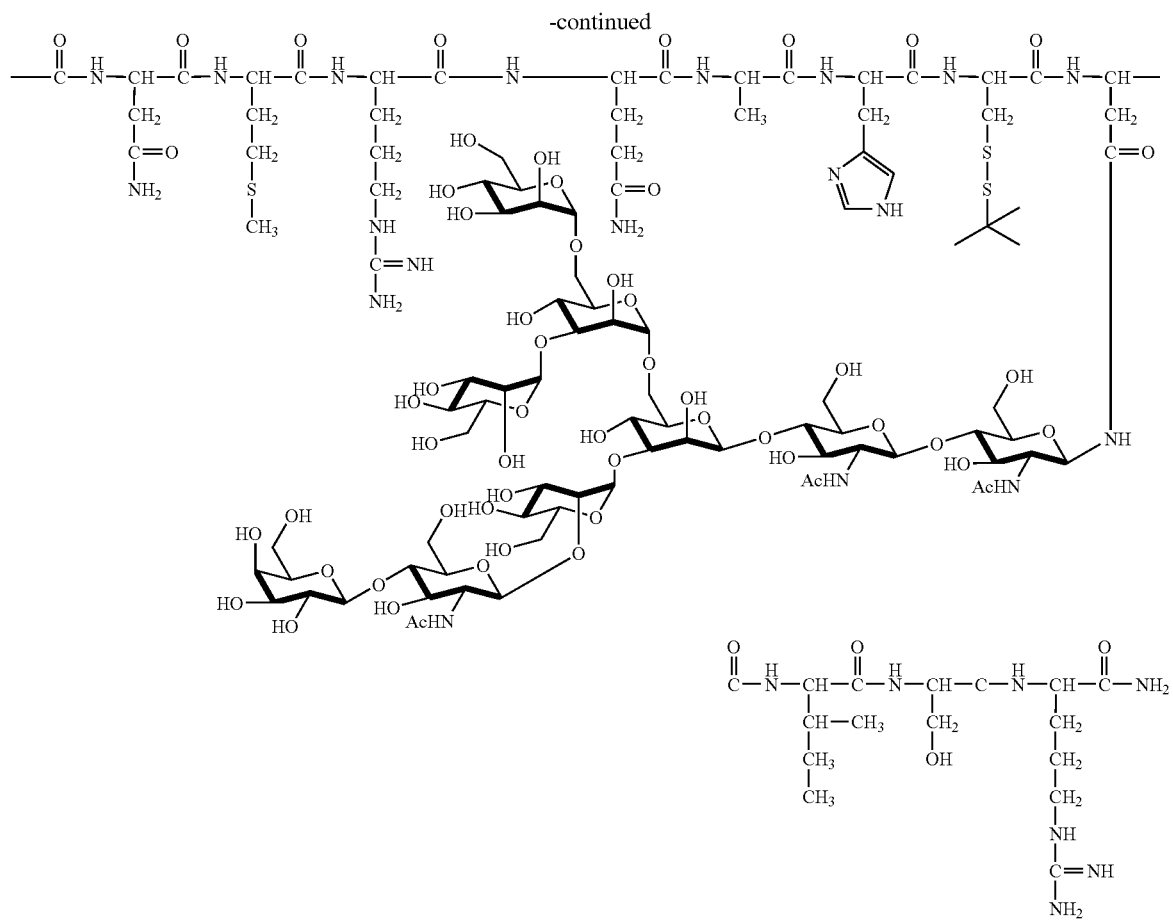

Compound 39 was Prepared Similar to 34.

EXAMPLE 34

General Methods: Reagents obtained from commercial suppliers were used without further purification unless otherwise noted. THF, toluene, and methylene chloride were obtained from a dry solvent system (passed through a prepacked column of alumina) and used without further drying. All air and water sensitive reactions were performed in flame-dried glassware under a positive pressure of prepurified argon gas. NMR ($^1$H and $^{13}$C) spectra were recorded on Bruker AMX-400 MHz or Bruker Advance DRX-500 MHz as noted individually, referenced internally to solvent residual protons, or in the case of $D_2O$, to an external standard of 3-(Trimethylsilyl)-1-propanesulfonic acid, sodium salt. Optical rotations were obtained on a JASCO model DIP-370 digital polarimeter. Analytical thin-layer chromatography was performed on E. Merck silica gel 60 F254 plates. Compounds which were not UV active were visualized by dipping the plates in para-anisaldehyde, potassium permanganate, cerium ammonium molybdate, or orcinol/$H_2SO_4$ solution and heating. Preparative thin layer chromatography was performed using the indicated solvent on Whatman (LK6F Silica gel 60 Å 250 µM or 1000 µM) TLC plates.

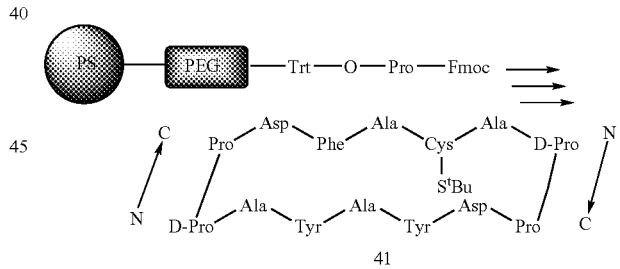

Cyclic peptide 41: NovaSyn TGT resin (purchased from NovaBiochem) was chlorinated, then esterified with Fmoc-Pro-OH, and then immediately Fmoc-deprotected according to a literature procedure (See *Fmoc Solid Phase Peptide Synthesis: A Practical Approach*. Ed. Chan, W. C. and White, P. D. Oxford University Press, New York, 2000. pp 50 and 217). Fmoc quantitation of the resin prior to deprotection indicated a loading of 0.180 mmol/g. 0.999 g of this resin was subjected continuous flow automated peptide synthesis. For coupling steps, resin was treated with with a 3-fold excesses of HATU and Fmoc amino acids in DIEA/DMF, and for deblocking, a solution of 2% Piperidine/2% DBU in DMF was used. The amino acids used were, in order of synthesis, Fmoc-D-Pro-OH, Fmoc-Ala-OH, Fmoc-Tyr(tBu)-OH, Fmoc-Ala-OH, Fmoc-Tyr(tBu)-OH, Fmoc-Asp(tBu)-OH, Fmoc-Pro-OH, Fmoc-D-Pro-OH, Fmoc-Ala-OH, Fmoc-Cys(StBu)-OH, Fmoc-Ala-OH, Fmoc-Phe-OH, Fmoc-Asp(tBu)-OH. The resin was then transferred to a manual peptide synthesis vessel, treated with a cleavage solution of 10 mL of 20% trifluoroethanol in dichloromethane for 2 hours. The beads were filtered, rinsed with another 10 mL cleavage solution, filtered again, and then treated for another 2 hours with 10 mL of cleavage solution. This process was repeated for a total of 3 2-hour cleavage cycles, and the combined filtrate was concentrated in vacuo to afford 290 mg crude linear protected peptide (ESI MS analysis showed predominantly the desired product peak, 1809.9 (M+H)). This material was redissolved in 100 mL of 1% v/v DIEA in DMF. HOAt (65.9 mg, 0.484 mmol, 3 equiv.) was added, followed by HATU (184 mg, 0.484 mmol, 3 equiv.). After 1 hour, the solvent was removed in vacuo (using a rotovap, ~1 mm Hg, 30C). The remaining residue was left on a pump (~0.25 mm Hg) for another 3 minutes before being resuspended in 10 mL dichloromethane, at which point crystals of HATU/HOAt-related material crashed out and were filtered off through a cotton plug. The resulting solution was subjected to a short silica column in 8% MeOH/dichloromethane, and all fractions were combined except those containing baseline material by TLC, which were discarded. The combined fractions were concentrated in vacuo, affording the crude cyclic protected peptide (ESI MS analysis showed predominantly the desired product peak, 1791.9 (M+H)). This material was then redissolved in a solution of 87.5%TFA/5% water/5% phenol/2.5% triethylsilane, and stirred for 30 minutes. Solvent was removed in vacuo, then the residue was triturated with 25 mL diethyl ether 4 times to afford 160 mg crude peptide 41. This was purified in four batches by preparative reverse-phase HPLC using a gradient of 20-50% acetonitrile in water (with a constant TFA concentration of 0.04-0.05%) over 40 min, flow rate 80 mL/min. The retention time of 41 was 19.9 minutes (ESI MS analysis showed a clean product spectrum with a base peak of 1567.7 (M+H)). The column used was a 41×250 mm Dynamax C18 column, 60 Å pore size, 8☐M particle size to afford 110 mg pure 41 (0.070 mmol, 39% yield based on Proline-loaded resin).

EXAMPLE 35

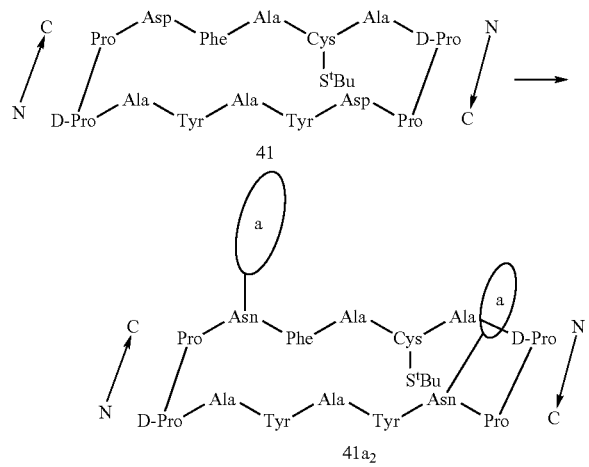

Divalent Glycopeptide $41a_2$: Solutions of each reaction participant were prepared with a stir bar in flame-dried vials under argon as follows: Peptide 41 (5.8 mg, 3.7 μmol, 1.02 equiv., dissolved in 300 μL DMSO), glycosylamine a-$NH_2$ (14.9 mg, 7.91 μmol, 2.2 equiv., dissolved in 200 μL DMSO), HATU (10.9 mg dissolved in 500 mL DMSO). 4 μL of dry DIEA was added to the vial containing peptide 41, followed by 145 μL (8.14 μmol, 2.26 equiv.) of the HATU solution, producing a strong yellow color. As quickly as possible (~30 sec), 438 μL of this activated peptide solution was transferred to the vial containing the solution of glycosylamine a. After 1 hour, LC/MS analysis of the crude reaction mixture (10-50%B over 40 min, same solvent system as above, Microsorb C18, 300-5, 2×150 mm, 0.2 mL/min) showed 70% yield of divalent glycopeptide (RT 25 min) by integration of UV signal. The crude reaction mixture was injected onto preparative reverse-phase HPLC using a gradient of 10-50%B over 40 minutes, flow rate 16 mL/min. The column used was a 21.4× 250 mm Dynamax C18, 60 Å pore size, 5 μM particle size. Retention time for divalent glycopeptide was 24 minutes. After concentrating the fractions from this peak, the material was redissolved in DMF/water and repurified on the same column in five batches using a slower gradient (20-35%B over 15 min), this time collecting only the center of the peak for the purest fractions (ESI MS analysis showed a clean product spectrum with base peaks of 2648.1 (M+2H) and 1765.7 (M+3H). Concentration of these fractions yielded 6.6 mg $41a_2$ (1.25 μmol 35% yield).

EXAMPLE 36

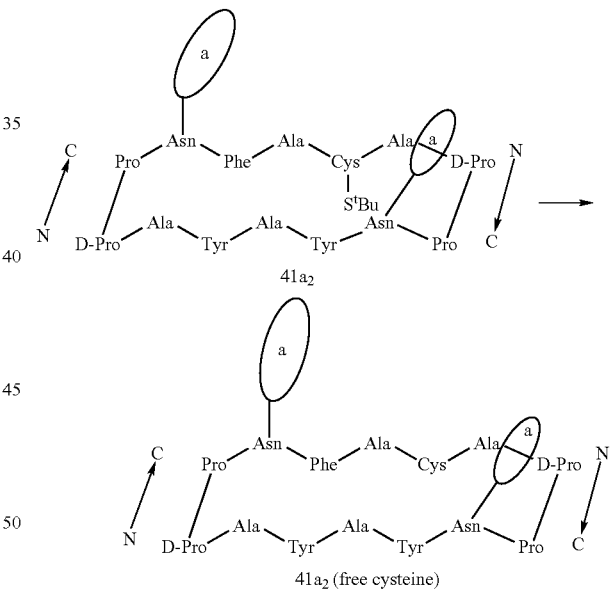

Cysteine-disulfide deprotection of $41a_2$: To a solution of 6.6 mg $41a_2$ (1.25 μmol) in 1.4 mL DMF and 175 μL water was added 87 μL DIEA. Argon was bubbled through the reaction mixture for 15 minutes and then mercaptoethane sulfonic acid, sodium salt was added (20.5 mg, 0.125 mmol, 100 equiv.). After 9 hours, LC/MS analysis in 10-40%B over 30 min showed >90% conversion (product R.T. 18.3 min), with a trace of mixed $41a_2$-MESNa disulfide beginning to appear (R.T. 15 min). The crude reaction mixture was then injected, with minimal handling in air, onto preparative reverse-phase HPLC, using a gradient of 10-40%B over 30 min (see procedure for 41 for description of solvent). Product fractions were collected at 20.4 minutes and immediately shell-frozen and lyophilized. The solid product of this reaction is prone to air-oxidation and is most reliably preserved by storage under vacuum.

ABBREVIATIONS AND GLOSSARY

A: alanine
Ac: acetyl
ACT: α1-antichymotrypsin
Ala: alanine
Arg: arginine
Asn: asparagine
Asp: aspartic acid
Bn: benzyl
Boc: tert-butyloxycarbonyl
BPH: benign prostatic hyperplasia
BSP: benzenesulfinyl piperidine
Bu: butyl
Bz: benzoyl
CAN: ceric ammonium nitrate
coll: sym-collidine
C-terminus: peptide carbonyl terminus
Cys: cysteine
D: aspartic acid
DIEA: N,N-diisopropylethylamine
DMF: dimethyl formamide
DMSO: dimethyl sulfoxide
DTBMP: di-tert-butylmethylpyridine
DTBP: di-tert-butylpyridine
Et: ethyl
Fmoc: 9-fluorenylmethyloxycarbonyl
G: glycine
Gal: galactose
Glc: glucose
Gln: glutamine
Glu: glutamic acid
Gly: glycine
H: histidine
HATU: 7-azahydroxybenzotriazolyl tetramethyluronium hexafluorophosphate
His: histidine
Ile: isoleucine
K: lysine
kDa: kilodaltons
KLH: keyhole limpet hemocyanin
L: leucine
Leu: leucine
Lys: lysine
Man: mannose
MES-Na: 2-mercaptoethanesulfonic acid, sodium salt
MHC: major histocompatibility complex
N: asparagine
NAc: N-acetyl
NCL: native chemical ligation
N-terminus: peptide amine terminus
linked: linked through an ethereal oxygen
Pam3Cys: tripalmitoyl-S-glycerylcysteinylserine
PBS: phosphate-buffered saline
Ph: phenyl
Phth: phthalimido-
PMB: p-methoxybenzyl
Pro: proline
Gp120: prostate specific antigen
Py: pyridine
QS21: a glycosteroidal immunoaduvant
R: arginine
S: serine
sat. aq.: saturated aqueous
Ser: serine
T: threonine
TBAF: :tetra-n-butylammonium fluoride
TBS: tert-butyldimethylsilyl
tBu: tert-butyl
Tf: trifluoromethanesulfonate
THF: tetrahydrofuran
Thr: threonine
t-Gp120: total prostate specific antigen
Trp: tryptophan
V: valine
Val: valine
W: tryptophan

What is claimed is:

1. A multi-antigenic construct comprising two or more carbohydrate domains having the structure:

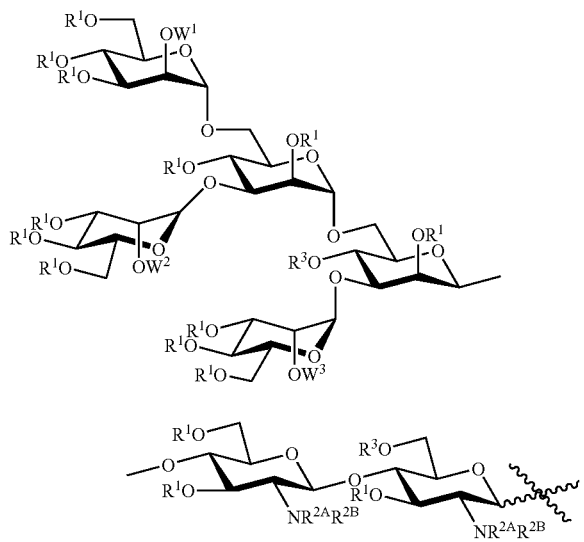

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

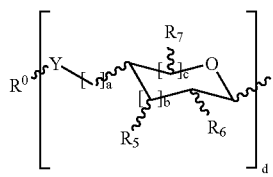

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently $R^1$, $R^3$, or optionally substituted mannose, galactose or lactosamine moieties;

wherein each carbohydrate domain is independently covalently bound to a linker system, said linker system being a cyclic peptide or dimerized peptide.

2. The construct of claim 1, wherein $W^3$ is $R^1$, $R^3$, as defined in claim 1, or a moiety having the structure:

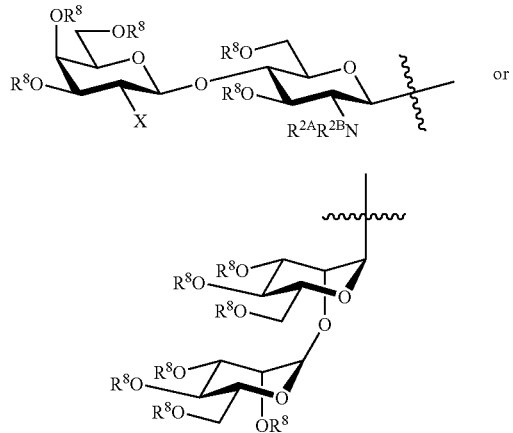

wherein X is $-OR^1$ or $-NR^{2A}R^{2B}$; and each occurrence of $R^8$ is independently $R^1$ or a sialic acid moiety.

3. The construct of claim 1, wherein $W^1$ and $W^2$ are independently $R^1$, $R^3$ or a moiety having the structure:

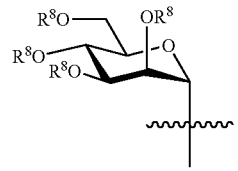

wherein each occurrence of $R^8$ is independently $R^1$ or a sialic acid moiety.

4. The construct of claim 1, wherein the linker system is designed to approximate the spatial position(s) of carbohydrate(s) in gp120.

5. The construct of claim 1, wherein the linker system is further attached to a carrier immunostimulant.

6. A multi-antigenic construct comprising a cyclic or dimeric peptide backbone, wherein two or more amino acids are independently substituted with a glycosidic moiety having the structure:

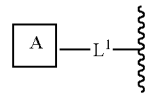

wherein each occurrence of $L^1$ is independently a substituted or unsubstituted, linear or branched, cyclic or acyclic, saturated or unsaturated aliphatic or heteroaliphatic moiety; and each occurrence of A is independently a carbohydrate domain of formula:

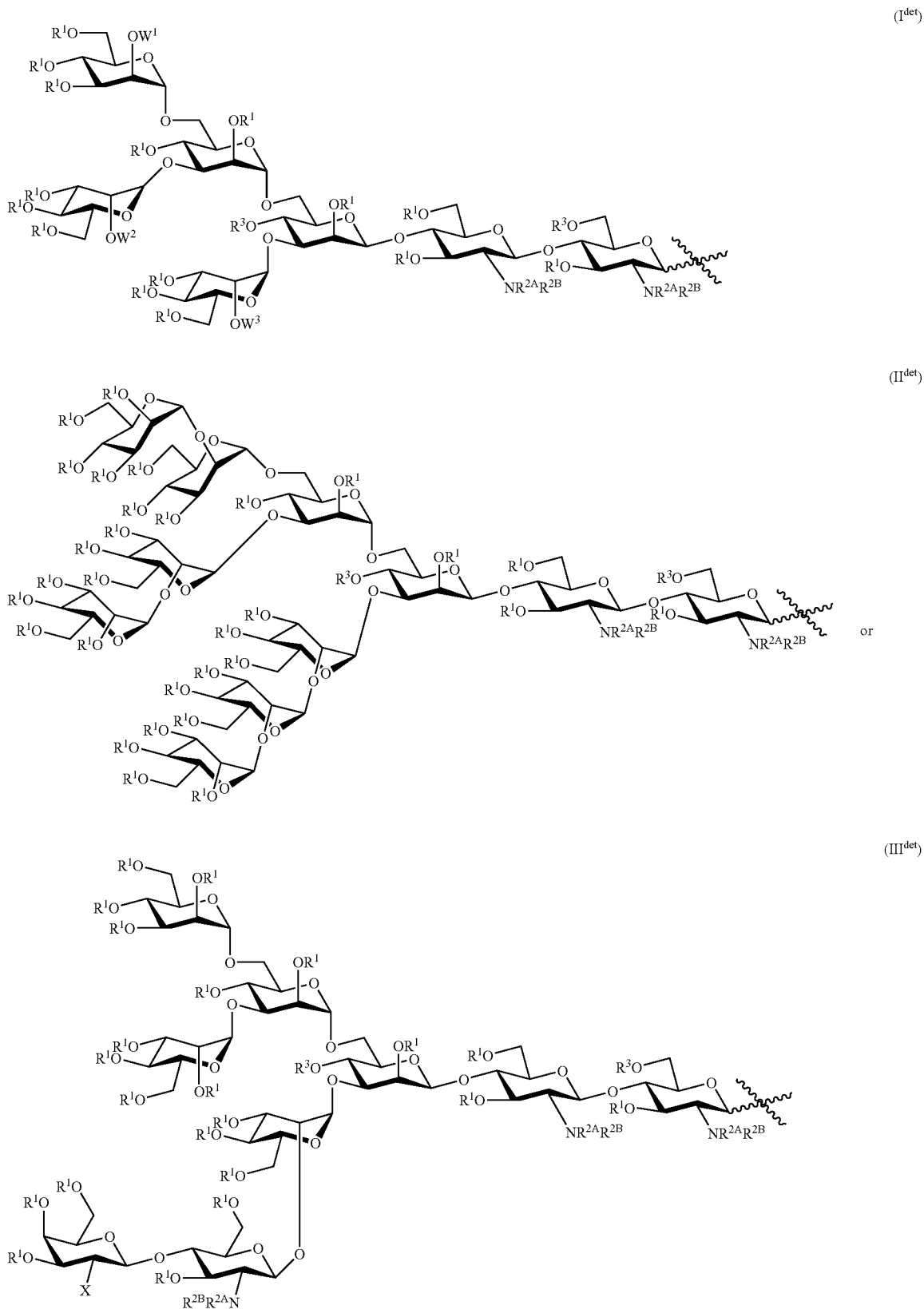

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

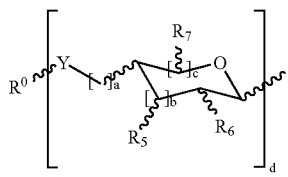

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group; and $W^1$, $W^2$ and $W^3$ are independently optionally substituted mannose, galactose or lactosamine moieties.

7. The construct of claim 6 having the structure:

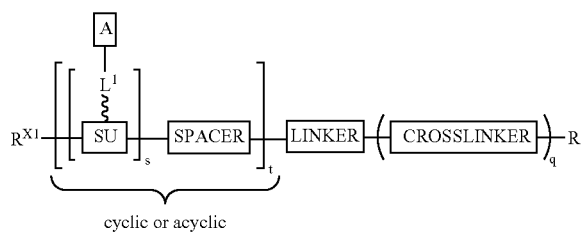

wherein q is 0 or 1;
each occurrence of s is independently an integer from 1-20;
t is an integer from 1-6;
wherein t+s>2;
$R^{X1}$ is hydrogen, alkyl, acyl, aryl, heteroaryl, -alkyl(aryl), -alkyl(heteroaryl) or a nitrogen x protecting group; or $R^{X1}$ is covalently bound to a substituent on the last occurrence of the spacer, thereby forming a cyclic backbone;
R is hydrogen or an immunogenic carrier;
each occurrence of the structural unit SU is independently a substituted or unsubstituted aliphatic, heteroaliphatic, aryl, heteroaryl or peptidic moiety;

each occurrence of the spacer is independently a substituted or unsubstituted aliphatic, heteroaliphatic, aryl, heteroaryl or peptidic moiety;

the linker is absent, or is —O—, $—NR_G—$, $—NR_G(CR_HR_J)_kNR_K—$, $—NR_G(CR_HR_J)_kNR_K(C=O)(CR_HR_J)_kS—$, $—(CR_HR_J)_kNR_K—$, $—O(CR_HR_J)_kNR_K—$, an oligoester fragment comprising from 2 to about 20 hydroxy acyl residues, a peptidic fragment comprising from 2 to about 20 amino acyl residues, or a linear or branched chain alkyl or aryl carboxylic ester, wherein each occurrence of k is independently 1-5;

wherein each occurrence of $R_G$, $R_H$, $R_J$ or $R_K$ is independently hydrogen, a linear or branched, substituted or unsubstituted, cyclic or acyclic alkyl moiety, or a substituted or unsubstituted aryl moiety;

the crosslinker is a moiety derived from a crosslinking reagent capable of conjugating the carrier with the linker, or when the linker is absent, with the t bracketed structure;

the carrier is a peptide, protein, protein complex or lipid;

each occurrence of $L^1$ is independently a substituted or unsubstituted aliphatic or heteroaliphatic moiety; and each occurrence of A is independently a carbohydrate domain of formula ($I^{det}$), ($II^{det}$) or ($III^{det}$).

8. The construct of claim 6 or 7, wherein each occurrence of $L^1$ is independently $—O(CHR^{aa})_n—$ or $—NHC(=O)(CHR^{aa})_n—$ wherein each occurrence of n is independently an integer from 1-10; and each occurrence of $R^{aa}$ is hydrogen, lower alkyl, aryl, heteroaryl, -alkyl(aryl) or alkyl(heteroaryl).

9. The construct of claim 7, wherein the structural unit SU, for each occurrence, is independently a substituted or unsubstituted amino acid residue or peptidyl moiety.

10. The construct of claim 7, wherein the t bracketed structure is a cyclic glycopeptide having the structure:

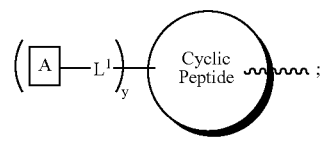

where y is an integer from 1-50; and
each occurrence of A is independently a carbohydrate domain of formula ($I^{det}$), ($II^{det}$) or ($III^{det}$).

11. The construct of claim 10, wherein the cyclic peptide has the structure:

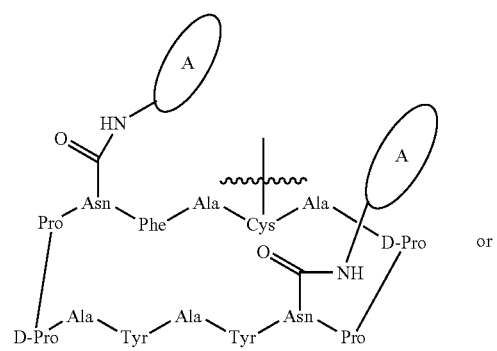

or

-continued

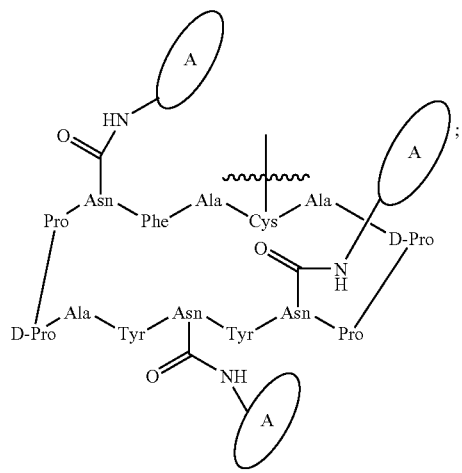

wherein each occurrence of A is independently a carbohydrate domain of formula ($I^{det}$), ($II^{det}$) or ($III^{det}$).

12. The construct of claim 11, wherein each occurrence of A has the structure:

13. The construct of claim 6, wherein the construct is a dimeric glycopeptide having the structure:

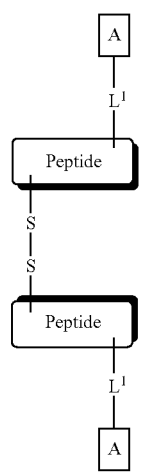

wherein each peptide may be the same or different; and each occurrence of A is independently a carbohydrate domain having the structure:

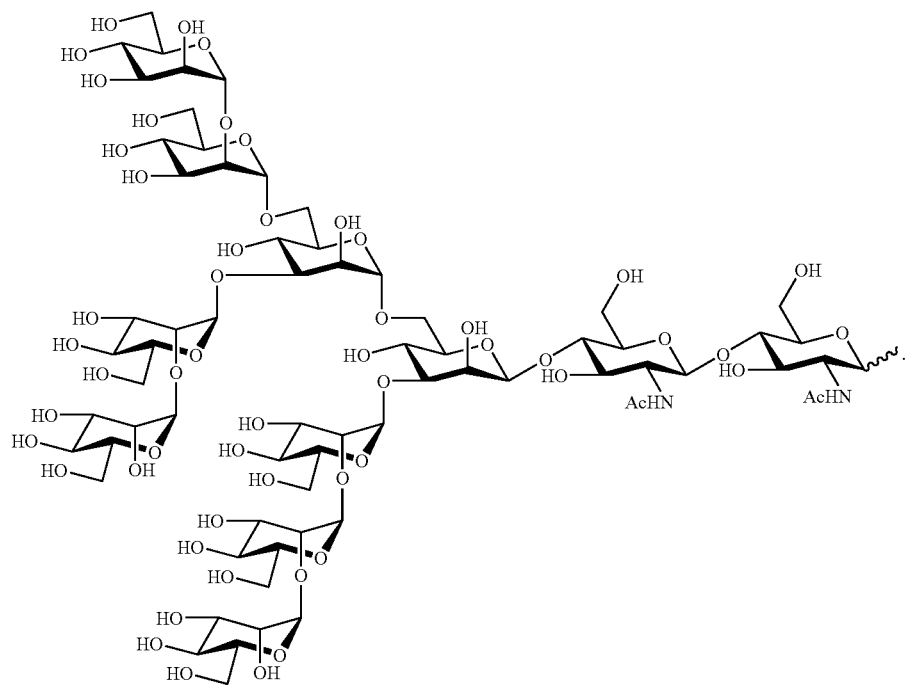

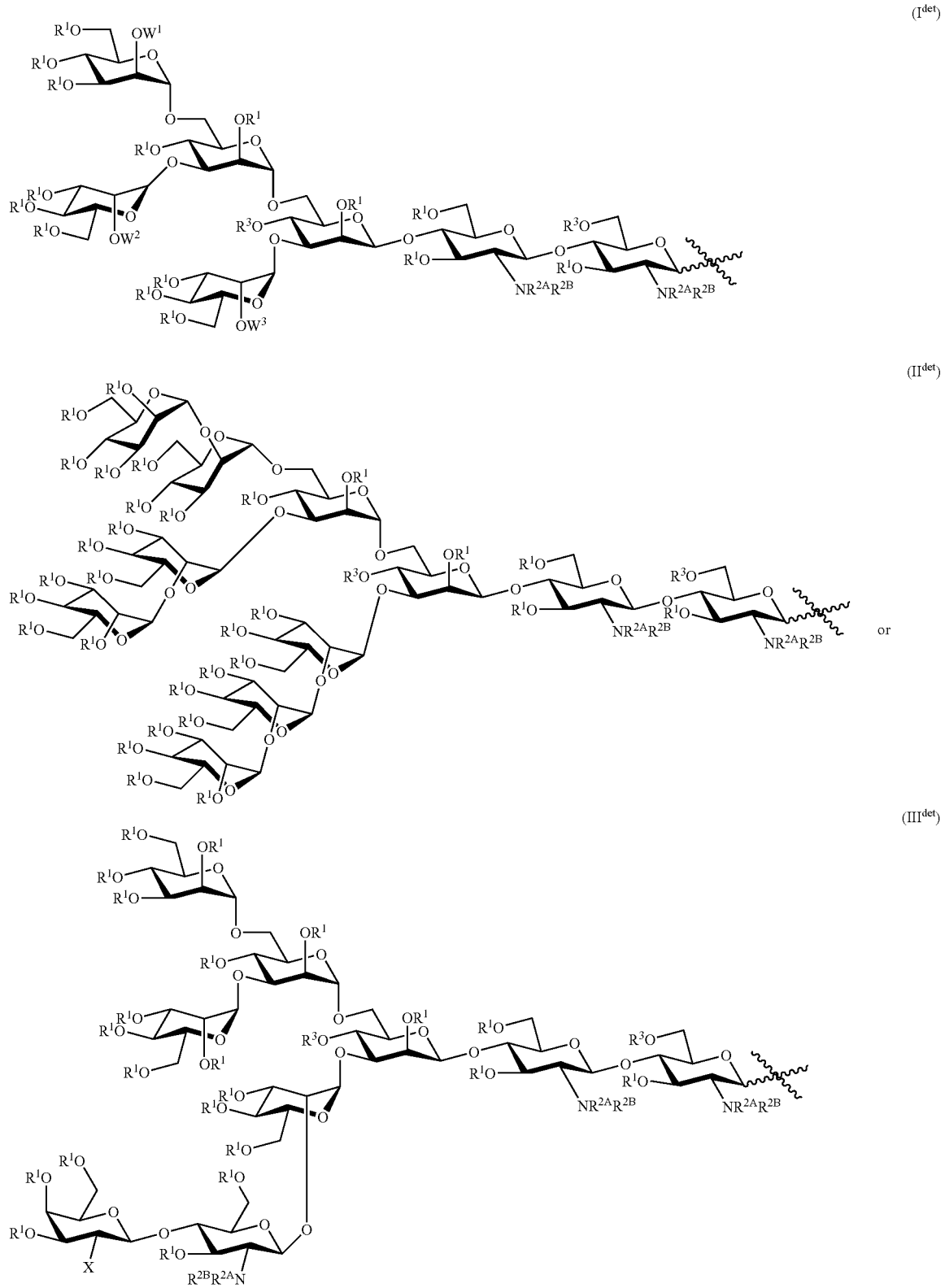
wherein each occurrence of $R^1$ is independently hydrogen or an oxygen protecting group;
each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

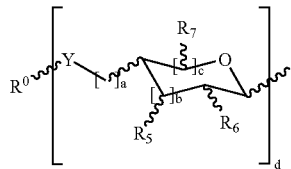

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alicyl, arylaikyl or aryl group;

$W^1$, $W^2$ and $W^3$ are independently optionally substituted mannose, galactose or lactosamine moieties.

14. The glycopeptide of claim 13, wherein each occurrence of $L^1$ is independently —O(CHR$^{aa}$)$_n$— or —NHC(=O)(CHR$^{aa}$)$_n$— wherein each occurrence of n is independently an integer from 1-10; and each occurrence of $R^{aa}$ is hydrogen, lower alkyl, aryl, heteroaryl, -alkyl(aryl) or -alkyl(heteroaryl).

15. The glycopeptide of claim 13, wherein each occurrence of $L^1$ is an aspartyl side chain.

16. The glycopeptide of claim 13, wherein the peptide has a structure that is either identical or closely related to that of gp120 near an N-glycosylation site.

17. The glycopeptide of claim 16, wherein the peptide comprises the amino acid sequence: Cys-Asn-Ile-Ser-Arg (SEQ ID NO: 3), wherein any one or more of the amino acid residues may bear one or more protecting groups.

18. The glycopeptide of claim 16, wherein the peptide comprises the amino acid sequence: Ala-Phe-Val-Thr-Ile-Gly-Lys-Ile-Gly-Asn-Met-Arg-Gln-Ala-His-Cys-Asn-Ile-Ser-Arg (SEQ ID NO: 4), wherein any one or more of the amino acid residues may bear one or more protecting groups.

19. The glycopeptide of claim 12 having the structure:

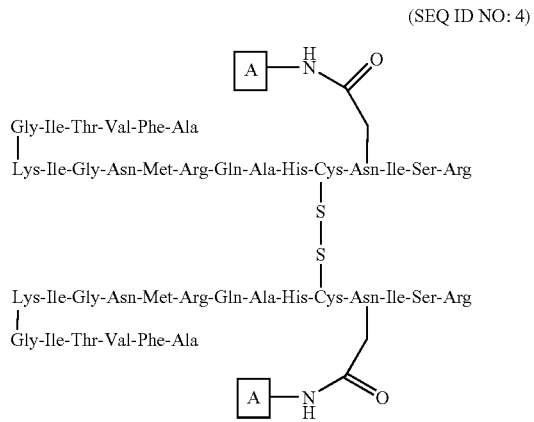

wherein each occurrence of A is independently a carbohydrate domain having one of the structures:

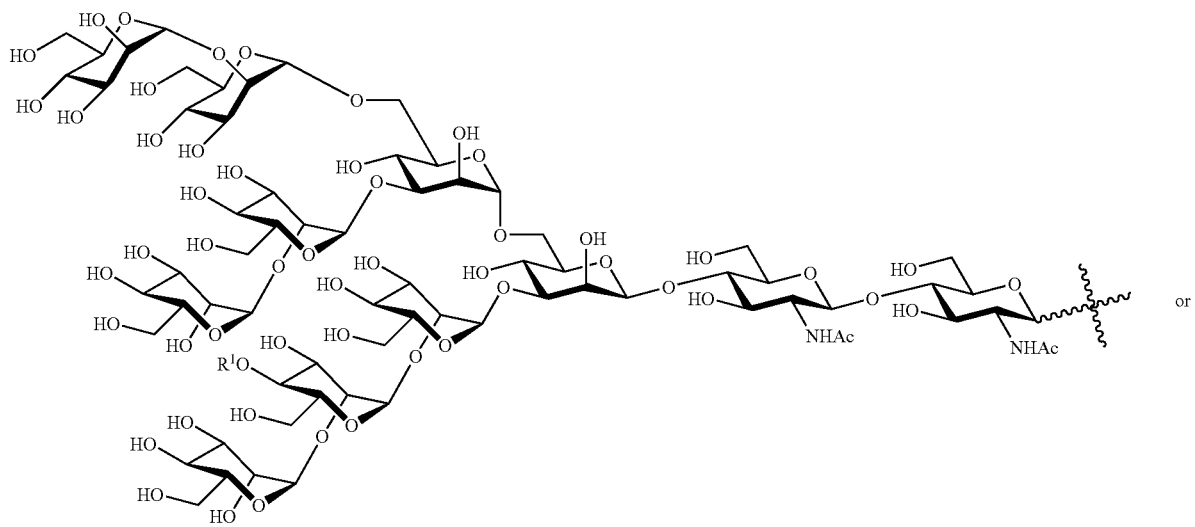

-continued
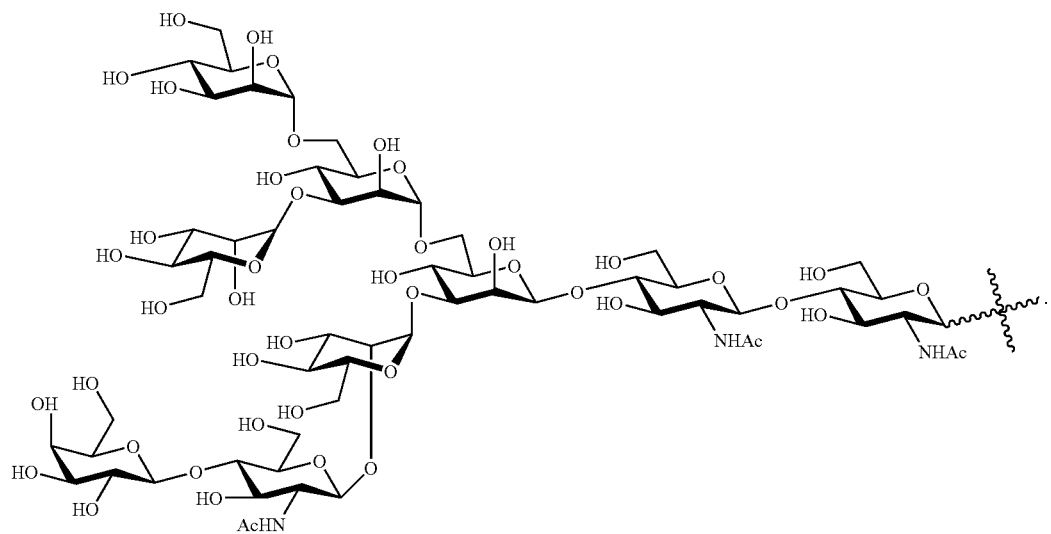
20. The glycopeptide of claim 13 having the structure:
(SEQ ID NO: 3)
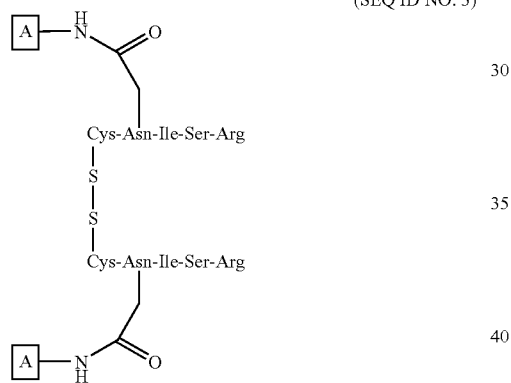
wherein each occurrence of A is independently a carbohydrate domain having one of the structures:
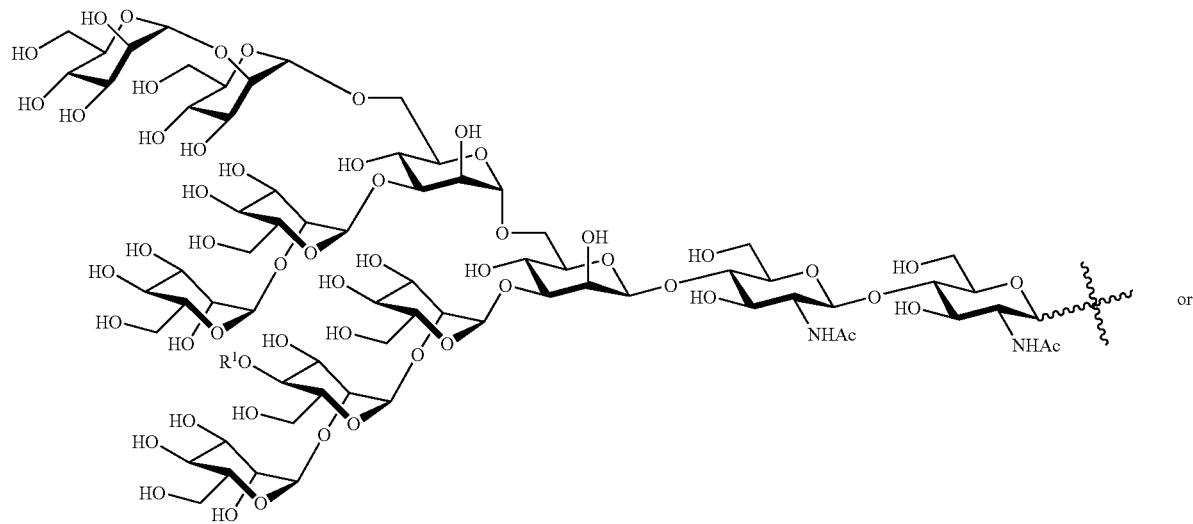
or -continued

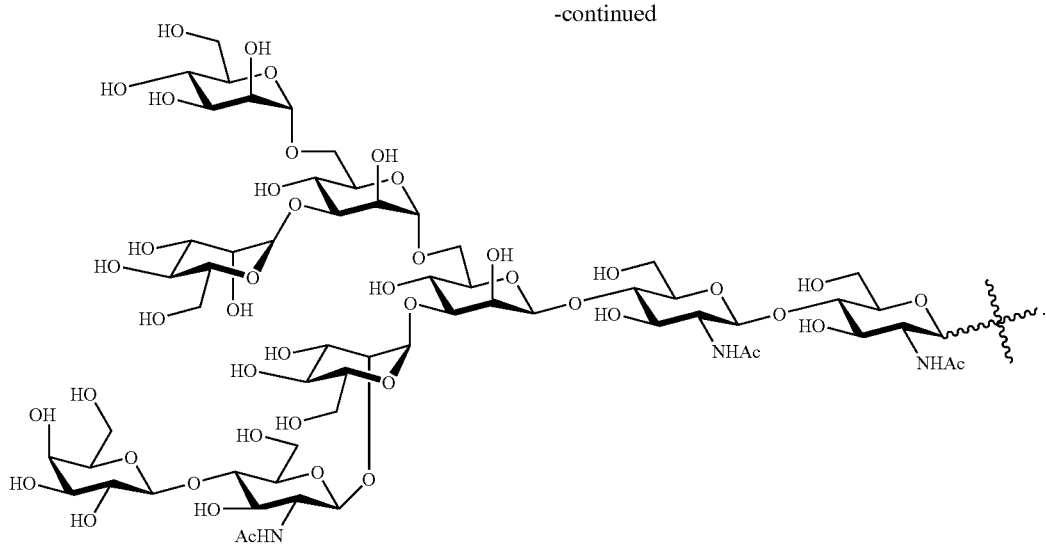

21. An isolated multi-antigenic compound comprising two or more carbohydrate domains having the structure:

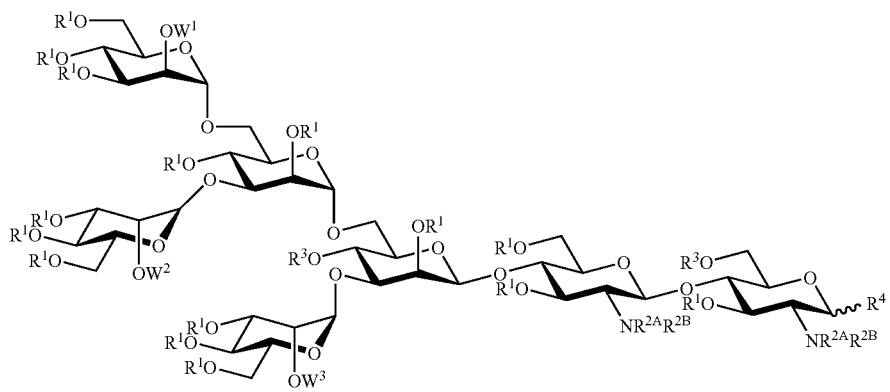

(I)

wherein each occurrence of $R^1$ is independently hydrogen or an oxygen protecting group;
each occurrence of $R^{2A}$ and $R^{2B}$ is independently hydrogen or a nitrogen protecting group;
each occurrence of $R^3$ is independently hydrogen, a protecting group or a carbohydrate domain comprising a saccharide moiety having the structure:

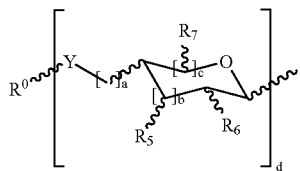

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently $R^1$, $R^3$, or optionally substituted mannose, galactose or lactosamine moieties;
and wherein $R^4$ is —$OR^{4A}$ or —$NHR^{4A}$; wherein $R^{4A}$ is an amino acyl moiety, an amino acyl residue of a peptide, an amino acyl residue of a protein, or $R^{4A}$ comprises a peptide moiety covalently linked to the rest of the construct, or to the N or O atom to which it is attached, either directly or through a crosslinker;

wherein $R^4$ comprises a cyclic or dimeric peptide.

22. The compound of claim 21, wherein $W^3$ is $R^1$, $R^3$, or a moiety having the structure:

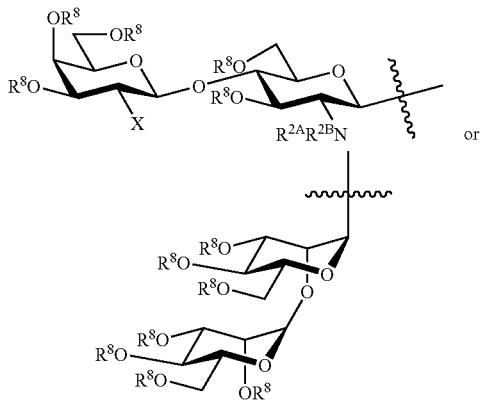

or wherein X is $-OR^1$ or $-NR^{2A}R^{2B}$; and each occurrence of $R^8$ is independently $R^1$ or a sialic acid moiety.

23. The compound of claim 21, wherein $W^1$ and $W^2$ are independently $R^1$, $R^3$ or a moiety having the structure:

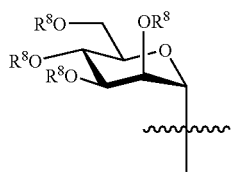

wherein each occurrence of $R^8$ is independently $R^1$ or a sialic acid moiety.

24. An isolated multi-antigenic compound comprising two or more carbohydrate domains having the structure:

each occurrence of $R^3$ is independently hydrogen, a protecting group or a carbohydrate domain comprising a saccharide moiety having the structure:

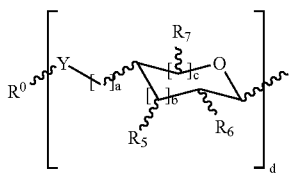

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylailcyl or aiyl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylailcyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

$W^1$, $W^2$ and $W^3$ are independently optionally substituted mannose, galactose or lactosamine moieties;

and wherein $R^4$ is $-NHR^{4A}$; wherein $R^{4A}$ is covalently linked to the rest of the construct, or to the N atom to which it is attached, either directly or through a crosslinker;

(I)

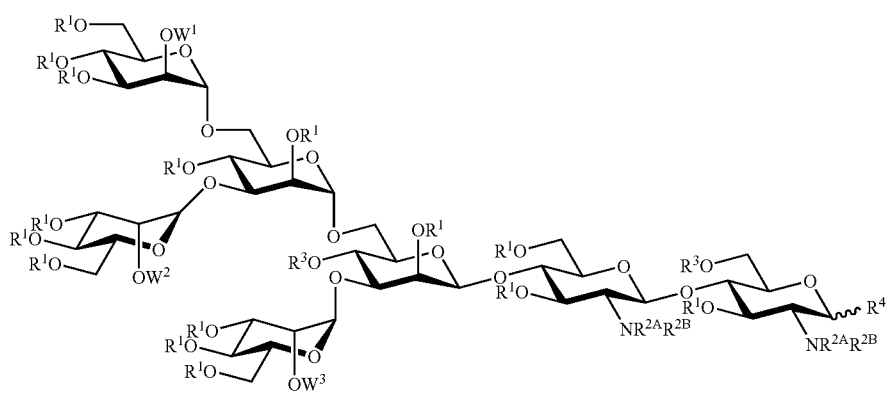

wherein each occurrence of $R^1$ is independently hydrogen or an oxygen protecting group;

each occurrence of $R^{2A}$ and $R^{2B}$ is independently hydrogen or a nitrogen protecting group;

wherein $R^{4A}$ comprises an Asparagine residue (Asn) of a peptide whose structure is either identical or closely related to that of gp120 near an N-glycosylation site and the saccharide unit bearing $R^4$ has the structure:

(SEQ ID NO: 3)

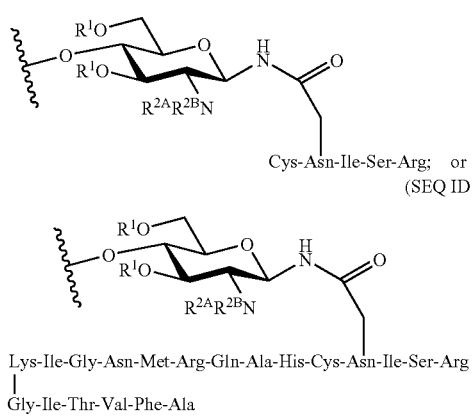

Cys-Asn-Ile-Ser-Arg; or (SEQ ID NO: 4)

Lys-Ile-Gly-Asn-Met-Arg-Gln-Ala-His-Cys-Asn-Ile-Ser-Arg
|
Gly-Ile-Thr-Val-Phe-Ala wherein any of the amino acid residues may bear one or more protecting groups.

25. The compound of claim 24, wherein the saccharide unit bearing $R^4$ has the structure:

(SEQ ID NO: 3)

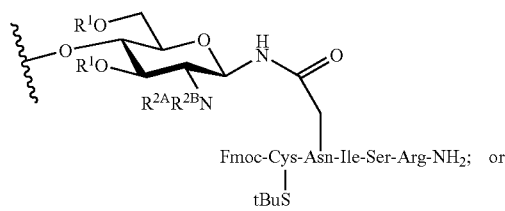

Fmoc-Cys-Asn-Ile-Ser-Arg-NH$_2$; or
|
tBuS

-continued (SEQ ID NO: 4)

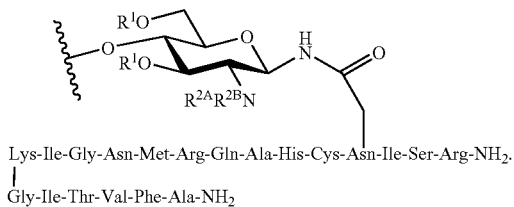

ivDde
|
Lys-Ile-Gly-Asn-Met-Arg-Gln-Ala-His-Cys-Asn-Ile-Ser-Arg-NH$_2$.
|                                                        |
Gly-Ile-Thr-Val-Phe-Ala-Fmoc                            tBuS

26. The compound of claim 24, wherein the saccharide unit bearing $R^4$ has the structure:

(SEQ ID NO: 4)

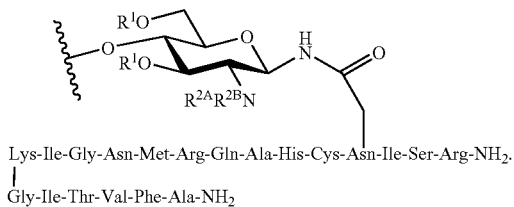

Lys-Ile-Gly-Asn-Met-Arg-Gln-Ala-His-Cys-Asn-Ile-Ser-Arg-NH$_2$.
|
Gly-Ile-Thr-Val-Phe-Ala-NH$_2$

27. A compound having the structure:

(SEQ ID NO: 3)

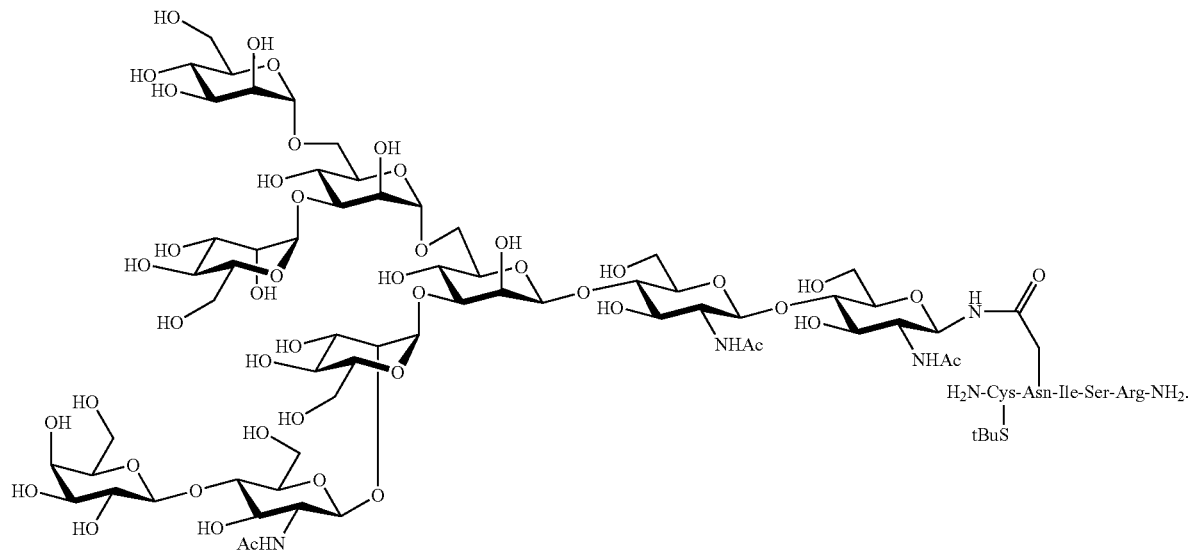

28. A compound having the structure:
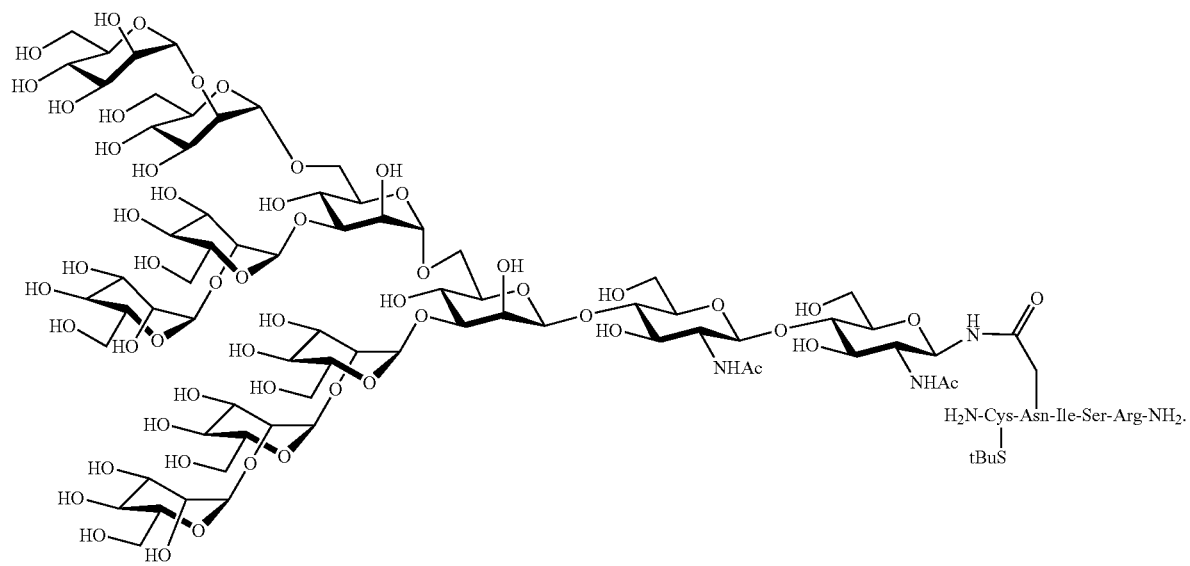
(SEQ ID NO: 3)
29. A compound having the structure:
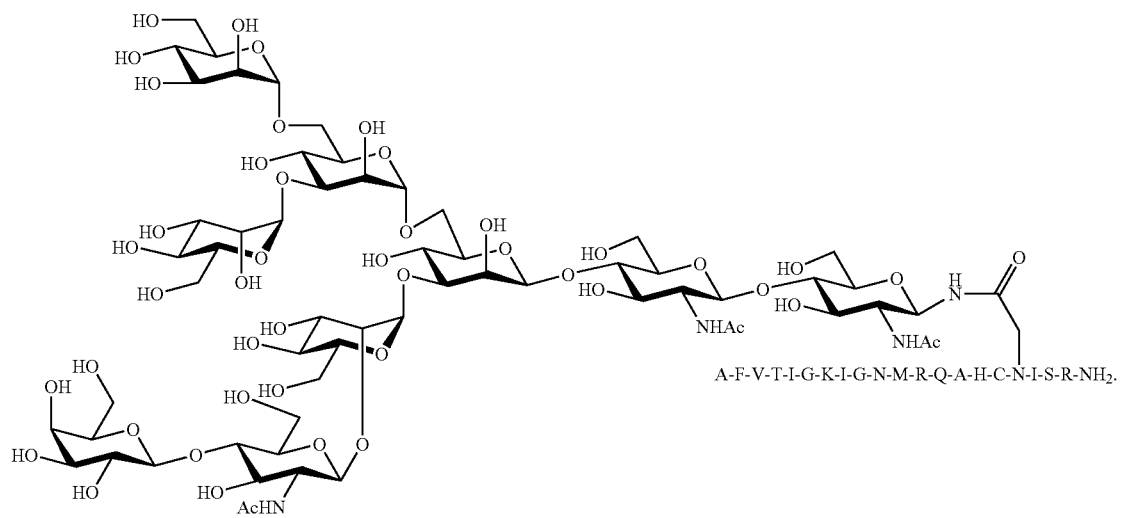
(SEQ ID NO: 4)

30. A compound having the structure:

(SEQ ID NO: 4)

A-F-V-T-I-G-K-I-G-N-M-R-Q-A-H-C-N-I-S-R-NH₂.

31. A pharmaceutical composition comprising an effective amount of a construct of claim 6; in admixture with a pharmaceutically suitable diluent or carrier.

32. The composition of claim 31, wherein the composition is for eliciting an immune response in a subject and the compound is present in an amount effective to induce antibodies in the subject.

33. A method of eliciting antibodies in a subject comprising administering to the subject a composition of claim 32.

34. A method of treating or preventing an HIV infection comprising administering to a subject an effective amount of a composition of claim 31.

35. A method of eliciting an immune response wherein the response is directed against an antigen comprising a carbohydrate epitope expressed on the surface of gp120, said antigen being a construct of claim 1.

36. The method of claim 35 further comprising administering an adjuvant.

37. The multi-antigenic construct of claim 1, wherein the linker system is a cyclic peptide that adopts a β-sheet conformation in which alternating residues point their side chains above and below the macrocycle.

38. The multi-antigenic construct of claim 37, wherein all amino acids bearing a carbohydrate domain point their side chains in the same direction.

39. The multi-antigenic construct of claim 38, wherein the number of amino acids bearing a carbohydrate domain is an integer between two and six, inclusive.

40. The multi-antigenic construct of claim 38, wherein the number of amino acids bearing a carbohydrate domain is three.

41. The multi-antigenic construct of claim 38, wherein the number of amino acids bearing a carbohydrate domain is two.

42. The multi-antigenic construct of claim 38, further comprising a cysteine residue side chain that points in the opposite direction of the amino acid side chains bearing a carbohydrate domain.

43. The multi-antigenic construct of claim 38, wherein the linker system is further covalently attached to a carrier immunostimulant selected from the group consisting of KLH, OMPC, Pam₃Cys, bovine serum albumin, and polysine.

44. The multi-antigenic construct of claim 43, wherein the carrier immunostimulant is linked to the rest of the construct through a crosslinker.

45. The multi-antigenic construct of claim 44, where the carrier immunostimulant is OMPC.

\* \* \* \* \*